US011179457B2

(12) United States Patent
Iyer et al.

(10) Patent No.: US 11,179,457 B2
(45) Date of Patent: Nov. 23, 2021

(54) SENECAVIRUS A IMMUNOGENIC COMPOSITIONS AND METHODS THEREOF

(71) Applicant: Boehringer Ingelheim Animal Health USA Inc., Duluth, GA (US)

(72) Inventors: Arun V. Iyer, Ames, IA (US); Abby Rae Patterson, Story City, IA (US); Joseph Gilbert Victoria, Ames, IA (US); Eric Martin Vaughn, Ames, IA (US); Luis Alejandro Hernandez, Story City, IA (US); Jennifer L. English, Marshalltown, IA (US)

( * ) Notice: Subject to any disclaimer, the term of this patent is extended or adjusted under 35 U.S.C. 154(b) by 0 days.

(21) Appl. No.: 16/629,525

(22) PCT Filed: Jul. 9, 2018

(86) PCT No.: PCT/US2018/041321

§ 371 (c)(1),
(2) Date: Jan. 8, 2020

(87) PCT Pub. No.: WO2019/014144

PCT Pub. Date: Jan. 17, 2019

(65) Prior Publication Data

US 2020/0306362 A1 Oct. 1, 2020

Related U.S. Application Data

(60) Provisional application No. 62/590,209, filed on Nov. 22, 2017, provisional application No. 62/531,578, filed on Jul. 12, 2017.

(51) Int. Cl.

| | |
|---|---|
| ***A61K 39/125*** | (2006.01) |
| ***A61P 31/14*** | (2006.01) |
| ***C07K 14/005*** | (2006.01) |
| ***C12N 7/00*** | (2006.01) |
| ***C07K 16/10*** | (2006.01) |
| ***G01N 33/569*** | (2006.01) |
| *A61K 39/00* | (2006.01) |

(52) U.S. Cl.

CPC ............ *A61K 39/125* (2013.01); *A61P 31/14* (2018.01); *C07K 14/005* (2013.01); *C07K 16/1009* (2013.01); *C12N 7/00* (2013.01); *G01N 33/56983* (2013.01); *A61K 2039/5252* (2013.01); *A61K 2039/552* (2013.01); *C12N 2770/32011* (2013.01); *C12N 2770/32022* (2013.01); *C12N 2770/32034* (2013.01)

(58) Field of Classification Search

None

See application file for complete search history.

(56) References Cited

FOREIGN PATENT DOCUMENTS

| | | |
|---|---|---|
| CN | 107184969 A | 9/2017 |
| WO | 2006101841 A2 | 9/2006 |
| WO | 2017181070 A1 | 10/2017 |

OTHER PUBLICATIONS

Chen et al., Construction andcharacterizationofafull-lengthcDNAinfectious clone ofemergingporcineSenecavirusA, 2016, Virology, vol. 497, pp. 111-124.*

Yang, Fan, et al. "Immunogenicity and protective efficacy of an inactivated cell culture-derived Seneca Valley virus vaccine in pigs." Vaccine 36.6 (2018): 841-846.

Zhang, X., et al. "Review of Seneca Valley Virus: A Call for Increased Surveillance and Research." Frontiers in microbiology 9 (2018): 940.

* cited by examiner

*Primary Examiner* — Benjamin P Blumel

(74) *Attorney, Agent, or Firm* — Jamie Graham; John Ezcurra

(57) ABSTRACT

The present invention relates to killed/inactivated and/or recombinant Senecavirus A immunogenic compositions and vaccines, and methods of preventing or treating animals in need of with such an immunogenic compositions and vaccines.

19 Claims, 13 Drawing Sheets

Specification includes a Sequence Listing.

Figure 4:
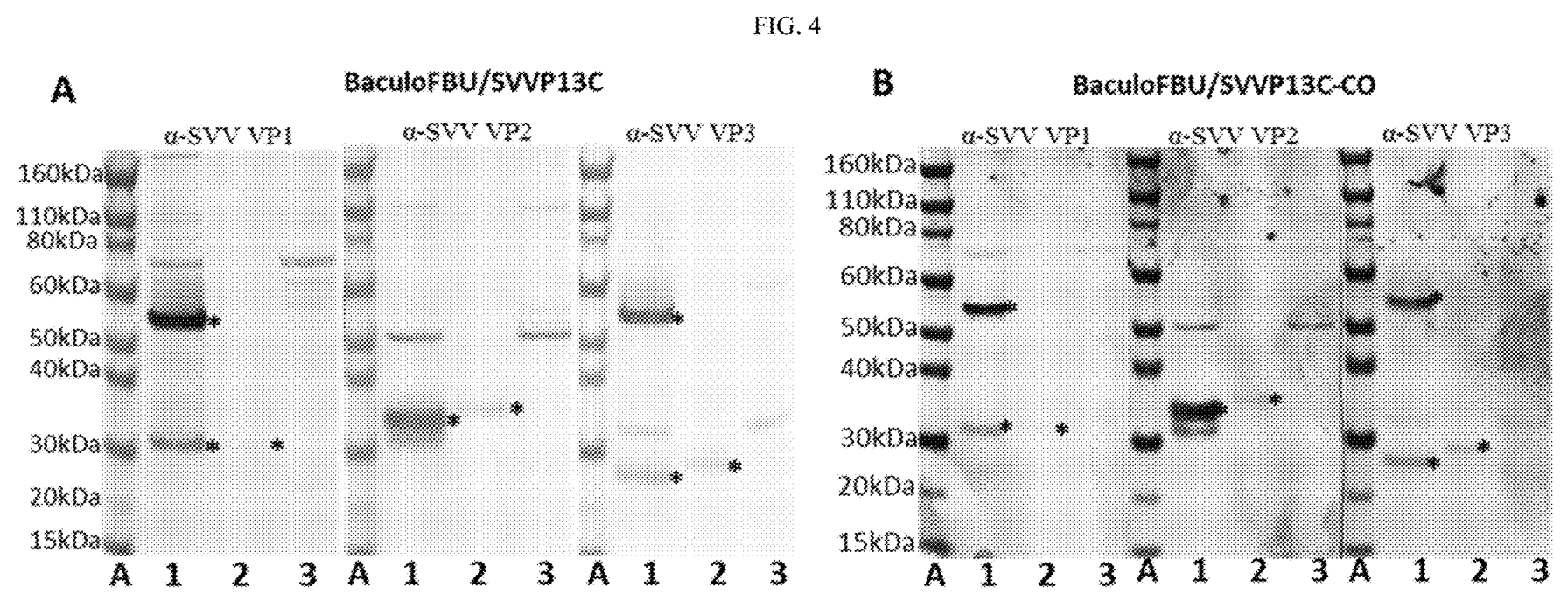

A

BaculoFBU/SVVP13C

α-SVV VP1 α-SVV VP2 α-SVV VP3

160kDa 110kDa 80kDa 60kDa 50kDa 40kDa 30kDa 20kDa 15kDa

A 1 2 3 A 1 2 3 A 1 2 3

B

BaculoFBU/SVVP13C-CO

α-SVV VP1 α-SVV VP2 α-SVV VP3

160kDa 110kDa 80kDa 60kDa 50kDa 40kDa 30kDa 20kDa 15kDa

Figure 6:
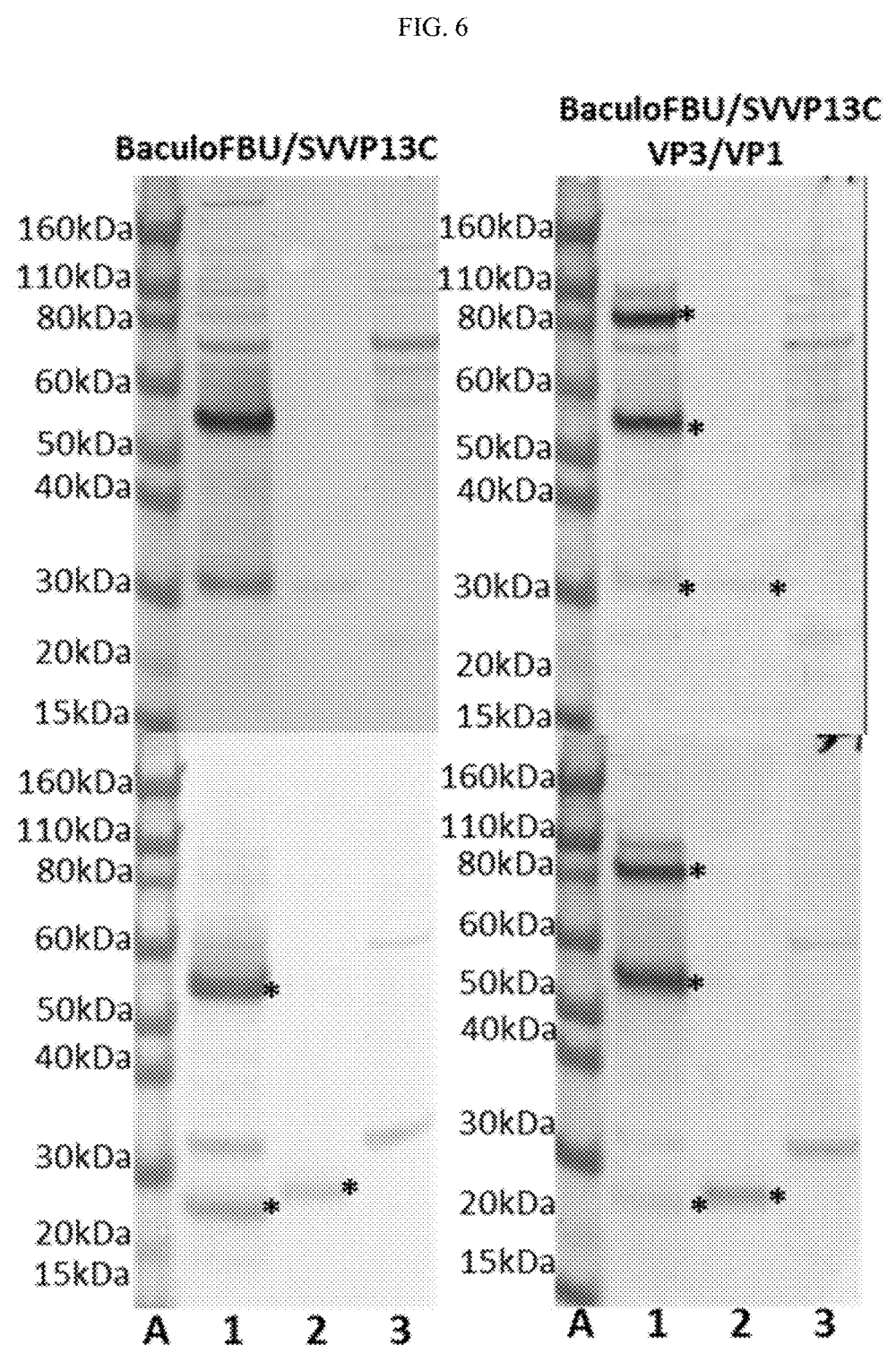

BaculoFBU/SVVP13C

BaculoFBU/SVVP13C VP3/VP1

160kDa
110kDa
80kDa
60kDa
50kDa
40kDa
30kDa
20kDa
15kDa

160kDa
110kDa
80kDa
60kDa
50kDa
40kDa
30kDa
20kDa
15kDa

160kDa
110kDa
80kDa
60kDa
50kDa
40kDa
30kDa
20kDa
15kDa

160kDa
110kDa
80kDa
60kDa
50kDa
40kDa
30kDa
20kDa
15kDa

A 1 2 3

A 1 2 3

BaculoFBU/SVVP13CVP3/VP1 Sucrose Fractions

FIG. 8

BaculoFBU/SVVP13CD

α-SVV VP1 α-SVV VP2 α-SVV VP3

160kDa
110kDa
80kDa
60kDa
50kDa
40kDa
30kDa
20kDa
15kDa

Figure 9:
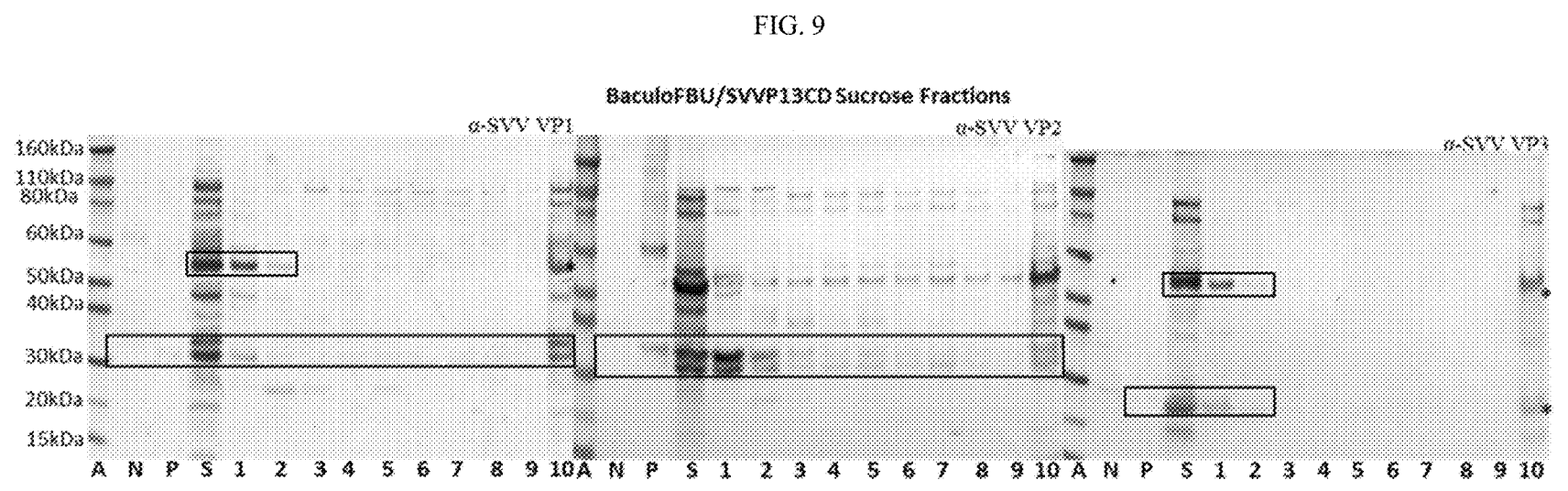

BaculoFBU/SVVP13CD Sucrose Fractions

α-SVV VP1 α-SVV VP2 α-SVV VP3

A N P S 1 2 3 4 5 6 7 8 9 10

160kDa 110kDa 80kDa 60kDa 50kDa 40kDa 30kDa 20kDa 15kDa

SENECAVIRUS A IMMUNOGENIC COMPOSITIONS AND METHODS THEREOF

CROSS-REFERENCE TO OTHER APPLICATIONS

This application is a national stage application of International Application No. PCT/US2018/041321, filed Jul. 9, 2018, which claims the benefit of U.S. Provisional Application Nos. 62/531,578 and 62/590,209, filed Jul. 12, 2017 and Nov. 22, 2017, respectively, the entire contents of which are hereby incorporated by reference herein.

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

A. Field of the Invention

The present invention relates to Seneca Valley Virus A or Senecavirus A (SVA) and its use as an immunogenic composition or vaccine to treat animals affected by Senecavirus A.

B. Description of the Related Art

SVA is a non-enveloped, single-stranded, positive-sense RNA virus within the family Picornaviridae. Foot and Mouth Disease Virus (FMDV) and swine vesicular disease virus (SVDA) are also member of family Picornaviridae.

The virus was originally discovered as a contaminant from cell-culture medium (See, Hales, L. M., et al., *Complete genome sequence analysis of Seneca Valley virus*-001, *a novel oncolytic picornavirus*. J Gen Virol, 2008. 89(Pt 5): p. 1265-75, incorporated by reference in its entirety); however, neutralizing antibodies against the virus have been detected in swine, bovine, murine and humans (See, Knowles, N. J., et al., *Epidemiology of Seneca Valley Virus: Identification and Characterization of Isolates from Pigs in the United States, in The Northern Lights EUROPIC* 2006-14*th meeting of the European Study Group on the Molecular Biology of Picornaviruses*. 2006: Saairselka, Inari, Finland, incorporated by reference in its entirety). Reported clinical signs following infection include vesicular lesions on the snout and coronary band, acute lameness, ulceration of the coronary band and sloughing of the hoof (Singh, K., et al., *Seneca Valley Virus and vesicular lesions in a pig with idiopathic vesicular disease*. J Vet Sci Technol, 2012. 3(6) and Pasma, T., S. Davidson, and S. L. Shaw, *Idiopathic vesicular disease in swine in Manitoba*. CVJ, 2008. 49: p. 84-85, both incorporated by reference in their entirety). In 2016, Koch's postulate was fulfilled when a cell culture-propagated SVA isolate was used to inoculate conventional animals and vesicular lesions were observed four days post inoculation (Montiel, N., et al., *Vesicular Disease in 9-Week-Old Pigs Experimentally Infected with Senecavirus A*. Emerg Infect Dis, 2016. 22(7): p. 1246-8, incorporated by reference in its entirety).

U.S. Pat. No. 8,039,606 describes the use of a Seneca Valley Virus to treat tumors. However, this Seneca Valley virus differs from the SVA of the present invention.

There has been an unexplained increase in cases of SVA in the US, Canada, Australia, Italy, New Zealand and Brazil. Further, because of the similarity of clinical signs to FMDV, this virus is of interest to the swine industry. The Center for Veterinary Biologics (CVB) notice 16-03 confirmed that the CVB was interested in licensing biologics and/or prophylactics for SVA virus.

SUMMARY OF THE INVENTION

The present invention provides immunogenic compositions, vaccines, and related methods that overcome deficiencies in the art. The compositions and methods provide immunogenic compositions which include inactivated/killed and/or recombinant forms of a non-enveloped (+) single-stranded RNA virus of SVA. In particular, the application provides a vaccine for generating an immune response in porcine for protection against diseases associated with Senecavirus A. The present Senecavirus A isolate NAC #20150909 (SEQ ID NO: 1, SEQ ID NO: 2 and/or SEQ ID NO: 3) was isolated from vesicular fluid collected from 5 month old swine exhibiting vesicular lesions on the snout and coronary band.

Immunogenic compositions and vaccines of the invention comprise SEQ ID NO: 1, SEQ ID NO: 2 and/or SEQ ID NO: 3.

Exemplary compositions of the invention comprise the polypeptide sequences of SEQ ID NO: 3, or fragments thereof that are immunoreactive to SVA.

Immunogenic compositions and vaccines of the invention comprise a SVA antigen, expressed in one non-limiting example in insect cells via a recombinant baculovirus expressing a modified SVA P1, 2A, partial 2B and 3B, and 3C protease, e.g., modified SVA nucleic acid sequence (SEQ ID NO:18) encoding amino acid sequence (SEQ ID NO: 19) and typically also includes an adjuvant. The vaccine may also include other components, such as preservative(s), stabilizer(s) and antigens against other porcine pathogens.

A preferred P1-2A-P3 nucleic acid sequence suitable for use in the invention is a polynucleotide encoding a P1-2A-P3polypeptide, said polynucleotide having at least at least 80%, 81%, 82%, 83%, 84%, 85%, 86%, 87%, 88%, or 89%, more preferably at least 90%, 91%, 92%, 93%, or 94%, and most preferably at least 95%, 96%, 96.1%, 96.2%, 96.3%, 96.4%, 96.5%, 96.6%, 96.7%, 96.8%, 96.9%, 97%, 97.1%, 97.2%, 97.3%, 97.4%, 97.5%, 97.6%, 97.7%, 97.8%, 97.9%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%. 99.9% sequence identity to SEQ ID NO: 18, 20, 22, 24, 32, and 33. "As used herein, it is in particular understood that the term "sequence identity to SEQ ID NO:X" or "identical SEQ ID NO:X", respectively, is equivalent to the term "sequence identity with the sequence of SEQ ID NO:X over the length of SEQ ID NO: X" or "identical to the sequence of SEQ ID NO:X over the length of SEQ ID NO: X", respectively, wherein in this context "X" is any integer selected from 18, 20, 22, 24, 32, and 33."

A preferred P1-2A-P3 polypeptide suitable for use in the invention is the polypeptide having the sequence set out in SEQ ID NO: 19, 21, 23, 25, 27, and 29 having at least 80% homology with SEQ ID NO: 19, 21, 23, 25, 27, and 29 for example at least 85% homology with SEQ ID NO: 19, 21, 23, 25, 27, and 29, such as a least 85% homology with SEQ ID NO: 19, 21, 23, 25, 27, and 29, such as at least 90% homology with SEQ ID NO: 19, 21, 23, 25, 27, and 29, for example at least 95%, at least 98% or at least 99% homology SEQ ID NO: 19, 21, 23, 25, 27, and 29.

In another aspect the invention provides nucleic acid sequences that encode one or more polypeptides, antibody constructs, or antibody conjugates. The gene sequences coding for the polypeptides comprise a nucleic acid sequence that is at least 95%, 90%, 85%, or even 80% homologous to and/or identical with the sequence of SEQ ID NO: 1 or SEQ ID NO: 2, or fragments thereof coding for a polypeptide that is immunoreactive to SVA. Exemplary nucleic acid sequences of the invention include any one of the sequences of SEQ ID NO: 1, SEQ ID NO: 2, and fragments thereof that encode a polypeptide that is immunoreactive to SVA.

Moreover a polypeptide of the invention as used herein includes but is not limited to a polypeptide that comprises:

i) a polypeptide comprising the amino acid sequence of SEQ ID NO: 3;
ii) a polypeptide that is at least 80% homologous to and/or identical with a polypeptide of i);
iii) a fragment of the polypeptides of i) and/or ii);
iv) a polypeptide of i) or ii);
v) a fragment of iii) or iv) comprising at least 5, preferably 8, more preferably 10, even more preferably 15 contiguous amino acids included in the sequences of SEQ ID NO: 3;
vi) a polypeptide that is encoded by a polynucleotide comprising the sequence of SEQ ID NO: 1 or 2;
vii) a polypeptide that is encoded by a polynucleotide that is at least 80% homologous to or identical with polynucleotides of vi);
viii) a protein fragment that is encoded by a polynucleotide that comprises at least 15, preferably 24, more preferably 30, even more preferably 45 contiguous nucleotides included in the sequences of SEQ ID NO: 1 or SEQ ID NO: 2.

Immunogenic compositions of the invention which comprise at least one or more SVA polypeptides as defined herein may further comprise a physiologically-acceptable vehicle such as a pharmaceutically or veterinarily acceptable carrier, adjuvant, or combination thereof.

Any of the SVA polypeptides provided herewith or any immunogenic compositions comprising one or more of these SVA polypeptides provided herewith can be used as a medicament, preferably as a vaccine or immunogenic composition, most preferably for the prophylaxis or treatment of a subject against a SVA infection.

Those of skill in the art will understand that the compositions used herein may incorporate known injectable, physiologically acceptable sterile solutions. For preparing a ready-to-use solution for parenteral injection or infusion, aqueous isotonic solutions, e.g. saline or plasma protein solutions, are readily available. In addition, the immunogenic and vaccine compositions of the present invention can include veterinary-acceptable carriers, diluents, isotonic agents, stabilizers, or adjuvants.

Methods of the invention include, but are not limited to, a method of provoking an immune response against an SVA infection in a subject comprising the step of administering to the subject an immunogenic composition comprising one or more SVA polypeptides as defined herein. Compositions of the invention may be used to treat or alternatively to prevent an SVA infection. Preferably, such immune response reduces the incidence of or severity of one or more clinical signs associated with or caused by the infection with SVA serotypes.

Herein, suitable subjects and subjects in need to which compositions of the invention may be administered include animals in need of either prophylactic or treatment for a viral associated infection, disease, or condition. Animals in which the immune response is stimulated by use of compositions or methods of the invention include livestock, such as swine, bovines, goats, and sheep. Preferred animals include porcines, murids, equids, lagomorphs, and bovids. Most preferably, an immune response is stimulated in swine.

The invention also provides a method of reducing the incidence of or severity of one or more clinical signs associated with or caused by SVA infection, comprising the step of administering an immunogenic composition of the invention that comprises one or more SVA peptides as provided herewith and preferably a carrier molecule, such that the incidence of or the severity of a clinical sign of the SVA infection is reduced by at least 10%, preferably at least 20%, even more preferred at least 30%, even more preferred at least 50%, even more preferred at least 70%, most preferred at least 100% relative to a subject that has not received the immunogenic composition as provided herewith.

Such clinical signs include vesicular disease such as open or closed blisters or lesions located on the snout, oral mucosa, and/or at the junction where the skin and the hoof wall meet (Coronary band), nail bed hemorrhages, sudden lameness with redness and swelling at or around the coronary band; and breeding females that are suddenly off feed, lethargic, anorexic and/or have a fever up to 105° Fahrenheit (~40.6° Celsius).

There appears to be a short term (4-10 days) increase in mortality in neonatal piglets (less than 7 days) that may or may not have diarrhea associated with it. Morbidity and mortality estimates are 30-70% for a short time period. It is usually upon investigation of the increase in neonatal mortality, that the vesicular lesions in the breeding age animals are noted. This type of infection in swine resulting in snout and coronary band vesicles has also been termed idiopathic vesicular disease in swine.

According to a further aspect, the present invention also relates to a method for the prophylaxis of an SVA infection, wherein said SVA infection may be caused by Seneca Valley Virus A, comprising the step of administering an immunogenic composition of the invention that comprises one or more SVA peptides as provided herewith.

The invention also provides a method of preparing any of the immunogenic compositions provided herewith that method comprises mixing one or more SVA peptides as provided herewith with a carrier molecule, preferably such that the one or more SVA peptides and carrier molecule are covalently coupled or conjugated to one another. Such conjugates may be multivalent or univalent. Multivalent compositions or vaccines include an immuno-conjugation of multiple SVA peptides with a carrier molecule. In a further aspect, the invention provides a method of producing one or more SVA peptides that method comprises transforming a host cell, preferably a prokaryotic cell such as *E. coli* with a nucleic acid molecule that codes for any of the SVA peptides as provided herewith. Alternatively, the host cell may be a eukaryotic cell such as an animal cell, protist cell, plant cell, or fungal cell. Preferably the eukaryotic cell is a mammalian cell such as CHO, BHK or COS, or a fungal cell such as *Saccharomyces cerevisiae*, or an insect cell such as Sf9.

Another aspect of the invention provides a method of producing one or more SVA peptides that induce an immune response against SVA. This comprises culturing a transformed expression vector coding for and expressing one or more SVA peptides disclosed herein. The expressed proteins are either retained by the expression organism or secreted into the culture medium. Expression is conducted under conditions sufficient to produce a SVA peptide capable of inducing an immune response to SVA.

A method of producing a recombinantly expressed P1-2A-P3 antigen vaccine generated in insect cells via a recombinant baculovirus expressing a modified SVA P1-2A-P3 protein is also provided. The method in one exemplary embodiment includes cloning the SVA P1-2A-P3 sequence into a vector pVL1393 (BD Biosciences) and co-transfect Sf9 insect cells. For the inactivated recombinant SVA material, SVA baculoviral harvest was inactivated for 24 hours using 5 mM BEI, clarified and 0.45 μm filtered. Typically, the inactivated virus is further processed, e.g., by concentration and blending with other components, to produce a commercial formulation. For example, the fluids containing the inactivated virus may be concentrated and blended with an adjuvant and/or antigen(s) to one or more other porcine pathogens.

Methods of making compositions of the invention may further comprise mixing the conjugate of one or more SVA peptides or inactivated whole-virus preparations and a carrier molecule with a physiologically-acceptable vehicle such as a pharmaceutically- or veterinary-acceptable carrier, adjuvant, or combination thereof. Those of skill in the art will recognize that the choice of vehicle, adjuvant, or combination will be determined by the delivery route, personal preference, and animal species among others.

In another aspect, the invention provides a method of diagnosing a SVA infection in a subject. That method comprises providing one or more SVA peptides; contacting the one or more SVA peptides with a sample obtained from the subject; and identifying the subject as having an SVA infection if an antibody capable of binding the one or more SVA peptides is detected in the sample.

In another respect, the invention provides a method of ascertaining that a subject has been previously exposed to a SVA infection and is able to express an immune response to SVA. That method comprises providing one or more SVA peptides; contacting the one or more SVA peptides with a sample obtained from the subject; and identifying the subject as having a SVA infection if an antibody capable of binding the one or more SVA peptides is detected in the sample.

The invention also provides kits that comprise an immunogenic composition that comprises one or more SVA peptides, preferably together with a carrier molecule; a container for packaging the immunogenic composition; a set of printed instructions; and a dispenser capable of administering the immunogenic composition to an animal. Optionally, the one or more SVA peptides and the carrier molecule may be packaged as a conjugate or as separate compounds. When supplied separately, a means of conjugating the one or more SVA peptides and carrier molecule, as well as appropriate printed instructions, is also supplied.

The invention also provides kits for vaccinating an animal comprising a set of printed instructions; a dispenser capable of administering the immunogenic composition provided herewith comprising one or more SVA peptides to an animal; and wherein at least one of SVA peptides effectively immunizes the animal against at least one disease associated with SVA infection. Preferably, the one or more SVA peptides are selected from those provided herewith. Kits of the invention may further comprise a veterinary acceptable carrier, adjuvant, or combination thereof.

The dispenser in a kit of the invention is capable of dispensing its contents as droplets; and the immunogenic composition comprises the SVA peptides as provided herewith included in the kit is capable of reducing the severity of at least one clinical sign of a SVA infection when administered intranasally, orally, intradermally, or intramuscularly to an animal. Preferably, the severity of a clinical sign is reduced by at least 10% preferably by at least 20%, even more preferred by at least 30%, even more preferred by at least 50%, even more preferred by at least 70%, most preferred by at least 100% as compared to an untreated, infected animal.

Methods for the treatment or prophylaxis of infections caused by SVA are also disclosed. The method comprises administering an effective amount of the immunogenic composition of the present invention to a subject, wherein said treatment or prophylaxis is selected from the group consisting of reducing signs of SVA infection, reducing the severity of or incidence of clinical signs of SVA infection, reducing the mortality of subjects from SVA infection, and combinations thereof.

Compositions of the invention further comprise a veterinarily acceptable carrier, adjuvant, or combination thereof. Such compositions may be used as a vaccine and comprise an inactivated vaccine. Such vaccines elicit a protective immunological response against at least one disease associated with SVA.

Those of skill in the art will understand that the compositions used herein may incorporate known injectable, physiologically acceptable sterile solutions. For preparing a ready-to-use solution for parenteral injection or infusion, aqueous isotonic solutions, e.g., saline or plasma protein solutions are readily available. In addition, the immunogenic and vaccine compositions of the present invention can include pharmaceutical- or veterinary-acceptable carriers, diluents, isotonic agents, stabilizers, or adjuvants.

Methods of the invention may also comprise admixing a composition of the invention with a veterinarily acceptable carrier, adjuvant, or combination thereof. Those of skill in the art will recognize that the choice of carrier, adjuvant, or combination will be determined by the delivery route, personal preference, and animal species among others.

Methods for the treatment or prophylaxis of infections caused by SVA are also disclosed. The method comprises administering an effective amount of the immunogenic composition of the present invention to an animal, wherein said treatment or prophylaxis is selected from the group consisting of reducing signs of SVA infection, reducing the severity of or incidence of clinical signs of SVA infection, reducing the mortality of animals from SVA infection, and combinations thereof.

Preferred routes of administration include intranasal, oral, intradermal, and intramuscular. Administration via the intramuscular route, most preferably in a single dose, is preferred. The skilled artisan will recognize that compositions of the invention may also be administered in two or more doses, as well as, by other routes of administration. For example, such other routes include subcutaneously, intracutaneously, intravenously, intravascularly, intraarterially, intraperitoneally, intrathecally, intratracheally, intracutaneously, intracardially, intralobally, intramedullarly, intrapulmonarily, or intravaginally. Depending on the desired duration and effectiveness of the treatment, the compositions according to the invention may be administered once or several times, also intermittently, for instance on a daily basis for several days, weeks or months and in different dosages.

The invention also provides kits for vaccinating an animal comprising a set of printed instructions; a dispenser capable of administering a vaccine to an animal; and at least one isolate from a SVA culture. Kits of the invention may further comprise a veterinarily acceptable carrier, adjuvant, or combination thereof.

The dispenser in a kit of the invention is capable of dispensing its contents as droplets; and the isolate included in the kit is capable of reducing the severity of at least one clinical sign of a SVA infection when administered intranasally, orally, intradermally, or intramuscularly to an animal. In some kits, the isolate is also capable of reducing the severity of at least one clinical sign of a SVA infection. Preferably, the severity of a clinical sign is reduced by at least 10% as compared to an untreated, infected animal.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 4 shows Western blots of BaculoFBU/SVVP13C(A) (SEQ ID NO:18) and BaculoFBU/SVVP13C-CO (B) (SEQ ID NO:20) supernatant samples compared to native SVV antigen detected with anti-alpha-SVV VP1, anti-alpha-SVV VP2 and anti-alpha-SVV VP3 cross-absorbed rabbit polyclonal antibodies. Lane A is the protein standard, Line 1 is SVV Baculo Harvest Supernatant, Line 2 is SVV Antigen (SEQ ID NO:3) and Lane 3 is Baculo Harvest Supernatant Negative Control. Expected Band Sizes: Full length SVV P1=around 95 kDa (SEQ ID NO:19, amino acids 1-859), VP1=around 29 kDa (SEQ ID NO:19, amino acids 596-859), VP2-around 32 kDa (SEQ ID NO:19, amino acids 73-356), VP3=around 26 kDa (SEQ ID NO:19, amino acids 357-595).

FIG. 6 shows Western blots of BaculoFBU/SVVP13C (SEQ ID NO:18) and BaculoFBU/VVP13C VP3/VP1 (SEQ ID NO:22) supernatant harvests with α-SVV VP1 (top row) and α-SVV VP3 (bottom row) rabbit polyclonal antibodies. Lane A-Protein Standard, Lane 1-SVV Baculo Harvest Supernatant Lane 2-SVV Antigen and Lane 3-Baculo Harvest Supernatant Neg. Control.

FIG. 8 shows Western Blots of BaculoFBU/VVP13CD (SEQ ID NO:24) Supernatant Harvest detected with an anti-SVV VP1, anti-SVV VP2 and anti-SVV VP3 rabbit polyclonal antibodies. Lane A is the Protein Standard, Lane 1 is SVV Baculo Harvest Supernatant, Lane 2 is SVV Antigen (SEQ ID NO:3) and Lane 3 is Baculo Harvest Supernatant Negative Control. Expected Band Sizes: Full length SVV P1=around 95 kDa (SEQ ID NO:19, amino acids 1-859), VP1=around 29 kDa (SEQ ID NO:19, amino acids 596-859), VP2-around 32 kDa (SEQ ID NO:19, amino acids 73-356), VP3=around 26 kDa (SEQ ID NO:19, amino acids 357-595).

FIG. 9 shows Western Blots of BaluloFBU/SVVP13CD (SEQ ID NO:24) sucrose fractions with anti-SVV VP1, anti-SVV VP2, and anti-SVV VP3 rabbit polyclonal antibodies. Lane A is the Protein Standard, Lane 1 is SVV Baculo Harvest Supernatant, Lane N is BaculoFBU/No Insert Negative Control, P is Positive Control Native inactivated SVV (SEQ ID NO.3), S is SVVP13CD (SEQ ID NO.25) pellet re-suspended in TBA and Lane 1-10 is Sucrose Fractions 1-10. Expected Band Sizes: Full length SVV P1=around 95 kDa (SEQ ID NO:19, amino acids 1-859), VP1=around 29 kDa (SEQ ID NO:19, amino acids 596-859), VP2-around 32 kDa (SEQ ID NO:19, amino acids 73-356), VP3=around 26 kDa (SEQ ID NO:19, amino acids 357-595).

DETAILED DESCRIPTION

Figure 1:
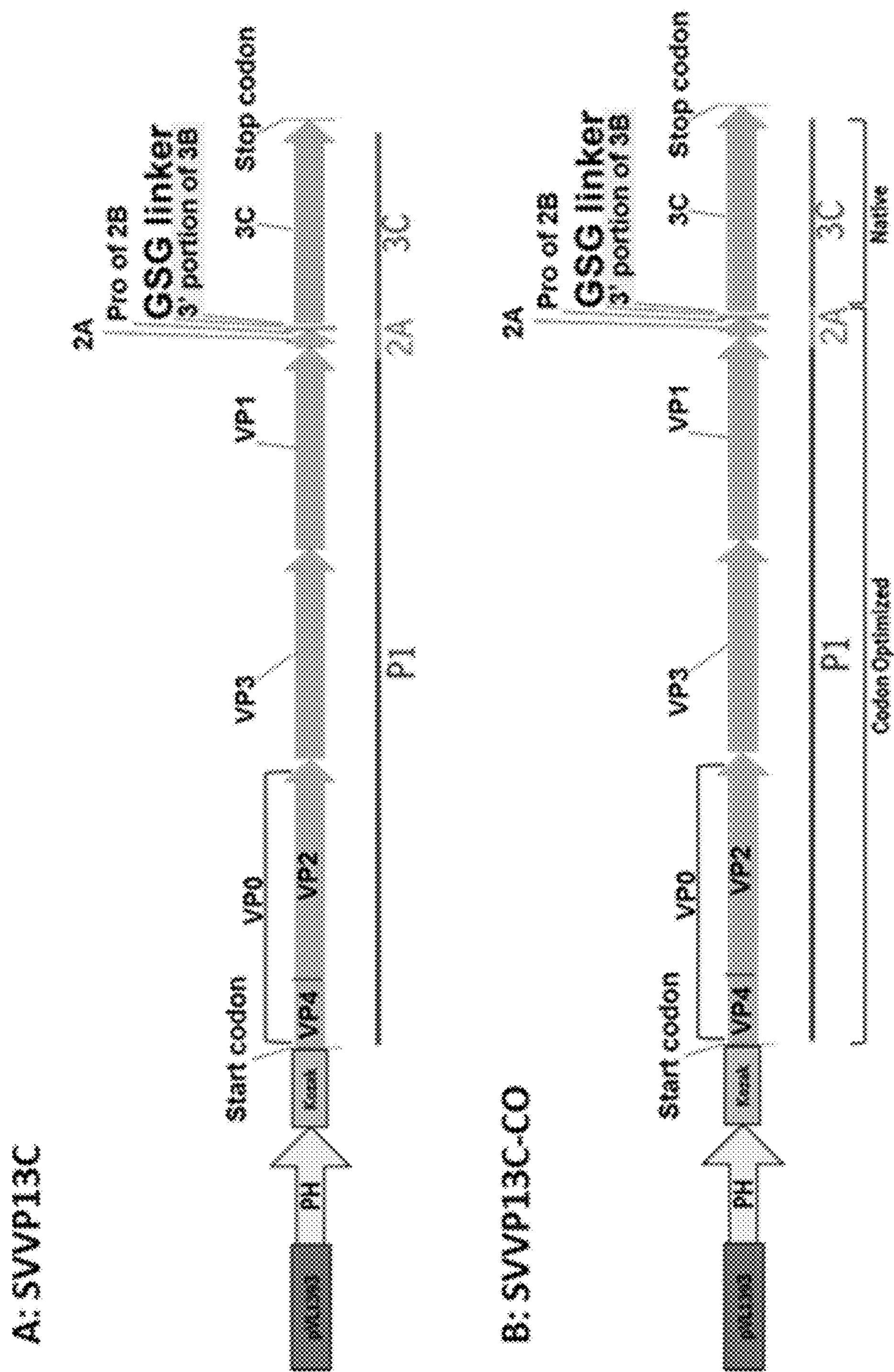
FIG. 1 shows the SVVP13C construct design (A) (SEQ ID NO:18) and SVVP 13C-CO (codon optimized) construct design (B) (SEQ ID NO:20) for the baculovirus expression system.
Figure 2:
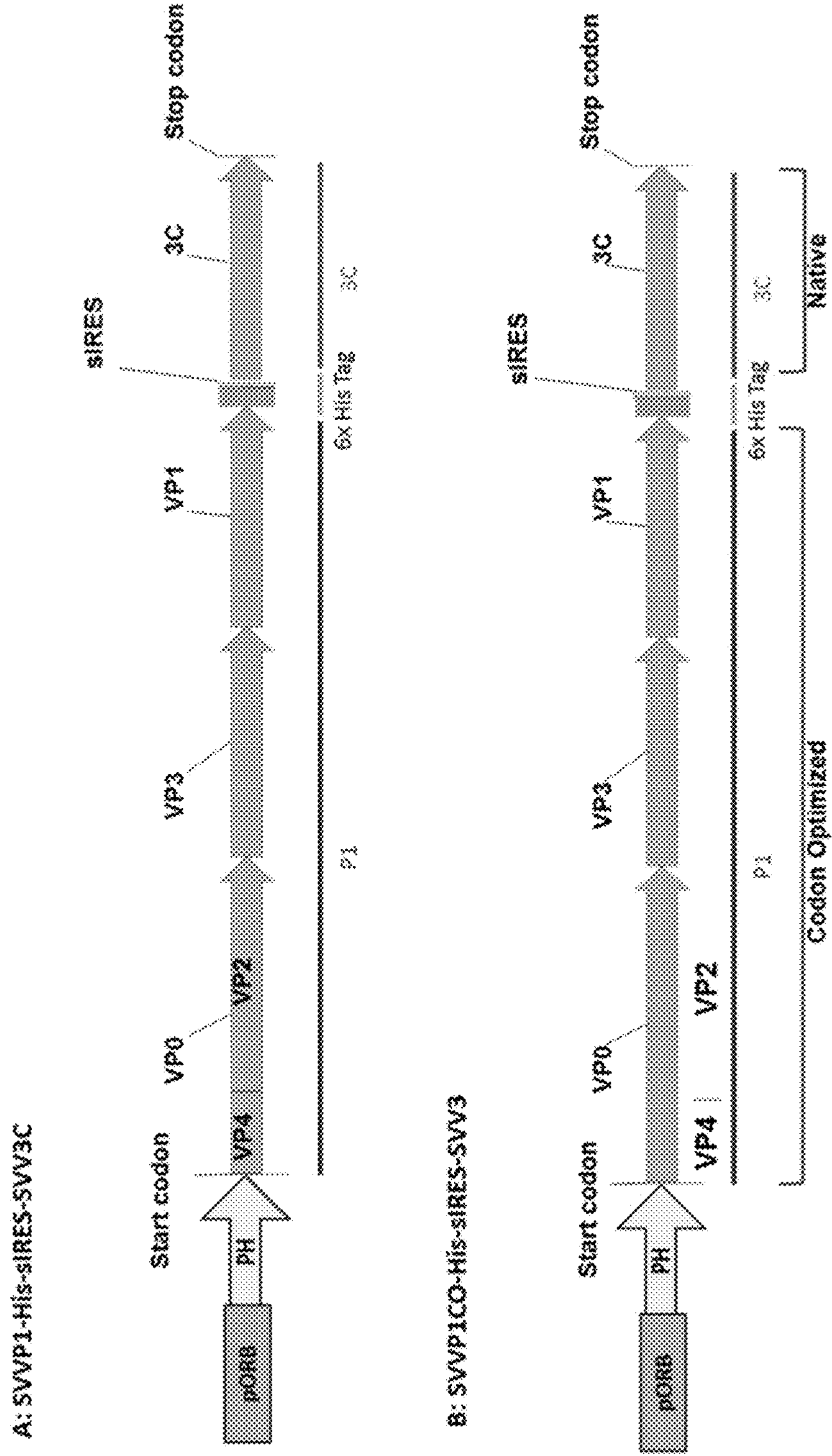
FIG. 2 shows the SVVP1-His-sIRES-SVV3C construct design (A) (SEQ ID NO:32) and SVVP1CO-His-sIRES-SVV3C (codon optimized) construct design (B) (SEQ ID NO:33) for the baculovirus expression system.

The practice of the present invention will employ, unless otherwise indicated, conventional techniques of molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "an antigen" includes a mixture of two or more antigens; reference to "an excipient" includes mixtures of two or more excipients, and the like.

A. Definitions

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

"Protection against disease", "protective immunity", "functional immunity" and similar phrases, means a response against a disease or condition generated by administration of one or more therapeutic compositions of the invention, or a combination thereof, that results in fewer deleterious effects than would be expected in a non-immunized subject that has been exposed to disease or infection. That is, the severity of the deleterious effects of the infection is lessened in a vaccinated subject. Infection may be reduced, slowed, or possibly fully prevented, in a vaccinated subject. Herein, where complete prevention of infection is meant, it is specifically stated. If complete prevention is not stated then the term includes partial prevention.

Herein, "reduction of the incidence and/or severity of clinical signs" or "reduction of clinical symptoms" means, but is not limited to, reducing the number of infected subjects in a group, reducing or eliminating the number of subjects exhibiting clinical signs of infection, or reducing the severity of any clinical signs that are present in one or more subjects, in comparison to wild-type infection. For example, it should refer to any reduction of pathogen load, pathogen shedding, reduction in pathogen transmission, or reduction of any clinical sign symptomatic of malaria. Preferably these clinical signs are reduced in one or more subjects receiving the therapeutic composition of the present invention by at least 10% in comparison to subjects not receiving the composition and that become infected. More preferably clinical signs are reduced in subjects receiving a composition of the present invention by at least 20%, preferably by at least 30%, more preferably by at least 40%, and even more preferably by at least 50%.

The term "increased protection" herein means, but is not limited to, a statistically significant reduction of one or more clinical symptoms which are associated with infection by an infectious agent, preferably SVA, respectively, in a vaccinated group of subjects vs. a non-vaccinated control group of subjects. The term "statistically significant reduction of clinical symptoms" means, but is not limited to, the frequency in the incidence of at least one clinical symptom in the vaccinated group of subjects is at least 10%, preferably 20%, more preferably 30%, even more preferably 50%, and even more preferably 70% lower than in the non-vaccinated control group after the challenge the infectious agent.

"Long-lasting protection" shall refer to "improved efficacy" that persists for at least 3 weeks, but more preferably at least 3 months, still more preferably at least 6 months. In the case of livestock, it is most preferred that the long lasting protection shall persist until the average age at which animals are marketed for meat.

An "immunogenic or immunological composition" refers to a composition of matter that comprises at least one SVA immunogenic composition, or immunogenic portion thereof, that elicits an immunological response in the host of a cellular or antibody-mediated immune response to the composition. In a preferred embodiment of the present invention, an immunogenic composition induces an immune response and, more preferably, confers protective immunity against one or more of the clinical signs of a SVA infection.

An "immunogenic" or "antigen" as used herein refer to a polypeptide or protein that elicits an immunological response as described herein. An "immunogenic" SVA protein or polypeptide includes the full-length sequence of any of the SVA identified herein or analogs or immunogenic fragments thereof. The term "immunogenic fragment" or "immunogenic portion" refers to a fragment or truncated and/or substituted form of an SVA that includes one or more epitopes and thus elicits the immunological response described herein. In general, such truncated and/or substituted forms, or fragments will comprise at least six contiguous amino acids from the full-length SVA protein. More preferably, the truncated or substituted forms, or fragments will have at least 10, more preferably at least 15, and still more preferably at least 19 contiguous amino acids from the full-length SVA protein. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known and described in the art, see e.g., U.S. Pat. No. 4,708,871; Geysen et al. (1984) Proc. Natl. Acad. Sci. USA 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, Jun. 28-Jul. 3, 1998. (The teachings and content of which are all incorporated by reference herein.)

An “immune response” or “immunological response” means, but is not limited to, the development of a cellular and/or antibody-mediated immune response to the composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

Herein, “specifically immunoreactive” refers to an immunoreactive protein or polypeptide that recognizes an antigen characteristic of SVA infection but does not react with an antigen characteristic of a strict challenge control.

As used herein, “a pharmaceutical- or veterinary-acceptable carrier” includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

In some embodiments, the immunogenic composition of the present invention contains an adjuvant. “Adjuvants” as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), John Wiley and Sons, NY, pp 51-94 (1995) and Todd et al., Vaccine 15:564-570 (1997). Exemplary adjuvants are the SPT emulsion described on page 147 of “Vaccine Design, The Subunit and Adjuvant Approach” edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL® (Lubrizol)) are particularly appropriate. They are cross-linked with an allyl sucrose or with allyl pentaerythritol. Among then, there may be mentioned Carbopol 974P, 934P and 971P. Most preferred is the use of Carbopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Safety" refers to the absence of adverse consequences in a vaccinated animal following vaccination, including but not limited to: potential reversion of a bacterium-based vaccine to virulence, clinically significant side effects such as persistent, systemic illness or unacceptable inflammation at the site of vaccine administration.

The terms "vaccination" or "vaccinating" or variants thereof, as used herein means, but is not limited to, a process which includes the administration of an immunogenic composition of the invention that, when administered to an animal, elicits, or is able to elicit—directly or indirectly—an immune response in the animal against SVA.

"Mortality", in the context of the present invention, refers to death caused by SVA infection, and includes the situation where the infection is so severe that an animal is euthanized to prevent suffering and provide a humane ending to its life.

Herein, "effective dose" means, but is not limited to, an amount of antigen that elicits, or is able to elicit, an immune response that yields a reduction of clinical symptoms in an animal to which the antigen is administered.

As used herein, the term "effective amount" means, in the context of a composition, an amount of an immunogenic composition capable of inducing an immune response that reduces the incidence of or lessens the severity of infection or incident of disease in an animal. Particularly, an effective amount refers to colony forming units (CFU) per dose. Alternatively, in the context of a therapy, the term "effective amount" refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

The term "fragment" refers to a fragment or truncated and/or substituted form of a SVA peptide or a gene coding for such SVA peptide that includes one or more epitopes and thus elicits the immunological response against SVA. Preferably, such fragment is a fragment or truncated and/or substituted form of any of the SVA peptides or any of the SVA genes provided herewith. In general, such truncated and/or substituted forms, or fragments will comprise at least six contiguous amino acids from the full-length SVA sequence. More preferably, the truncated or substituted forms, or fragments will have at least 10, more preferably at least 15, and still more preferably at least 19 contiguous amino acids from the full-length SVA sequence. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known and described in the art, see e.g., U.S. Pat. No. 4,708,871; Geysen et al. (1984) Proc. Natl. Acad. Sci. USA 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, Jun. 28-Jul. 3, 1998. (The teachings and content of which are all incorporated by reference herein.)

The term "variant" with respect to sequences (e.g., a polypeptide or nucleic acid sequence) is intended to mean substantially similar sequences. For nucleotide sequences comprising an open reading frame, variants include those sequences that, because of the degeneracy of the genetic code, encode the identical amino acid sequence of the native protein. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein for the purposes of codon optimization. Generally, nucleotide sequence variants of the invention will have at least at least 80%, 81%, 82%, 83%, 84%, 85%, 86%, 87%, 88%, or 89%, more preferably at least 90%, 91%, 92%, 93%, or 94%, and most preferably at least 95%, 96%, 96.1%, 96.2%, 96.3%, 96.4%, 96.5%, 96.6%, 96.7%, 96.8%, 96.9%, 97%, 97.1%, 97.2%, 97.3%, 97.4%, 97.5%, 97.6%, 97.7%, 97.8%, 97.9%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9% sequence identity compared to a reference sequence using one of the alignment programs described using standard parameters.

The term "immunoreactive to SVA" as used herein means that the peptide or fragment elicits the immunological response against SVA.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homolog sequence comprises at least a stretch of 50, even more preferred of 100, even more preferred of 250, even more preferred of 500 nucleotides.

A “conservative substitution” refers to the substitution of an amino acid residue or nucleotide with another amino acid residue or nucleotide having similar characteristics or properties including size, hydrophobicity, etc., such that the overall functionality does not change significantly.

“Sequence Identity” as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are “identical” at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% “sequence identity” to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms “sequence identity” or “percent identity” are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically and preferred in the scope of the present invention, the comparison will be carried out over the full length of the two sequences being compared. However, sequence identity may be carried out over a region of, for example, twenty, fifty, one hundred or more contiguous amino acid residues.

As used herein, it is in particular understood that the term "having at least X % sequence identity with the nucleic acid/amino acid sequence according to SEQ ID NO:Y" (or, alternatively, the term "having at least X % sequence identity with the nucleic acid/amino acid sequence of/set forth in SEQ ID NO:Y") is equivalent to the term "having at least X % sequence identity with the nucleic acid/amino acid sequence according to SEQ ID NO:Y over the length of SEQ ID NO:Y" or to the term "having at least X % sequence identity with the nucleic acid/amino acid sequence according to SEQ ID NO:Y over the whole length of SEQ ID NO:Y", respectively.

Vectors and methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382, 425, PCT publications WO 94/16716, WO 96/39491, WO 95/30018; Paoletti, "Applications of pox virus vectors to vaccination: An update, "PNAS USA 93: 11349-11353, October 1996; Moss, "Genetically engineered poxviruses for recombinant gene expression, vaccination, and safety," PNAS USA 93: 11341-11348, October 1996; Smith et al., U.S. Pat. No. 4,745,051 (recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector, "Molecular and Cellular Biology March 1984, Vol. 4, No. 3, p. 406; EPA0 370 573; U.S. application Ser. No. 920,197, filed Oct. 16, 1986; EP Patent publication No. 265785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93: 11313-11318, October 1996; Robertson et al., "Epstein-Barr virus vectors for gene delivery to B lymphocytes", PNAS USA 93: 11334-11340, October 1996; Frolov et al., "Alphavirus-based expression vectors: Strategies and applications," PNAS USA 93: 11371-11377, October 1996; Kitson et al., J. Virol. 65, 3068-3075, 1991; U.S. Pat. Nos. 5,591,439, 5,552,143; WO 98/00166; allowed U.S. application Ser. Nos. 08/675, 556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April, 1990; Prevec et al., J. Gen Virol. 70, 42434; PCT WO 91/11525; Feigner et al. (1994), J. Biol. Chem. 269, 2550-2561, Science, 259: 1745-49, 1993; and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996; and U.S. Pat. Nos. 5,591,639, 5,589, 466, and 5,580,859, as well as WO 90/11092, WO93/19183, WO94/21797, WO95/11307, WO95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach et al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein.

Preferred viral vectors include baculovirus such as BaculoGold (BD Biosciences Pharmingen, San Diego, Calif.), in particular provided that the production cells are insect cells. Although the baculovirus expression system is preferred, it is understood by those of skill in the art that other expression systems will work for purposes of the present invention.

B. Carriers Molecules

The carrier molecules to which the SVA peptides of the invention can be conjugated or covalently linked are preferably those described above. Preferred carriers for animal use are bovine serum albumin and Keyhole Limpet Hemocyanin. Protein carriers suitable for human use include tetanus toxoid, diphtheria toxoid, acellular pertussis vaccine (LPF toxoid), cross-reacting materials (CRM's) which are antigenically similar to bacterial toxins but are non-toxic by means of mutation. For example, CRM 197 obtained according to Pappenheimer, et al, Immunochemistry, 9, 891-906 (1972), and other bacterial protein carriers, for example meningococcal outer membrane protein may be used. Preferably, the carrier protein itself is an immunogen.

The SVA peptides of the invention may be covalently coupled to the carrier by any convenient method known to the art. While use of a symmetric linker such as adipic acid dihydrazide, as described by Schneerson et al, J. Experimental Medicine, 152, 361-376 (1980), or a heterobifunctional linker such as N-succinimidyl 3-(2-pyridyldithio) propionate as described by Fattom et al, Infection and Immunity, 56, 2292-2298 (1988) are within the scope of the invention, it is preferred to avoid the use of any linker but instead couple a SVA peptide of the invention directly to the carrier molecule. Such coupling may be achieved by means of reductive amination as described by Landi et al J. Immunology, 127, 1011-1019 (1981).

The size of the immunogenic composition, as defined by average molecular weight, is variable and dependent upon the chosen SVA peptide(s) and the method of coupling of the SVA peptide(s) to the carrier. Therefore, it can be as small as 1,000 daltons ($10^3$) or greater than $10^6$ daltons. With the reductive amination coupling method, the molecular weight of the SVA peptide(s) is usually within the range of 5,000 to 500,000, for example 300,000 to 500,000, or for example 5,000 to 50,000 daltons.

Carrier molecules, i.e. peptides, derivatives and analogs thereof, and peptide mimetics that specifically bind a SVA peptide of the invention can be produced by various methods known in the art, including, but not limited to solid-phase synthesis or by solution (Nakanishi et al., 1993, Gene 137:51-56; Merrifield, 1963, J. Am. Chem. Soc. 15:2149-2154; Neurath, H. et al., Eds., The Proteins, Vol II, 3d Ed., p. 105-237, Academic Press, New York, N.Y. (1976), incorporated herein in their entirety by reference).

The SVA peptides of the invention or the antibodies or binding portions thereof of the present invention may be administered in injectable dosages by solution or suspension of in a diluent with a pharmaceutical or veterinary carrier.

Toxicity and therapeutic efficacy of such molecules can be determined by standard pharmaceutical procedures in cell cultures or experimental animals, e.g., for determining the $LD_{50}$ (the dose lethal to 50% of the population).

The vaccines of the invention may be multivalent or univalent. Multivalent vaccines are made from immunoconjugation of multiple SVA peptides with a carrier molecule.

In one aspect, the SVA peptide compositions comprise an effective immunizing amount of the immunogenic conjugate, preferably in combination with an immunostimulant; and a physiologically acceptable vehicle. As used in the present context, "immunostimulant" is intended to encompass any compound or composition which has the ability to enhance the activity of the immune system, whether it is a specific potentiating effect in combination with a specific antigen, or simply an independent effect upon the activity of one or more elements of the immune response. Immunostimulant compounds include but are not limited to mineral gels, e.g., aluminum hydroxide; surface active substances such as lysolecithin, PLURONIC® polyols; polyanions; peptides; oil emulsions; alum, and MDP. Methods of utilizing these materials are known in the art, and it is well within the ability of the skilled artisan to determine an optimum amount of stimulant for a given vaccine. More than one immunostimulant may be used in a given formulation. The immunogen may also be incorporated into liposomes, or conjugated to polysaccharides and/or other polymers for use in a vaccine formulation.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to a mammal, especially a pig. Associated with such container(s) can be a notice in the form prescribed by a governmental agency regulating the manufacture, use or sale of pharmaceuticals or biological products, which notice reflects approval by the agency of manufacture, use or sale for human administration.

C. Adjuvants

In order to further increase the immunogenicity of the immunogenic compositions provided herewith, and which contain one or more SVA peptides may also comprise one or more adjuvants.

The adjuvant may be purified by any of the techniques described previously or known in the art. The preferred purification technique is silica gel chromatography, in particular the "flash" (rapid) chromatographic technique, as described by W. Clark Still et al, J. Organic Chemistry, 43, 2923-2925 (1978). However, other chromatographic methods, including HPLC, may be used for purification of the adjuvant. Crystallization may also be used to purify the adjuvant. In some cases, no purification is required as a product of analytical purity is obtained directly from the synthesis.

The vaccine compositions of the invention are prepared by physically mixing the adjuvant with the SVA peptide(s) under appropriate sterile conditions in accordance with known techniques to produce the adjuvanted composition. Complexation of the SVA peptide(s) and the adjuvant is facilitated by the existence of a net negative charge on the conjugate which is electrostatically attracted to the positive charge present on the long chain alkyl compound adjuvant.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01% to 75%, preferably at a concentration of about 2% to 30%, more preferably at a concentration of about 5% to 25%, still more preferably at a concentration of about 7% to 22%, and most preferably at a concentration of 10% to 20% by volume of the final product.

D. Physiologically-Acceptable Vehicles

The vaccine compositions of this invention may be formulated using techniques similar to those used for other pharmaceutical polypeptide compositions. Thus, the adjuvant and SVA peptide(s), preferably conjugated to carrier molecule and/or admixed with an adjuvant may be stored in lyophilized form and reconstituted in a physiologically acceptable vehicle to form a suspension prior to administration. Alternatively, the adjuvant and conjugate may be stored in the vehicle. Preferred vehicles are sterile solutions, in particular, sterile buffer solutions, such as phosphate buffered saline. Any method of combining the adjuvant and the conjugate in the vehicle such that improved immunological effectiveness of the immunogenic composition is appropriate.

The volume of a single dose of the vaccine of this invention may vary but will be generally within the ranges commonly employed in conventional vaccines. The volume of a single dose is preferably between about 0.1 ml and about 3 ml, preferably between about 0.2 ml and about 1.5 ml, more preferably between about 0.2 ml and about 0.5 ml at the concentrations of conjugate and adjuvant noted above.

The vaccine compositions of the invention may be administered by any convenient means.

E. Formulations

Immunogenic conjugates comprising a SVA peptide coupled to a carrier molecule can be used as vaccines for immunization against SVA. The vaccines, comprising the immunogenic conjugate in a physiologically acceptable vehicle, are useful in a method of immunizing animals, preferably swine, for treatment or prevention of infections by SVA.

Antibodies generated against immunogenic conjugates of the present invention by immunization with an immunogenic conjugate can be used in passive immunotherapy and generation of anti-idiotypic antibodies for treating or preventing infections of SVA.

The subject to which the composition is administered is preferably an animal, including but not limited to cows, horses, sheep, pigs, poultry (e.g. chickens), goats, cats, dogs, hamsters, mice and rats, most preferably the mammal is swine.

The formulations of the invention comprise an effective immunizing amount of one or more immunogenic compositions or antibodies thereto and a physiologically acceptable vehicle. Vaccines comprise an effective immunizing amount of one or more immunogenic compositions and a physiologically acceptable vehicle. The formulation should suit the mode of administration.

The immunogenic composition, if desired, can also contain minor amounts of wetting or emulsifying agents, or pH buffering agents. The immunogenic composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

F. Effective Dose

The compounds described herein can be administered to a subject at therapeutically effective doses to treat SVA-associated diseases. The dosage will depend upon the host receiving the vaccine as well as factors such as the size, weight, and age of the host.

The precise amount of immunogenic conjugate or antibody of the invention to be employed in a formulation will depend on the route of administration and the nature of the subject (e.g., species, age, size, stage/level of disease), and should be decided according to the judgment of the practitioner and each subjects circumstances according to standard clinical techniques. An effective immunizing amount is that amount sufficient to treat or prevent a SVA infectious disease in a subject. An example of an appropriate dose is about 6 to 7 log TCID50/mL. Alternatively, effective doses may also be extrapolated from dose-response curves derived from animal model test systems and can vary from 0.001 mg/kg to 100 mg/kg.

Toxicity and therapeutic efficacy of compounds may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in animals, especially swine. The dosage of such compounds lies preferably within a range of circulating concentrations that include the $ED_{50}$ with little or no toxicity. The dosage can vary within this range depending upon the dosage form employed and the route of administration utilized. For any compound used in the methods of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in subjects. Levels in plasma can be measured, for example, by high performance liquid chromatography.

Immunogenicity of a composition can be determined by monitoring the immune response of test subjects following immunization with the composition by use of any immunoassay known in the art. Generation of a humoral (antibody) response and/or cell-mediated immunity, may be taken as an indication of an immune response. Test subjects may include animals such as pigs, mice, hamsters, dogs, cats, rabbits, cows, horses, sheep, poultry (e.g. chickens, ducks, geese, and turkeys).

The immune response of the test subjects can be analyzed by various approaches such as: the reactivity of the resultant immune serum to the immunogenic conjugate, as assayed by known techniques, e.g., enzyme linked immunosorbent assay (ELISA), immunoblots, immunoprecipitation, etc.; or, by protection of immunized hosts from infection by the pathogen and/or attenuation of symptoms due to infection by the pathogen in immunized hosts as determined by any method known in the art, for assaying the levels of an infectious disease agent, e.g., the bacterial levels (for example, by culturing of a sample from the subject), or other technique known in the art. The levels of the infectious disease agent may also be determined by measuring the levels of the antigen against which the immunoglobulin was directed. A decrease in the levels of the infectious disease agent or an amelioration of the symptoms of the infectious disease indicates that the composition is effective.

The therapeutics of the invention can be tested in vitro for the desired therapeutic or prophylactic activity, prior to in vivo use in animals or humans For example, in vitro assays that can be used to determine whether administration of a specific therapeutic is indicated include in vitro cell culture assays in which appropriate cells from a cell line or cells cultured from a subject having a particular disease or disorder are exposed to or otherwise administered a therapeutic, and the effect of the therapeutic on the cells is observed.

Alternatively, the therapeutic may be assayed by contacting the therapeutic to cells (either cultured from a subject or from a cultured cell line) that are susceptible to infection by the infectious disease agent but that are not infected with the infectious disease agent, exposing the cells to the infectious disease agent, and then determining whether the infection rate of cells contacted with the therapeutic was lower than the infection rate of cells not contacted with the therapeutic. Infection of cells with an infectious disease agent may be assayed by any method known in the art.

In addition, the therapeutic can be assessed by measuring the level of the molecule against which the antibody is directed in the animal model or human subject at suitable time intervals before, during, or after therapy. Any change or absence of change in the amount of the molecule can be identified and correlated with the effect of the treatment on the subject. The level of the molecule can be determined by any method known in the art.

After vaccination of an animal to a SVA infection using the methods and compositions of the present invention, any binding assay known in the art can be used to assess the binding between the resulting antibody and the particular molecule. These assays may also be performed to select antibodies that exhibit a higher affinity or specificity for the particular antigen.

G. Detection and Diagnostic Methods

Antibodies, or binding portions thereof, resulting from the use of SVA peptides of the present invention are useful for detecting in a sample the presence of SVA virus. This detection method comprises the steps of providing an isolated antibody or binding portion thereof raised against an SVA peptide of the invention, adding to the isolated antibody or binding portion thereof a sample suspected of containing a quantity of SVA, and detecting the presence of a complex comprising the isolated antibody or binding portion thereof bound to SVA.

The antibodies or binding portions thereof of the present invention are also useful for detecting in a sample the presence of a SVA peptide. This detection method comprises the steps of providing an isolated antibody or binding portion thereof raised against a SVA peptide, adding to the isolated antibody or binding portion thereof a sample suspected of containing a quantity of the SVA peptide, and detecting the presence of a complex comprising the isolated antibody or binding portion thereof bound to the SVA peptide.

Immunoglobulins, particularly antibodies, (and functionally active fragments thereof) that bind a specific molecule that is a member of a binding pair may be used as diagnostics and prognostics, as described herein. In various embodiments, the present invention provides the measurement of a member of the binding pair, and the uses of such measurements in clinical applications. The immunoglobulins in the present invention may be used, for example, in the detection of an antigen in a biological sample whereby subjects may be tested for aberrant levels of the molecule to which the immunoglobulin binds, and/or for the presence of abnormal forms of such molecules. By "aberrant levels" is meant increased or decreased relative to that present, or a standard level representing that present, in an analogous sample from a portion of the body or from a subject not having the disease. The antibodies of this invention may also be included as a reagent in a kit for use in a diagnostic or prognostic technique.

In one aspect, an antibody of the invention that immunospecifically binds to a SVA peptide may be used to diagnose, prognosis or screen for a SVA infection.

In another aspect, the invention provides a method of diagnosing or screening for the presence of a SVA infection or immunity thereto, comprising measuring in a subject the level of immunospecific binding of an antibody to a sample derived from the subject, in which the antibody immunospecifically binds a SVA peptide in which an increase in the level of said immunospecific binding, relative to the level of said immunospecific binding in an analogous sample from a subject not having the infectious disease agent, indicates the presence of SVA.

Examples of suitable assays to detect the presence of SVA peptides or antagonists thereof include but are not limited to ELISA, radioimmunoassay, gel-diffusion precipitation reaction assay, immunodiffusion assay, agglutination assay, fluorescent immunoassay, protein A immunoassay, or immunoelectrophoresis assay.

Immunoassays for the particular molecule will typically comprise incubating a sample, such as a biological fluid, a tissue extract, freshly harvested cells, or lysates of cultured cells, in the presence of a detectably labeled antibody and detecting the bound antibody by any of a number of techniques well-known in the art.

The binding activity of a given antibody may be determined according to well-known methods. Those skilled in the art will be able to determine operative and optimal assay conditions for each determination by employing routine experimentation.

An additional aspect of the present invention relates to diagnostic kits for the detection or measurement of SVA. Kits for diagnostic use are provided, that comprise in one or more containers an anti-SVA peptide antibody, and, optionally, a labeled binding partner to the antibody. Alternatively, the anti-SVA peptide antibody can be labeled (with a detectable marker, e.g., a chemiluminescent, enzymatic, fluorescent, or radioactive moiety). Accordingly, the present invention provides a diagnostic kit comprising, an anti-SVA peptide antibody and a control immunoglobulin. In a specific embodiment, one of the foregoing compounds of the container can be detectably labeled. A kit can optionally further comprise, in a container, a predetermined amount of a SVA peptide recognized by the antibody of the kit, for use as a standard or control.

Preferred routes of administration include but are not limited to intranasal, oral, intradermal, and intramuscular. Administration via the intramuscular route, most preferably in a single dose, is desirable. The skilled artisan will recognize that compositions of the invention may also be administered in one, two or more doses, as well as, by other routes of administration. For example, such other routes include subcutaneously, intracutaneously, intravenously, intravascularly, intraarterially, intraperitoneally, intrathecally, intratracheally, intracutaneously, intracardially, intralobally, intramedullary, intrapulmonarily, and intravaginally. Depending on the desired duration and effectiveness of the treatment, the compositions according to the invention may be administered once or several times, also intermittently, for instance on a daily basis for several days, weeks or months and in different dosages.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

SEQUENCE LISTING

This application contains a sequence listing. The sequence listing comprises the following sequences:

SEQ ID NO:1 denotes the RNA sequence of the near-complete genome of the SVA strain of the present invention.

SEQ ID NO:2 denotes a subset of the genomic RNA sequence that encodes the viral polyprotein (SVV antigen; SEQ ID NO:3).

SEQ ID NO:3 denotes the amino acid sequence of the viral polyprotein (SVV antigen) encoded by SEQ ID NO:2.

SEQ ID NO:4 denotes GenBank_KX377924.

SEQ ID NO:5 denotes GenBank_KT321458.

SEQ ID NO:6 denotes GenBank_KR063107.

SEQ ID NO:7 denotes GenBank_KR063108.

SEQ ID NO:8 denotes GenBank_KR063109.

SEQ ID NO:9 denotes GenBank_HJ999048.

SEQ ID NO:10 denotes GenBank_KC667560.

SEQ ID NO:11 denotes GenBank_GY488390.

SEQ ID NO:12 denotes GenBank_GV614995.

SEQ ID NO:13 denotes GenBank_DM060849.

SEQ ID NO:14 denotes GenBank_NC_011349.

SEQ ID NO:15 denotes GenBank_GY488390_CDS.

SEQ ID NO:16 denotes GenBank_GV614995_CDS.

SEQ ID NO:17 denotes GenBank_DM060849_CDS.

SEQ ID NO:18 denotes the nucleotide sequence of SVVP13C insert in construct BaculoFBU/SVVP13C (A).

SEQ ID NO:19 denotes the amino acid sequence of SVVP13C polyprotein expressed from BaculoFBU/SVVP13C.

SEQ ID NO:20 denotes the nucleotide sequence of SVVP13C insert in construct BaculoFBU/SVVP13C-CO where the SVV P1 region is codon optimized for expression in insect cells (B).

SEQ ID NO:21 denotes the amino acid sequence of SVVP13C polyprotein expressed from BaculoFBU/SVVP13C-CO.

SEQ ID NO:22 denotes BaculoFBU/VVP13C VP3/VP1.

SEQ ID NO:23 denotes the nucleic acid sequence of the SVVP13C VP3/VP1 insert of construct BaculoFBU/SVVP13C VP3/VP1.

SEQ ID NO:24 denotes the nucleic acid sequence of the SVVP13CD insert of construct BaculoFBU/SVVP13CD.

SEQ ID NO:25 denotes the amino acid sequence of SVVP13CD polyprotein expressed from BaculoFBU/SVVP13CD.

SEQ ID NO:26 denotes the nucleic acid sequence of the PCR product containing the coding sequence for SVVP1-His.

SEQ ID NO:27 denotes the amino acid sequence of SVVP1-His expressed from construct BaculoG/SVVP1-His-sIRES-SVV3C.

SEQ ID NO:28 denotes the nucleic acid sequence of the PCR product containing the coding sequence for SVVP1-His that has been codon optimized for expression in insect cells (SVVP1CO-His).

SEQ ID NO:29 denotes the amino acid sequence of SVVP1-His expressed from construct BaculoG/SVVP1CO-His-sIRES-SVV3C.

SEQ ID NO:30 denotes the nucleic acid sequence of the PCR product containing the coding sequence for SVV3C.

SEQ ID NO:31 denotes the amino acid sequence of SVV3C expressed from constructs BaculoG/SVVP1-His-sIRES-SVV3C and BaculoG/SVVP1CO-His-sIRES-SVV3C.

SEQ ID NO:32 denotes the nucleic acid sequence of the SVVP1-His-sIRES-SVV3C expression cassette in pORB-SVVP1-His-sIRES-SVV3C.

SEQ ID NO:33 denotes the nucleic acid sequence of the SVVP1CO-His-sIRES-SVV3C expression cassette in pORB-SVVP1CO-His-sIRES-SVV3C.

SEQ ID NO:34 denotes PCR primer P3219012A (SVVP1 Fwd).

SEQ ID NO:35 denotes PCR primer P3219039A (SVVP1 His Rev).

SEQ ID NO:36 denotes PCR primer P3219012C (SVVP1-CO Fwd).

SEQ ID NO:37 denotes PCR primer P3219039B (SVVP1-CO His Rev).

SEQ ID NO:38 denotes PCR primer P3219012E (SVV3C Fwd).

SEQ ID NO:39 denotes PCR primer P3219039C (SVV3C Rev).

SEQ ID NO:40 denotes PCR primer P3219165A (VP3/VP1 Fwd).

SEQ ID NO:41 denotes PCR primer P3219165B (VP3/VP1 Rev).

SEQ ID NO:42 denotes PCR primer P3219166A (SVV3D Fwd).

SEQ ID NO:43 denotes PCR primer P3219166B (SVV3C Rev).

SEQ ID NO:44 denotes PCR primer P3219166C (SVV3D Rev).

SEQ ID NO:45 denotes SVV3D coding sequence.

The invention further includes the following clauses:

1. A method of generating an immune response in a mammal, comprising administering an immunologically-effective amount of a killed Seneca Valley Virus A (SVA) comprising:

(a) a nucleic acid sequence of SEQ ID NO:1 or SEQ ID NO:2, or (b) a nucleic acid sequence 97% identical to SEQ ID NO:1, which encodes a polypeptide having immunologically-effective activity of a polypeptide of SEQ ID NO:3.

2. A method of generating an immune response in a mammal, comprising administering an immunologically-effective amount of a killed SVA comprising:

(a) having the amino acid sequence of SEQ ID NO:3;

(b) having an amino acid sequence 80% identical to SEQ ID NO:3 and having a biological or immunologically-effective activity of a polypeptide encoded by SEQ ID NO:3; or (c) that is a fragment of the amino acid sequence of SEQ ID NO:3 comprising at least 15 contiguous amino acids of SEQ ID NO:3and having an immunologically-effective activity.

3. A method of generating an immune response in a mammal, comprising administering an immunologically-effective amount of a killed SVA comprising:

(a) a nucleic acid sequence of SEQ ID NO:1 or SEQ ID NO:2, or (b) a nucleic acid sequence 97% identical to SEQ ID NO:1 or SEQ ID NO:2, which encodes a polypeptide having immunologically-effective activity of a polypeptide of SEQ ID NO:3.

4. A method of generating an immune response in a mammal, comprising administering an immunologically-effective amount of an immunogenic compositions according to clause 1.

5. A method of generating an immune response in a mammal, comprising administering an immunologically-effective amount of an immunogenic compositions according to clause 2.

6. A method of generating an immune response in a mammal, comprising administering an immunologically-effective amount of an immunogenic composition according to clause 3.

7. A method according to clause 1, wherein the mammal is a swine, and the immune response provides protective immunity to disease caused by SVA infection.

8. A method according to clause 2, wherein the mammal is a swine, and the immune response provides protective immunity to disease caused by SVA infection.

9. A method according to clause 3, wherein the mammal is a swine, and the immune response provides protective immunity to disease caused by SVA infection.

10. A vaccine comprising one or more antigens of Senecavirus A (SVA), wherein the SVA is any SVA comprising:

(a) a nucleic acid encoded by SEQ ID NO:1, and/or comprises the sequence of SEQ ID NO:1 and/or comprises the RNA equivalent of SEQ ID NO:1;

(b) a nucleic acid which sequence is at least 99% identical with SEQ ID NO:1 and/or is at least 99% identical with the RNA equivalent of SEQ ID. NO:1;

(c) a polypeptide that is encoded by a polynucleotide comprising the sequence of SEQ ID NO: 1 or 2;

(d) a polypeptide that is encoded by a polynucleotide that is at least 80% homologous to or identical with polynucleotides of a);

(e) a protein fragment that is encoded by a polynucleotide that comprises at least 15, preferably 24, more preferably 30, even more preferably 45 contiguous nucleotides included in the sequences of SEQ ID NO: 1 or SEQ ID NO: 2;

(f) a polypeptide comprising the amino acid sequence of SEQ ID NO: 3;

(g) a polypeptide that is at least 80% homologous to and/or identical with a polypeptide of f);

(h) a fragment of the polypeptides of f) and/or g);

(i) a polypeptide of f) or g); or (j) a fragment of h) or i) comprising at least 5, preferably 8, more preferably 10, even more preferably 15 contiguous amino acids included in the sequences of SEQ ID NO: 3.

11. The vaccine of clause 10, wherein the vaccine is recombinant vaccine or a killed vaccine.

12. The vaccine of clause 10, wherein the vaccine is killed vaccine.

13. The vaccine of clause 10, wherein the Senecavirus A (SVA), is chemically inactivated.

14. The vaccine of clause 13, wherein the Senecavirus A (SVA), is chemically inactivated by treatment with a chemical inactivating agent which includes a compound selected from the group consisting of ethylenimine, binary ethylenimine, acetylethylenimine and mixtures thereof.

15. The vaccine of clause 14, wherein the Senecavirus A (SVA), is chemically inactivated by treatment with binary ethylenimine.

16. The vaccine of clause 10, wherein the vaccine further comprises an adjuvant.

17. The vaccine of clause 16, wherein the adjuvant is an EMULSIGEN® oil-in-water emulsion-based adjuvant.

18. The vaccine of clause 6, wherein the Senecavirus A (SVA) comprises SEQ ID NO:1, and/or comprises the RNA equivalent of SEQ ID NO:1.

19. The vaccine of clause 11, wherein the vaccine is recombinant vaccine.

20. The vaccine of clause 11, wherein such recombinant vaccine comprises one or more immunogenic components selected from the group consisting of:

(a) an isolated nucleic acid encoding an antigen of Senecavirus A (SVA), wherein the recombinant polypeptide has at least 90% homology with SEQ ID NO:3, (b) a vector comprising the isolated nucleic acid of a), (c) the recombinant protein encoded by the nucleic acid of a), and (d) any combination thereof.

21. The vaccine of clause 20, wherein such vaccine comprises a pharmaceutical acceptable carrier and/or excipient.

22. The vaccine of clause 21, wherein the excipient is one or more adjuvants.

23. The vaccine of clause 22, wherein the adjuvant is an EMULSIGEN® oil-in-water emulsion-based adjuvant.

24. The vaccine of clause 20, wherein the vaccine further comprises one or more additional antigens.

25. The vaccine of clause 20, wherein an immunogenic component is the isolated nucleic acid.

26. The vaccine of clause 20, wherein an immunogenic component is the vector.

27. The vaccine of clause 11, wherein an immunogenic component is the recombinant Senecavirus A (SVA) P1 protein.

28. The vaccine of clause 20, wherein an immunogenic component is a combination.

EXAMPLES

Example 1

This study utilized conventional animals to determine the preliminary feasibility of induction of a serological response following vaccine administration. The primary purpose of this study was to evaluate if inactivated whole-virus preparations using Senecavirus A (SVA) (SEQ ID NO:1 or SEQ ID NO:2, and/or a nucleic acid sequence 97% identical to SEQ ID NO:1, which encodes a polypeptide having immunologically-effective activity of a polypeptide of SEQ ID NO:3) seroconverted in conventional pigs to the SVA vaccine.

For virus isolation, 0.5 mL of vesicular fluid was filtered through a 0.2/0.8 μm syringe filter (Pall Acrodisc Cat 4658) and the filtrate was used for inoculation on to swine testes cells (ST cells). ST cells were grown in 6-well plates to 80-100% confluency. Media was aspirated and 0.25 mL of the filtrate was inoculated on to the cells. Following an hour of adsorption at 37° C., plain serum free media was added to cells. Plates were incubated at 37° C., 5% CO2 atmosphere and checked daily for cytopathic effects (CPE). CPE was typically complete in 24-28 hours. Harvested virus was passed several times and was used to generate serials.

The viral stock was prepared by inoculating flasks planted with AI-ST cells with 5 mL viral stock and 160 mL of media (Minimum Essential Media+2.5% HEPES). Flasks were incubated for approximately 48 hrs. Flasks were frozen and then thawed at room temperature. Material was 0.2 μm filtered. Viral harvest was inactivated with a combination of 10 mM BEI and 0.2% formaldehyde with constant agitation at 37° C. for 72 hrs. The inactivation was neutralized with sodium thiosulfate (17% of BEI volume added) and sodium bisulfite. Inactivation was confirmed by two passages of material on AI-ST cells. For the initial passage, 10 mL of inactivated material was inoculated onto a T75 flask of AI-ST cells. Flasks were incubated for seven days at 37° C.+5% $CO_2$ and periodically evaluated for the presence of cytopathic effect. For the second passage, flasks were frozen, then thawed. Material was centrifuged and 10 mL of the supernatant was inoculated onto a T75 flask of AI-ST cells. Flasks were incubated for seven days at 37° C.+5% $CO_2$ and periodically evaluated for the presence of cytopathic effect. Positive and negative controls samples were included in the assay. Results confirmed lack of growth in both lots. Inactivated viral harvest was concentrated to 12.4× using a 10 k, 650 $cm^2$ ultrafiltration hollow fiber cartridge. The concentrated serial was aseptically combined with EMULSIGEN® D (commercially available from Phibro Animal Health Corporation) to achieve a 12.5% formulation. The mixture was stirred for 30 minutes at room temperature and then aseptically dispensed into 30 mL vaccine bottles and stored at 4° C. Material was tested for bacterial sterility by routine culture (anaerobic and aerobic) on blood agar plates at 37° C. for 48 hours. No bacterial contamination was detected.

Twenty pigs were randomized into two groups as shown in Table 1. See Table 1 below for group descriptions and housing structure. On D0, pigs were administered a 2 mL intramuscular dose of the SVA vaccine or a placebo. On D21, animals received a booster administration of the SVA vaccine or placebo. Blood was collected from all pigs prior to administration of the treatment at each vaccination (D0 and D21) and on D35. Subsets of serum samples were assayed for evidence of seroconversion to SVA. General health observations were recorded throughout the study. Injection sites were observed for reactions for a minimum of three days following administration of the vaccine. Animals were humanely euthanized at the end of the trial.

TABLE 1

| Study Design | | | | |
|---|---|---|---|---|
| Group | Room | n | Vaccine treatment | Dose/Route |
| 1 | 114 | 11 | SVA inactivated prototype vaccine (Senecavirus A; x + 10; 0.2 μm filtered; pre-inactivation titers (two batches were pooled) = 6.95/6.51 log TCID50/mL; inactivated with 10 mM BEI + 0.2% formaldehyde; neutralized with sodium bisulfite and sodium thiosulfate; 12.4X concentrated (10kD hollow-fiber); adjuvanted with 12.5% EMULSIGEN ® D) | 2 mL/IM |
| 2 | 114<br>219 | 7<br>2 | Placebo (1xPBS (Gibco, catalog# 10010-023, L#1793111) adjuvanted with 12.5% EMULSIGEN ® D) | 2 mL/IM |

This study demonstrated 100% seroconversion (as measured by virus neutralization) to SVA following administration of two doses of the BEI-inactivated SVA prototype adjuvanted with 12.5% EMULSIGEN® D. See Table 2 for the schedule of key events and sample collection.

TABLE 2

| Schedule of key events and sample collection | |
|---|---|
| Study Day | Study Event |
| D-3 | Collection of blood from animals |
| D-1 | Transfer of animals from study |
| D0 | Vaccination #1 |
| | Injection site observations for three days following vaccination |
| | Collection of blood from animals |
| D14 | Collection of blood from animals |
| | Vaccination #2 |
| D21 | Collection of blood from animals |
| | Injection site observations for three days following vaccination* |
| D0-D34 | General health observations (1× daily) |
| D34 | Necropsy |
| | Collection of terminal blood (1 × 250 mL bottle) from all animals |

*Note that observations continued until reactions resolved

To avoid bias, treatments were administered on D0 and D21 by personnel not involved with clinical monitoring of the animals. On D0, the 2 mL dose of vaccine was administered to healthy pigs into the musculature of the right neck using an appropriately-sized, sterile needle and syringe. On D21, the process was identical with the exception that the injection was given on the left side of the neck. The lot number, dosage amount, animal identification numbers and timing of administration of vaccine material were recorded on the Vaccine Dose Confirmation Record.

During the vaccination period, animals were evaluated daily using a general health observation form. Specifically, if all animals were normal, an N was entered for status. If an abnormal pig was found, an A was entered for status and the specific animal identification number and abnormality was listed. Injection site areas were monitored for the presence of redness, swelling, heat and pain (either present or absent) and size (cm) for a minimum of three days following each vaccination. If lesions were apparent, they were monitored until resolution.

On blood collection dates, three to eight mL of venous whole blood was collected by the Investigator or designee via the anterior vena cava from each pig using an appropriately sized VACUTAINER® needle, a VACUTAINER® needle holder (both commercially available from Becton Dickinson and Company Corporation) and appropriately sized serum separator tubes (SST).

Serum samples were held at 2-8° C. until testing. Processing was completed within 48 hours of receipt. Blood tubes were centrifuged at 1960×g for 10 minutes at 4° C. The serum was separated from the clot by centrifugation and decanted into two screw-cap cryogenic vials labeled with at least study number, day of study, and animal ID. Aliquots were stored at −70° C.±10° C. The samples were stored for a minimum of six months after the completion of this study.

Selected serum samples were tested by a virus neutralizing assay using SVA isolate NAC #20150909.

At the time of off-test, animals were deeply anesthetized and 1×250 mL centrifuge bottle of blood was collected from each animal. The animal was euthanized and the injection site was palpated. All animals were rendered in accordance with the AUP and facility standard operating procedures.

The pig was considered the experimental unit. A list of available pigs born to sow no.'s 9, 116, 787 and 895 (n=30) and from sow no.'s 141 and 145 (n=6) were used for randomization. Specifically, pigs were assigned a random number (using random.org). Pigs were sorted by sow, then random number. Pen assignments were assigned a random number (using random.org). The pen assignments were then sorted by random number and combined with the animal list.

The statistical analyses and data summaries were conducted by the study monitor. All data were imported into JMP® version 11.1.1 for analysis. Data listings and summary statistics by treatment group were generated.

An internally developed virus neutralization assay was used to measure seroconversation in animals following vaccination. No animals had a detectable serological response prior to vaccination. By D35, all vaccinated animals (Group 1) had a detectable response. The assay was run at a 1:80 dilution and animals were considered either positive or negative. See Table 3 below for a summary of the SVA VN results.

TABLE 3

SVA VN results by group and study day

| Group | Description | Study day D0 | Study day D35 |
|---|---|---|---|
| 1 | SVA inactivated prototype vaccine | 0/11 | 11/11 |
| 2 | Placebo | 0/9 | 0/9 |

The primary objective of this study was to evaluate whether conventional pigs seroconvert to SVA following vaccination with SVA vaccine.

In regards to the SVA vaccine, 100% of pigs vaccinated with the inactivated SVA prototype vaccine were able to generate a neutralizing antibody response. In conclusion, this study was able to demonstrate reasonable expectation of efficacy for the prototype inactivated SVA vaccine.

Example 2

Two gene sequences were ordered in the pUCIDT-Amp vector (Integrated DNA Technologies) The SVVP13C gene (SEQ ID NO:18) is native sequence of the full length P1 polyprotein with 2A and partial 2B and 3B sequences connecting the P1 polyprotein and 3C self-cleaving protease. The SVVP13C-CO gene (SEQ ID NO: 20) is an insect codon optimized version of the SVVP13C with the P1, 2A and 2B sequences codon-optimized using the IDT Codon Optimization Tool while the 3B and 3C remained as native sequences. Both genes have a Kozak sequence before the start codon, as well as BamHI and NotI restriction sites at the 5' and 3' ends, respectively. The SVVP13C (SEQ ID NO:18) and SVVP13C-CO (SEQ ID NO: 20) inserts were excised from pUCIDT-AMP-SVVP13C and pUCIDT-AMP-SVVP13C-CO plasmids by BamHI and NotI digestion, respectively, and ligated into the pVL1393 vector (BD Biosciences). See FIG. 1 for construct design of the native and codon optimized pVL1393 constructs.

PCR amplification was performed to amplify the SVVP1-His (SEQ ID NO:26) and SVVP1CO-His (SEQ ID NO:27) sequence from pIDT-AMP-SVVP13C and pIDT-AMP-SVVP13C-CO respectively using primers that added the coding sequence for a 6×His tag on the 3' end of each gene (SEQ ID NO: 34, 35, 36 and 37). The SVV3C sequence (SEQ ID NO:30) was amplified from pIDT-AMP-SVVP13C using primers to add a 5' SpeI site and a 3' SacI site (SEQ ID: 38 and 39). (See Table 4 for primers).

TABLE 4

Primer Sequences for SVVP1-His-SVV3C and SVVP1CO-His-SVV3C

| Primer | Sequence (5'-3') | SEQ ID NO: |
|---|---|---|
| P3219012A (SVVP1 Fwd) | GGATCCGCCACCATGGGTAATGTTCA | 34 |
| P3219039A (SVVP1 His Rev) | GCGGCCGCTCAGTGGTGGTGGTGGTGGTGTTGCATCAGCATCTT TTGCTTGTAGCTGC | 35 |
| P3219012C (SVVP1-CO Fwd) | GGATCCGCCACCATGGGCAACG | 36 |
| P3219039B (SVVP1-CO His Rev) | GCGGCCGCTCAGTGGTGGTGGTGGTGGTGTTGCATAAGCATCTT CTGTTTATAGCTACGG | 37 |
| P3219012E (SVV3C Fwd) | ACTAGTATGCAGCCCAACGTGGACATGGGCTTT | 38 |
| P3219039C (SSV3C Rev) | GAGCTCTCATTGCATTGTAGCCAGAGGCTCACCGG | 39 |

TABLE 5

Primer Sequences for SVVP13C VP3/VP1 and SVVP13CD

| Primer | Sequence (5'-3') | SEQ ID NO: |
|---|---|---|
| P3219165A (VP3/VP1 Fwd) | CTTCCTACGTGCCTCAGGGGGTTGACAACGCCGAGACTGGG | 40 |
| P3219165B (VP3/VP1 Rev) | CCCAGTCTCGGCGTTGTCAACCCCCTGAGGCACGTAGGAAG | 41 |
| P3219166A (SVV3D Fwd) | TACAATGCAAGGACTGATGACTGAGCTAGAGCCTG | 42 |
| P3219166B (WVV3C Rev) | TCAGTCATCAGTCCTTGCATTGTAGCCAGAG | 43 |
| P3219166C (SVV3D Rev) | GCGGCCGCTCAGTCGAACAAGGCCCTCCATCT | 44 |

The SVV3C insert (SEQ ID NO:30) was ligated into the second multiple cloning site (MCS2) of pORB-MCS1-sIRES-MCS2 vector (Allele Biotechnology) using the SpeI and SacI restriction sites. Subsequently, either SVVP1-His or SVVP1CO-His were ligated into MCS1 of pORB-MCS1-sIRES-SVV3C utilizing the BamHI and NotI restriction sites to generate pORB-SVVP1-His-sIRES-SVV3C (SEQ ID NO:32) and pORB-SVVP1CO-His-sIRES-SVV3C (SEQ ID NO:33) respectively.

Figure 3:
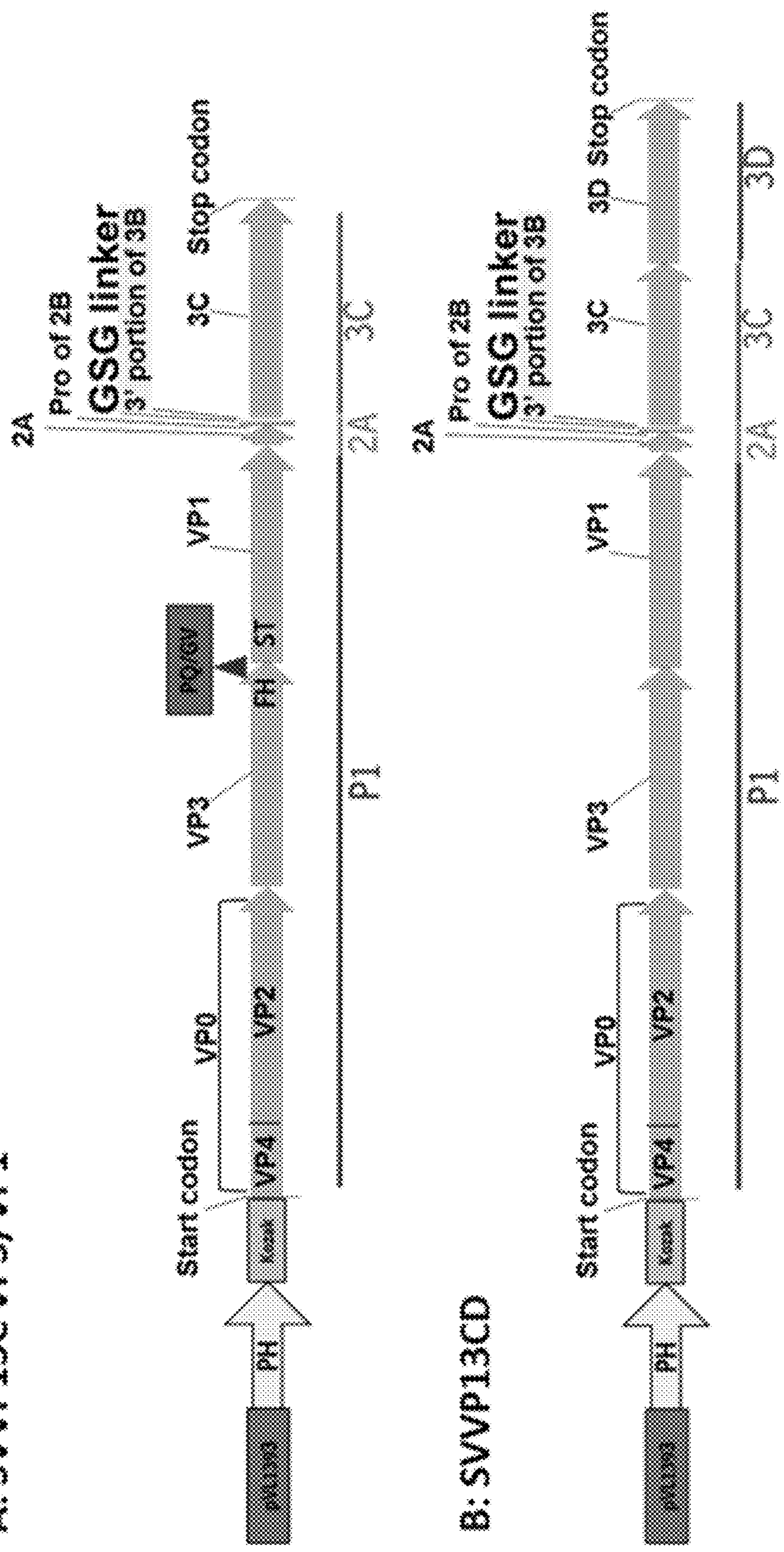
FIG. 3 shows SVVP13C VP3/VP1 construct design (A) (SEQ ID NO:22) to mutate the VP3/VP1 cleavage site and SVVP13CD construct design (B) (SEQ ID NO:24) for the baculovirus expression system

Primers were designed to mutate the VP3/VP1 cleavage site (nucleotides 1786-1797) of the SVVP13C sequence (SEQ ID NO:18) in pUCIDT-AMP-SVVP13C from FH/ST to PQ/GV (See Table 5 above for primers, SEQ ID NO:40 and 41) using the Lightning Quik Site Directed Mutagenesis kit (Stratagene). The mutated sequence, SVVP13C VP3/VP1 (SEQ ID NO: 22) was excised from pUCIDT-AMP-SVVP13C VP3/VP1 and ligated into the pVL1393 vector to produce pVL1393-SVVP13C VP3/VP1 An additional construct fused the SVV3D coding sequence (SEQ ID NO:45) to the 3' end of the SVVP13C sequence (SEQ ID NO:18) by overlap extension PCR (OE-PCR) using overlapping primer sets (SEQ ID NO: 34, 42, 43, and 44). The resulting PCR product, SVVP13CD (SEQ ID NO: 24) was cloned into pVL1393 using BamHI and NotI restriction sites. (See FIG. 3 for diagrams of the SVVP13C VP3/VP1 (SEQ ID NO: 22) and SVVP13CD constructs (SEQ ID NO: 24)).

The recombinant SVV capsid constructs in the pVL1393-based plasmids were co-transfected with FlashBAC ULTRA (FBU) baculovirus DNA (Oxford Expression Technologies) into Sf9 cells, whereas the pORB-based plasmids were co-transfected with BaculoGold baculovirus DNA (BD Biosciences) into Sf9 insect cells using the ESCORT transfection reagent (Sigma Aldrich) as per Manufacturer's instructions. Cell culture supernatants from the transfected Sf9 cells were harvested and clarified by centrifugation at 1,000×g for 5 min to pellet the cellular debris. The clarified supernatant was collected, 0.2 μM-filtered and stored as the P1 transfection harvest. Sf9 insect cells were used to generate P2 stocks, and the P2 stocks were then used to generate P3 and P4 amplifications of the SVV constructs for protein expression evaluations in SF+ insect cells. Baculovirus-infected SF+ cells were harvested and clarified at 10,000×g for 10 min at 4° C. The cultures of baculovirus-infected SF+ cells were sampled daily to monitor total cells/mL, viable cells/mL, percent viability and cell diameter by Vi-Cell analysis. Amplifications were harvested when viability was ≤30% viability or when viable cells were ≤$1\times10^6$ cells/mL. Additional one mL daily samples were collected to evaluate protein expression as the infections progressed and were processed as described above. Collected supernatant and cell pellet samples were stored at −70° C. until evaluation.

Lysis of Insect Cell Pellets to Separate Soluble and Insoluble Fractions

SF+ insect cell culture samples were centrifuged to pellet the cells after which the media was removed and the cell pellets were frozen until lysis. Pellets were re-suspended in lysis buffer containing the following: 20 mM Tris, 1% Triton X-100, Protease Inhibitor Cocktail for His-tagged Proteins (10 μL/mL) and Benzonase (250 units/mL) in de-ionized water with a pH of 7.4. The re-suspended insect cell lysates were vortexed for 10 sec, incubated at room temperature for 5 min, vortexed again for 10 sec than centrifuged at 19,090×g for 10 min at 4° C. to pellet insoluble material. The soluble lysates were pipetted off the insoluble fractions and stored in tubes at −70° C.

Purification of SVV Recombinant Capsid Proteins

Supernatant harvests containing the expressed recombinant SVV capsid proteins were 0.2 μM-filtered, dispensed into ultracentrifuge tubes, and centrifuged at 100,000×g for two hours at 4° C. to pellet protein and possible VLPs. The clarified supernatant was carefully decanted and the pelleted material was re-suspended in TBS and stored at 4° C. Discontinuous 10%-60% sucrose gradients were used to further purify recombinant SVV capsid proteins for the respective constructs. The respective re-suspended materials were added to the top of the gradient and centrifuged at 100,000×g for two hours at 4° C. Fractions from the sucrose gradients were collected equally into tubes (with fraction 1 starting at the top of the gradient surface) and stored at 4° C.

SDS-PAGE & Western

SD S-PAGE was performed using the NuPAGE electrophoresis system and 4-12% Bis-Tris IVIES mini gels. Samples were separated under reducing conditions using 0.05M DTT at 175V for the appropriate time. Gels were stained for total protein using an eStain 2.0 Protein Staining Device or transferred to nitrocellulose membranes using the iBlot system for Western blots. Western blots were performed with anti-SVV peptide rabbit polyclonal antibodies (anti-VP1-2, anti-VP2-2, and anti-VP3-1, varying dilutions) and goat anti-rabbit peroxidase-labeled secondary antibody (1:500) by the Snap ID Protein Detection System (EMD Millipore), utilizing negative control baculovirus antigen in the antibody diluent, and developed using TMB membrane peroxidase substrate.

Dialysis and Concentration of Purified SVV Recombinant Capsid Proteins

Sucrose gradient fractions containing the recombinant protein as determined by Western blot were pooled together and dispensed into a 10,000 MWCO or 50,000 MWCO cellulose membrane dialysis cassette. The dialysis cassette was placed in 3.5 L of TBS with a magnetic stir bar, covered, and placed on a stir plate at 4° C. for a minimum of 6 hrs. The dialysis cassette was then placed into a fresh beaker of 3.5 L of TBS, and further dialyzed with stirring overnight or longer. The sample was removed from the dialysis cassette and concentrated, if needed, depending on the volume of the dialyzed sample. Concentration was performed using a size-exclusion filter unit and centrifugation according to Manufacturer's directions until desired sample volume was achieved.

Electron Microscope (EM) Imaging

The sucrose gradient-purified and dialyzed recombinant SVV capsid protein samples were evaluated by transmission electron microscopy (EM) at the USDA NADC Facility for the visualization of VLPs. The expected size of the icosahedral viral capsid for native SVV is approximately 27 nm in diameter.

Results and Discussion

The native SVV P1 polyprotein (SEQ ID NO:19, amino acids 1-859) is processed by a self-cleaving protease to form the individual viral capsid subunit proteins, VP1-VP4. The SVV baculovirus constructs described in this invention were designed in a manner similar to that used for FMDV baculovirus constructs utilizing self-cleavage of the expressed polyprotein into individual protein subunits for formation of an empty capsid or VLP. Constructs encoding full length SVV P1 polyprotein, 2A, partial 2B and 3B, and 3C (SEQ ID NO:18) were prepared with native coding sequence or with the P1, 2A and 2B sequences codon-optimized (SEQ ID NO:20) for insect cells. Previous research with the similar pVL1393-based FMDV baculovirus constructs revealed SF+ cell toxicity attributed to 3C expression. Concern as to potential SVV 3C toxicity was addressed by also generating pORB-based baculovirus constructs for evaluation. The pORB-based constructs utilize an internal ribosomal entry site (WSSV sIRES) (SEQ ID NO:32, nucleic acids 2647-2826) allowing for the initiation of cap-independent mRNA translation, which differs from the 5' cap dependent translation of the sequence most adjacent to the 3'-end of the polyhedrin promoter. Several studies have shown that the use of a sIRES, such as that from WSSV, has often resulted in decreased protein expression of the translated sequence placed after the sIRES. In the context of the described SVV baculovirus constructs (SEQ ID NOs:32 and 33), the utilization of the sIRES may reduce expression of the SVV 3C self-cleaving protease, which in turn may alleviate 3C toxicity issues without reducing expression of SVVP1. The pORB-based and pVL1393-based constructs were similar in that they both utilized the same SVVP1 sequence and included a C-terminal 6×-His tag. However, the key difference between the pORB- or pVL1393-based constructs was that the pORB-based constructs placed the SVV3C protease sequence behind the sIRES site. After evaluations of these initial sets of constructs, two more constructs were created modifying the original SVV DNA sequence. One construct modified the VP3/VP1 cleavage site sequence (SEQ ID NO:22) and the other construct further incorporated the SVV3D DNA sequence at the end of the SVV3C sequence (SEQ ID NO:24). All constructs were evaluated for expression of the capsid subunits as well as for the production of VLPs.

Expression of SVV Capsid Proteins in Baculovirus-Infected Insect Cells

The BaculoFBU/SVVP13C (SEQ ID NO:18) and BaculoFBU/SVVP13C-CO (SEQ ID NO:20) constructs were used to infect SF+ cells with samples collected to evaluate the expression of SVV capsid proteins. Protein bands of expected sizes for VP1 (SEQ ID NO:19, amino acids 596-859), VP2 (SEQ ID NO:19, amino acids 73-356) and VP3 (SEQ ID NO:19, amino acids 357-595) capsid subunits were detected by Western blot with anti-SVV P1 subunit-specific antibodies in the supernatant from the baculovirus-infected insect cells, which were similar in size to native SVV capsid proteins (FIG. 4). Interestingly, an additional protein band of 55 kDa was detected in the alpha-SVV VP1 and alpha-SVV VP3 Western blots. The 55 kDa band was not detected in the native SVV antigen sample or the negative control (FIG. 4). The presence of the additional protein of 55 kDa in size suggests that it may comprise an uncleaved VP3-VP1 protein product.

FIG. 4 also provides a comparison of SVV capsid protein expression levels between the native (A) (SEQ ID NO:18) and the codon-optimized (B) (SEQ ID NO:20) SVV DNA sequences in baculovirus-infected SF+ cells. Based on these Western blots, there was no apparent difference in SVV capsid protein expression levels between the codon-optimized BaculoFBU/SVVP13C-CO (SEQ ID NO:20) and the original, native BaculoFBU/SVVP13C (SEQ ID NO:18), therefore only the BaculoFBU/SVVP13C (SEQ ID NO:18) construct was evaluated further. The second set of constructs with the 3C protease placed behind the sIRES did not produce detectable SVV capsid subunit proteins during infection of SF+ insect cells. Not only did the sIRES constructs not produce detectable levels of the SVV capsid subunit proteins, no SF+ cytotoxicity issues were observed. Consequently, the sIRES constructs were not further evaluated. Based on these overall observations, the supernatant harvest for BaculoFBU/SVVP13C-infected SF+ insect cells was the most promising construct to move forward for sucrose gradient purification and evaluation for the presence of VLPs.

Figure 5:
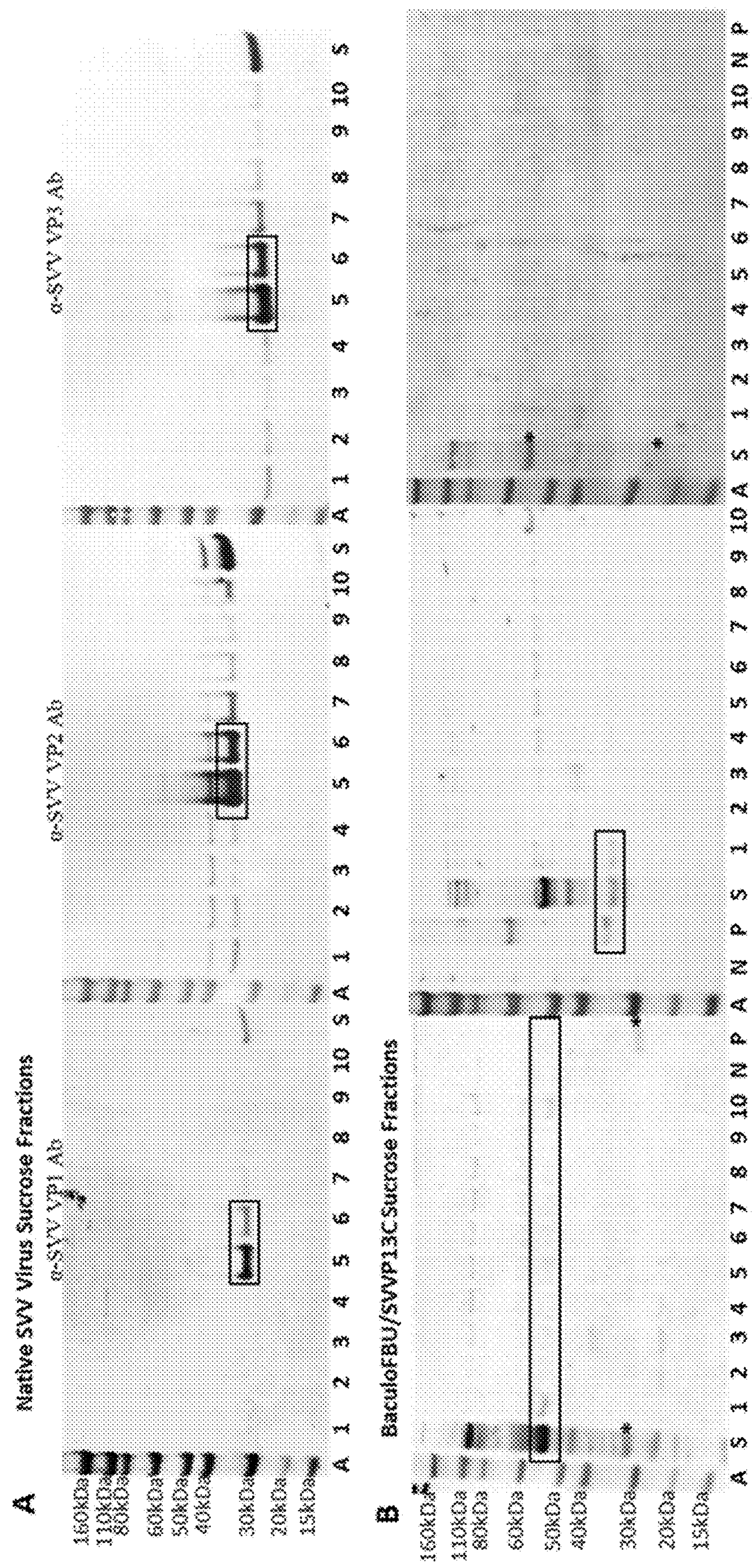
FIG. 5 shows western blots of native SVV virus sucrose fractions (A) and BauloFBU/SVVP13C sucrose fractions (B) with alpha-SVV VP1, alpha-SVV VP2 and alpha-SVV PV3 rabbit polyclonal antibodies. Lane A is the protein standard, Lanes 1-10 is sucrose fractions 1-10, N-BaculoFBU/No Insert Negative Control, P is Positive Control Native inactivated SVV and S is starting sample for sucrose gradient. Expected Band sizes: Full length SVV P1=around 95 kDa (SEQ ID NO:19, amino acids 1-859), VP1=around 29 kDa (SEQ ID NO:19, amino acids 596-859), VP2-around 32 kDa (SEQ ID NO:19, amino acids 73-356), VP3=around 26 kDa (SEQ ID NO:19, amino acids 357-595).

To determine the expected mobility of BaculoFBU/SVVP13C-derived SVV capsid proteins in a sucrose gradient, pelleted native SVV virus was separated on a sucrose gradient and analyzed by Western blot (FIG. 5A). The majority of native SVV subunit proteins were detected in fractions 5 and 6 after sucrose gradient purification for native SVV. It was anticipated that if VLPs were formed in the baculovirus-infected SF+ cells they would present in a similar or slightly higher range of collected gradient fractions.

Harvest supernatant from the BaculoFBU/SVVP13C construct was also processed for sucrose gradient purification. Western blots of the sucrose gradient fractions only detected a small portion of the recombinant SVV VP2 capsid protein in sucrose fraction one (FIG. 5B). VP1 and VP3 were not detected in the sucrose fractions, although a faint protein band at 55 kDa, thought to be uncleaved VP3-VP1, was detected throughout the sucrose fractions by α-SVV VP1 Western blot. No recombinant SVV capsid proteins were detected in fractions 5 and 6 in contrast to the detection of expected proteins from native SVV. These results suggest that the capsid subunit proteins expressed in BaculoFBU/SVVP13C-infected insect cells do not form VLPs.

Even though BaculoFBU/SVVP13C (SEQ ID NO:18) produced recombinant SVV capsid proteins, detected as subunit proteins with alpha-SVV antibodies, VLPs were not observed. The capsid subunit proteins were of similar size when compared to the native SVV virus proteins, but several other protein bands were also detected in the baculovirus-infected SF+ cells, including a protein band at 55 kDa in the alpha-SVV VP1 and alpha-SVV VP3 Western blots, suggesting an uncleaved VP3-VP1 protein product not present in the native SVV virus. This may be an indication of an issue with the efficient cleavage and separation of the VP3-VP1 subunits which in turn may hinder VLP formation in baculovirus-infected insect cells.

Evaluation of Modified BaculoFBU/SVVP13C Constructs

To investigate the possibility of the SVV capsid subunit proteins VP1 and VP3 not separating completely, two new constructs were designed based on previous publications. The 2008 publication by Hales et al. stated that the SVV P1 VP3/VP1 cleavage site, FH/ST, was atypical of picornaviruses including the genus most closely related to SVV, Cardiovirus. In comparison, the typical cleavage site of PQ/GV is conserved in many known picornaviruses. Therefore, mutation of the VP3/VP1 cleavage site to a typical picornavirus cleavage sequence may enhance cleavage of the VP3 and VP1 capsid subunits. The BaculoFBU/

SVVP13C (SEQ ID NO:18) construct was mutated to contain a PQ/GV sequence at the VP3/VP1 interface resulting in a construct designated as BaculoFBU/SVVP13C VP3/VP1 (SEQ ID NO:22). This new construct was used to infect SF+ cells and evaluated in protein expression assessments in a similar fashion as to that of the BaculoFBU/SVVP13C construct (SEQ ID NO:18). Western blot analysis of BaculoFBU/SVVP13C VP3/VP1-derived supernatant samples using alpha-SVV VP1 or alpha-SVV VP3 antibodies detected the putative uncleaved VP3-VP1 protein product and individual subunits of VP3 or VP1 bands in the same proportion as was observed from BaculoFBU/SVVP13C (SEQ ID NO:18) (FIG. 6). A protein band at the expected full length of the SVV P1 polyprotein, ~95 kDa, was also detected in the BaculoFBU/SVVP13C VP3/VP1 harvest supernatants.

Figure 7:
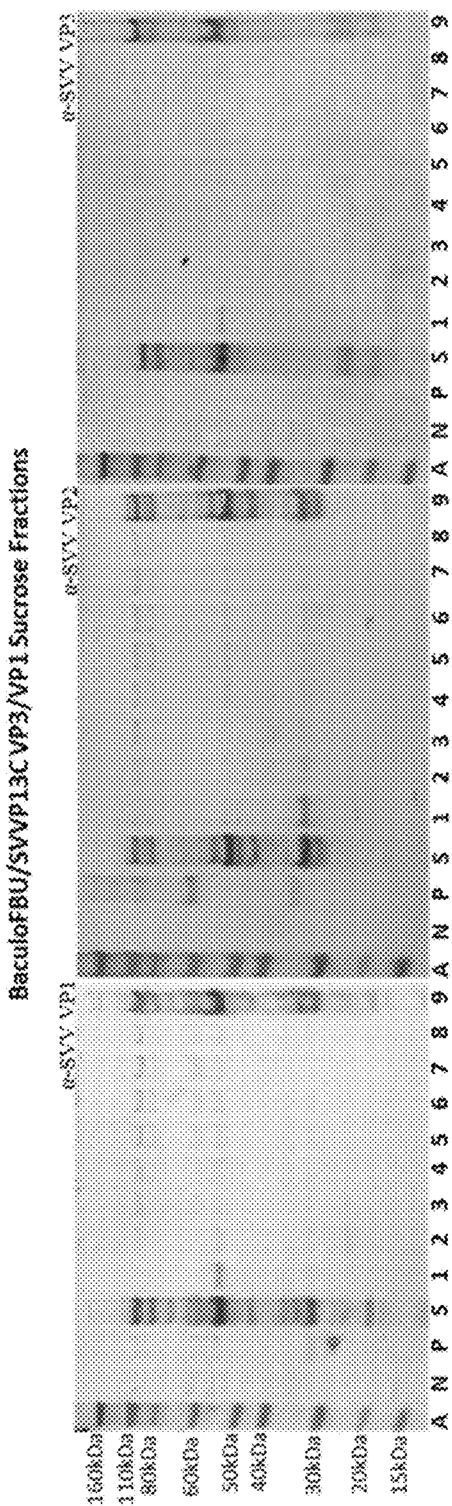
FIG. 7 shows Western Blots of BaculoFBU/VVP13C VP3/VP1 (SEQ ID NO:22) sucrose fractions with an anti-SVV VP1, anti-SVV VP2 and anti-SVV VP3 rabbit polyclonal antibodies. Lane A is the Protein Standard, N is BaculoFBU/No insert native control, P is positive control native inactivated SVV (SEQ ID NO:3), S is SVVP13C VP3/VP1 (SEQ ID NO:22,) pellet re-suspended in TBS and Lane 1-9 is sucrose fractions 1-9. Full length SVV P1=around 95 kDa (SEQ ID NO:19, amino acids 1-859), VP1=around 29 kDa (SEQ ID NO:19, amino acids 596-859), VP2-around 32 kDa (SEQ ID NO:19, amino acids 73-356), VP3=around 26 kDa (SEQ ID NO:19, amino acids 357-595).

Additionally, Western blot evaluations of the sucrose gradient fractions of the harvest supernatant (FIG. 7) were comparable to the results of BaculoFBU/SVVP13C (SEQ ID NO:18). The α-SVV VP2 Western blot detected the recombinant SVV VP2 capsid protein throughout the sucrose fractions with the majority in fractions one and nine. Subunit VP1 and VP3 proteins were not detected in the sucrose fractions, although a protein band at 55 kDa was detected throughout the sucrose fractions of the α-VP1 Western and in sucrose fractions one and nine of the α-VP3 Western that is possibly the VP3-VP1 uncleaved proteins. All three Westerns had several protein bands detected in the very last sucrose fraction that appeared similar to the starting sample of the sucrose gradient. This suggests the SVV capsid proteins may aggregate and pellet to the bottom of the gradient. Capsid proteins were not detected in the last fraction of the BaculoFBU/SVVP13C (SEQ ID NO:18) sucrose gradient Westerns in FIG. 5*b*, but were observed in previous evaluations (NB 3219-123). It appears from these Western evaluations that the mutation of the cleavage sequence from FH/ST to PQ/GV had no effect on the presence of the 55 kDa band thought to be VP3-VP1 uncleaved. Compared to the original construct no increase in the amount of subunit VP3 and VP1 protein was detected and no VLP formation was observed.

Figure 8:
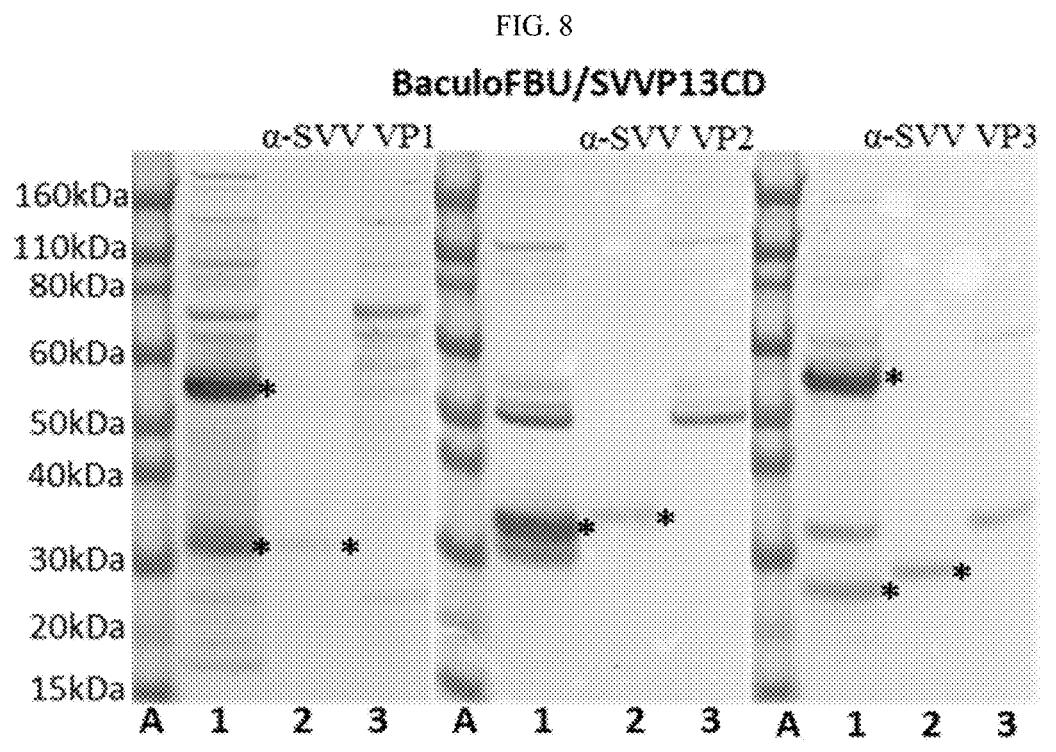

Other genera within picornavirus including enteroviruses and apthoviruses have shown more efficient cleavage of VP3-VP1 when having the 3CD protease in the native virus; therefore, a second Senecavirus construct, BaculoFBU/SVVP13CD (SEQ ID NO:24), was designed. BaculoFBU/SVVP13CD (SEQ ID NO:24) was expressed in SF+ cells and the supernatant harvest was evaluated by Western blot (FIG. 8). Results comparable to the previous VLP assessments were observed, with detection of VP1, VP2 and VP3 subunits as well as the suspected uncleaved VP3-VP1 protein of 55 kDa in the α-SVV VP1 and α-SVV VP3 Western blots.

In contrast to SVV protein expression assessments with other SVV baculovirus constructs, Western blot evaluations of the sucrose fractions for BaculoFBU/SVVP13CD (SEQ ID NO:24) exhibited monomeric SVV VP1, VP2 and VP3 capsid subunit proteins present in sucrose fractions 1 and 2 with VP1 and VP2 detected throughout the sucrose fractions. The 55 kDa protein band was present in the α-SVV VP1 and α-SVV VP3 Western blots in sucrose fractions 1 and 2, but not in the negative control sample or α-SVV VP2 Western blots (FIG. 9). Similar to the BaculoFBU/SVVP13C VP3/VP1 (SEQ ID NO:22) sucrose fraction evaluations, a majority of the SVV capsid proteins aggregated and pelleted to the bottom of the sucrose gradient for BaculoFBU/SVVP13CD (SEQ ID NO:24). However, detection of SVV VP1 and VP2 subunit proteins throughout the fractions derived from BaculoFBU/SVVP13CD-infected SF+ cells construct suggest the possibility of VLP formation.

Despite unclear results from the sucrose gradient evaluations of each construct, fractions expected to contain VLPs were evaluated by electron microscopy (EM) at the USDA NADC. Pooled sucrose fractions from supernatant harvests BaculoFBU/SVVP13C (SEQ ID NO:18), BaculoFBU/SVVP13C VP3/VP1 (SEQ ID NO:22) and BaculoFBU/SVVP13CD (SEQ ID NO:24) were dialyzed in TBS and concentrated in preparation for EM imaging. The samples had high background making it difficult to clearly depict VLPs by EM negative staining Some spherical shapes were seen sparsely in the BaculoFBU/SVVP13C VP3/VP1 (SEQ ID NO:22) and BaculoFBU/SVVP13CD (SEQ ID NO:24) pooled sucrose fractions that were similar in size to expected SVV VLPs, but there were not enough of them throughout the sample to confirm the presence of VLPs.

Recombinant SVV Proteins are Expressed Inside the SF+ Insect Cells

Figure 10:
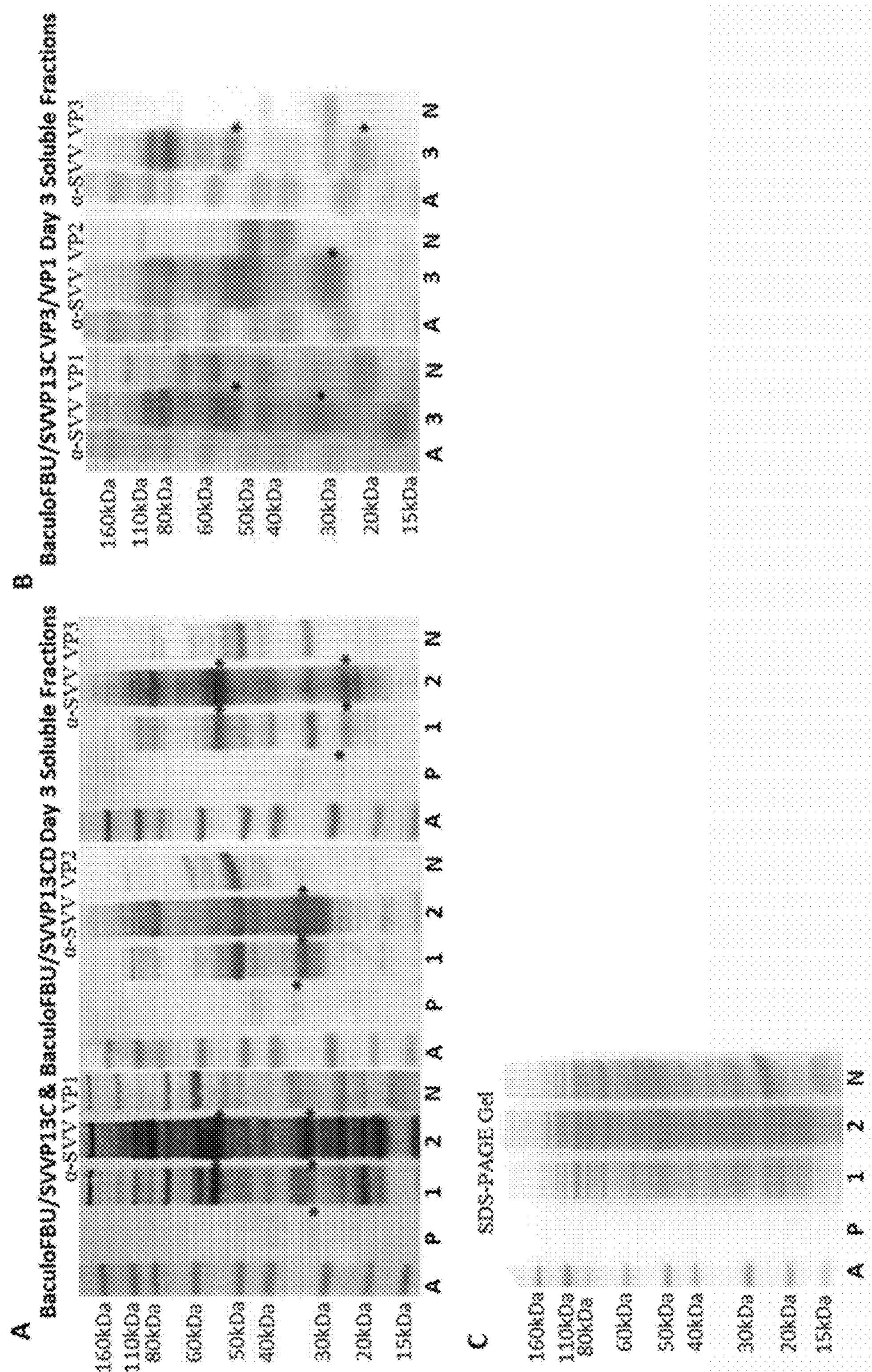
FIG. 10 shows Western Blots of BaculoFBU/SVVP13C (A) (SEQ ID NO:18), BaculoFBU/SVVP13CD (A) (SEQ ID NO:24), and BaculoFBU/SVVP13CVP3/VP1 (B) (SEQ ID NO:22). Day 3 soluble fractions with α-SVV VP1, α-SVV VP2 and α-SVV VP3 rabbit polyclonal antibodies. SDS-PAGE gel for BaculoFBU/SVVP13C and BaculoFBU/SVVP13CD (C). Lane A-Protein Standard, Lane P—Positive Control Native SVV Antigen, Lane 1—Day 3 Soluble Fraction SVVP13C, Lane 2—Day 3 Soluble Fraction SVVP13CD, Lane 3—Day 3 Soluble Fraction SVVP13C VP3/VP1 and Lane N—Negative Control BaculoFBU/No Insert Soluble Fraction. Expected Band Sizes: Full length SVV P1=around 95 kDa (SEQ ID NO:19, amino acids 1-859), VP1=around 29 kDa (SEQ ID NO:19, amino acids 596-859), VP2-around 32 kDa (SEQ ID NO:19, amino acids 73-356), VP3=around 26 kDa (SEQ ID NO:19, amino acids 357-595).
Figure 11:
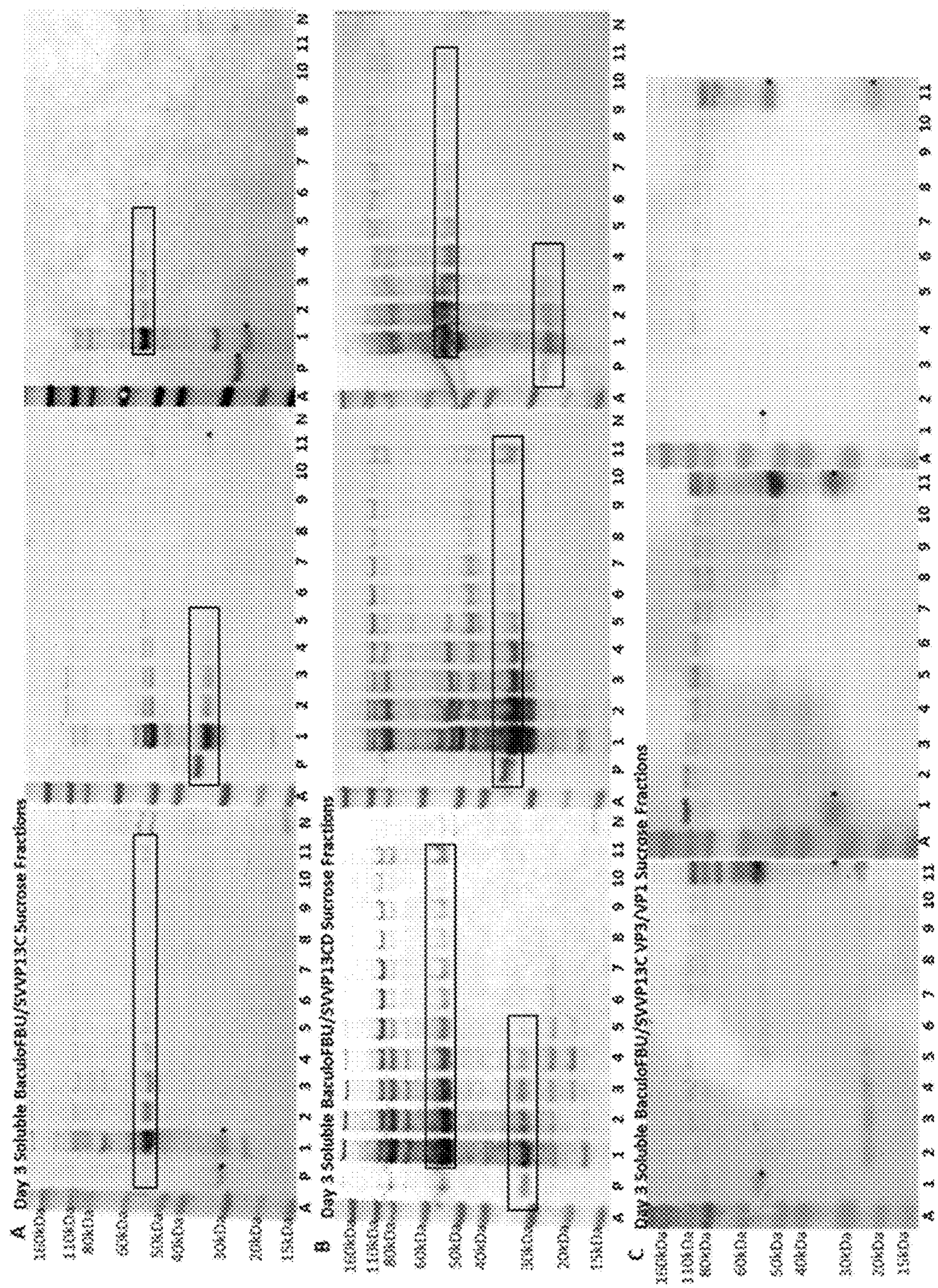
FIG. 11 shows Western blots of sucrose fractions of Day 3 Soluble BaculoFBU/SVVP13C (SEQ ID NO:18), BaculoFBU/SVVP13CD (SEQ ID NO:24) and BaculoFBU/SVVP13C VP3/VP1 (SEQ ID NO:22) with anti-alpha-SVV VP1, anti-alpha-SVV VP2 and anti-alpha-SVV VP3 rabbit polyclonal antibodies. Lane A is Protein Standard, P is Positive Control Native Inactivated SVV, Lane 1-11 is Sucrose fractions 1-11 and N is Negative Control BaculoFBU/No Insert Soluble Fraction. Expected Band Sizes: Full length SVV P1=around 95 kDa (SEQ ID NO:19, amino acids 1-859), VP1=around 29 kDa (SEQ ID NO:19, amino acids 596-859), VP2-around 32 kDa (SEQ ID NO:19, amino acids 73-356), VP3=around 26 kDa (SEQ ID NO:19, amino acids 357-595)

One possibility as to why the individual recombinant SVV viral capsid proteins are detected in the supernatant, but do not appear to form VLPs is that VLPs might dissociate shortly after release into the supernatant due to the low pH of the insect cell media. To test this hypothesis, cell pellet samples from day 3, when viability of the cells was still relatively high, of BaculoFBU/SVVP13C (SEQ ID NO:18), BaculoFBU/SVVP13C VP3/VP1 (SEQ ID NO:22) and BaculoFBU/SVVP13CD (SEQ ID NO:24) infections were lysed in physiological pH buffer to obtain the soluble protein fraction for evaluation of recombinant SVV subunit proteins by Western blot (FIG. 10). As seen with the supernatant harvest samples of the baculo SVV constructs, there were detectable levels of subunit capsid proteins VP1, VP2 and VP3 in the Day 3 soluble fractions. An ~55 kDa band suspected to be uncleaved VP3-VP1 proteins was also detected in the α-SVV VP1 and α-SVV VP3 Westerns in the baculo SVV sample lanes as observed previously. The Day 3 soluble fraction samples were sucrose gradient purified and evaluated by Western blot to observe if VLPs were present in the cells before lysis (FIG. 11).

The sucrose fractions from the Day 3 soluble fractions had comparable results as seen with the supernatant harvest sucrose fractions from insect cells infected with BaculoFBU/SVVP13C (SEQ ID NO:18), BaculoFBU/SVVP13C VP3/VP1 (SEQ ID NO:22) and BaculoFBU/SVVP13CD (SEQ ID NO:24), respectively. The protein bands expected to be the SVV capsid proteins were detected mostly in fractions one and two and/or pelleted to the bottom suggesting the SVV subunit proteins inside the insect cells do not form VLPs prior to cell lysis. EM was performed on pooled sucrose fractions of BaculoFBU/SVVP13C VP3/VP1 (SEQ ID NO:22) Day 3 soluble sample with no VLPs being observed for this sample. BaculoFBU/SVVP13C (SEQ ID NO:18) and BaculoFBU/SVVP13CD (SEQ ID NO:24) Day 3 soluble sucrose fractions were not evaluated by EM.

Conclusions

Although it was determined that recombinant SVV viral capsid proteins VP1, VP2 and VP3 were expressed to some extent as fully cleaved proteins, they did not result in VLP formation based on sucrose gradient purification and EM imaging In the Western blot evaluations of sucrose gradient fractions, the recombinant SVV capsid proteins were detected in the first few fractions and/or in the last fractions of the gradient. These results suggest that the proteins do not assemble into VLPs, but rather remain as non-associated monomers or form large aggregates indicative of misfolded or misassembled proteins. Electron microscopy supports these results as VLPs were not detected in the pooled sucrose fractions which contained the SVV capsid subunit proteins.

Example 3

This study utilizes conventional animals to determine the preliminary feasibility of induction of a serological response following vaccine administration. The primary purpose of this study is to evaluate whether administration of prototype vaccines BaculoFBU/SVVP13C (SEQ ID NO:18), BaculoFBU/SVVP13C VP3/VP1 (SEQ ID NO:22) and BaculoFBU/SVVP13CD (SEQ ID NO:24) results in seroconversion in conventional pigs.

Forty pigs are randomized into four groups as shown in Table 1. See Table 6 below for group descriptions and housing structure. On D0, pigs are administered a 2 mL intramuscular dose of the prototype vaccines or a placebo. On D21, animals receive a booster administration of the prototype vaccines or placebo. Blood is collected from all pigs prior to administration of the treatment at each vaccination (D0 and D21) and on D35. Subsets of serum samples are assayed for evidence of seroconversion to SVA. General health observations are recorded throughout the study. Injection sites are observed for reactions for a minimum of three days following administration of the vaccine. Animals are humanely euthanized at the end of the trial. See Table 7 for the schedule of key events and sample collection.

TABLE 6

| Study Design | | | |
|---|---|---|---|
| Group | n | Vaccine treatment | Dose/Route |
| 1 | 10 | BaculoFBU/SVVP13C (SEQ ID NO: 18); inactivated with 5-10 mM BEI; adjuvanted with 12.5% EMULSIGEN ® D) | 2 mL/IM |
| 2 | 10 | BaculoFBU/SVVP13C VP3/VP1 (SEQ ID NO: 22) inactivated with 5-10 mM BEI; adjuvanted with 12.5% EMULSIGEN ® D) | 2 mL/IM |
| 3 | 10 | BaculoFBU/SVVP13CD (SEQ ID NO: 24); inactivated with 5-10 mM BEI; adjuvanted with 12.5% EMULSIGEN ® D) | 2 mL/IM |
| 4 | 10 | Placebo (BaculoFBU/empty); inactivated with 5-10 mM BEI; adjuvanted with 12.5% EMULSIGEN ® D) | 2 mL/IM |

TABLE 7

| Schedule of key events and sample collection | |
|---|---|
| Study Day | Study Event |
| D-3 | Collection of blood from animals |
| D-1 | Transfer of animals from study |
| D0 | Vaccination #1<br>Injection site observations for three days following vaccination<br>Collection of blood from animals |
| D14 | Collection of blood from animals |
| D21 | Vaccination #2<br>Collection of blood from animals<br>Injection site observations for three days following vaccination* |
| D0-D34 | General health observations (1× daily) |
| D34 | Necropsy<br>Collection of terminal blood (1 × 250 mL bottle) from all animals |

*Note that observations continued until reactions resolved

To avoid bias, treatments are administered on D0 and D21 by personnel not involved with clinical monitoring of the animals. On D0, the 2 mL dose of vaccine is administered to healthy pigs into the musculature of the right neck using an appropriately-sized, sterile needle and syringe. On D21, the process is identical with the exception that the injection was given on the left side of the neck. The lot number, dosage amount, animal identification numbers and timing of administration of vaccine material are recorded on the Vaccine Dose Confirmation Record.

During the vaccination period, animals are evaluated daily using a general health observation form. Specifically, if all animals are normal, an N is entered for status. If an abnormal pig is found, an A is entered for status and the specific animal identification number and abnormality is listed. Injection site areas are monitored for the presence of redness, swelling, heat and pain (either present or absent) and size (cm) for a minimum of three days following each vaccination. If lesions are apparent, they are monitored until resolution.

On blood collection dates, three to eight mL of venous whole blood are collected by the Investigator or designee via the anterior vena cava from each pig using an appropriately sized VACUTAINER® needle, a VACUTAINER® needle holder (both commercially available from Becton Dickinson and Company Corporation) and appropriately sized serum separator tubes (SST).

Serum samples are held at 2-8° C. until testing. Processing is completed within 48 hours of receipt. Blood tubes are centrifuged at 1960×g for 10 minutes at 4° C. The serum is separated from the clot by centrifugation and decanted into two screw-cap cryogenic vials labeled with at least study number, day of study, and animal ID. Aliquots are stored at −70° C.±10° C. The samples are stored for a minimum of six months after the completion of this study.

Example 4

This study utilized conventional animals to evaluate the efficacy of a two-dose, Senecavirus A vaccine, inactivated, whole virus against a heterologous challenge with a heterologous Senecavirus A field isolate. A total of 25 pigs were used for the study. Animals were randomized into two treatment groups. On D0, thirteen pigs in the SVA-Vx group were inoculated intramuscularly (IM) with Senecavirus A vaccine, inactivated, whole virus, while the remaining twelve pigs in the Placebo group received a control product. On D14, a booster vaccine was administered intramuscularly to all pigs using the appropriate material. On D35, all pigs were challenged with a total volume of 5 mL (2 mL orally and 3 mL intranasally) of 8.36 log TCID50/dose heterologous Senecavirus A field isolate (viral harvest). All pigs were housed comingled within one room. Pigs were monitored daily for general health from D0 through D33. From D34 through D49, pigs were monitored daily for clinical signs associated with SVA infection. Blood and rectal temperatures were taken periodically throughout the study. All animals were necropsied on D49 (14 days post challenge). See Table 8 for experimental design summary.

TABLE 8

| Study design | | | | | |
|---|---|---|---|---|---|
| Group | n | Room | Vaccine (D0, D14) | Challenge (D35) | Off-test |
| SVA-Vx | 13 | 316 | Senecavirus A vaccine, inactivated, whole virus | 8.36 log TCID50/5 mL dose; heterologous | D49 |
| Placebo | 12 | 316 | Placebo | Senecavirus A field isolate (viral harvest) | |

See Table 9 below for a summary of the vaccine and control product formulations. Routine culture and a *Mycoplasma* sp. PCR were performed on the vaccine material; no growth (anaerobic or aerobic on blood agar) or mycoplasma DNA contamination was detected. The vaccines were administered on D0, intramuscularly into the right side of the neck, midway between the base of the ear and point of the shoulder, using appropriately-sized sterile needles and syringes. On D14, the vaccine was administered in the same location as previously described but on the left side of the neck. All groups received a 2 mL dose.

TABLE 9

| Vaccine and Control | |
|---|---|
| Group | Treatment |
| SVA-Vx | Senecavirus A; pre-MSV; 0.2 μm filtered; pre-inactivation titer = 7.71 log $TCID_{50}$/mL; inactivated with 10 mM BEI + 0.2% formaldehyde; neutralized with sodium bisulfite and sodium thiosulfate; adjuvanted with 12.5% Emulsigen D; Lot#3423-022. |
| Placebo | Mock infected media; inactivated with 10 mM BEI + 0.2% formaldehyde; neutralized with sodium bisulfite and sodium thiosulfate; adjuvanted with 12.5% Emulsigen D; Lot#3423-023. |

Based on reports from field cases and previous publications, animals were monitored for lameness, hoof lesions, and the presence of vesicles. If an animal had any clinical abnormality throughout the study, it was considered affected. Table 10 reports the frequency of affected animals by group. The preventative fraction estimate 0.322 (0.004, 0.539; 95% CI) indicates vaccination reduced the number of affected animals. Mitigated fraction analysis was also done on the number of days an animal displayed an abnormal clinical sign. The mitigated fraction estimate of 0.710 (0.333, 0.935; 95% CI) indicates vaccination reduced the number of days an animal was considered affected.

TABLE 10

| Frequency distribution of presence/absence of clinical signs by group during the challenge phase | | | | | |
|---|---|---|---|---|---|
| | Affected?* | | | | |
| | No | | Yes | | |
| Group | N | % | N | % | total n |
| SVA-Vx | 4 | 31 | 9 | 69 | 13 |
| Placebo | 0 | 0 | 11 | 100 | 11[†] |

*Affected = a clinical sign was observed at least once during the study

[†]Animal #648 was removed from the analysis

Figure 12:
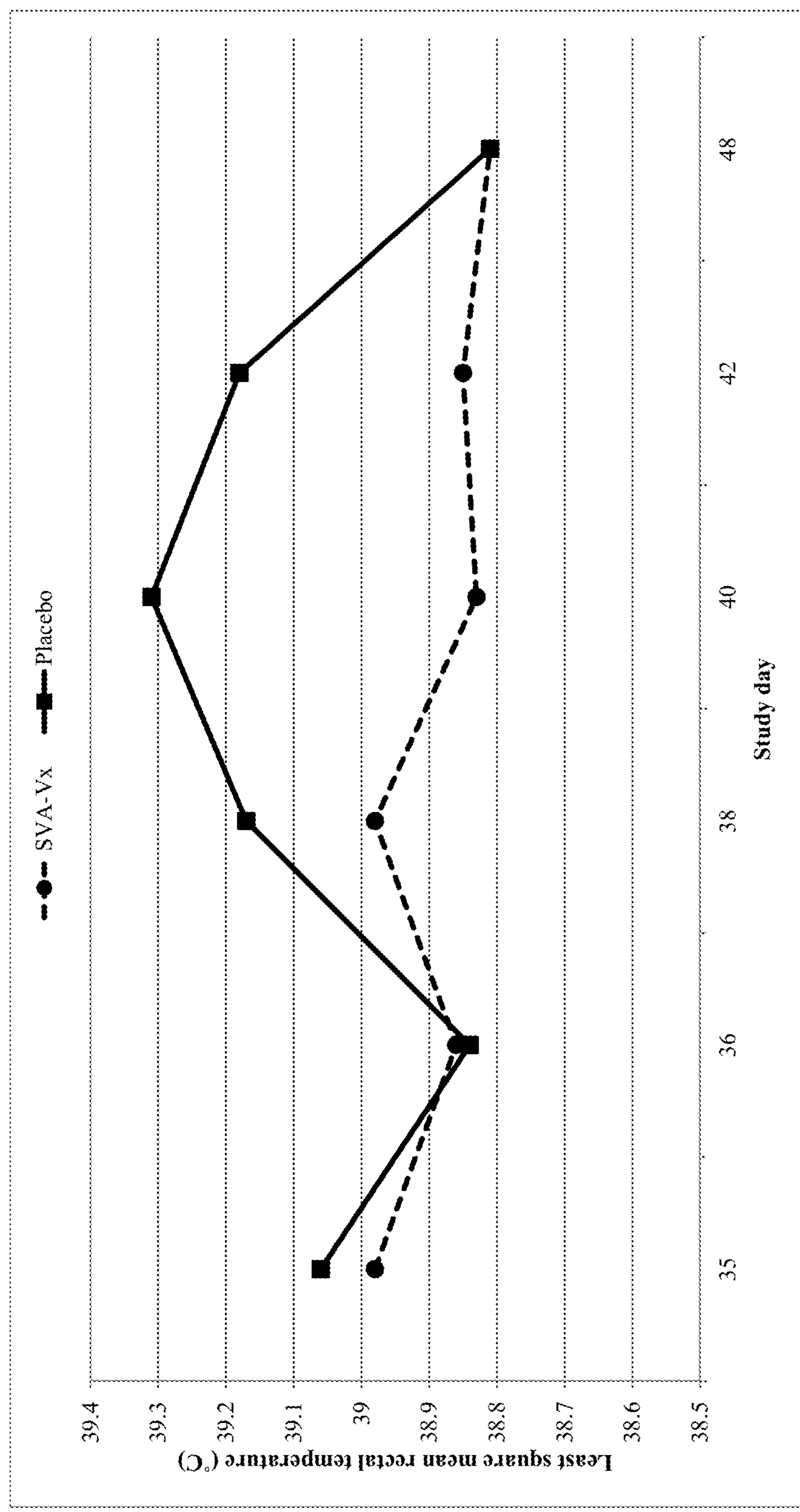
FIG. 12 shows the least square mean rectal temperatures (° C.) by study day and group.

Rectal temperatures were collected during the challenge period; least square mean rectal temperatures by study day and group are presented in FIG. 12. Vaccination resulted in significantly lower temperatures at D40 and 42.

Serum samples from D0, 14, 35, and 49 were evaluated by a virus neutralization assay. Geometric mean titers by group and study day are presented in Table 11. Following two doses of vaccine, 13/13 (100%) of animals had neutralizing titers greater than 400.

TABLE 11

Summary statistics for virus neutralization titers by study day and group. Values of <40 were reported as 20; values >2560 were set to 2560.

| Group | Study Day | n | Geometric Mean | Min | Max | % animals positive (>40) |
|---|---|---|---|---|---|---|
| SVA-Vx | 0 | 13 | 20.00 | 20 | 20 | 0.00 |
| | 14 | 13 | 68.17 | 20 | 160 | 69.23 |
| | 35 | 13 | 440.64 | 80 | 1280 | 100.00 |
| | 49 | 13 | 640.76 | 80 | 2560 | 100.00 |
| Placebo | 0 | 12 | 20.00 | 20 | 20 | 0.00 |
| | 14 | 12 | 20.00 | 20 | 20 | 0.00 |
| | 35 | 12 | 21.19 | 20 | 40 | 0.00 |
| | 49 | 11 | 2256.9 | 640 | 2560 | 100.00 |

Figure 13:
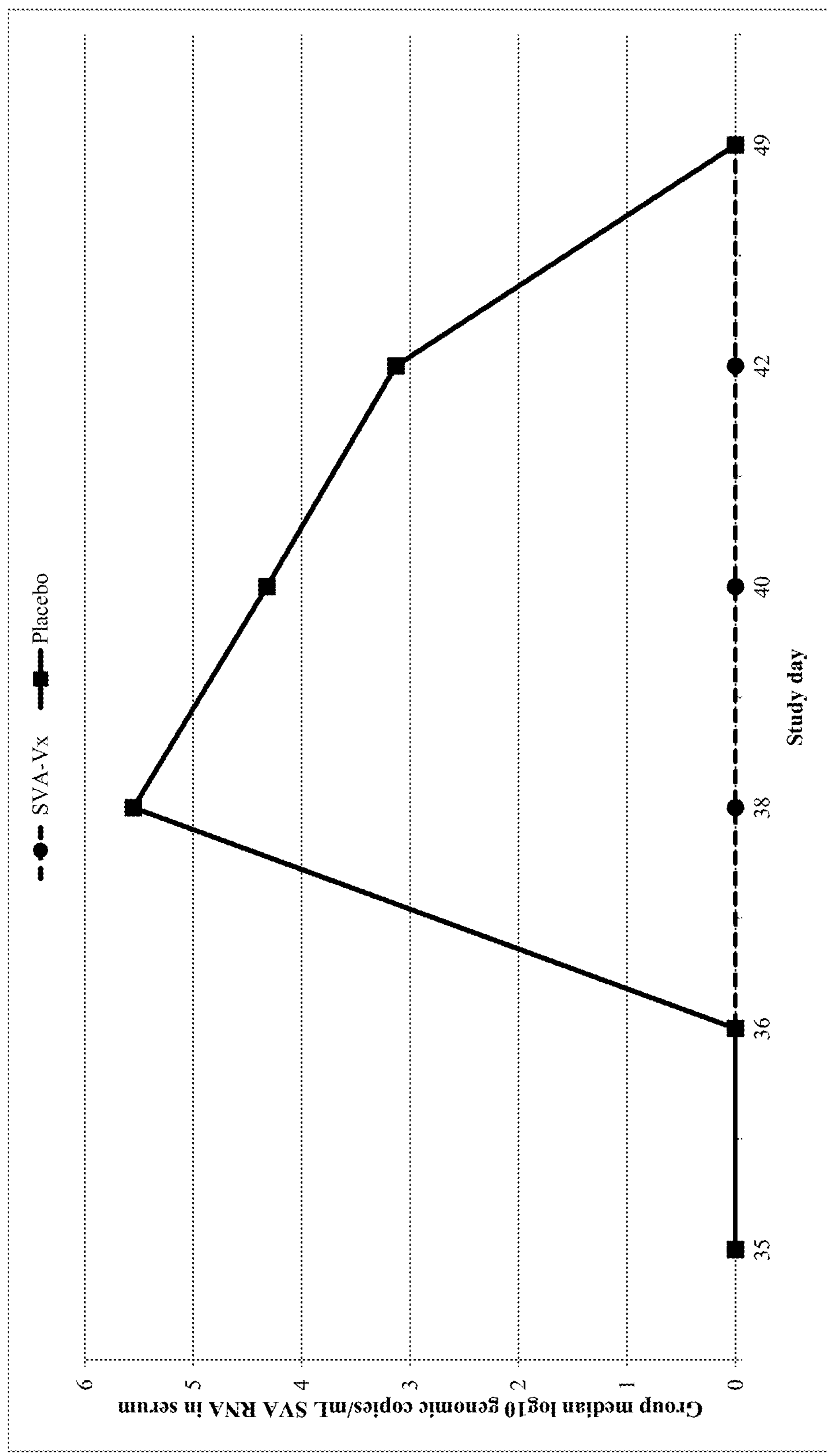
FIG. 13 shows the group median $\log_{10}$ genomic copies/mL SVA RNA in serum by group and day.

The presence of viral RNA in the serum was detected by a qRT-PCR assay. FIG. 13 displays group median quantities ($log_{10}$ genomic copies/mL) of SVA RNA in serum. SVA RNA was not detected in vaccinated animals at any time during the study. In comparison, viremia was detected in the placebo group from D36 through D42.

In conclusion, vaccination with two doses of Senecavirus A vaccine, inactivated, whole virus, resulted in complete reduction of viremia, a statistically significant reduction in clinical signs (PF=0.322; 95% CI=0.004, 0.539), and greater than four-fold virus neutralization titers in 13/13 vaccinated animals prior to challenge.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

The invention claimed is:

1. A nucleic acid of a chemically inactivated virus comprising a polynucleotide, a complement of the polynucleotide, or a DNA equivalent of the polynucleotide or the polynucleotide complement, wherein the polynucleotide: (i) comprises 99% sequence identity to SEQ ID NO: 1; (ii) comprises 95% sequence identity to SEQ ID NO: 2; and/or (iii) encodes a polypeptide having the amino acid sequence of SEQ ID NO: 3, wherein the chemically inactivated virus is chemically inactivated by treatment with a chemical inactivating agent which includes a compound selected from the group consisting of: binary ethylenimine (BED), formaldehyde, ethylenimine, acetylethylenimine and mixtures thereof.

2. The nucleic acid of claim 1, wherein the virus is a Senecavirus A (SVA).

3. The nucleic acid of claim 2, wherein the SVA is able infect a swine having at least one clinical sign arising from SVA infection selected from: vesicular disease, nail bed hemorrhages, sudden/acute lameness with redness and swelling at or around a coronary band, ulceration of the coronary band and sloughing of a hoof, going off feed, lethargy, anorexia, and fever.

4. A SVA comprising the nucleic acid of claim 1, wherein the nucleic acid is a ribonucleic acid and wherein the SVA is chemically inactivated by treatment with a chemical inactivating agent which includes a compound selected from the group consisting of, binary ethylenimine (BEI), formaldehyde, ethylenimine, acetylethylenimine and mixtures thereof.

5. A nucleic acid of a chemically inactivated Senecavirus A (SVA) comprising a polynucleotide, a complement of the polynucleotide, or a DNA equivalent of the polynucleotide or the polynucleotide complement, wherein the polynucleotide: (i) comprises 99% sequence identity to SEQ ID NO: 1; (ii) comprises 95% sequence identity to SEQ ID NO: 2; and/or (iii) encodes a polypeptide having the amino acid sequence of SEQ ID NO: 3, wherein the chemically inactivated SVA is chemically inactivated by treatment with a chemical inactivating agent which includes a compound selected from the group consisting of: binary ethylenimine (BED), formaldehyde, ethylenimine, acetylethylenimine and mixtures thereof.

6. A vector comprising a nucleic acid of a recombinant or chemically inactivated virus comprising a polynucleotide, a complement of the polynucleotide, or a DNA equivalent of the polynucleotide or the polynucleotide complement, wherein the polynucleotide: (i) comprises 99% sequence identity to SEQ ID NO: 1; (ii) comprises 95% sequence identity to SEQ ID NO: 2; and/or (iii) encodes a polypeptide having the amino acid sequence of SEQ ID NO: 3.

7. An isolated host cell comprising the vector of claim 6.

8. A polypeptide of a chemically inactivated virus comprising an amino acid sequence that: (i) is encoded by a polynucleotide comprising 99% sequence identity to SEQ ID NO: 1 and/or 95% sequence identity to SEQ ID NO:2; (ii) has the amino acid sequence of SEQ ID NO: 3; (iii) corresponds to a P1-2A-P3 polypeptide and is encoded by a polynucleotide comprising 90% sequence identity to SEQ ID NO: 18, 20, 22, 24, 32, and/or 33; and/or (iv) has at least 90% sequence identity to SEQ ID NO: 19, 21, 23, 25, 27, and/or 29, wherein the chemically inactivated virus is chemically inactivated by treatment with a chemical inactivating agent which includes a compound selected from the group consisting of: binary ethylenimine (BED), formaldehyde, ethylenimine, acetylethylenimine and mixtures thereof.

9. An immunogenic composition comprising the nucleic acid of claim 1 and a pharmaceutically acceptable carrier and/or excipient.

10. A vaccine comprising a nucleic acid of a chemically inactivated virus comprising a polynucleotide, a complement of the polynucleotide, or a DNA equivalent of the polynucleotide or the polynucleotide complement, wherein the polynucleotide: (i) comprises 99% sequence identity to SEQ ID NO: 1; (ii) comprises 95% sequence identity to SEQ ID NO: 2; and/or (iii) encodes a polypeptide having the amino acid sequence of SEQ ID NO: 3 and a pharmaceutically acceptable carrier, excipient, and/or adjuvant, wherein the chemically inactivated virus is chemically inactivated by treatment with a chemical inactivating agent which includes a compound selected from the group consisting of: binary ethylenimine (BED), formaldehyde, ethylenimine, acetylethylenimine and mixtures thereof.

11. A method of inducing an immune response against SVA infection, comprising administering to a swine the immunogenic composition of claim 9.

12. A method for eliciting an immune response in a swine that is effective to reduce or eliminate subsequent SVA infection clinical signs in the swine relative to a non-immunized control subject of the same species, comprising:

administering to the swine the immunogenic composition of claim 9, wherein the clinical signs comprise at least one of the following: vesicular disease, nail bed hemorrhages, sudden/acute lameness with redness and swelling at or around a coronary band, ulceration of the coronary band and sloughing of a hoof, going off feed, lethargy, anorexia, and fever.

13. A kit for vaccinating a swine against SVA, comprising:

the vaccine of claim 10; and a dispenser capable of administering the recombinant or killed vaccine to the swine.

14. An immunogenic composition comprising the polypeptide of claim 8 and a pharmaceutically acceptable carrier and/or excipient.

15. A vaccine comprising the polypeptide of claim 8 and a pharmaceutically acceptable carrier, excipient, and/or adjuvant.

16. The immunogenic composition of claim 9 wherein the virus is Senecavirus A (SVA) and the nucleic acid is a ribonucleic acid.

17. The immunogenic composition of claim 16 wherein the SVA is chemically inactivated.

18. The vaccine of claim 10 wherein the virus is Senecavirus A (SVA) and the nucleic acid is a ribonucleic acid.

19. The vaccine of claim 18 wherein the SVA is chemically inactivated.

* * * * *

SEQUENCE LISTING

```
<160> NUMBER OF SEQ ID NOS: 45

<210> SEQ ID NO 1
<211> LENGTH: 7221
<212> TYPE: RNA
<213> ORGANISM: Senecavirus

<400> SEQUENCE: 1

cuguguuugc uagaggcaca gaggagcaac auccaaccug cuuuuguggg gaacggugcg      60

gcuccaauuc cugcgucgcc aaagguguua gcgcacccaa acggcgcauc uaccaaugcu     120

auuggugugg ucugcgaguu cuagccuacu cguuucuccc cuacucacuc auucacgcac     180

aaaaacugug uuguaacuau aagauuuagc ccucgcacgg gaugugcgau aaccgcaaga     240

uugacucaag cgcggaaagc gcuguaacca caugcuguua gucccuuuau ggcugcgaga     300

uggcuaucca ccucggauca cugaacugga gcucgacccu ccuuaguaag ggaaccgaga     360

ggccuucuug caacaagcuc cgacacagag uccacgugau ugcuaccacc augaguacau     420

gguucucccc ucucgaccca ggacuucuuu uugaauaucc acggcucgau ccagagggug     480

gggcaugauc ccccuagcau agcgagcuac agcgggaacu guagcuaggc cuuagcgugc     540

cuuggauacu gccugauagg gcgacggccu agucgugucg guucuauagg uagcacauac     600

aaguaugcag aacucucauu uuucuuucga uacagccucu ggcaccuuug aagacguaac     660

cggaacaaaa gucaagaucg uugaacaccc cagaucggug aacaauggug uuuacgauuc     720

guccacucau uuagagauac ugaaccuaca gggugaaauu gaaauuuuaa agucuuucaa     780

cgaauaccaa auucgcgccg ccaaacaaca acuuggacug gacaucguau acgaacuaca     840

ggguaauguu cagacaaccu caaagaauga uuuugauucc cgcggcaaua augguaacau     900

gaccuucaau uacuacgcaa acacuuacca gaauucagua gacuucucga ccuccucguc     960

ggcgucaggc gccggacccg ggaacucccg gggcggauua gcgggucucc ucacaaauuu    1020

caguggaauc uugaacccuc uuggcuaccu caaagaucac aauaccgaag aaauggaaaa    1080

cucugccgau cgagucauaa cgcaaacggc gggcaacacu gccauaaaca cgcaaucauc    1140

acugggugug uugugugccu acguugaaga cccgaccaaa ucugacccuc cguccagcag    1200

cacagaucaa cccaccacca cuuuuacugc caucgacagg ugguacacug gacgccucaa    1260

uucuuggaca aaagcuguaa aaaccuucuc uuuucaggcc guuccgcucc cuggagccuu    1320

ccugucuaga cagggaggcc ucaacggagg ggccuucacg gccacccuac auagacauuu    1380

cuuaaugaag ugcgggguggc agguggcaggu ucaaugcaau uugacgcaau uccaccaagg    1440

ugcucuucuu guugccaugg uccccgaaac cacccuugau gucaaaccug acggcaaggc    1500

aaagagcuua caggagcuga augaagagca gugggguggaa augucugacg acuaccggac    1560

cgggaaaaac augccuuuuc agucucuugg cacauacuau cggcccccua acuggacuug    1620

gggccccaau uuuauuaacc ccuaucaagu aacagucuuc ccacaccaaa uucugaacgc    1680
```

```
gagaaccucu accucgguag acauaagugu cccguacauc ggggagacuc cuacacaauc   1740
cucagagaca cagaacuccu ggacccuccu uguuauggug cuuguccccc uggacuacaa   1800
ggagggagcc acaacugacc cagaaauuac auuuucugua aggccuacaa gucccuacuu   1860
caaugggcuu cguaaccguu ucaagaccgg gacggacgag gaacaggggc ccauucccac   1920
agcacccaga gaaaauucgc uuauguuucu cucaaccauc ccugacgaca cugucccugc   1980
uuacgggaau gugcguaccc cucccgucaa uuaccucccc ggugaaauaa ccgaccucuu   2040
acaacuggcc cguauaccca cucucauggc guuugggcgg gcgucugaac ccgagccugc   2100
cucagacgca uaugugcccu acguugccgu uccugcccag uucgacgaca agccucucau   2160
cuccuucccg aucacccuuu cagauccugu cuaccagaac acccugguag gcgccaucag   2220
uucgaacuuc gccaacuacc gggggiguau ccaaaucacu cugacauuuu guggacccau   2280
gauggcaaga gggaaauucc ugcucucgua uucuccccca aauggagcac aaccacagac   2340
ccuuucugaa gcuaugcagu gcacauacuc uauuugggau auaggcuuga acucuaguug   2400
gaccuuuguc auccccuaca ucucgcccag ugauuaccgu gaaacucggg cuauuaccaa   2460
cucaguuuau ucugcugaug guugguuuag cuugcacaag cugaccaaaa uuacucuacc   2520
accugacugc ccacagaguc ccuguauucu cuuuuucgcc ucugcuggug aggauuacac   2580
ccuccgucuc ccuguugauu guaauccuuc cuacguguuc cacuccaccg acaacgccga   2640
gacuggggu auugaggcag guaacacuga caccgauuuc ucuggugaac uggcggcucc   2700
uggcucuaac cauacuaaug ucaaauuccu guuugaccga ucucgacuac ugaauguaau   2760
uaagguacug gagaaggacg ccgucuuccc ccguccuuuc cccacagcaa caggugcaca   2820
gcaggacgau gguuacuuuu gucuucuaac accccgccca acagucgcuu cccgaccccgc  2880
cacucguuuc ggccuguacg ucaacccguc ugacaguggc guucucgcua acacuucacu   2940
ggauuucaau uuuuacaguu uggccuguuu cacuuacuuu agaucagacc uugaagucac   3000
gguggucuca cuggagccag auuuggaguu cgccgugggg ugguuccccu cuggcaguga   3060
guaccaggcu ucuagcuuug ucuacgacca acugcaugua cccuaccacu uuacugggcg   3120
cacuccccgc gcuuucacca gcaagggugg aaagguaucu uucgugcucc cuuggaacuc   3180
ugucucuucc gugcuucccg ugcgcugggg gggcgccucc aagcuuucuu cugccacgcg   3240
gggucugccg gcucaugcug acugggggac cauuuacgcc uuuauccccc gucccaacga   3300
gaagaaaagc accgcuguaa agcacguggc gguguacguu cgguacaaga acgcgcgugc   3360
cuggugcccc agcaugcuuc ccuuucgcag cuacaagcag aagaugcuga ugcaaucagg   3420
cgacgucgag accaacccug gcccugcuuc ugacaacccg aucuuggagu uucuugaagc   3480
ggaaaacgau cuagucacuc uggccucucu cuggaagaug guacacucug uucaacagac   3540
cuggagaaag uaugugaaga acgacaauuu uuggcccaac uugcucagug agcuagoggg   3600
ggaaggcucc aucgccuugg ccgccacgcu aucuaaccaa gcuucaguga aagcucucuu   3660
gggccugcau uuucucucuc gagggcucaa uuacacagau uuuuacucuu uacugauaga   3720
gaaaugcucu aguuucuuua cuguagaacc gccuccucca ccagcugaaa aucugaugac   3780
caagcccucc gugaagucga aauuccgaaa gcuguuuaag augcaaggac ccauggacac   3840
agucaaagac uggaaccaaa uagccgccgg cuugaagaau uuccaauuug uucgugaccu   3900
agucaaagag gugguugacu ggcuccaggc cuggaucaau aaagagaaag ccagcccugu   3960
ccuccaguac cagcuggaga ugaagaagcu cgggcccgug gcuuuggcuc augaugccuu   4020
cauggccggu uccgggcccc cucuugguga cgaccagauu gaauaccucc agaaccucaa   4080
```

-continued

```
aucucuugcc cuaacacugg gaaagacuaa uuuggcccaa agucucacca cuaugaucaa   4140

cgccaagcag agcuccgccc aacgagucga acccguugug gugguccuca gaggcaagcc   4200

gggaugcggc aaaagcuugg ccuccacguu gauugcccag gcugugucua agcgucucua   4260

cggcucacag agugguauu cucuuccucc ggacccagac uucuucgacg gauauaaagg   4320

acaguuugua accuugaugg acgaucuggg acaaaacccg gaugggcaag auuucuccac   4380

cuuuugucag auggugucga ccgcccaauu ucuucccaac auggcggacc uugcagagaa   4440

ggggcgucccc uucaccucca aucuuaucau ugcaacuaca aaccucccuc acuuuagccc   4500

ugucaccauu gcugacccuu cugcagucuc ucggcguauc aacuacgacc ugacucuaga   4560

aguaucugag gccuacaaga agcacacgcg gcugaauuuc gaccuggcuu ucagacgcac   4620

ugacgccccc cccauuuauc cuuuugcugc ccaugugccc uucguggacg uggcugugcg   4680

cuucaaaaau ggucaucaaa gcuucaaucu ccuggaguug gucgacucua uuugugcaga   4740

cauucgggcc aagcaacaag gugcccgaaa uaugcagacu cugguucuac agagcccuaa   4800

cgagaacgac gacacccccg ucgacgaggc guuggguaga guucucaccc ccgcugcggu   4860

cgacgaggcg cuugucgacc ucgcuccaga ugccgacccg guuggccgcu uagcuauucu   4920

cgccaagcua ggucuugccc uagcugcggu cacuccuggu uugauaaucu uggcagugg   4980

acucuacaag uacuucucug gcucugauac agaccaagaa gaaacagaaa gugaggagcc   5040

ugcuaaagug ccuaggagcg agaaugcuua ugacggccca aagaaaaacu ccaagccccc   5100

uggagcgcuc ucucuuaugg aaaugcaaca gcccaacgug gacaugggcu uugaggcugc   5160

aguugcuaag aaaguggucg uccccauuac cuucaugguu cccaacagac cuuccggacu   5220

uacacagucc gcucuucuug uggccggccg gaccuuccua aucaaugagc auacaugguc   5280

caaccccucc uggaccagcu ucacaauccg uggugaggug cacacucgug augagcccuu   5340

ccaaacgguu cauuuuacuc accauggucu ucccacagau cugaugaugg uacgucucgg   5400

accgggcaac ucuuucccua acaaucuaga uaaguuugga cuugaccaga ugccggcacg   5460

uaacucccgu gugguuggcg uuucggcuag uuacgguaac uucuucuucu cugggaacuu   5520

ccucggguuu guugacucca ucaccucuga ccaaggaacc uaugcgagac uuuucaggua   5580

cagggugacg acuuacaagg gauggugcgg uucggcccug gucugugagg ccgguggugu   5640

ccgacgcauc auuggcaugc auucugcugg ugccgcuggu aucggcgccg ggacuuacau   5700

cucaaaauua ggacugauca aagcccuuaa acaccucggu gagccucugg cuacaaugca   5760

aggacugaug acugagcuag agccuggagu caccguacau guaccccgaa aaucuaaauu   5820

gagaaagacg accgcacacg cgguguacaa accggaguuu gaaccugcug uguugucaaa   5880

auuugauccc agacugaaca aggauguuga ccuagaugag guaauuuggu cuaaacacac   5940

cgccaacguc ccuuaucaac cuccuuuguu cuacacauac augucagagu acgcucaucg   6000

gguuuucucc uuuugggaa aagacaauga cauucugacc gucaaagaag caauccuggg   6060

caucccugga cuagacccua uggaucccca cacagcuccg gguuugcccu acgccauuag   6120

cggccuucga cguacugauc ucgucgauuu ugcgaacggc acgguagacc cggcacuggc   6180

caugcagauc cagaaauucu uagacgguga cuacucugau caugucuucc aaacuuuucu   6240

gaaagaugaa aucagacccu cagagaaggu ccgggcggga aaaacccgca uugucgaugu   6300

gcccucccug gcgcacugca uugugggcag aaugcugcuu gggcgcuuug ccgccaaguu   6360

ucaaucccau ccuggcuuuc uccuuggcuc cgcuaucggg ucugacccug augucuucug   6420
```

-continued

```
gaccgucaua ggggcucagc ucgagggaag aaagaacacg uaugacgugg acuacagugc   6480

cuuugacucu ucacacggca cuggcuccuu cgaggcucuc aucucucacu uuuucaccgu   6540

ggacaauggu uucagcccug cgcugggacc guaucucaga ucccuggcug ucucggugca   6600

cgcuuacggc gagcgucgca ucaagauuac cggaggccuc cccucugguu gugccgcgac   6660

cagccugcug aacacagugc ucaacaaugu gaucaucagg acugcucugg cauugaccua   6720

caaggaauuu gaauaugaca ugguugauau caucgccuac ggugacgacc uucugguugg   6780

uacggauuau gaucuggacu ucaaugaggu ggcgcggcgc gcugccaaac uggggguaua   6840

gaugacuccu gccaacaagg guucugucuu cccuccgacu ucccucucu ccgaugcugu   6900

uuuucuaaaa cgcaaauucg uccaaaacaa ugacggcuua uauaaaccag uuauggauuu   6960

aaagaauuug gaagccaugc ucuccuacuu caaaccagga acacuacucg agaagcugca   7020

aucuguuucu auguuggcuc aacauucugg aaaagaagaa uacgauagau ugaugcaccc   7080

cuucgcugac uaugguggccg uaccgaguca cgaguaccug caggcaagau ggagggccuu   7140

guucgacuga ccuggauagc cuaacgcgcu ucggugcugc cggcgauucu gggagaaccc   7200

agucggaaca gaaaagggga a                                             7221
```

```
<210> SEQ ID NO 2
<211> LENGTH: 6546
<212> TYPE: RNA
<213> ORGANISM: Senecavirus

<400> SEQUENCE: 2

augcagaacu cucauuuuuc uuucgauaca gccucuggca ccuuugaaga cguaaccgga     60

acaaaaguca agaucguuga acaccccaga ucggugaaca auggguguuua cgauucgucc    120

acucauuuag agauacugaa ccuacagggu gaaauugaaa uuuuaaaguc uuucaacgaa    180

uaccaaauuc gcgccgccaa acaacaacuu ggacuggaca ucguauacga acuacagggu    240

aauguucaga caaccucaaa gaaugauuuu gauucccgcg gcaauaaugg uaacaugacc    300

uucaauuacu acgcaaacac uuaccagaau ucaguagacu ucucgaccuc cucgucggcg    360

ucaggcgccg gacccgggaa cucccggggc ggauuagcgg gucuccucac aaauuucagu    420

ggaaucuuga acccucuugg cuaccucaaa gaucacaaua ccgaagaaau ggaaaacucu    480

gccgaucgag ucauaacgca aacggcgggc aacacugcca uaaacacgca aucaucacug    540

ggugugugu gugccuacgu ugaagacccg accaaaucug acccuccguc cagcagcaca    600

gaucaaccca ccaccacuuu uacugccauc gacaggugu acacuggacg ccucaauucu    660

uggacaaaag cuguaaaaac cuucucuuuu caggccguuc cgcucccugg agccuuccug    720

ucuagacagg gaggccucaa cggaggggcc uucacggcca cccuacauag acauuucuua    780

augaagugcg gguggcaggu gcagguucaa ugcaauuuga cgcaauucca ccaaggugcu    840

cuucuuguug ccauggucccc cgaaaccacc cuugauguca aaccugacgg caaggcaaag    900

agcuuacagg agcugaauga agagcagugg guggaaaugu cugacgacua ccggaccggg    960

aaaaacaugc cuuuucaguc ucuuggcaca uacuaucggc ccccuaacug gacuuggggc   1020

cccaauuuua uuaaccccua ucaaguaaca gucuucccac accaaauucu gaacgcgaga   1080

accucuaccu cgguagacau aagugucccg uacaucgggg agacuccuac acaauccuca   1140

gagacacaga acuccuggac ccuccuuguu auggugcuug ucccccugga cuacaaggag   1200

ggagccacaa cugacccaga aauuacauuu ucuguaaggc cuacaagucc cuacuucaau   1260

gggcuucgua accguuucaa gaccgggacg gacgaggaac aggggcccau ucccacagca   1320
```

-continued

```
cccagagaaa auucgcuuau guuucucuca accaucccug acgacacugu cccugcuuac   1380
gggaaugugc guaccccucc cgucaauuac cuccccggug aaauaaccga ccucuuacaa   1440
cuggcccgua uacccacucu cauggcguuu gggcgggcgu cugaacccga gccugccuca   1500
gacgcauaug ugcccuacgu ugccguuccu gcccaguucg acgacaagcc ucucaucucc   1560
uucccgauca cccuuucaga uccugucuac cagaacaccc ugguaggcgc caucaguucg   1620
aacuucgcca acuaccgggg guguauccaa aucacucuga cauuuugugg acccaugaug   1680
gcaagaggga aauuccugcu cucguauucu cccccaaaug gagcacaacc acagacccuu   1740
ucugaagcua ugcagugcac auacucuauu ugggauauag gcuugaacuc uaguuggacc   1800
uuugucaucc ccuacaucuc gcccagugau uaccgugaaa cucgggcuau uaccaacuca   1860
guuuauucug cugaugguug guuuagcuug cacaagcuga ccaaaauuac ucuaccaccu   1920
gacugcccac agagucccug uauucucuuu uucgccucug cuggugagga uuacacccuc   1980
cgucucccug uugauuguaa uccuuccuac guguuccacu ccaccgacaa cgccgagacu   2040
gggguuauug aggcagguaa cacugacacc gauuucucug gugaacuggc ggcuccuggc   2100
ucuaaccaua cuaaugucaa auuccuguuu gaccgaucuc gacuacugaa uguaauuaag   2160
guacuggaga aggacgccgu cuucccccgu ccuuucccca cagcaacagg ugcacagcag   2220
gacgaugguu acuuuugucu ucuaacaccc cgcccaacag ucgcuucccg acccgccacu   2280
cguuucggcc uguacgucaa cccgucugac aguggcguuc ucgcuaacac uucacuggau   2340
uucaauuuuu acaguuuggc cuguuucacu uacuuuagau cagaccuuga agucacggug   2400
gucucacugg agccagauuu ggaguucgcc gugggguggu uccccucugg cagugaguac   2460
caggcuucua gcuuugucua cgaccaacug cauguacccu accacuuuac ugggcgcacu   2520
ccccgcgcuu ucaccagcaa ggguggaaag guaucuuucg ugcucccuug gaacucuguc   2580
ucuuccgugc uucccgugcg cugggggggc gccuccaagc uuucuucugc cacgcggggu   2640
cugccggcuc augcugacug gggaccauu uacgccuuua ucccccgucc caacgagaag   2700
aaaagcaccg cuguaaagca cguggcggug uacguucggu acaagaacgc gcgugccugg   2760
ugccccagca ugcuucccuu ucgcagcuac aagcagaaga ugcugaugca aucaggcgac   2820
gucgagacca acccuggccc ugcuucugac aacccgaucu uggaguuucu ugaagcggaa   2880
aacgaucuag ucacucuggc cucucucugg aagaugguac acucuguuca acagaccugg   2940
agaaaguaug ugaagaacga caauuuuugg cccaacuugc ucagugagcu aguggggaa   3000
ggcuccaucg ccuuggccgc cacgcuaucu aaccaagcuu cagugaaagc ucucuugggc   3060
cugcauuuuc ucucucgagg gcucaauuac acagauuuuu acucuuuacu gauagagaaa   3120
ugcucuaguu ucuuuacugu agaaccgccu ccuccaccag cugaaaaucu gaugaccaag   3180
cccuccguga agucgaaauu ccgaaagcug uuuaagaugc aaggacccau ggacacaguc   3240
aaagacugga accaaauagc cgccggcuug aagaauuucc aauuuguucg ugaccuaguc   3300
aaagaggugg uugacuggcu ccaggccugg aucaauaaag agaaagccag cccuguccuc   3360
caguaccagc uggagaugaa gaagcucggg cccguggcuu uggcucauga ugccuucaug   3420
gccgguuccg ggcccccucu uggugacgac cagauugaau accuccagaa ccucaaaucu   3480
cuugcccuaa cacugggaaa gacuaauuug gcccaaaguc ucaccacuau gaucaacgcc   3540
aagcagagcu ccgcccaacg agucgaaccc guuguggugg uccucagagg caagccggga   3600
ugcggcaaaa gcuuggccuc cacguugauu gcccaggcug ugucuaagcg ucucuacggc   3660
```

```
ucacagagug uguauucucu ucccuccggac ccagacuucu ucgacggaua uaaaggacag   3720
uuuguaaccu ugauggacga ucugggacaa aacccggaug ggcaagauuu cuccaccuuu   3780
ugucagaugg ugucgaccgc ccaauuucuu cccaacaugg cggaccuugc agagaagggg   3840
cgucccuuca ccuccaaucu uaucauugca acuacaaacc ucccucacuu uagcccuguc   3900
accauugcug acccuucugc agucucucgg cguaucaacu acgaccugac ucuagaagua   3960
ucugaggccu acaagaagca cacgcggcug aauuucgacc uggcuuucag acgcacugac   4020
gcccccccca uuuauccuuu ugcugcccau gugcccuucg uggacguggc ugugcgcuuc   4080
aaaaaugguc aucaaagcuu caaucuccug gaguuggucg acucuauuug ugcagacauu   4140
cgggccaagc aacaaggugc ccgaaauaug cagacucugg uucuacagag cccuaacgag   4200
aacgacgaca cccccgucga cgaggcguug gguagaguuc ucacccccgc ugcggucgac   4260
gaggcgcuug ucgaccucgc uccagaugcc gacccgguug gccgcuuagc uauucucgcc   4320
aagcuagguc uugcccuagc ugcggucacu ccugguuuga uaaucuuggc agugggacuc   4380
uacaaguacu ucucuggcuc ugauacagac caagaagaaa cagaaaguga ggagccugcu   4440
aaagugccua ggagcgagaa ugcuuaugac ggcccaaaga aaaacuccaa gcccccugga   4500
gcgcucucuc uuauggaaau gcaacagccc aacguggaca ugggcuuuga ggcugcaguu   4560
gcuaagaaag uggucguccc cauuaccuuc augguuccca acagaccuuc cggacuuaca   4620
caguccgcuc uucuugugge cggccggacc uuccuaauca augagcauac augguccaac   4680
cccuccugga ccagcuucac aauccguggu gaggugcaca cucgugauga gcccuuccaa   4740
acgguucauu uuacucacca uggucuuccc acagaucuga ugaugguacg ucucggaccg   4800
ggcaacucuu ucccuaacaa ucuagauaag uuuggacuug accagaugcc ggcacguaac   4860
ucccgugugg uuggcguuuc ggcuaguuac gguaacuucu ucuucucugg gaacuuccuc   4920
ggguuuguug acuccaucac cucugaccaa ggaaccuaug cgagacuuuu cagguacagg   4980
gugacgacuu acaagggaug gugcgguucg gcccuggucu gugaggccgg uggugucgga   5040
cgcaucauug gcaugcauuc ugcuggugcc gcugguaucg gcgccgggac uuacaucuca   5100
aaauuaggac ugaucaaagc ccuuaaacac cucggugagc cucuggcuac aaugcaagga   5160
cugaugacug agcuagagcc uggagucacc guacauguac cccgaaaauc uaaauugaga   5220
aagacgaccg cacacgcggu guacaaaccg gaguuugaac cugcuguguu gucaaaauuu   5280
gaucccagac ugaacaagga uguugaccua gaugagguaa uuuggucuaa acacaccgcc   5340
aacgucccuu aucaaccucc uuuguucuac acauacaugu cagaguacgc ucaucggguu   5400
uucuccuuuu ugggaaaaga caaugacauu cugaccguca aagaagcaau ccugggcauc   5460
ccuggacuag acccuaugga uccccacaca gcuccggguu ugcccuacgc cauuagcggc   5520
cuucgacgua cugaucucgu cgauuuugcg aacggcacgg uagacccggc acuggccaug   5580
cagauccaga aauucuuaga cggugacuac ucugaucaug ucuuccaaac uuuucugaaa   5640
gaugaaauca gacccucaga gaagguccgg gcgggaaaaa cccgcauugu cgaugugccc   5700
ucccuggcgc acugcauugu gggcagaaug cugcuugggc gcuuugccgc caaguuucaa   5760
ucccauccug gcuuucuccu uggcuccgcu aucgggucug acccugaugu cuucuggacc   5820
gucauagggg cucagcucga gggaagaaag aacacguaug acguggacua cagugccuuu   5880
gacucuucac acggcacugg cuccuucgag gcucucaucu cucacuuuuu caccguggac   5940
aaugguuuca gcccugcgcu gggaccguau cucagauccc uggcugucuc ggugcacgcu   6000
uacggcgagc gucgcaucaa gauuaccgga ggccuccccu cugguugugc cgcgaccagc   6060
```

```
cugcugaaca cagugcucaa caaugugauc aucaggacug cucuggcauu gaccuacaag   6120

gaauuugaau augacauggu ugauaucauc gccuacggug acgaccuucu gguugguacg   6180

gauuaugauc uggacuucaa ugagguggcg cggcgcgcug ccaaacuggg guauaagaug   6240

acuccugcca acaaggguuc ugucuucccu ccgacuuccu cucucuccga ugcuguuuuu   6300

cuaaaacgca aauucgucca aaacaaugac ggcuuauaua aaccaguuau ggauuuaaag   6360

aauuuggaag ccaugcucuc cuacuucaaa ccaggaacac uacucgagaa gcugcaaucu   6420

guuucuaugu uggcucaaca uucuggaaaa gaagaauacg auagauugau gcaccccuuc   6480

gcugacuaug gugccguacc gagucacgag uaccugcagg caagauggag ggccuuguuc   6540

gacuga                                                              6546
```

<210> SEQ ID NO 3
<211> LENGTH: 2181
<212> TYPE: PRT
<213> ORGANISM: Senecavirus

<400> SEQUENCE: 3

```
Met Gln Asn Ser His Phe Ser Phe Asp Thr Ala Ser Gly Thr Phe Glu
1               5                   10                  15

Asp Val Thr Gly Thr Lys Val Lys Ile Val Glu His Pro Arg Ser Val
            20                  25                  30

Asn Asn Gly Val Tyr Asp Ser Ser Thr His Leu Glu Ile Leu Asn Leu
        35                  40                  45

Gln Gly Glu Ile Glu Ile Leu Lys Ser Phe Asn Glu Tyr Gln Ile Arg
    50                  55                  60

Ala Ala Lys Gln Gln Leu Gly Leu Asp Ile Val Tyr Glu Leu Gln Gly
65                  70                  75                  80

Asn Val Gln Thr Thr Ser Lys Asn Asp Phe Asp Ser Arg Gly Asn Asn
                85                  90                  95

Gly Asn Met Thr Phe Asn Tyr Tyr Ala Asn Thr Tyr Gln Asn Ser Val
            100                 105                 110

Asp Phe Ser Thr Ser Ser Ser Ala Ser Gly Ala Gly Pro Gly Asn Ser
        115                 120                 125

Arg Gly Gly Leu Ala Gly Leu Leu Thr Asn Phe Ser Gly Ile Leu Asn
    130                 135                 140

Pro Leu Gly Tyr Leu Lys Asp His Asn Thr Glu Glu Met Glu Asn Ser
145                 150                 155                 160

Ala Asp Arg Val Ile Thr Gln Thr Ala Gly Asn Thr Ala Ile Asn Thr
                165                 170                 175

Gln Ser Ser Leu Gly Val Leu Cys Ala Tyr Val Glu Asp Pro Thr Lys
            180                 185                 190

Ser Asp Pro Pro Ser Ser Ser Thr Asp Gln Pro Thr Thr Thr Phe Thr
        195                 200                 205

Ala Ile Asp Arg Trp Tyr Thr Gly Arg Leu Asn Ser Trp Thr Lys Ala
    210                 215                 220

Val Lys Thr Phe Ser Phe Gln Ala Val Pro Leu Pro Gly Ala Phe Leu
225                 230                 235                 240

Ser Arg Gln Gly Gly Leu Asn Gly Gly Ala Phe Thr Ala Thr Leu His
                245                 250                 255

Arg His Phe Leu Met Lys Cys Gly Trp Gln Val Gln Val Gln Cys Asn
            260                 265                 270

Leu Thr Gln Phe His Gln Gly Ala Leu Leu Val Ala Met Val Pro Glu
```

```
        275                 280                 285

Thr Thr Leu Asp Val Lys Pro Asp Gly Lys Ala Lys Ser Leu Gln Glu
    290                 295                 300

Leu Asn Glu Glu Gln Trp Val Glu Met Ser Asp Asp Tyr Arg Thr Gly
305                 310                 315                 320

Lys Asn Met Pro Phe Gln Ser Leu Gly Thr Tyr Tyr Arg Pro Pro Asn
                325                 330                 335

Trp Thr Trp Gly Pro Asn Phe Ile Asn Pro Tyr Gln Val Thr Val Phe
            340                 345                 350

Pro His Gln Ile Leu Asn Ala Arg Thr Ser Thr Ser Val Asp Ile Ser
        355                 360                 365

Val Pro Tyr Ile Gly Glu Thr Pro Thr Gln Ser Ser Glu Thr Gln Asn
    370                 375                 380

Ser Trp Thr Leu Leu Val Met Val Leu Val Pro Leu Asp Tyr Lys Glu
385                 390                 395                 400

Gly Ala Thr Thr Asp Pro Glu Ile Thr Phe Ser Val Arg Pro Thr Ser
                405                 410                 415

Pro Tyr Phe Asn Gly Leu Arg Asn Arg Phe Lys Thr Gly Thr Asp Glu
            420                 425                 430

Glu Gln Gly Pro Ile Pro Thr Ala Pro Arg Glu Asn Ser Leu Met Phe
        435                 440                 445

Leu Ser Thr Ile Pro Asp Asp Thr Val Pro Ala Tyr Gly Asn Val Arg
    450                 455                 460

Thr Pro Pro Val Asn Tyr Leu Pro Gly Glu Ile Thr Asp Leu Leu Gln
465                 470                 475                 480

Leu Ala Arg Ile Pro Thr Leu Met Ala Phe Gly Arg Ala Ser Glu Pro
                485                 490                 495

Glu Pro Ala Ser Asp Ala Tyr Val Pro Tyr Val Ala Val Pro Ala Gln
            500                 505                 510

Phe Asp Asp Lys Pro Leu Ile Ser Phe Pro Ile Thr Leu Ser Asp Pro
        515                 520                 525

Val Tyr Gln Asn Thr Leu Val Gly Ala Ile Ser Ser Asn Phe Ala Asn
    530                 535                 540

Tyr Arg Gly Cys Ile Gln Ile Thr Leu Thr Phe Cys Gly Pro Met Met
545                 550                 555                 560

Ala Arg Gly Lys Phe Leu Leu Ser Tyr Ser Pro Pro Asn Gly Ala Gln
                565                 570                 575

Pro Gln Thr Leu Ser Glu Ala Met Gln Cys Thr Tyr Ser Ile Trp Asp
            580                 585                 590

Ile Gly Leu Asn Ser Ser Trp Thr Phe Val Ile Pro Tyr Ile Ser Pro
        595                 600                 605

Ser Asp Tyr Arg Glu Thr Arg Ala Ile Thr Asn Ser Val Tyr Ser Ala
    610                 615                 620

Asp Gly Trp Phe Ser Leu His Lys Leu Thr Lys Ile Thr Leu Pro Pro
625                 630                 635                 640

Asp Cys Pro Gln Ser Pro Cys Ile Leu Phe Phe Ala Ser Ala Gly Glu
                645                 650                 655

Asp Tyr Thr Leu Arg Leu Pro Val Asp Cys Asn Pro Ser Tyr Val Phe
            660                 665                 670

His Ser Thr Asp Asn Ala Glu Thr Gly Val Ile Glu Ala Gly Asn Thr
        675                 680                 685

Asp Thr Asp Phe Ser Gly Glu Leu Ala Ala Pro Gly Ser Asn His Thr
    690                 695                 700
```

-continued

```
Asn Val Lys Phe Leu Phe Asp Arg Ser Arg Leu Leu Asn Val Ile Lys
705                 710                 715                 720

Val Leu Glu Lys Asp Ala Val Phe Pro Arg Pro Phe Pro Thr Ala Thr
                725                 730                 735

Gly Ala Gln Gln Asp Asp Gly Tyr Phe Cys Leu Leu Thr Pro Arg Pro
            740                 745                 750

Thr Val Ala Ser Arg Pro Ala Thr Arg Phe Gly Leu Tyr Val Asn Pro
        755                 760                 765

Ser Asp Ser Gly Val Leu Ala Asn Thr Ser Leu Asp Phe Asn Phe Tyr
    770                 775                 780

Ser Leu Ala Cys Phe Thr Tyr Phe Arg Ser Asp Leu Glu Val Thr Val
785                 790                 795                 800

Val Ser Leu Glu Pro Asp Leu Glu Phe Ala Val Gly Trp Phe Pro Ser
                805                 810                 815

Gly Ser Glu Tyr Gln Ala Ser Ser Phe Val Tyr Asp Gln Leu His Val
            820                 825                 830

Pro Tyr His Phe Thr Gly Arg Thr Pro Arg Ala Phe Thr Ser Lys Gly
        835                 840                 845

Gly Lys Val Ser Phe Val Leu Pro Trp Asn Ser Val Ser Ser Val Leu
    850                 855                 860

Pro Val Arg Trp Gly Gly Ala Ser Lys Leu Ser Ser Ala Thr Arg Gly
865                 870                 875                 880

Leu Pro Ala His Ala Asp Trp Gly Thr Ile Tyr Ala Phe Ile Pro Arg
                885                 890                 895

Pro Asn Glu Lys Lys Ser Thr Ala Val Lys His Val Ala Val Tyr Val
            900                 905                 910

Arg Tyr Lys Asn Ala Arg Ala Trp Cys Pro Ser Met Leu Pro Phe Arg
        915                 920                 925

Ser Tyr Lys Gln Lys Met Leu Met Gln Ser Gly Asp Val Glu Thr Asn
    930                 935                 940

Pro Gly Pro Ala Ser Asp Asn Pro Ile Leu Glu Phe Leu Glu Ala Glu
945                 950                 955                 960

Asn Asp Leu Val Thr Leu Ala Ser Leu Trp Lys Met Val His Ser Val
                965                 970                 975

Gln Gln Thr Trp Arg Lys Tyr Val Lys Asn Asp Asn Phe Trp Pro Asn
            980                 985                 990

Leu Leu Ser Glu Leu Val Gly Glu  Gly Ser Ile Ala Leu  Ala Ala Thr
        995                 1000                1005

Leu Ser  Asn Gln Ala Ser Val  Lys Ala Leu Leu Gly  Leu His Phe
    1010                 1015                 1020

Leu Ser  Arg Gly Leu Asn Tyr  Thr Asp Phe Tyr Ser  Leu Leu Ile
    1025                 1030                 1035

Glu Lys  Cys Ser Ser Phe Phe  Thr Val Glu Pro Pro  Pro Pro Pro
    1040                 1045                 1050

Ala Glu  Asn Leu Met Thr Lys  Pro Ser Val Lys Ser  Lys Phe Arg
    1055                 1060                 1065

Lys Leu  Phe Lys Met Gln Gly  Pro Met Asp Thr Val  Lys Asp Trp
    1070                 1075                 1080

Asn Gln  Ile Ala Ala Gly Leu  Lys Asn Phe Gln Phe  Val Arg Asp
    1085                 1090                 1095

Leu Val  Lys Glu Val Val Asp  Trp Leu Gln Ala Trp  Ile Asn Lys
    1100                 1105                 1110
```

```
Glu Lys  Ala Ser Pro Val Leu  Gln Tyr Gln Leu Glu  Met Lys Lys
    1115                 1120                 1125

Leu Gly  Pro Val Ala Leu Ala  His Asp Ala Phe Met  Ala Gly Ser
    1130                 1135                 1140

Gly Pro  Pro Leu Gly Asp Asp  Gln Ile Glu Tyr Leu  Gln Asn Leu
    1145                 1150                 1155

Lys Ser  Leu Ala Leu Thr Leu  Gly Lys Thr Asn Leu  Ala Gln Ser
    1160                 1165                 1170

Leu Thr  Thr Met Ile Asn Ala  Lys Gln Ser Ser Ala  Gln Arg Val
    1175                 1180                 1185

Glu Pro  Val Val Val Val Leu  Arg Gly Lys Pro Gly  Cys Gly Lys
    1190                 1195                 1200

Ser Leu  Ala Ser Thr Leu Ile  Ala Gln Ala Val Ser  Lys Arg Leu
    1205                 1210                 1215

Tyr Gly  Ser Gln Ser Val Tyr  Ser Leu Pro Pro Asp  Pro Asp Phe
    1220                 1225                 1230

Phe Asp  Gly Tyr Lys Gly Gln  Phe Val Thr Leu Met  Asp Asp Leu
    1235                 1240                 1245

Gly Gln  Asn Pro Asp Gly Gln  Asp Phe Ser Thr Phe  Cys Gln Met
    1250                 1255                 1260

Val Ser  Thr Ala Gln Phe Leu  Pro Asn Met Ala Asp  Leu Ala Glu
    1265                 1270                 1275

Lys Gly  Arg Pro Phe Thr Ser  Asn Leu Ile Ile Ala  Thr Thr Asn
    1280                 1285                 1290

Leu Pro  His Phe Ser Pro Val  Thr Ile Ala Asp Pro  Ser Ala Val
    1295                 1300                 1305

Ser Arg  Arg Ile Asn Tyr Asp  Leu Thr Leu Glu Val  Ser Glu Ala
    1310                 1315                 1320

Tyr Lys  Lys His Thr Arg Leu  Asn Phe Asp Leu Ala  Phe Arg Arg
    1325                 1330                 1335

Thr Asp  Ala Pro Pro Ile Tyr  Pro Phe Ala Ala His  Val Pro Phe
    1340                 1345                 1350

Val Asp  Val Ala Val Arg Phe  Lys Asn Gly His Gln  Ser Phe Asn
    1355                 1360                 1365

Leu Leu  Glu Leu Val Asp Ser  Ile Cys Ala Asp Ile  Arg Ala Lys
    1370                 1375                 1380

Gln Gln  Gly Ala Arg Asn Met  Gln Thr Leu Val Leu  Gln Ser Pro
    1385                 1390                 1395

Asn Glu  Asn Asp Asp Thr Pro  Val Asp Glu Ala Leu  Gly Arg Val
    1400                 1405                 1410

Leu Thr  Pro Ala Ala Val Asp  Glu Ala Leu Val Asp  Leu Ala Pro
    1415                 1420                 1425

Asp Ala  Asp Pro Val Gly Arg  Leu Ala Ile Leu Ala  Lys Leu Gly
    1430                 1435                 1440

Leu Ala  Leu Ala Ala Val Thr  Pro Gly Leu Ile Ile  Leu Ala Val
    1445                 1450                 1455

Gly Leu  Tyr Lys Tyr Phe Ser  Gly Ser Asp Thr Asp  Gln Glu Glu
    1460                 1465                 1470

Thr Glu  Ser Glu Glu Pro Ala  Lys Val Pro Arg Ser  Glu Asn Ala
    1475                 1480                 1485

Tyr Asp  Gly Pro Lys Lys Asn  Ser Lys Pro Pro Gly  Ala Leu Ser
    1490                 1495                 1500

Leu Met  Glu Met Gln Gln Pro  Asn Val Asp Met Gly  Phe Glu Ala
```

```
    1505                1510                1515

Ala Val  Ala Lys Lys Val Val  Val Pro Ile Thr Phe  Met Val Pro
    1520                1525                1530

Asn Arg  Pro Ser Gly Leu Thr  Gln Ser Ala Leu Leu  Val Ala Gly
    1535                1540                1545

Arg Thr  Phe Leu Ile Asn Glu  His Thr Trp Ser Asn  Pro Ser Trp
    1550                1555                1560

Thr Ser  Phe Thr Ile Arg Gly  Glu Val His Thr Arg  Asp Glu Pro
    1565                1570                1575

Phe Gln  Thr Val His Phe Thr  His His Gly Leu Pro  Thr Asp Leu
    1580                1585                1590

Met Met  Val Arg Leu Gly Pro  Gly Asn Ser Phe Pro  Asn Asn Leu
    1595                1600                1605

Asp Lys  Phe Gly Leu Asp Gln  Met Pro Ala Arg Asn  Ser Arg Val
    1610                1615                1620

Val Gly  Val Ser Ala Ser Tyr  Gly Asn Phe Phe Phe  Ser Gly Asn
    1625                1630                1635

Phe Leu  Gly Phe Val Asp Ser  Ile Thr Ser Asp Gln  Gly Thr Tyr
    1640                1645                1650

Ala Arg  Leu Phe Arg Tyr Arg  Val Thr Thr Tyr Lys  Gly Trp Cys
    1655                1660                1665

Gly Ser  Ala Leu Val Cys Glu  Ala Gly Gly Val Arg  Arg Ile Ile
    1670                1675                1680

Gly Met  His Ser Ala Gly Ala  Ala Gly Ile Gly Ala  Gly Thr Tyr
    1685                1690                1695

Ile Ser  Lys Leu Gly Leu Ile  Lys Ala Leu Lys His  Leu Gly Glu
    1700                1705                1710

Pro Leu  Ala Thr Met Gln Gly  Leu Met Thr Glu Leu  Glu Pro Gly
    1715                1720                1725

Val Thr  Val His Val Pro Arg  Lys Ser Lys Leu Arg  Lys Thr Thr
    1730                1735                1740

Ala His  Ala Val Tyr Lys Pro  Glu Phe Glu Pro Ala  Val Leu Ser
    1745                1750                1755

Lys Phe  Asp Pro Arg Leu Asn  Lys Asp Val Asp Leu  Asp Glu Val
    1760                1765                1770

Ile Trp  Ser Lys His Thr Ala  Asn Val Pro Tyr Gln  Pro Pro Leu
    1775                1780                1785

Phe Tyr  Thr Tyr Met Ser Glu  Tyr Ala His Arg Val  Phe Ser Phe
    1790                1795                1800

Leu Gly  Lys Asp Asn Asp Ile  Leu Thr Val Lys Glu  Ala Ile Leu
    1805                1810                1815

Gly Ile  Pro Gly Leu Asp Pro  Met Asp Pro His Thr  Ala Pro Gly
    1820                1825                1830

Leu Pro  Tyr Ala Ile Ser Gly  Leu Arg Arg Thr Asp  Leu Val Asp
    1835                1840                1845

Phe Ala  Asn Gly Thr Val Asp  Pro Ala Leu Ala Met  Gln Ile Gln
    1850                1855                1860

Lys Phe  Leu Asp Gly Asp Tyr  Ser Asp His Val Phe  Gln Thr Phe
    1865                1870                1875

Leu Lys  Asp Glu Ile Arg Pro  Ser Glu Lys Val Arg  Ala Gly Lys
    1880                1885                1890

Thr Arg  Ile Val Asp Val Pro  Ser Leu Ala His Cys  Ile Val Gly
    1895                1900                1905
```

```
Arg Met  Leu Leu Gly Arg Phe  Ala Ala Lys Phe Gln  Ser His Pro
    1910                 1915                 1920

Gly Phe  Leu Leu Gly Ser Ala  Ile Gly Ser Asp Pro  Asp Val Phe
    1925                 1930                 1935

Trp Thr  Val Ile Gly Ala Gln  Leu Glu Gly Arg Lys  Asn Thr Tyr
    1940                 1945                 1950

Asp Val  Asp Tyr Ser Ala Phe  Asp Ser Ser His Gly  Thr Gly Ser
    1955                 1960                 1965

Phe Glu  Ala Leu Ile Ser His  Phe Phe Thr Val Asp  Asn Gly Phe
    1970                 1975                 1980

Ser Pro  Ala Leu Gly Pro Tyr  Leu Arg Ser Leu Ala  Val Ser Val
    1985                 1990                 1995

His Ala  Tyr Gly Glu Arg Arg  Ile Lys Ile Thr Gly  Gly Leu Pro
    2000                 2005                 2010

Ser Gly  Cys Ala Ala Thr Ser  Leu Leu Asn Thr Val  Leu Asn Asn
    2015                 2020                 2025

Val Ile  Ile Arg Thr Ala Leu  Ala Leu Thr Tyr Lys  Glu Phe Glu
    2030                 2035                 2040

Tyr Asp  Met Val Asp Ile Ile  Ala Tyr Gly Asp Asp  Leu Leu Val
    2045                 2050                 2055

Gly Thr  Asp Tyr Asp Leu Asp  Phe Asn Glu Val Ala  Arg Arg Ala
    2060                 2065                 2070

Ala Lys  Leu Gly Tyr Lys Met  Thr Pro Ala Asn Lys  Gly Ser Val
    2075                 2080                 2085

Phe Pro  Pro Thr Ser Ser Leu  Ser Asp Ala Val Phe  Leu Lys Arg
    2090                 2095                 2100

Lys Phe  Val Gln Asn Asn Asp  Gly Leu Tyr Lys Pro  Val Met Asp
    2105                 2110                 2115

Leu Lys  Asn Leu Glu Ala Met  Leu Ser Tyr Phe Lys  Pro Gly Thr
    2120                 2125                 2130

Leu Leu  Glu Lys Leu Gln Ser  Val Ser Met Leu Ala  Gln His Ser
    2135                 2140                 2145

Gly Lys  Glu Glu Tyr Asp Arg  Leu Met His Pro Phe  Ala Asp Tyr
    2150                 2155                 2160

Gly Ala  Val Pro Ser His Glu  Tyr Leu Gln Ala Arg  Trp Arg Ala
    2165                 2170                 2175

Leu Phe  Asp
    2180
```

<210> SEQ ID NO 4
<211> LENGTH: 7300
<212> TYPE: RNA
<213> ORGANISM: Senecavirus

<400> SEQUENCE: 4

```
uuugaaaugg ggggcugggc ccucaugccc aguccuuccu uuccccuucc gggggguaaa      60

ccggcugugu uugcuagagg cacagaggag caacauccaa ccugcucuug uggggaacgg     120

ugcggcucca auuccugcgu cgccaaaggu guuagcgcac ccaaacggcg caucuaccaa     180

ugcuauuggu guggucugcg aguucuagcc uacucguuuc uccccuaucc acucacucac     240

gcacaaaaag uguguuguaa cuacaagacu uagcccucgc acgagaugug cgauaaccgc     300

aagauugacu caagcgcgga aagcgcugua accacaugcu guuagucccu uuauggcugc     360

gagauggcua uccaccucgg aucacugaac uggagcucga cccuccuuag uaagggaacc     420
```

```
gagaggccuu cuugcaacaa gcuccgacac agaguccacg ugauugcuac caccaugagu    480
acaugguucu ccccucucga cccaggacuu cuuuuugaau auccacggcu cgauccagag    540
gguggggcau gaucccccua gcauagcgag cuacagcggg aacuguagcu aggccuuagc    600
gugcuuugga uacugccuga uagggcgacg gccuagucgu gucgguucua uagguagcac    660
auacaaauau gcagaacucu cauuuuucuu ucgauacagc cucuggcacc uuugaagacg    720
uaaccggaac aaaagucaag aucguugaau acccuagauc ggugaacaau ggugguuuacg    780
auucguccac ucauuuagag auacugaacc uacagggguga aauugaaauu uuaaggucuu    840
ucaaugaaua ccaaauucgc gccgccaaac aacaacuugg acuggacauc guauaugaac    900
uacaggguaa uguucagaca accucaaaga augauuuuga uucccgcggc aauaauggua    960
acaugaccuu caauuacuac gcaaacacuu aucagaauuc aguagacuuc ucgaccuccu   1020
cgucggcguc aggcgccgga cccgggaacu cccggggcgg auuagcgggu cuccucacaa   1080
auuucagugg aaucuugaac ccucuuggcu accucaaaga ccacaauacc gaagaaaugg   1140
aaaacucugc ugaucgaguc auaacacaaa cggcgggcaa cacugccaua aacacgcaau   1200
caucacuggg ugugauugugu gccuacguug aagacccgac caaaucugac ccuccgucca   1260
gcagcacaga ucaacccacc accacuuuua cugccaucga cagguguggac acuggacgcc   1320
ucaauucuug gacaaaagcu guaaaaaccu ucucuuuuca ggccgucccg cucccuggag   1380
ccuuccuguc uagacaggga ggccucaaug gaggggccuu cacggcuacc cuacauagac   1440
auuucuuaau gaagugcggg uggcaggugc agguccaaug caauuugaca caauuccacc   1500
aaggugcucu ucuuguugcc augguccccg aaaccacccu ugaugucaag cccgacggca   1560
aggcaaagag ccuacaggag cugaaugaag agcagugggu agaaaugucu gacgauuacc   1620
ggaccgggaa aaacaugccu uuucagucuc uuggcacaua cuaucggccc ccuaacugga   1680
cuuggggccc uaauuucauc aaccccuauc aaguaacagu uuucccacac caaauucuga   1740
acgcgagaac cucuaccucg guagacauaa gugucccaua caucggggag acuccuacac   1800
aauccucaga gacacagaac uccuggaccc uccucguuau ggugcuuguc ccccuggacu   1860
acaaggaggg agccacaacu gacccagaaa uuacauuuuc cguaaggccu acaaguccuu   1920
acuucaaugg gcuucguaac cgcuacaaga ccgggacgga cgaggaacag gggcccauuc   1980
ccacagcacc cagagaaaau ucgcuuaugu uucucucgac caucccugac gacacugucc   2040
cugcuuacgg gaaugugcgu accccucccg ucaauuaccu uccuggugaa auaaccgacc   2100
ucuuacaacu ggcccguaua cccacucuca uggcguuugg gcgggugccu gaaccugaac   2160
cugccucaga cgcuuaugug cccuacguug ccguucccac ccaguucgau gacaagccuc   2220
ucaucuccuu cccgaucacc cuuucagauc cugucuacca gaauacucug guaggcgcca   2280
ucaguucaaa uuucgccaac uaccgggggu guauccaaau cacucugaca uuuuguggac   2340
cuaugauggc aagagggaaa uuccuacucu cguauucucc cccaaaugga acacaaccac   2400
agacccuuuc ugaagccaug cagugcacau auucuauuug ggauauaggc uuaaacucua   2460
guuggaccuu ugucaucccc uacaucucgc ccagugacua ccgugaaacu cgggccauua   2520
ccaauucggu uuauucugcu gauggcuggu uuagccugca caagcugacc aaaauuacuc   2580
uaccaccuga uugcccacag agccccugua uucucuuuuu cgccucugcu ggugaggauu   2640
acacccuccg ucuccccguu gauuguaauc cuucuuaugu guuccacucc accgacaacg   2700
ccgagacugg gguuauugag gcggguaaca cugacaccga uuucucuggu gaauuggcgg   2760
```

-continued

```
cuccuggcuc uaaccacacu aaugucaagu uccuguuuga ccgaucucga uuacugaaug   2820
uaauuaaggu acuggagaag gacgccgucu ucccccgccc uuuccccaca gcaacuggua   2880
cacaacagga cgaugguuac uuuugucuuc uaacaccccg cccaacaguc gccucccgac   2940
ccgccacucg uuucggccug uacgucaguc cgucugacag uggcguucuc gccaacacuu   3000
cacuggauuu caauuuuuac agcuuggccu guuucacuua cuuuagauca gaccuugaag   3060
ucacggugcu cucacuggag ccagaucugg aauucgcugu agggugguuc cccucuggca   3120
gugaguacca ggcuuccagc uuugucuacg accaacugca uguacccuac cacuuuacug   3180
ggcgcacucc ccgcgcuuuc gccagcaagg gugggaaggu aucuuucgug cucccuugga   3240
acucugucuc auccgugcuu cccgugcgcu gggggggcgc uuccaagcuu ucuucugcca   3300
cgcggggucu gccggcucau gcugacuggg ggacuauuua cgccuuuauc ccccguccca   3360
acgagaagaa aagcaccgcu guaaagcaug uggccgugua cguucgguac aagaacgcgc   3420
gugccuggug ccccagcaug cuucccuuuc gcagcuacaa gcagaagaug cugaugcaau   3480
caggcgacgu cgagaccaac ccaggcccug cuucugacaa cccaaucuug gaauuucuug   3540
aagcagaaaa ugaucuaguc acucuggccu cucucuggaa gaugguacac ucuguucaac   3600
agaccuggag aaaguaugug aagaacgaca auuuuuggcc caauuuacuc agugaguuag   3660
ugggggaagg cuccaucgcc uuggccgcca cgcugucuaa ccaagcuuca guaaaagcuc   3720
ucuugggccu gcauuuucuc ucucgagggc ucaauuacac agacuuuuac ucuuuacuga   3780
uagagaaaug cucuaguuuc uuuacuguag aaccgccucc uccaccagcu gaaaaucuga   3840
ugaccaagcc cuccgugaag ucgaaauucc gaaagcuguu uaagaugcaa ggacccaugg   3900
acaaagucaa agacuggaac caaauagccg ccggcuugaa gaauuuucaa uuuguucgug   3960
accuagucaa agaggugguc gacuggcucc aggccuggau caacaaagag aaagccagcc   4020
cuguccucca guaccaguug gagaugaaga agcucgggcc cguggcuuug gcucaugaug   4080
ccuucauggc cgguuccggg cccccucuua gugacgacca gauugaauac cuccaaaacc   4140
ucaaaucucu ugcccuaaca cuggggaaga cuaauuuggc ccaaagucuc accacuauga   4200
ucaaugccaa gcaaaguucc gcccaacgag ucgaacccgu uguggugguc cucagaggca   4260
agccgggaug cggcaagagc uuggccucca cguugauugc ccaggcugug uccaagcguc   4320
ucuacggcuc acaaagugug uauucucuuc cuccggaccc agacuucuuc gacggauaca   4380
aaggacaguu uguaaccuug auggaugauu ugggacaaaa cccggauggg caagauuucu   4440
ccaccuuuug ucagauggug ucgaccgccc aauuucuucc caacauggcg gaccuugcag   4500
agaaggggcg ccccuuuacc uccaaucuua ucauugcaac uacaaaccuc ccccacuuca   4560
gcccugucac cauugcugau ccuucugcgg ucucucgucg gaucaacuac gacuugacuc   4620
uagaaguauc ugaggccuac aaaaagcaca cacggcugaa uuuugaccug gcuuucaggc   4680
gcacagacgc cccccccauu uauccuuuug cugcccaugu gccuuucgug gacguggcug   4740
ugcgcuucaa aaauggccac cagagcuuca aucuccuaga guuggucgac ucuauuugug   4800
cagacauucg agccaagcaa caaggugccc gaaauaugca gacucuaguu cuacagagcc   4860
cuaacgagaa ugaugacacc cccgucgacg aggcgcuggg uagaguucuc acucccgcug   4920
cggucgacga ggcgcuuguc gaccucgcuc aagaggccga uccgguuggc cgcuuggcua   4980
uucuugccaa acuagggcuu gcucuagcug cggucacccc cggcuugaua aucuuggcag   5040
ugggacucua uagguacuuc ucuggcucug augcagacca agaagaaacg gaaagugagg   5100
aaccugcuaa agcgccuagg agcgagaaug cuuaugacgg cccgaagaaa aacucuaagc   5160
```

ccccuggagc gcucucucuu auggaaaugc aacagcccaa cguggacaug ggcuuugagg 5220
cugcggucgc uaagaaagug gucgucccca uuacauucau gguucccaac agaccuucug 5280
gacuuacaca guccgcccuu cuuguggccg gccggaccuu ccuaauuaau gagcauacau 5340
gguccaaccc cuccuggacc aguuucacaa uccguggùga ggugcacacu cgugaugagc 5400
cuuuccaaac gguucauuuu acucaccaug guguucccac agaccugaug augguacguc 5460
ucggaccggg caacucuuuc ccuaacaauc uagacaaguu uggacuugac cagaugccgg 5520
cacguaacuc ccguguggu ggcguuucgg cuaguuacgg uaauuucuuc uucucuggga 5580
auuuccuugg guuuguugac uccaucaccu cugaacaagg aacuuaugca agacuuuuua 5640
gguacagggu gaccaccuac aagggauggu gcgguucggc ccuggucugu gaggccggug 5700
guguccggcg caucauuggc cugcauucug cuggugccgc ugguaucggc gccgggaccu 5760
acaucucaaa auuaggacug aucaaagccc uuaaacaccu cggugaaccu cuggcuacaa 5820
ugcaaggacu gaugacugag cuagagccug gagucaccgu gcauguaccc cggaaaucua 5880
aauugagaaa gacgaccgca cacgcggugu acaaaccgga guuugaaccu gcuguguugu 5940
caaaauuuga ucccagacug aacaaggaug uugaccuaga ugagguaauu uggucuaaac 6000
acacugccaa cgucccuuau caaccuccuu uguucuacac auacauguca gaguacgcuc 6060
aucggguuuu cuccuuuuug ggaaaagaca augacauucu gaccguuaaa gaagcaaucc 6120
ugggcauccc uggacuagac ccuauggauc cccacacagc ucggguucug cccuacgcca 6180
uuagcggccu ucgacguacu gaucucgucg auuuugugaa cgguacggua gacgcagcac 6240
uggccaugca aauccagaaa uucuuagacg gugacuacuc ugaucauguc uuccaaacuu 6300
uucugaaaga ugaaaucaga cccucagaga agguccgagc gggaaaaacc cgcauugucg 6360
augugcccuc ccuggcacac ugcauugugg gcagaaugcu gcucgggcgu uucgccgcca 6420
aguuucaauc ccaucccggc uuucuucuug guucugcuau cggguccgac ccugaugucu 6480
ucuggaccgu cauaggggcu cagcucgagg gaagaaagaa cacguacgac guggacuaca 6540
gugccuuuga cucuucacac ggcacuggcu ccuucgaggc ucucaucucu cacuuuuuca 6600
ccguugacaa ugguuuuagc ccugcgcugg gaccguaucu cagaucccug gcugucucgg 6660
ugcacgcuua cggcgagcgu cgcaucaaga uuaccggagg ccuucccucu gguugugccg 6720
cgaccagccu ucugaucaca gugcucaaca augugaucau caggacugcu cuggcauuga 6780
cuuacaagga auuugaguau gacaugguug auaucaucgc cuacggugac gaccuuuugg 6840
uugguacgga uuaugaucug gacuucaaug aaguggcgcg gcgcgcugcc aaacuggggu 6900
auaagaugac uccugccaac aaggguuccg ucuucccucc gacuuccucu cucuccgaug 6960
cuguuuuucu aaaacgcaaa uucguccaaa acaaugacgg cuuauauaaa ccaguuaugg 7020
auuuaaagaa uuuggaagcc augcucuccu acuucaaacc aggaacacua cucgagaagc 7080
ugcaaucugu uucuauguug gcucaacauu cuggaaaaga agaauaugau agauugaugc 7140
gccccuucgc ugacuacggu gccguaccga gucacgagua ccugcaggca agauggaggg 7200
ccuuguucga uugaccuaga uagcccaacg cgcuucggug ccgccggcga uucugggaga 7260
acucagucgg aacagaaaag ggaaaaaaaa aaaaaaaaaa 7300

<210> SEQ ID NO 5
<211> LENGTH: 7286
<212> TYPE: RNA
<213> ORGANISM: Senecavirus

<400> SEQUENCE: 5

```
uuugaaaugg ggggcugggc ccucaugccc aguccuuccu uuccccuucc ggggggguaaa     60
ccggcugugu uugcuagagg cacagaggag caacauccaa ccugcucuug uggggaacgg    120
ugcggcucca auuccugcgu cgccaaaggu guuagcgcac ccaaacggcg caucuaccaa    180
ugcuauuggu guggucugcg aguucuagcc uacucguuuc uccccuaucc acucacucac    240
gcacaaaaag uguguuguaa cuacaagacu uagcccucgc acgagaugug cgauaaccgc    300
aagauugacu caagcgcgga aagcgcugua accacaugcu guuagucccu uuauggcugc    360
gagauggcua uccaccucgg aucacugaac uggagcucga cccuccuuag uaagggaacc    420
gagaggccuu cuugcaacaa gcuccgacac agaguccacg ugauugcuac caccaugagu    480
acaugguucu ccccucucga cccaggacuu cuuuuugaau auccacggcu cgauccagag    540
ggugggggcau gaucccccua gcauagcgag cuacagcggg aacuguagcu aggccuuagc    600
gugcuuugga uacugccuga uagggcgacg gccuagucgu gucgguucua uagguagcac    660
auacaaauau gcagaacucu cauuuuucuu ucgauacagc cucuggcacc uuugaagacg    720
uaaccggaac aaaagucaag aucguugaau acccuagauc ggugaacaau gguguuuacg    780
auucguccac ucauuuagag auacugaacc uacaggguga aauugaaauu uuaaggucuu    840
ucaaugaaua ccaaauucgc gccgccaaac aacaacuugg acuggacauc guauaugaac    900
uacaggguaa uguucagaca accucaaaga augauuuuga uucccgcggc aauaaauggua    960
acaugaccuu caauuacuac gcaaacacuu aucagaauuc aguagacuuc ucgaccuccu   1020
cgucggcguc aggcgccgga cccgggaacu cccggggcgg auuagcgggu cuccucacaa   1080
auuucagugg aaucuugaac ccucuuggcu accucaaaga ccacaauacc gaagaaaugg   1140
aaaacucugc ugaucgaguc auaacacaaa cggcgggcaa cacugccaua aacacgcaau   1200
caucacuggg uguguugugu gccuacguug aagacccgac caaaucugac ccuccgucca   1260
gcagcacaga ucaacccacc accacuuuua cugccaucga cagguggauac acuggacgcc  1320
ucaauucuug gacaaaagcu guaaaaaccu ucucuuuuca ggccgucccg cucccuggag   1380
ccuuccuguc uagacaggga ggccucaaug gaggggccuu cacggcuacc cuacauagac   1440
auuucuuaau gaagugcggg uggcaggugc agguccaaug caauuugaca caauuccacc   1500
aaggugcucu ucuuguugcc augguccccg aaaccacccu ugaugucaag cccgacggca   1560
aggcaaagag ccuacaggag cugaaugaag agcagugggu agaaaugucu gacgauuacc   1620
ggaccgggaa aacaugccu uuucagucuc uuggcacaua cuaucggccc ccuaacugga    1680
cuuggggccc uaauuucauc aaccccuauc aaguaacagu uuucccacac caaauucuga   1740
acgcgagaac cucuaccucg guagacauaa gugucccaua caucggggag acuccuacac   1800
aauccucaga gacacagaac uccuggaccc uccucguuau ggugcuuguc ccccuggacu   1860
acaaggaggg agccacaacu gacccagaaa uuacauuuuc cguaaggccu acaaguccuu   1920
acuucaaugg gcuucguaac cgcuacacga ccgggacgga cgaggaacag gggcccauuc   1980
ccacagcacc cagagaaaau ucgcuuaugu uucucucgac caucccugac gacacugucc   2040
cugcuuacgg gaaugugcgu accccucccg ucaauuaccu uccuggugaa auaaccgacc   2100
ucuuacaacu ggcccguaua cccacucuca uggcguuugg gcgggugccu gaaccugaac   2160
cugccucaga cgcuuaugug cccuacguug ccguucccac ccaguucgau gacaagccuc   2220
ucaucuccuu cccgaucacc cuuucagauc cugucuacca gaauacucug guaggcgcca   2280
ucaguucaaa uuucgccaac uaccgggggu guauccaaau cacucugaca uuuuguggac   2340
```

```
cuaugauggc aagagggaaa uuccuacucu cguauucucc cccaaaugga acacaaccac   2400
agacccuuuc ugaagccaug cagugcacau auucuauuug ggauauaggc uuaaacucua   2460
guuggaccuu ugucaucccc uacaucucgc ccagugacua ccgugaaacu cgggccauua   2520
ccaauucggu uuauucugcu gauggcuggu uuagccugca caagcugacc aaaauuacuc   2580
uaccaccuga uugcccacag agccccugua uucucuuuuu cgccucugcu ggugaggauu   2640
acacccuccg ucuccccguu gauuguaauc cuucuuaugu guuccacucc accgacaacg   2700
ccgagacugg gguuauugag gcggguaaca cugacaccga uuucucuggu gaauuggcgg   2760
cuccuggcuc uaaccacacu aaugucaagu uccuguuuga ccgaucucga uuacugaaug   2820
uaauuaaggu acuggagaag gacgccgucu ucccccgccc uuuccccaca gcaacuggua   2880
cacaacagga cgaugguuac uuuugucuuc uaacaccccg cccaacaguc gccucccgac   2940
ccgccacucg uuucggccug uacgucaguc cgucugacag uggcguucuc gccaacacuu   3000
cacuggauuu caauuuuuac agcuuggccu guuucacuua cuuuagauca gaccuugaag   3060
ucacggugu cucacuggag ccagaucugg aauucgcugu agggugguuc cccucuggca   3120
gugaguacca ggcuuccagc uuugucuacg accaacugca uguacccuac cacuuuacug   3180
ggcgcacucc ccgcgcuuuc gccagcaagg gugggaaggu aucuuucgug cucccuugga   3240
acucugucuc auccgugcuu cccgugcgcu ggggggggcgc uuccaagcuu ucuucugcca   3300
cgcggggucu gccggcucau gcugacuggg ggacuauuua cgccuuuauc ccccguccca   3360
acgagaagaa aagcaccgcu guaaagcaug uggccgugua cguucgguac aagaacgcgc   3420
gugccuggug ccccagcaug cuucccuuuc gcagcuacaa gcagaagaug cugaugcaau   3480
caggcgacgu cgagaccaac ccaggcccug cuucugacaa cccaaucuug gaauuucuug   3540
aagcagaaaa ugaucuaguc acucuggccu cucucuggaa gaugguacac ucuguucaac   3600
agaccuggag aaaguaugug aagaacgaca auuuuuggcc caauuuacuc agugaguuag   3660
ugggggaagg cuccaucgcc uuggccgcca cgcugucuaa ccaagcuuca guaaaagcuc   3720
ucuugggccu gcauuuucuc ucucgagggc ucaauuacac agacuuuuac ucuuuacuga   3780
uagagaaaug cucuaguuuc uuuacuguag aaccgccucc uccaccagcu gaaaaucuga   3840
ugaccaagcc cuccgugaag ucgaaauucc gaaagcuguu uaagaugcaa ggacccaugg   3900
acaaagucaa agacuggaac caaauagccg ccggcuugaa gaauuuucaa uuuguucgug   3960
accuagucaa agagguggguc gacuggcucc aggccuggau caacaaagag aaagccagcc   4020
cuguccucca guaccaguug gagaugaaga agcucgggcc cguggcuuug gcucaugaug   4080
ccuucauggc cgguuccggg cccccucuua gugacgacca gauugaauac cuccaaaacc   4140
ucaaaucucu ugcccuaaca cuggggaaga cuaauuuggc ccaaagucuc accacuauga   4200
ucaaugccaa gcaaaguucc gcccaacgag ucgaacccgu ugugguggguc cucagaggca   4260
agccgggaug cggcaagagc uuggccucca cguugauugc ccaggcugug uccaagcguc   4320
ucuacggcuc acaaagugug uauucucuuc cuccggaccc agacuucuuc gacggauaca   4380
aaggacaguu uguaaccuug auggaugauu ugggacaaaa cccggauggg caagauuucu   4440
ccaccuuuug ucagauggug ucgaccgccc aauuucuucc caacauggcg gaccuugcag   4500
agaaggggcg ccccuuuacc uccaaucuua ucauugcaac uacaaaccuc ccccacuuca   4560
gcccugucac cauugcugau ccuucugcgg ucucucgucg gaucaacuac gacuugacuc   4620
uagaaguauc ugaggccuac aaaaagcaca cacggcugaa uuuugaccug gcuuucaggc   4680
```

-continued

```
gcacagacgc cccccccauu uauccuuuug cugcccaugu gccuuucgug gacguggcug   4740

ugcgcuucaa aaauggccac cagagcuuca aucuccuaga guuggucgac ucuauuugug   4800

cagacauucg agccaagcaa caaggugccc gaaauaugca gacucuaguu cuacagagcc   4860

cuaacgagaa ugaugacacc cccgucgacg aggcgcuggg uagaguucuc acucccgcug   4920

cggucgacga ggcgcuuguc gaccucgcuc aagaggccga uccgguuggc cgcuuggcua   4980

uucuugccaa acuaggucuu gcucuagcug cggucacccc cggcuugaua aucuuggcag   5040

ugggacucua uagguacuuc ucuggcucug augcagacca agaagaaacg gaaagugagg   5100

aaccugcuaa agcgccuagg agcgagaaug cuuaugacgg cccgaagaaa aacucuaagc   5160

ccccuggagc gcucucucuu auggaaaugc aacagcccaa cguggacaug ggcuuugagg   5220

cugcggucgc uaagaaagug gucgucccca uuacauucau gguucccaac agaccuucug   5280

gacuuacaca guccgcccuu cuuguggccg gccggaccuu ccuaauuaau gagcauacau   5340

gguccaaccc cuccuggacc aguuucacaa uccguggnuga ggugcacacu cgugaugagc   5400

cuuuccaaac gguucauuuu acucaccaug guguucccac agaccugaug augguacguc   5460

ucggaccggg caacucuuuc ccuaacaauc uagacaaguu uggacuugac cagaugccgg   5520

cacguaacuc ccgugugguu ggcguuucgg cuaguuacgg uaauuucuuc uucucuggga   5580

auuuccuugg guuuguugac uccaucaccu cugaacaagg aacuuaugca agacuuuuua   5640

gguacagggu gaccaccuac aagggauggu gcgguucggc ccuggucugu gaggccggug   5700

guguccggcg caucauuggc cugcauucug cugguguccgc ugguaucggc gccgggaccu   5760

acaucucaaa auuaggacug aucaaagccc uuaaacaccu cggugaaccu cuggcuacaa   5820

ugcaaggacu gaugacugag cuagagccug gagucaccgu gcauguaccc cggaaaucua   5880

aauugagaaa gacgaccgca cacgcggugu acaaaccgga guuugaaccu gcuguguugu   5940

caaaauuuga ucccagacug aacaaggaug uugaccuaga ugagguaauu uggucuaaac   6000

acacugccaa cgucccuuau caaccuccuu uguucuacac auacauguca gaguacgcuc   6060

aucggguuuu cuccuuuuug ggaaaagaca augacauucu gaccguuaaa gaagcaaucc   6120

ugggcauccc uggacuagac ccuauggauc cccacacagc uccgggucug cccuacgcca   6180

uuagcggccu ucgacguacu gaucucgucg auuuugugaa cgguacggua gacgcagcac   6240

uggccaugca aauccagaaa uucuuagacg gugacuacuc ugaucauguc uuccaaacuu   6300

uucugaaaga ugaaaucaga cccucagaga agguccgagc gggaaaaacc cgcauugucg   6360

augugcccuc ccuggcacac ugcauugugg gcagaaugcu gcucgggcgu uucgccgcca   6420

aguuucaauc ccaucccggc uuucuucuug guucugcuau cggguccgac ccugaugucu   6480

ucuggaccgu cauaggggcu cagcucgagg gaagaaagaa cacguacgac guggacuaca   6540

gugccuuuga cucuucacac ggcacuggcu ccuucgaggc ucucaucucu cacuuuuuca   6600

ccguugacaa ugguuuuagc ccugcgcugg gaccguaucu cagaucccug gcugucucgg   6660

ugcacgcuua cggcgagcgu cgcaucaaga uuaccggagg ccuucccucu gguugugccg   6720

cgaccagccu ucugaacaca gugcucaaca augugaucau caggacugcu cuggcauuga   6780

cuuacaagga auuugaguau gacaugguug auaucaucgc cuacggugac gaccuuuugg   6840

uugguacgga uuaugaucug gacuucaaug aaguggcgcg gcgcgcugcc aaacuggggu   6900

auaagaugac uccugccaac aaggguuccg ucuucccucc gacuuccucu cucuccgaug   6960

cuguuuuucu aaaacgcaaa uucguccaaa acaaugacgg cuuauauaaa ccaguuaugg   7020

auuuaaagaa uuuggaagcc augcucuccu acuucaaacc aggaacacua cucgagaagc   7080
```

ugcaaucugu uucuauguug gcucaacauu cuggaaaaga agaauaugau agauugaugc 7140
accccuucgc ugacuacggu gccguaccga gucacgagua ccugcaggca agauggaggg 7200
ccuuguucga uugaccuaga uagcccaacg cgcuucggug ccgccggcga uucugggaga 7260
acucagucgg aacagaaaag ggaaaa 7286

<210> SEQ ID NO 6
<211> LENGTH: 7270
<212> TYPE: RNA
<213> ORGANISM: Senecavirus

<400> SEQUENCE: 6
cugggcccuc augcccaguc cuuccuuucc ccuuccgggg gguaaaccgg cuguguuugc 60
uagaggcaca gaggagcaac auccaaccug cuuuuguggg gaacggugcg gcuccaauuc 120
cugcgucgcc aaaggugua gcgcacccaa acggcgcauc uaccaaugcu auuggugugg 180
ucugcgaguu cuagccuacu cguuucuccc cuauccacuc acucacgcac aaaaagugug 240
cuguaauuac aagauuuagc ccucgcacga gaugugcgau aaccgcaaga uugacucaag 300
cgcggaaagc gcuguaacca caugcuguua gucccuucau ggcugcgaga uggcuaucca 360
ccucggauca cugaacugga gcucgacccu ccuuaguaag ggaaccgaga ggccuucuug 420
caacaagcuc cgacacagag uccacgugau ugcuaccacc augaguacau gguucucccc 480
ucucgaccca ggacuucuuu uugaauaucc acggcucgau ccagagggug gggcaugauc 540
ccccuagcau agcgagcuac agcgggaacu guagcuaggc cuuagcgugc cuuggauacu 600
gccugauagg gcgacggccu agucgugucg guucuauagg uagcacauac aaauaugcag 660
aacucucacu uuucuuucga uacagccucu ggcaccuuug aagacguaac cggaacaaaa 720
gucaagaucg uugaauaccc uagaucggug aacaauggug uuuacgauuc guccacucau 780
uuagagauac ugaaccuaca gggugaaauu gaaauuuuaa agucuuucaa ugaauaccaa 840
auucgcgccg ccaaacaaca acuuggacug gacaucguau acgaacuaca ggguaauguu 900
cagacaaccu caaagaauga uuuugauucc cgcgguaaua augguaacau gaccuucaau 960
uacuacgcaa acacuuacca gaauucagua gacuucucga ccuccucguc ggcgucaggc 1020
gccggacccg ggaacucccg ggcggauua gcgggucucc ucacaaauuu caguggaauc 1080
uugaacccuc uuggcuaccu caaagaucac aauaccgaag aaauggaaaa cucugcugau 1140
cgagucauaa cgcaaacggc gggcaacacu gccauaaaca cgcaaucauc acugggugug 1200
uugugugccu acguugaaga cccgaccaaa ucugacccuc cguccagcag cacagaucaa 1260
cccaccacca cuuuuacugc caucgacagg ugguacacug gacgccucaa uucuuggaca 1320
aaagcuguaa aaaccuucuc uuuucaggcc gucccgcucc cuggagccuu ccugucuaga 1380
cagggaggcc ucaacggagg ggccuucacg gcuacccuac auagacauuu cuuaaugaag 1440
ugcggguggc aggugcaggu ccaaugcaau uugacgcaau uccaccaagg ugcucuucuu 1500
guugccaugg uccccgaaac cacccuugau gucaaaccug acggcaaggc aaagagcuua 1560
caggagcuga augaagaaca gugggugga augucugacg auuaccggac cgggaaaaac 1620
augccuuucc agucucuugg cacauacuau cggcccccua acuggacuug ggcccccaau 1680
uucaucaacc ccuaucaagu aacaguuuuc ccacaccaaa uucugaacgc gagaaccucu 1740
accucgguag acauaagugu cccauacauc ggggagacuc cuacacaauc cucagagaca 1800
cagaacuccu ggacccuccu cguuauggug cuuguccccc uggacuacaa ggagggagcc 1860

-continued

```
acaacugacc cagaaauuac auuuucugua aggccuacaa guccuuacuu caaugggcua   1920
cguaaccguu ucacgaccgg gacggacgag gaacaggggc ccauucccac agcacccaga   1980
gaaaauucgc uuauguuucu cucaaccauc ccugacgaca cugucccugc uuacgggaau   2040
gugcguaccc cucccgucaa uuaccucccu ggugaaauaa ccgaccucuu acaacuggcc   2100
cguauaccca cucucauggc guucgggcgg gugucugaac ccgagccugc cucagacaca   2160
uaugugcccu acguugccgu uccugcccag uucgacgaca agccucucau cuccuucccg   2220
aucacccuuu cagauccugu cuaccagaac acccugguag gcgccaucag uucgaauuuc   2280
gccaacuacc gggggguguau ccaaaucacu cugacauuuu guggacccau gauggcaaga   2340
gggaaauucc uacucucgua uucuccucca aauggagcac aaccacagac ccuuucugaa   2400
gcuaugcagu gcacguacuc uauuugggau auaggcuuga acucuaguug gaccuuuguc   2460
auccccuaca ucucgcccag ugauuaccgu gaaacucggg cuauuaccaa cucaguuuau   2520
ucugcugaug guugguuuag ccugcacaag cugacuaaaa uuacucuacc accugacugc   2580
ccacagaguc ccuguauucu cuuuuucgcc ucugcuggug aggauuacac ccuccgucuc   2640
ccuguugauu guaauccuuc cuacguguuc cacuccaccg acaacgccga gacugggguu   2700
auugaggcgg guaacacuga caccgacuuc ucuggugagc uggcggcucc uggcucuaac   2760
cacacuaaug ucaaguuccu guuugaucga ucucgauuac ugaauguaau uaagguacug   2820
gagaaggacg ccgucuuccc ccguccuuuc cccacagcaa caggugcaca gcaggacgau   2880
gguuacuuuu gccuucuaac accccgccca acagucgcuu cccgacccgc cacucguuuc   2940
ggccuguacg ucaauccguc ugacaguggc guucucgcua acacuucacu ggauuucaau   3000
uuuuacagcu uggccuguuu cacuuacuuu agaucagacc uugaagucac gguggucuca   3060
cuggagccag aucuggaauu cgcuguaggg ugguuccccu cuggcaguga guaccaggcu   3120
uccagcuuug ucuacgacca acugcaugua cccuaccacu uuacugggcg cacuccccgc   3180
gcuuucacca gcaagggugg aaagguaucu uucgugcuuc cuuggaacuc ugucucaucc   3240
gugcuucccg ugcgcugggg gggcgcuucc aagcuuucuu ccgccacgcg gggucuaccg   3300
gcucaugcug acugggggac cauuuacgcc uucauccccc guccuaauga gaagaaaagc   3360
accgcugcaa agcacguggc gguguacguu cgguacaaga acgcgcgugc cuggugcccc   3420
agcaugcucc ccuuccgcag cuacaagcag aagaugcuga ugcaaucagg cgacgucgag   3480
accaacccug gcccugcuuc ugacaaccca aucuuggagu uucuugaagc ugaaaacgau   3540
cuagucacuc uggccucucu cuggaagaug guacacucug uucaacagac cuggagaaag   3600
uaugugaaga augacaauuu uuggcccaau uugcucagug agcuaguggg ggaaggcucc   3660
aucgccuugg ccgccacgcu aucuaaccaa gcuucaguaa aagcucucuu aggccugcau   3720
uuucucuccc gagggcucaa uuauacagau uuuuacucuu uacugauaga gaaaugcucu   3780
aguuucuuua cuguagaacc gccuccucca ccagcugaaa aucugaugac caagccccucc   3840
gugaggucga aauuccgaaa gcuguuuaag augcaaggac ccauggacac agucaaagac   3900
uggaaccaaa uagccgccgg ccugaagaau uuccaauuug uucgugaccu ggucaaagag   3960
guggucgauu ggcuccaggc cuggauuaau aaagagaaag ccagcccugu ccuccaguac   4020
cagcuggaga ugaagaaacu cggacccgug gcuuuggcuc augaugccuu cauggccggu   4080
uccgggcccc cucuuaguga cgaccagauu gaauaucucc agaaccucaa aucucuugcc   4140
cuaacacugg ggaagacuaa uuuggcccaa agucucacca cuaugaucaa ugccaagcaa   4200
agcuccgcuc aacgagucga acccguugug gugguccuua gaggcaagcc gggauguggc   4260
```

```
aagagcuugg ccuccacguu gauugcccag gcugugucca agcgucucua cggcucacaa   4320
aguguguauu cucuuccucc ggauccagac uucuucgacg gauacaaagg acaguuugua   4380
accuugaugg acgaucuggg acaaaacccg gaugggcaag auuucuccac cuuuugucag   4440
augguguucga ccgcccaauu ucuucccaac auggcggacc uuacagagaa ggggcguccc   4500
uucaccucca aucuuaucau ugcaacuaca aaccucccuc acuucagccc ugucaccauu   4560
gcugauccuu cugcagucuc ucgucguauc aacuacgacc ugacucuaga aguaucugag   4620
gccuauaaga agcacacacg gcugaauuuu gaccuggcuu ucagacgcac agacgccccc   4680
cccauuuauc cuuuugcugc ccaugugccc uucguggacg uggcugugcg cuucaaaaau   4740
ggucaucaga gcuucaaucu ccuagaguug gucgacucua uuugugcaga cauucgagcc   4800
aagcaacaag gugcccgaaa uaugcagacu cugguucuac agagccccaa cgagaacgac   4860
gacaccccccg ucgacgaggc guuggguaga guucucaccc ccgcugcggu cgacgaggcg   4920
cuugucgacc ucgcuccaga ugccgacccg guuggccguu uggcuauucu cgccaagcua   4980
ggucuugccc uagcugcggu caccccuggu uugauaaucu uggcaguggg acucuacagg   5040
uacuucucug gcucugauac agaccaagaa gaaacagaag gugaggagcc ugcuaaagcg   5100
ccuaggagcg agaaugcuua ugacggcccg aagaaaaacu cuaagccccc uggagcgcuc   5160
ucccuuaugg aaaugcaaca gcccaacgug gacaugggcu uugaggcugc ggucgcuaag   5220
aaaguggucg uccccauuac cuucaugguu cccaacagac cuucuggacu uacacagucc   5280
gcucuucuug uggccggccg gaccuuccua auuaaugagc auacaugguc caaccccucc   5340
uggaccagcu ucacaauccg uggugaggug cacacccgug augagccuuu ccaaacgguu   5400
cauuuuacuc accauggugu ucccacagau cuggugaugg uacgucucgg accgggcaac   5460
uccuucccua acaaucuaga caaguuugga cuugaucaga ugccggcacg uaacuccccgu   5520
gugguuggcg uuucggcuag uuacggcaac uucuucuucu cugggaacuu ccucggguuu   5580
guugacucca ucaccucuga ccaaggaacu uaugcgagac uuuuuaggua cagggugacg   5640
accuacaagg gguggugcgg uucggcccug guuugugagg ccgguggugu ccggcgcauc   5700
auuggccugc auucugcugg ugccgcuggu aucggcgccg ggacuuacau cucaaaauua   5760
ggacugauca aagcccucaa acaccucggu gaaccucugg cuacaaugca aggacugaug   5820
acugagcuag agccuggagu caccgugcau guaccccgga aaucuaaauu gagaaagacg   5880
accgcacacg cgguguacaa accggaguuu gaaccugcug uguugucaaa auuugauccc   5940
agacugaaca aggauguuga ccuagaugag guaauuuggu cuaaacacac ugccaacguc   6000
ccuuaucaac cuccuuuguu cuacacauac augucagagu acgcucaucg gguuuucucc   6060
uuuuugggaa aagacaauga cauucugacc gucaaagaag caaucuuggg aaucccugga   6120
cuagacccua uggaucccca cacagcuccg ggucugcccu acgccauuag cggccuucga   6180
cguacugauc ucgucgauuu ugcgaacggc acgguggacc cgacacuggc cguacaaauc   6240
caaaaauucu uagacgguga cuacucugau caugucuucc aaacuuuucu gaaagaugaa   6300
aucagacccu cagagaaggu ccgagcggga aaaacccgca uugucgaugu gcccucccug   6360
gcgcacugca uugugggcag aauguugcuu gggcgcuuug ccgccaaguu ucaaucccau   6420
ccuggcuuuc uccuuggcuc ugcuaucggg ucugacccug augucuucug gaccgucaua   6480
ggggcucagc ucgagggaag aaagaacacg uaugacgugg acuacagugc cuuugacucu   6540
ucacacggca cuggcuccuu cgaggcucuc aucucucacu uuuucaccgu ggacaauggu   6600
```

```
uuuagcccug cgcugggauc guaucucaga ucccuggcug ucucggugca cgcuuacggc   6660
gagcgucgca ucaagauuac cggaggccuc cccucugguu gugccgcgac cagccugcug   6720
aacacagugc ucaacaaugu gaucaucagg acugcucugg cauugaccua caaggaauuu   6780
gaauaugaca ugguugauau caucgccuac ggugacgacc uucugguugg uacggauuac   6840
gaucuggacu ucaaugaggu ggcgcggcgc gcugccaaac uggggguaaa gaugacuccu   6900
gccaacaaag guucugucuu cccuccgacu ucccucucu ccgacgcugu uuuucuaaaa   6960
cgcaaauucg uccaaaacaa ugacggcuua uacaaaccag uuauggauuu aaagaauuug   7020
gaagccaugc ucuccuacuu caaaccagga acacuacucg agaagcugca aucuguuucu   7080
auguuggcuc aacauucugg aaaagaagaa uaugauagau ugaugcaccc cuuugcugac   7140
uacggugccg uaccgaguca cgaguaccug caggcaagau ggagggccuu guucgacuga   7200
ccuagauagc ccaacgcgcu ccggugcugc cggcgauucu gggagaacuc agucggaaca   7260
gaaaagggaa                                                           7270
```

<210> SEQ ID NO 7
<211> LENGTH: 7270
<212> TYPE: RNA
<213> ORGANISM: Senecavirus

<400> SEQUENCE: 7

```
cugggcccuc augcccaguc cuuccuuucc ccuuccgggg gguaaaccgg cuguguuugc     60
uagaggcaca gaggagcaac auccaaccug cuuuuguggg gaacggugcg gcuccaauuc    120
cugcgucgcc aaagguguua gcgcacccaa acggcgcauc uaccaaugcu auuggugugg    180
ucugcgaguu cuagccuacu cguuucuccc cuauccacuc acucacgcac aaaaagugug    240
cuguaauuac aagauuuagc ccucgcacga gaugugcgau aaccgcaaga uugacucaag    300
cgcggaaagc gcuguaacca caugcuguua gucccuucau ggcugcgaga uggcuaucca    360
ccucggauca cugaacugga gcucgacccu ccuuaguaag ggaaccgaga ggccuucuug    420
caacaagcuc cgacacagag uccacgugau ugcuaccacc augaguacau gguucucccc    480
ucucgaccca ggacuucuuu uugaauaucc acggcucgau ccagagggug gggcaugauc    540
ccccuagcau agcgagcuac agcgggaacu guagcuaggc cuuagcgugc cuuggauacu    600
gccugauagg gcgacggccu agucgugucg guucuauagg uagcacauac aaauaugcag    660
aacucucacu uuucuuucga uacagccucu ggcaccuuug aagacguaac cggaacaaaa    720
gucaagaucg uugaauaccc uagaucggug aacaauggug uuuacgauuc guccacucau    780
uuagagauac ugaaccuaca gggugaaauu gaaauuuuaa agucuuucaa ugaauaccaa    840
auucgcgccg ccaaacaaca acuuggacug gacaucguau acgaacuaca ggguaauguu    900
cagacaaccu caaagaauga uuuugauucc cgcgguaaua augguaacau gaccuucaau    960
uacuacgcaa acacuuacca gaauucagua gacuucucga ccuccucguc ggcgucaggc   1020
gccggacccg ggaacucccg ggcggauua gcgggucucc ucacaaauuu caguggaauc    1080
uugaacccuc uuggcuaccu caaagaucac aauaccgaag aaauggaaaa cucugcugau   1140
cgagucauaa cgcaaacggc gggcaacacu gccauaaaca cgcaaucauc acugggugug   1200
uugugugccu acguugaaga cccgaccaaa ucugacccuc cguccagcag cacagaucaa   1260
cccaccacca cuuuuacugc caucgacagg ugguacacug gacgccucaa uucuuggaca   1320
aaagcuguaa aaaccuucuc uuuucaggcc gucccgcucc cuggagccuu ccugucuaga   1380
cagggaggcc ucaacggagg ggccuucacg gcuacccuac auagacauuu cuuaaugaag   1440
```

```
ugcggguggc aggugcaggu ccaaugcaau uugacgcaau uccaccaagg ugcucuucuu   1500
guugccaugg uccccgaaac cacccuugau gucaaaccug acggcaaggc aaagagcuua   1560
caggagcuga augaagaaca gugggugggaa augucugacg auuaccggac cgggaaaaac   1620
augccuuucc agucucuugg cacauacuau cggccccccua acuggacuug gggccccaau   1680
uucaucaacc ccuaucaagu aacaguuuuc ccacaccaaa uucugaacgc gagaaccucu   1740
accucgguag acauaagugu cccauacauc ggggagacuc cuacacaauc cucagagaca   1800
cagaacuccu ggacccuccu cguuauggug cuuguccccc uggacuacaa ggagggagcc   1860
acaacugacc cagaaauuac auuuucugua aggccuacaa guccuuacuu caaugggcua   1920
cguaaccguu ucacgaccgg gacggacgag gaacaggggc ccauucccac agcacccaga   1980
gaaaauucgc uuauguuucu cucaaccauc ccugacgaca cugucccugc uuacgggaau   2040
gugcguaccc cucccgucaa uuaccucccu ggugaaauaa ccgaccucuu acaacuggcc   2100
cguauaccca cucucauggc guucgggcgg gugucugaac ccgagccugc cucagacaca   2160
uaugugcccu acguugccgu uccugcccag uucgacgaca agccucucau cuccuucccg   2220
aucacccuuu cagauccugu cuaccagaac acccugguag gcgccaucag uucgaauuuc   2280
gccaacuacc gggggguguau ccaaaucacu cugacauuuu guggacccau gauggcaaga   2340
gggaaauucc uacucucgua uucuccucca aauggagcac aaccacagac ccuuucugaa   2400
gcuaugcagu gcacguacuc uauuugggau auaggcuuga acucuaguug gaccuuuguc   2460
auccccuaca ucucgcccag ugauuaccgu gaaacucggg cuauuaccaa cucaguuuau   2520
ucugcugaug guugguuuag ccugcacaag cugacuaaaa uuacucuacc accugacugc   2580
ccacagaguc ccuguauucu cuuuuucgcc ucugcuggug aggauuacac ccuccgucuc   2640
ccuguugauu guaauccuuc cuacguguuc cacuccaccg acaacgccga gacugggguu   2700
auugaggcgg guaacacuga caccgacuuc ucuggugagc uggcggcucc uggcucuaac   2760
cacacuaaug ucaaguuccu guuugaucga ucucgauuac ugaauguaau uaagguacug   2820
gagaaggacg ccgucuuccc ccguccuuuc ccccacagcaa caggugcaca gcaggacgau   2880
gguuacuuuu gccuucuaac accccgccca acagucgcuu cccgacccgc cacucguuuc   2940
ggccuguacg ucaauccguc ugacaguggc guucucgcua acacuucacu ggauuucaau   3000
uuuuacagcu uggccuguuu cacuuacuuu agaucagacc uugaagucac gguggucuca   3060
cuggagccag aucuggaauu cgcuguaggg ugguuccccu cuggcaguga guaccaggcu   3120
uccagcuuug ucuacgacca acugcaugua cccuaccacu uuacugggcg cacucccccgc   3180
gcuuucacca gcaagggugg aaagguaucu uucgugcuuc cuuggaacuc ugucucaucc   3240
gugcuucccg ugcgcugggg gggcgcuucc aagcuuucuu ccgccacgcg gggucuaccg   3300
gcucaugcug acugggggac cauuuacgcc uucauccccc guccuaauga gaagaaaagc   3360
accgcugcaa agcacguggc gguguacguu cgguacaaga acgcgcgugc cuggugcccc   3420
agcaugcucc ccuuccgcag cuacaagcag aagaugcuga ugcaaucagg cgacgucgag   3480
accaacccug gcccugcuuc ugacaaccca aucuuggagu uucuugaagc ugaaaacgau   3540
cuagucacuc uggccucucu cuggaagaug guacacucug uucaacagac cuggagaaag   3600
uaugugaaga augacaauuu uuggcccaau uugcucagug agcuaguggg ggaaggcucc   3660
aucgccuugg ccgccacgcu aucuaaccaa gcuucaguaa aagcucucuu aggccugcau   3720
uuucucuccc gagggcucaa uuauacagau uuuuacucuu uacugauaga gaaaugcucu   3780
```

```
aguuucuuua cuguagaacc gccuccucca ccagcugaaa aucugaugac caagccuucc   3840
gugaggucga aauuccgaaa gcuguuuaag augcaaggac ccauggacac agucaaagac   3900
uggaaccaaa uagccgccgg ccugaagaau uuccaauuug uucgugaccu ggucaaagag   3960
gugguucgauu ggcuccaggc cuggauuaau aaagagaaag ccagcccugu ccuccaguac   4020
cagcuggaga ugaagaaacu cggacccgug gcuuuggcuc augaugccuu cauggccggu   4080
uccgggcccc cucuuaguga cgaccagauu gaauaucucc agaaccucaa aucucuugcc   4140
cuaacacugg ggaagacuaa uuuggcccaa agucucacca cuaugaucaa ugccaagcaa   4200
agcuccgcuc aacgagucga acccguugug gugguccuua gaggcaagcc gggauguggc   4260
aagagcuugg ccuccacguu gauugcccag gcuguguucca agcgucucua cggcucacaa   4320
aguguguauu cucuuccucc ggauccagac uucuucgacg gauacaaagg acaguuugua   4380
accuugaugg acgaucuggg acaaaacccg gaugggcaag auuucuccac cuuuugucag   4440
auggugucga ccgcccaauu ucuucccaac auggcggacc uuacagagaa ggggcguccc   4500
uucaccucca aucuuaucau ugcaacuaca aaccucccuc acuucagccc ugucaccauu   4560
gcugauccuu cugcagucuc ucgucguauc aacuacgacc ugacucuaga aguaucugag   4620
gccuauaaga agcacacacg gcugaauuuu gaccuggcuu ucagacgcac agacgccccc   4680
cccauuuauc cuuuugcugc ccaugugccc uucguggacg uggcugugcg cuucaaaaau   4740
ggucaucaga gcuucaaucu ccuagaguug gucgacucua uuugugcaga cauucgagcc   4800
aagcaacaag gugcccgaaa uaugcagacu cugguucuac agagccccaa cgagaacgac   4860
gacacccccg ucgacgaggc guuggguaga guucucaccc ccgcugcggu cgacgaggcg   4920
cuugucgacc ucgcuccaga ugccgacccg guuggccguu uggcuauucu cgccaagcua   4980
ggucuugccc uagcugcggu caccccuggu uugauaaucu uggcaguggg acucuacagg   5040
uacuucucug gcucugauac agaccaagaa gaaacagaag gugaggagcc ugcuaaagcg   5100
ccuaggagcg agaaugcuua ugacggcccg aagaaaaacu cuaagccccc uggagcgcuc   5160
ucccuuaugg aaaugcaaca gcccaacgug gacaugggcu uugaggcugc ggucgcuaag   5220
aaaguggucg uccccauuac cuucaugguu cccaacagac cuucuggacu uacacagucc   5280
gcucuucuug uggccggccg gaccuuccua auuaaugagc auacaugguc caaccccucc   5340
uggaccagcu ucacaauccg ugguaggug cacacccgug augagccuuu ccaaacgguu   5400
cauuuuacuc accauggugu ucccacagau cuggugaugg uacgucucgg accgggcaac   5460
uccuucccua acaaucuaga caaguuugga cuugaucaga ugccggcacg uaacucccgu   5520
gugguuggcg uuucggcuag uuacggcaac uucuucuucu cugggaacuu ccucggguuu   5580
guugacucca ucaccucuga ccaaggaacu uaugcgagac uuuuuaggua cagggugacg   5640
accuacaagg ggugguggcgg uucggcccug guuugugagg ccgguggugu ccggcgcauc   5700
auuggccugc auucugcugg ugccgcuggu aucggcgccg ggacuuacau cucaaaauua   5760
ggacugauca aagcccucaa acaccucggu gaaccucugg cuacaaugca aggacugaug   5820
acugagcuag agccuggagu caccgugcau guaccccgga aaucuaaauu gagaaagacg   5880
accgcacacg cgguguacaa accggaguuu gaaccugcug uguugucaaa auuugauccc   5940
agacugaaca aggauguuga ccuagaugag guaauuuggu cuaaacacac ugccaacguc   6000
ccuuaucaac cuccuuuguu cuacacauac augucagagu acgcucaucg gguuuucucc   6060
uuuuugggaa aagacaauga cauucugacc gucaaagaag caaucuuggg aaucccugga   6120
cuagacccua uggaucccca cacagcuccg ggucugcccu acgccauuag cggccuucga   6180
```

cguacugauc ucgucgauuu ugcgaacggc acgguggacc cgacacuggc cguacaaauc 6240
caaaaauucu uagacgguga cuacucugau caugucuucc aaacuuuucu gaaagaugaa 6300
aucagacccu cagagaaggu ccgagcggga aaaacccgca uugucgaugu gcccucccug 6360
gcgcacugca uuguggggcag aauguugcuu gggcgcuuug ccgccaaguu ucaaucccau 6420
ccuggcuuuc uccuuggcuc ugcuaucggg ucugacccug augucuucug gaccgucaua 6480
ggggcucagc ucgagggaag aaagaacacg uaugacgugg acuacagugc cuuugacucu 6540
ucacacggca cuggcuccuu cgaggcucuc aucucucacu uuuucaccgu ggacaauggu 6600
uuuagcccug cgcugggauc guaucucaga ucccuggcug ucucggugca cgcuuacggc 6660
gagcgucgca ucaagauuac cggaggccuc cccucugguu gugccgcgac cagccugcug 6720
aacacagugc ucaacaaugu gaucaucagg acugcucugg cauugaccua caaggaauuu 6780
gaauaugaca ugguugauau caucgccuac ggugacgacc uucugguugg uacggauuac 6840
gaucuggacu ucaaugaggu ggcgcggcgc gcugccaaac ugggguauaa gaugacuccu 6900
gccaacaaag guucugucuu cccuccgacu uccucucucu ccgacgcugu uuuucuaaaa 6960
cgcaaauucg uccaaaacaa ugacggcuua uacaaaccag uuauggauuu aaagaauuug 7020
gaagccaugc ucuccuacuu caaaccagga acacuacucg agaagcugca aucuguuucu 7080
auguuggcuc aacauucugg aaaagaagaa uaugauagau ugaugcaccc cuuugcugac 7140
uacggugccg uaccgaguca cgaguaccug caggcaagau ggagggccuu guucgacuga 7200
ccuagauagc ccaacgcgcu ccggugcugc cggcgauucu gggagaacuc agucggaaca 7260
gaaaagggaa 7270

<210> SEQ ID NO 8
<211> LENGTH: 7270
<212> TYPE: RNA
<213> ORGANISM: Senecavirus

<400> SEQUENCE: 8
cugggcccuc augcccaguc cuuccuuucc ccuuccgggg gguaaaccgg cuguguuugc 60
uagaggcaca gaggagcaac auccaaccug cuuuugaggg gaacggugcg gcuccaauuc 120
cugcgucgcc aaagguguua gcgcacccaa acggcgcauc uaccaaugcu auuggugugg 180
ucugcgaguu cuagccuacu cguuucuccc uuauccacuc acucacgcac aaaaagugug 240
cuguaacuac aagauuuagc ccucgcacga gaugugcgau aaccgcaaga uugacucaag 300
cgcggaaagc gcuguaacca caugcuguua gucccuucau ggcugcgaga uggcuaucca 360
ccucggauca cugaacugga gcucgacccu ccuuaguaag ggaaccgaga ggccuucuug 420
caacaagcuc cgacacagag uccacgugau ugcuaccacc augaguacau gguucucccc 480
ucucgaccca ggacuucuuu uugaauaucc acggcucgau ccagagggug gggcaugauc 540
ccccuagcau agcgagcuac agcgggaacu guagcuaggc cuuagcgugc cuuggauacu 600
gccugauagg gcgacggccu agucgugucg guucuauagg uagcacauac aaauaugcag 660
aacucucauu uuucuuucga uacagccucu ggcaccuuug aagacguaac cggaacaaaa 720
gucaagaucg uugaacaccc uagaucggug aacaauggug uuuacgauuc guccacucau 780
uuagagauac ugaaccuaca gggugaaauu gaaauuuuaa agucuuucaa ugaauaccaa 840
auucgcgccg ccaaacaaca acuuggacug gacaucguau acgaacuaca ggguaauguu 900
cagacaaccu caaagaauga uuuugauucc cgcgguaaua augguaacau gaccuucaau 960

```
uacuacgcaa acacuuacca gaauucagua gacuucucga ccuccucguc ggcgucaggc   1020

gccggacccg ggaacucccg gggcggauua gcgggucucc ucacaaauuu caguggaauc   1080

uugaacccuc uuggcuaccu caaagaucac aauaccgaag aaauggaaaa cucugcugau   1140

cgagucauaa cgcaaacggc gggcaacacu gccauaaaca cgcaaucauc acugggugug   1200

uugugugccu acguugaaga cccgaccaaa ucugacccuc cguccagcag cacagaucaa   1260

cccaccacca cuuuuacugc caucgacagg ugguacacug gacgccucaa uucuuggaca   1320

aaagcuguaa aaaccuucuc uuuucaggcc gucccgcucc cuggagccuu ccugucuaga   1380

cagggaggcc ucaacggagg ggccuucacg gcuacccuac auagacauuu cuuaaugaag   1440

ugcggguggc aggugcaggu ccaaugcaau uugacgcaau uccaccaagg ugcucuucuu   1500

guugccaugg uccccgaaac cacccuugau gucaaaccug acggcaaggc aaagagcuua   1560

caggagcuga augaagaaca gugggugga augucugacg auuaccggac cgggaaaaac   1620

augccuuucc agucucuugg cacauacuau cggcccccua acuggacuug ggccccaau    1680

uucaucaacc ccuaucaagu aacaguuuuc ccacaccaaa uucugaacgc gagaaccucu   1740

accucgguag acauaagugu cccauacauc ggggagacuc cuacacaauc cucagagaca   1800

cagaacuccu ggacccuccu cguuauggug cuuguccccc uggacuacaa ggagggagcc   1860

acaacugacc cagaaauuac auuuucugua aggccuacaa guccuuauuu caaugggcua   1920

cguaaccguu ucacgaccgg gacggacgag gaacaggggc ccauucccac agcacccaga   1980

gaaaauucgc uuauguuucu cucaaccauc ccugacgaca cuguccugc uuacgggaau    2040

gugcguaccc cucccgucaa uuaccucccu ggugaaauaa ccgaccucuu acaacuggcc   2100

cguauaccca cucucauggc guuugggcgg gugucugaac ccgagccugc cucagacaca   2160

uaugugcccu acguugccgu uccugcccag uucgacgaca agccucucau cuccuucccg   2220

aucacccuuu cagauccugu cuaccagaac acccugguag gcgccaucag uucgaauuuc   2280

gccaacuacc gggggguau ccaaaucacu cugacauuuu guggacccau gauggcaaga    2340

gggaaauucc uacucucgua uucuccacca aauggagcac aaccacagac ccuuucugaa   2400

gcuaugcagu gcacguacuc uauuugggau auaggcuuga acucuaguug gaccuuuguc   2460

auccccuaca ucucgcccag ugauuaccgu gaaacucggg cuauuaccaa cucaguuuau   2520

ucugcugaug guugguuuag ccugcacaag cuaacuaaaa uuacucuacc accugacugc   2580

ccacagaguc ccuguauucu cuuuuucgcc ucugcuggug aggauuacac ccuccgucuc   2640

ccuguugauu guaauccuuc cuacguguuc cacuccaccg acaacgccga gacuggggu    2700

auugaggcgg guaacacuga caccgauuuc ucuggugagc uggcggcucc uggcucuaac   2760

cacacuaaug ucaaguuccu guuugaucga ucucgauuac ugaauguaau uaagguacug   2820

gagaaggacg ccgucuuccc ccguccuuuc cccacagcaa caggugcaca gcaggacgau   2880

gguuacuuuu gccuucuaac accccgccca acagucgcuu cccgacccgc cacccguuuc   2940

ggccuguacg ucaauccguc ugacaguggc guucucgcua acacuucacu ggauuucaau   3000

uuuuacagcu uggccuguuu cacuuacuuu agaucagacc uugaagucac gguggucuca   3060

cuggagccag aucuggaauu cgcuguaggg ugguuccccu cuggcaguga guaccaggcu   3120

uccagcuuug ucuacgacca acugcaugua cccuaccacu uuacugggcg cacuccccgc   3180

gcuuucacca gcaagggugg aaagguaucu uucgugcuuc cuuggaacuc ugucucaucc   3240

gugcuucccg ugcgcugggg gggcgcuucc aagcuuucuu ccgccacgcg gggucuaccg   3300

gcucaugcug acugggggac cauuuacgcc uucauccccc guccuaacga gaagaaaagc   3360
```

```
accgcuguaa agcacguggc gguguacguu cgguacaaga acgcgcgugc cuggugcccc   3420
agcaugcucc ccuuccgcag cuacaagcag aagaugcuga ugcaaucagg cgacgucgag   3480
accaacccug gcccugcuuc ugacaaccca aucuuggagu uucuugaagc ugaaaacgau   3540
cuagucacuc uggccucucu cuggaagaug guacacucug uucaacagac cuggagaaag   3600
uaugugaaaa acgacaauuu uuggcccaau uugcucagug agcuaguggg ggaaggcucc   3660
aucgccuugg ccgccacgcu aucuaaccaa gcuucaguaa aagcucucuu aggccugcau   3720
uuucucuccc gagggcucaa uuauacagau uuuuacucuu uacugauaga gaaaugcucu   3780
aguuucuuua cuguagaacc gccuccucca ccagcugaaa aucugaugac caagcccucc   3840
gugaggucga aauuccgaaa gcuguuuaag augcaaggac ccauggacac agucaaagac   3900
uggaaccaaa uagccgccgg ccugaagaau uuccaauuug uucgugaccu ggucaaagag   3960
gugguucgauu ggcuccaggc cuggauuaau aaagagaaag ccagcccugu ccuccaguac   4020
cagcuggaga ugaagaaacu cggacccgug gcuuuggcuc augaugccuu cauggccggu   4080
uccgggcccc cucuuaguga cgaccagauu gaauaucucc agaaccucaa aucucuugcc   4140
cuaacacugg ggaagacuaa uuuggcccaa agucucacca cuaugaucaa ugccaagcaa   4200
agcuccgcuc aacgagucga acccguugug gugguccuua gaggcaagcc gggauguggc   4260
aagagcuugg ccuccacguu gauugcccag gccgugucca agcgucucua cggcucacaa   4320
agugguguauu cucuuccucc ggauccagac uucuucgacg gauacaaagg acaguuugua   4380
accuugaugg acgaucuggg acaaaacccg gaugggcaag auuucuccac cuuuugucag   4440
auggugucga ccgcccaauu ucuucccaac auggcggacc uugcagaaaa ggggcguccc   4500
uucaccucca aucuuaucau ugcaacuaca aaccucccuc acuucagccc ugucaccauu   4560
gcugauccuu ccgcagucuc ucgucguauc aacuacgacc ugacucuaga aguaucugag   4620
gccuauaaga agcacacacg gcugaauuuu gaccuggcuu ucagacgcac agacgccccc   4680
cccauuuauc cuuuugcugc ccaugugccc uucguggacg uggcugugcg cuucaaaaau   4740
ggucaucaga gcuucaaucu ccuagaguug gucgacucua uuugugcaga cauucgagcc   4800
aagcaacaag gugcucgaaa uaugcagacu cugguucuac agagccccaa cgagaacgac   4860
gacacccccg ucgacgaggc guuggguaga guucucaccc ccgcugcggu cgacgaggcg   4920
cuugucgacc ucgcuccaga ugccgacccg guuggccguu uggcuauucu cgccaagcua   4980
ggucuugccc uagcugcggu caccccuggu uugauaaucu uggcaguggg acucuacagg   5040
uacuucucug gcucugauac agaccaagaa gaaacagaaa gugaggagcc ugcuaaagcg   5100
ccuaggagcg agaaugcuua ugacggcccg aagaaaaacu ccaagccccc uggagcgcuc   5160
ucccuuaugg aaaugcaaca gcccaacgug gacaugggcu uugaggcugc ggucgcuaag   5220
aaagugguucg uccccauuac cuucaugguu cccaacagac cuucuggacu uacacagucc   5280
gcucuucuug uggccggccg gaccuuccua auuaaugagc auacaugguc caaccccucc   5340
uggaccagcu ucacaauccg uggugaggug cacgcucgug augagccuuu ccaaacgguu   5400
cauuuuacuc accauggugu ucccacagau cuagugaugg uacgucucgg accgggcaac   5460
ucuuucccua acaaucuaga caaguuugga cuugaucaga ugccggcacg uaacuccegu   5520
gugguuggcg uuucggcuag uuacggcaac uucuucuucu cugggaacuu ccucgggguuu   5580
guugacucca ucaccucuga ccaaggaacu uaugcgagac uuuuuaggua cagggugacg   5640
acuuacaagg gauggugcgg uucggcccug guuugugagg ccggugggugu ccggcgcauc   5700
```

```
auuggccugc auucugcugg ugccgcuggu aucggcgccg ggacuuacau cucaaaauua   5760
ggacugauca aagcccucaa acaccucggu gaaccucugg cuacaaugca agggcugaug   5820
acugagcuag agccuggagu caccgugcau guaccccgga aaucuaaauu gagaaagacg   5880
accgcacacg cgguguacaa accggaguuu gaaccugcug uguugucaaa auuugauccc   5940
agacugaaca aggauguuga ccuagaugag gcaauuuggu cuaaacacac ugccaacguc   6000
ccuuaucaac cuccuuuguu cuacacauac augucagagu acgcucaucg gguuuucucc   6060
uuuuugggaa aagacaauga cauucugacc gucaaagaag caauuuuggg aaucccugga   6120
cuagacccua uggaucccca cacagcuccg ggucugcccu acgccauuag cggccuucga   6180
cguacugauc ucgucgauuu ugcgaacggc acgguagacc cgauacuggc caugcaaauc   6240
caaaaauucu uagacggug a cuacucugau caugucuucc aaacuuuucu gaaagaugaa   6300
aucagacccu cagagaaggu ccgagcggga aaaacccgca uugucgaugu gcccucccug   6360
gcgcacugca uugugggcag aauguugcuu gggcgcuuug ccgccaaguu ucaaucccau   6420
ccuggcuuuc uccuuggcuc ugcuauuggg ucugacccug augucuucug gaccgucaua   6480
ggggcucagc ucgagggaag aaagaacacg uaugacgugg acuacagugc cuuugacucu   6540
ucacacggca cuggcuccuu cgaggcucuc aucucucacu uuuucaccgu ggacaauggu   6600
uuuagcccug cgcugggacc guaucucaga ucccuggcug ucucggugca cgcuuacggc   6660
gagcgucgca ucaagauuac cggaggccuc cccucugguu gugccgcgac cagccugcug   6720
aacacagugc ucaacaaugu gaucaucagg acugcucugg cauugaccua caaggaauuu   6780
gaauaugaca ugguugauau caucgccuac ggugacgacc uucugguugg uacggauuac   6840
gaucuggacu ucaaugaggu ggcgcggcgc gcugccaaac ugggguauaa gaugacuccu   6900
gccaacaaag guucugucuu cccuccgacu uccucucucu ccgacgcugu uuuucuaaaa   6960
cgcaaauucg uccaaaacaa ugacggcuua uacaaaccag uuauggauuu aaagaauuug   7020
gaagccaugc ucuccuacuu caaaccagga acacuacucg agaagcugca aucuguuucu   7080
auguuggcuc aacauucugg aaaagaagaa uaugauagau ugaugcaccc cuuugcugac   7140
uacggugccg uaccgaguca cgaguaccug caggcaagau ggagggccuu guucgacuga   7200
ccuagauagc ccaacgcgcu ccggugcugc cggcgauucu gggagaacuc agucggaaca   7260
gaaaagggaa                                                          7270
```

<210> SEQ ID NO 9
<211> LENGTH: 7310
<212> TYPE: RNA
<213> ORGANISM: Senecavirus

<400> SEQUENCE: 9

```
uuugaaaugg ggggcugggc ccugaugccc aguccuuccu uuccccuucc gggggguuaa     60
ccggcugugu uugcuagagg cacagagggg caacauccaa ccugcuuuug cggggaacgg    120
ugcggcuccg auuccugcgu cgccaaaggu guuagcgcac ccaaacggcg caccuaccaa    180
uguuauuggu guggucugcg aguucuagcc uacucguuuc ucccccgacc auucacucac    240
ccacgaaaag uguguuguaa ccauaagauu uaacccccgc acgggaugug cgauaaccgu    300
aagacuggcu caagcgcgga aagcgcugua accacaugcu guuagucccu uuauggcugc    360
aagauggcua cccaccucgg aucacugaac uggagcucga cccuccuuag uaagggaacc    420
gagaggccuu cgugcaacaa gcuccgacac agaguccacg ugacugcuac caccaugagu    480
acaugguucu ccccucucga cccaggacuu cuuuuugaau auccacggcu cgauccagag    540
```

```
ggugggggcau gaccccuagc auagcgagcu acagcgggaa cuguagcuag gccuuagcgu    600
gccuuggaua cugccugaua gggcgacggc cuagucgugu cgguucuaua gguagcacau    660
acaaauaugc agaacucuca uuuuucuuuc gauacagccu cuggcaccuu ugaagaugua    720
accggaacaa aagucaagau cguugaauac cccagaucgg ugaacaaugg uguuuacgau    780
ucgucuacuc auuuggagau acugaaccua cagggugaaa uugaaauuuu aaggucuuuc    840
aaugaauacc aaauucgcgc cgccaaacaa caacucggac uggacaucgu guacgaacua    900
caggguaaug uucagacaac gucaaagaau gauuuugauu cccguggcaa uaaugguaac    960
augaccuuca auuacuacgc aaacacuuau cagaauucag uagacuucuc gaccuccucg   1020
ucggcgucag gcgccggacc cgggaacucc cggggcggau uagcgggucu ccucacaaau   1080
uucaguggaa ucuugaaccc ucuuggcuac cucaaagauc acaacaccga agaaauggaa   1140
aacucugcug aucgagucac aacgcaaacg gcgggcaaca cugccauaaa cacgcaauca   1200
ucauugggug uguugugugc cuacguugaa gacccgacca aaucugaucc uccguccagc   1260
agcacagauc aacccaccac cacuuucacu gccaucgaca ggugguacac uggacgucuc   1320
aauucuugga caaaagcugu aaaaaccuuc ucuuuucagg ccgucccgcu ucccggggcc   1380
uuucugucua ggcagggagg ccucaacgga ggggccuuca cagcuacccu acauagacac   1440
uuuuugauga agugcgggug gcaggugcag guccaaugua auuugacaca auuccaccaa   1500
ggcgcucuuc uuguugccau gguuccugaa accacccuug augucaagcc cgacgguaag   1560
gcaaagagcu uacaggagcu gaaugaagaa caguggguggg aaaugucuga cgauuaccgg   1620
accgggaaaa acaugccuuu ucagucucuu ggcacauacu aucggccccc uaacuggacu   1680
ugggguccca auuucaucaa ccccuaucaa guaacgguuu ucccacacca aauucugaac   1740
gcgagaaccu cuaccucggu agacauaaac gucccauaca ucggggagac ccccacgcaa   1800
uccucagaga cacagaacuc cuggacccuc cucguuaugg ugcucguucc ccuagacuau   1860
aaggaaggag ccacaacuga cccagaaauu acauuuucug uaaggccuac aagucccuac   1920
uucaaugggc uucgcaaccg cuacacggcc gggacggacg aagaacaggg gcccauuccu   1980
acggcaccca gagaaaauuc gcuuauguuu cucucaaccc ucccugacga cacugucccu   2040
gcuuacggga augugcguac cccuccuguc aauuaccucc cuggugaaau aaccgaccuu   2100
uugcaacugg cccgcauacc cacucucaug gcauuugagc gggugccuga acccgugccu   2160
gccucagaca cauaugugcc cuacguugcc guucccaccc aguucgauga caggccucuc   2220
aucuccuucc cgaucacccu uucagauccc gucuaucaga acacccuggu uggcgccauc   2280
aguucaaauu ucgccaauua ccgugggugu auccaaauca cucugacauu uuguggaccc   2340
augauggcga gagggaaauu ccugcucucg uauucucccc caaauggaac gcaaccacag   2400
acucuuuccg aagcuaugca gugcacauac ucuauuuggg acauaggcuu gaacucuagu   2460
uggaccuucg ucguccccua caucucgccc agugacuacc gugaaacucg agccauuacc   2520
aacucgguuu acuccgcuga ugguugguuu agccugcaca aguugaccaa aauuacucua   2580
ccaccugacu guccgcaaag ucccugcauu cucuuuuucg cuucugcugg ugaggauuac   2640
acucuccguc uccccguuga uuguaauccu uccuaugugu uccacuccac cgacaacgcc   2700
gagaccgggg uuauugaggc ggguaacacu gacaccgauu ucucugguga acuggcggcu   2760
ccuggcucua accacacuaa ugucaaguuc cuguuugauc gaucucgauu auugaaugua   2820
aucaagguac uggagaagga cgccguuuuc ccccgcccuu ucccuacaca agaaggugcg   2880
```

-continued

```
cagcaggaug augguuacuu uugucuucug accccccgcc caacagucgc uucccgaccc   2940
gccacucguu ucggccugua cgccaauccg uccggcagug guguucuugc uaacacuuca   3000
cuggacuuca auuuuuauag cuuggccugu uucacuuacu uuagaucgga ccuugagguu   3060
acggugguc u cacuagagcc ggaucuggaa uuugcuguag ggugguuucc uucuggcagu   3120
gaauaccagg cuuccagcuu ugucuacgac cagcugcaug ugcccuucca cuuuacuggg   3180
cgcacucccc gcgcuuucgc uagcaagggu gggaagguau cuuucgugcu cccuuggaac   3240
ucugucucgu cugugcuccc cgugcgcugg gggggggcuu ccaagcucuc uucugcuacg   3300
cggggucuac cggcgcaugc ugauuggggg acuauuuacg ccuuugaccc ccguccuaau   3360
gagaagaaaa gcaccgcugu aaaacacgug gccguguaca uucgguacaa gaacgcacgu   3420
gccuggugcc ccagcaugcu ucccuuucgc agcuacaagc agaagaugcu gaugcaaucu   3480
ggcgauaucg agaccaaucc ugguccugcu ucugacaacc caauuuugga guuucuugaa   3540
gcagaaaaug aucuagucac ucuggccucu cucuggaaga uggugcacuc uguucaacag   3600
accuggagaa aguaugugaa gaacgaugau uuuuggccca auuuacucag cgagcuagug   3660
ggggaaggcu cugucgccuu ggccgccacg cuauccaacc aagcuucagu aaaggcucuu   3720
uugggccugc acuuucucuc ucgggggcuc aauuacacug acuuuuacuc uuuacugaua   3780
gagaaaugcu cuaguuucuu uaccguagaa ccaccuccuc caccagcuga aaaccugaug   3840
accaagcccu cagugaaguc gaaauuccga aaacuguuua agaugcaagg acccauggac   3900
aaagucaaag acuggaacca aauagcugcc ggcuugaaga auuucaauu uguucgugac   3960
cuagucaaag agguggucga uuggcugcag gccuggauca acaaagagaa agccagcccu   4020
guccuccagu accaguugga gaugaagaag cucgggccug uggccuuggc ucaugacgcu   4080
uucauggcug guuccgggcc cccucuuagc gacgaccaga uugaauaccu ccagaaccuc   4140
aaaucucuug cccuaacacu ggggaagacu aauuuggccc aaagucucac cacuaugauc   4200
aaugccaaac aaaguucagc ccaacgaguu gaacccguug ugguggcccu uagaggcaag   4260
ccgggaugcg gcaagagcuu ggccucuacg uugauugccc aggcugugc caagcgccuc   4320
uauggcuccc aaaguguaua uucucuuccc ccagauccag auuucuucga uggauacaaa   4380
ggacaguucg ugaccuugau ggaugauuug ggacaaaacc cggauggaca agauuucucc   4440
accuuuuguc agauggugc gaccgcccaa uuucucccca acauggcgga ccuugcagag   4500
aaagggcguc ccuuuaccuc caaucucauc auugcaacua caaaucuccc ccacuucagu   4560
ccugucacca uugcugaucc uucugcaguc ucucgccgua ucaacuacga ucugacucua   4620
gaaguaucug aggccuacaa gaaacacaca cggcugaauu uugacuuggc uuucaggcgc   4680
acagacgccc cccccauuua uccuuuugcu gcccaugugc ccuuugugga cguagcugug   4740
cgcuucaaaa augguucacca gaauuuuaau cuccuagagu uggucgauuc cauuuguaca   4800
gacauucgag ccaagcaaca aggugcccga aacaugcaga cucugguucu acagagcccc   4860
aacgagaaug augacacccc cgucgacgag gcguugggua gaguucucuc ccccgcugcg   4920
gucgaugagg cgcuugucga ccucacucca gaggccgacc cgguuggccg uuuggcuauu   4980
cuugccaagc uaggucuugc ccuagcugcg gucaccccug gucugauaau cuuggcagug   5040
ggacucuaca gguacuucuc uggcucugau gcagaccaag aagaaacaga aagugaggga   5100
ucugucaagg cacccaggag cgaaaaugcu uaugacggcc cgaagaaaaa cucuaagccc   5160
ccuggagcac ucucucucau ggaaaugcaa cagcccaacg uggacauggg cuuugaggcu   5220
gcggucgcua agaaaguggu cguccccauu accuucaugg uucccaacag accuucuggg   5280
```

```
cuuacacagu ccgcucuucu ggugaccggc cggaccuucc uaaucaauga acauacaugg   5340
uccaaucccu ccuggaccag cuucacaauc cgcggugagg uacacacucg ugaugagccc   5400
uuccaaacgg uucauuucac ucaccacggu auucccacag aucugaugau gguacgucuc   5460
ggaccgggca auucuuuccc uaacaaucua gacaaguuug gacuugacca gaugccggca   5520
cgcaacuccc guguggu ugg cguuucgucc aguuacggaa acuucuucuu cucuggaaau   5580
uuccucggau uuguugauuc caucaccucu gaacaaggaa cuuacgcaag acucuuuagg   5640
uacagggu ga cgaccuacaa aggauggugc ggcucggccc uggucuguga ggccggu ggc   5700
guccgacgca ucauuggccu gcauucugcu ggcgccgccg guaucggcgc cgggaccuau   5760
aucucaaaau uaggacuaau caaagcccug aaacaccucg gugaaccuuu ggccacaaug   5820
caaggacuga ugacugaauu agagccugga aucaccguac auguaccccg gaaauccaaa   5880
uugagaaaga cgaccgcaca cgcgguguac aaaccggagu uugagccugc uguguuguca   5940
aaauuugauc ccagacugaa caaggauguu gacuuggaug aaguaauuug gucuaaacac   6000
acugccaaug ucccuuacca accuccuuug uucuacacau acaugucaga guacgcucau   6060
cgagucuucu ccuucuuggg gaaagacaau gacauucuga ccgucaaaga agcaauucug   6120
ggcauccccg gacuagaccc cauggauccc cacacagcuc cggg ucugcc uuacgccauc   6180
aacggccuuc gacguacuga ucucgucgau uuugugaacg guacaguaga ugcggcgcug   6240
gcuguacaaa uccagaaauu cuuagacggu gacuacucug accaugucuu ccaaacuuuu   6300
cugaaagaug agaucagacc cucagagaaa guccgagcgg gaaaaacccg cauuguugau   6360
gugcccuccc uggcgcauug cauugugggc agaauguugc uugggcgcuu ugcugccaag   6420
uuucaauccc auccuggcuu ucuccucggc ucugcuaucg ggucugaccc ugauguuuuc   6480
uggaccguca uaggggcuca acucgagggg agaaagaaca cguaugacgu ggacuacagu   6540
gccuuugacu cuucacacgg cacuggcucc uucgaggcuc ucaucucuca cuuuuucacc   6600
guggacaaug guuuuagccc ugcgcuggga ccguaucuca gaucccuggc ugucucggug   6660
cacgcuuacg gcgagcgucg caucaagauu accgguggcc ucccc uccgg uugugccgcg   6720
accagccugc ugaacacagu gcucaacaau gugaucauca ggacugcucu ggcauugacu   6780
uacaaggaau uugaauauga caugguugau aucaucgccu acggugacga ccuucugguu   6840
ggcacggauu acgaucugga cuucaaugag guggcacgac gcgcugccaa guuggggguau   6900
aagaugacuc cugccaacaa ggguucuguc uucccuccga cuuccucucu uuccgaugcu   6960
guuuuucuaa agcgcaaauu cguccaaaac aacgacggcu uauacaaacc aguuauggau   7020
uuaaagaauu uggaagccau gcucuccuac uucaaaccag gaacacuacu cgagaagcug   7080
caaucuguuu cuauguuggc ucaacauucu ggaaaagaag aauaugauag auugaugcac   7140
cccuucgcug acuacggugc cguaccgagu cacgaguacc ugcaggcaag auggagggcc   7200
uuguucgacu gacccagaua gcccaaggcg cuucggugcu gccggcgauu cugggagaac   7260
ucagucggaa cagaaaaggg aaaaaaaaaa aaaaaaaaaa aaaaaaaaaa              7310
```

<210> SEQ ID NO 10
<211> LENGTH: 7356
<212> TYPE: RNA
<213> ORGANISM: Senecavirus

<400> SEQUENCE: 10

```
agggggggc ugggcccuca ugcccagucc uuccuuuccc cuuccggggg guaaaccggc     60
```

```
uguguuugcu agaggcacag aggagcaaca cccaaccugc uuuugugggg aacggugcgg 120
cuccgauucc ugcgucgcca aaggguguuag cgcacccaaa cggcgcaucu accaaugcua 180
uugguguggu cugcgaguuc uagccuacuc guuucucccc uauccauuca cucacgcaca 240
aaaagugugu uguaacuaca agauuuagcc cucgcacgag augugcgaua accgcaagac 300
ugacucaagc gcggaaagcg cuguaaccac augcuguuag ucccuuuaug gcugcgagau 360
ggcuauccac cucggaucac ugaacuggag cucgacccuc cuuaguaagg gaaccgagag 420
gccuucuugc aacaagcucc gacacagagu ccacgugauu gcuaccacca ugaguacaug 480
guucuccccu cucgacccag gacuucuuuu ugaauaucca cggcucgauc cagagggugg 540
ggcaugaucc cccuagcaua gcgagcuaca gcgggaacug uagcuaggcc uuagcgugcc 600
uuggauacug ccugauaggg cgacggccua gucgugucgg uucuauaggu agcacauaua 660
aauaugcaga acucucauuu uucuuucgau acagccucug gcaccuuuga agacguaacc 720
ggaacaaaag ucaagaucgu ugaauacccc agaucgguga acaauggugu uuacgauucg 780
uccacucauu uagagauacu gaaccuacag ggugaaauug aaauuuuaag gucuuucaau 840
gaauaccaaa uucgcgccgc caaacaacaa cuuggacugg acauuguaua cgaacuacag 900
gguaauguuc agacaaccuc aaagaaugau uuugauuccc gcggcaauaa cgguaacaug 960
accuucaauu acuacgcaaa cacuuaucag aauucaguag acuucucgac cuccucgucg 1020
gcgucaggcg ccgggcccgg gaacucccgg ggcggauuag cgggucuccu cacaaauuuc 1080
aguggaaucu ugaacccucu uggcuaccuc aaagaucaca auaccgaaga aauggaaaac 1140
ucugcugauc gagucauaac gcaaacggcg ggcaacacug ccauaaacac gcaaucauca 1200
cugggugugu ugugugccua uguugaagac ccgaccaaau cugacccucc guccagcagc 1260
acagaucaac ccaccaccac uuuuacugcc aucgacaggu gguacacugg acgccucaau 1320
ucuuggacaa aagcuguaaa aaccuucucu uuucaggccg ucccgcuccc uggagccuuc 1380
cugucuagac agggaggccu caacggaggg gccuucacgg cuacccuaca cagacauuuc 1440
uuaaugaagu gcggguggca ggugcagguc caaugcaauu ugacacaauu ccaccaaggu 1500
gcucuucuug uugccauggu ccccgaaacc acccuygaug ucaagcccga cggcaaggca 1560
aagagccuac aggagcugaa ugaagagcag uggguagaaa ugucugacga uuaccggacc 1620
gggaaaaaca ugccuuuuca gucucuuggc acauacuauc ggccccccuaa cuggacuugg 1680
ggcccuaauu ucaucaaccc cuaucaagua acaguuuucc cacaccaaau ucugaacgcg 1740
agaaccucua ccucgguaga cauaagugucc ccauacaucg gggagacucc uacacaaucc 1800
ucagagacac agaacuccug gacccuccuc guuauggugc uuguccccccu ggacuacaag 1860
gagggagcca caacugaccc agaaauuaca uuucuguaa ggccuacaag uccuuacuuc 1920
aaugggcuuc guaaccguua cacgaccggg acggacgagg aacaggggcc cauucccaca 1980
gcacccagag aaaauucgcu uauguuucuc ucaaccaucc cugacgacac ugucccugcu 2040
uacgggaaug ugcguacccc ucccgucaau uaccucccug gugaaauaac cgaccucuua 2100
caacuggccc guauacccac ucucauggcg uuugggcggg ugucugaacc cgagccugcc 2160
ucagacgcau augugcccua cguugccguu cccacccagu ucgaugacaa gccucucauc 2220
uccuucccga ucacccuuuc agauccuguc uaccagaaca cccugguagg cgccaucagu 2280
ucgaauuucg ccaacuaccg gggguguauc caaaucacuc ugacauuuug uggacccaug 2340
auggcaagag ggaaauuccu acucucguau ucuccccccaa auggaacgca accacagacu 2400
cuuucugaag ccaugcagug cacauacucc auuugggaua uaggcuugaa cucuaguugg 2460
```

```
accuuuguca uccccuacau cucgcccagu gacuaccgug aaacucgggc caucaccaac   2520
ucgguuuacu cugccgaugg uugguuuagc cugcacaagc ugaccaaaau cacucuaccg   2580
ccugacugcc cacagaaacc cuguauucuc uuuuucgccu cugcugguga ggauuacacc   2640
cuccgucucc ccguugauug uaauccuucc uacguguucc acuccaccga caacgccgag   2700
acuggggguua uugaggcggg uaacacugac accgauuucu cuggugaacu ggcggcuccu   2760
ggcucuaacc acacuaaugu caaguuccug uuugaucgau cucgauuacu gaauguaauu   2820
aagguacugg agaaggacgc cgucuucccc cguccuuucc ccacagaaac aggugcgcag   2880
caggacgaug guuacuuuug ucuucuaaca ccccgcccaa cagucgccuc ccgacccgcc   2940
acucguuucg gccuguacgu caauccgucu gacaguggcg uucucgccaa cacuucacug   3000
gauuucaauu uuuacagcuu ggccuguuuc acuuacuuua gaucagaccu ugaagucacg   3060
gugguucucac uggagccaga ucuggaauuu gcuguagggu gguuccccuc uggcagugag   3120
uaccaggcuu ccagcuuugu cuacgaccaa cugcauguac ccuaccacuu uaccgggcgc   3180
acuccccgcg cuuucaccag caagggguggg aagguaucuu ucgugcuccc uuggaacucu   3240
gucucauccg ugcuucccgu gcgcuggggg gcggcuucca agcucucuuc ugccacgcgg   3300
gguuugccgg cgcaugcuga cugggggacu auuuaugcuu ucguccccccg uccuaaugag   3360
aagaaaagca ccgcuguaaa gcacguggcc guguacguuc gguacaagaa cgcacgugcc   3420
uggugcccua gcaugcuucc cuuucgcagc uacaagcaga agaugcugau gcaaucuggc   3480
gauaucgaga ccaauccugg cccugcuucu gacaacccaa ucuuggaguu ucuugaggca   3540
gaaaacgauc uagucacucu ggccucucuc uggaagaugg uacacucugu ucagcagacc   3600
uggagaaagu acgugaagaa cgacaacuuu uggcccaauu uacucaguga gcugguggggg   3660
gaaggcucca ucgccuuggc cgccacacua uccaaccaag cuucaguaaa ggcucucuug   3720
ggccugcauu uucucucccg ggggcucaau uacacagacu uuuacuccuu acugauagag   3780
aaaugcucua guuucuucac uguagaacca ccuccuccac cagccgagaa ccugaugacc   3840
aagcccuccg ugaagucgaa auuccgaaag cuguuuaaga ugcaagggcc cauggacaaa   3900
gucaaagacu ggaaccaaau agccgccggu uugaagaauu uccaauuugu ccgugaccua   3960
gucaaagagg uggucgacug gcugcaggcc uggaucaaca aggagaaagc cagcccuguc   4020
cuccaguauc aguuagagau gaagaagcuc gggccugugg cucuggcuca ugaugcuuuc   4080
auggcugguu cugggccccc ucuuagugac gaucagauug aauaucucca gaaccuuaaa   4140
ucucuugccc uaacacuggg gaagacuaau uuggcccaaa gucucaccac uaugaucaau   4200
gccaaacaaa guuccgccca acgagucgaa cccguugugg ugguccuuag aggcaagccg   4260
ggaugcggca agagcuuggc cuccacgcug auugcccagg cuguguccaa gcgucucuac   4320
ggcucccaaa guguguauuc ucuucccccg gauccagauu ucuucgacgg auacaaagga   4380
caguuuguaa ccuugaugga ugaucuggga caaaacccgg auggacaaga uuucuccacc   4440
uuuugucaga uggugucgac cgcccaauuu cuccccaaca uggcggaccu ugcagagaag   4500
gggcgucccu ucaccuccaa ucuuaucauu gcaaccacaa accucccccca cuucagcccu   4560
gucaccauug cugauccuuc cgcagucucu cgucguauca acuacgaccu gacucuagaa   4620
guaucugagg ccuacaagaa gcauacacgg cugaauuuug accuggcuuu caggcgcaca   4680
gacgcccccc ccauuuaucc uuuugcugcc caugugcccu ucguggacgu agcugugcgc   4740
uucaaaaaug gucaccagaa cuuuaaucuc cuagaguugg ucgacuccau uugugcagac   4800
```

-continued

```
auucgagcca agcaacaagg ugcccggaac augcagacuu uggucuuaca gagcccuaau   4860

gagaaugaug acacccccgu cgacgaggcg uuggguagag uucucacccc cgcugcgguc   4920

gacgaggcgc uugucgaccu cgcuccagag gccgauccgg uuggccgcuu ggcuauucuu   4980

gccaagcuag gucuugcccu agcugcgguc accccugguu ugauaaucuu ggcaguggga   5040

cuuuacaggu acuucucugg cucugauaca gaccaagaug aaacagaaug ugaggaaucu   5100

accaaagcac cuaggagcga aaaugcuuau gacggcccga agaaaaacuc uaagcccccu   5160

ggagcacucu cucuuaugga aaugcaacag cccaacgugg acaugggcuu ugaggcugcg   5220

gucgcuaaga aaguggucgu ccccauuacc uucaugguuc ccaacagacc cucuggacuu   5280

acacaguccg cucuucuugu ggccggccgg accuuccuaa ucaaugagca cacaugguca   5340

aaucccuccu ggaccagcuu caccauccgu ggugaggugc auacucguga ugagccuuuu   5400

caaacgguuc auuuuaccca ccauggugu cccacagauc ugaugauggu acgucucgga   5460

ccgggcaacu cuuucccuaa caaucuagac aaguuuggac uugaccagau gccggcacgc   5520

aacucccgug ugguuggcgu uucgucuagu uacggcaauu ucuucuucuc ugggaauuuc   5580

cucggguucg uugacuccau caccucugaa caaggaacuu augcaagacu uuuuagguac   5640

agggugacga cuuacaaggg cuggugcggc ucggcccugg ucugugaggc cgguggugu    5700

cggcgcauca uuggccugca uucugcuggu gccgcuggua uuggugccgg gaccuacauc   5760

ucaaaauuag gacugaucaa agcucugaaa caccucggug aaccucuggc uacaaugcaa   5820

ggacugauga cugaguuaga gccuggaauc accguacaug uaccccggaa aucuaaauug   5880

agaaagacga ccgcacacgc aguguacaaa ccggaguuug aaccugcugu guugucaaaa   5940

uuugauccca gacugaacaa ggauguugac uuagaugagg uaauuugguc uaaacacacu   6000

gccaacgucc ccuaucaacc uccuuuguuc uacacauaca ugucagagua cgcucaucga   6060

guuuucuccu ucuugggaaa agacaaugac auucugaccg ucaaagaagc aauccugggc   6120

aucccuggac uagaccccau ggauccccac acagcuccgg gucugcccua ugccauuaac   6180

ggccuucgac guacugaucu cgucgacuuu gugaacggca cgguagacgc agcgcuggcc   6240

augcaaaucc agaaauucuu agacggugac uacucugauc augucuucca aacuuuucug   6300

aaagaugaaa ucagacccuc agagaagguc cgagcgggaa aaacccgcau ugucgaugug   6360

cccucccugg cgcauugcau ugugggcaga augcugcuug ggcgcuuugc cgccaaguuu   6420

caaucccauc cuggcuuucu ccuuggcucu gcuaucggcu cugacccuga uguuucugg    6480

accgucauag ggcucagcu cgagggaaga aagaacacgu augacgugga uuacagugcc    6540

uuugacucuu cacacggcac uggcuccuuc gaggcucuca ucucucacuu uuucaccgug   6600

gacaaugguu uuagcccugc gcugggaccg uaucucagau cccuggcugu cucggugcac   6660

gcuuacggcg agcgucgcau caagauuacc gguggccucc ccuccgguug ugccgcgacc   6720

agcuugcuga acacagugcu caacaaugug aucaucagga cugcucuggc auugacuuac   6780

aaggaauuug aguaugacau gguugauauc aucgccuacg gugacgaccu ucugguuggu   6840

acggauuacg aucuggacuu caaugaggug gcacgacgcg cugccaaacu gggguauaag   6900

augacucccg ccaacaaagg uuccgucuuc ccuccgacuu ccucucucuc cgaugcuguu   6960

uuucuaaaac gcaaauucgu ccaaaacaau gauggcuuau acaaaccagu uauggauuua   7020

aagaauuugg aagccaugcu cuccuacuuc aaaccaggaa cacuacucga gaagcugcaa   7080

ucuguuucua uguuggcuca acauucugga aaagaagaau augauagauu gaugcacccc   7140

uucgcugacu acggugccgu accgagucac gaguaccugc aggcaagaug gagggccuug   7200
```

```
uucgauugac ccagauagcc caaggcgcuu cgguguugcc ggcgauucug ggagaacuca   7260

gucggaacag aaaagggaaa aaaaaaawaa aaaaaaraaa aaaacaaaaa auaaaaacaa   7320

aaauaaacac gaccucacua cgagagcuga gacugc                             7356
```

<210> SEQ ID NO 11
<211> LENGTH: 7310
<212> TYPE: RNA
<213> ORGANISM: Senecavirus

<400> SEQUENCE: 11

```
uuugaaaugg ggggcugggc ccugaugccc aguccuuccu uucccccuucc ggggggguuaa     60

ccggcugugu uugcuagagg cacagagggg caacauccaa ccugcuuuug cggggaacgg    120

ugcggcuccg auuccugcgu cgccaaaggu guuagcgcac ccaaacggcg caccuaccaa    180

uguuauuggu guggucugcg aguucuagcc uacucguuuc ucccccgacc auucacucac    240

ccacgaaaag ugugguugaa ccauaagauu uaaccccccgc acgggaugug cgauaaccgu    300

aagacuggcu caagcgcgga aagcgcugua accacaugcu guuaguccu uuauggcugc    360

aagauggcua cccaccucgg aucacugaac uggagcucga cccuccuuag uaagggaacc    420

gagaggccuu cgugcaacaa gcuccgacac agaguccacg ugacugcuac caccaugagu    480

acaugguucu ccccucucga cccaggacuu cuuuuugaau auccacggcu cgauccagag    540

gguggggcau gaccccuagc auagcgagcu acagcgggaa cuguagcuag gccuuagcgu    600

gccuuggaua cugccugaua gggcgacggc cuagucgugu cgguucuaua gguagcacau    660

acaaauaugc agaacucuca uuuuucuuuc gauacagccu cuggcaccuu ugaagaugua    720

accggaacaa aagucaagau cguugaauac cccagaucgg ugaacaaugg uguuuacgau    780

ucgucuacuc auuuggagau acugaaccua cagggugaaa uugaaauuuu aaggucuuuc    840

aaugaauacc aaauucgcgc cgccaaacaa caacucggac uggacaucgu guacgaacua    900

caggguaaug uucagacaac gucaaagaau gauuuugauu cccguggcaa uaaugguaac    960

augaccuuca auuacuacgc aaacacuuau cagaauucag uagacuucuc gaccuccucg   1020

ucggcgucag gcgccggacc cgggaacucc cggggcggau uagcgggucu ccucacaaau   1080

uucaguggaa ucuugaaccc ucuuggcuac cucaaagauc acaacaccga agaaauggaa   1140

aacucugcug aucgagucac aacgcaaacg gcgggcaaca cugccauaaa cacgcaauca   1200

ucauugggug uguugugugc cuacguugaa gacccgacca aaucugaucc uccguccagc   1260

agcacagauc aacccaccac cacuuucacu gccaucgaca ggugguacac uggacgucuc   1320

aauucuugga caaaagcugu aaaaaccuuc ucuuuucagg ccgucccgcu ucccggggcc   1380

uuucugucua ggcagggagg ccucaacgga ggggccuuca cagcuacccu acauagacac   1440

uuuuugauga agugcgggug gcaggugcag guccaaugua auuugacaca auuccaccaa   1500

ggcgcucuuc uuguugccau gguuccugaa accacccuug augucaagcc cgacgguaag   1560

gcaaagagcu uacaggagcu gaaugaagaa cagugggugg aaaugucuga cgauuaccgg   1620

accgggaaaa acaugccuuu ucagucucuu ggcacauacu aucggccccc uaacuggacu   1680

uggggucccca auuucaucaa ccccuaucaa guaacgguuu ucccacacca aauucugaac   1740

gcgagaaccu cuaccucggu agacauaaac gucccauaca ucggggagac ccccacgcaa   1800

uccucagaga cacagaacuc cuggacccuc cucguuaugg ugcucguucc ccuagacuau   1860

aaggaaggag ccacaacuga cccagaaauu acauuuucug uaaggccuac aagucccuac   1920
```

```
uucaaugggc uucgcaaccg cuacacggcc gggacggacg aagaacaggg gcccauuccu   1980
acggcaccca gagaaaauuc gcuuauguuu cucucaaccc ucccugacga cacugucccu   2040
gcuuacggga augugcguac cccuccuguc aauuaccucc cuggugaaau aaccgaccuu   2100
uugcaacugg cccgcauacc cacucucaug gcauuugagc gggugccuga acccgugccu   2160
gccucagaca cauaugugcc cuacguugcc guucccaccc aguucgauga caggccucuc   2220
aucuccuucc cgaucacccu uucagauccc gucuaucaga acacccuggu uggcgccauc   2280
aguucaaauu ucgccaauua ccgugggugu auccaaauca cucugacauu uuguggaccc   2340
augauggcga gagggaaauu ccugcucucg uauucucccc caaauggaac gcaaccacag   2400
acucuuuccg aagcuaugca gugcacauac ucuauuuggg acauaggcuu gaacucuagu   2460
uggaccuucg ucguccccua caucucgccc agugacuacc gugaaacucg agccauuacc   2520
aacucgguuu acuccgcuga ugguugguuu agccugcaca aguugaccaa aauuacucua   2580
ccaccugacu guccgcaaag ucccugcauu cucuuuuucg cuucugcugg ugaggauuac   2640
acucuccguc uccccguuga uuguaauccu uccuaugugu uccacuccac cgacaacgcc   2700
gagaccgggg uuauugaggc ggguaacacu gacaccgauu ucucugguga acuggcggcu   2760
ccuggcucua accacacuaa ugucaaguuc cuguuugauc gaucucgauu auugaaugua   2820
aucaagguac uggagaagga cgccguuuuc ccccgcccuu ucccuacaca agaaggugcg   2880
cagcaggaug augguuacuu uugucuucug accccccgcc caacagucgc uucccgaccc   2940
gccacucguu ucggccugua cgccaauccg uccggcagug guguucuugc uaacacuuca   3000
cuggacuuca auuuuuauag cuuggccugu uucacuuacu uuagaucgga ccuugagguu   3060
acggugguc u cacuagagcc ggaucuggaa uuugcuguag ggugguuucc uucuggcagu   3120
gaauaccagg cuuccagcuu ugucuacgac cagcugcaug ugcccuucca cuuuacuggg   3180
cgcacucccc gcgcuuucgc uagcaagggu gggaagguau cuuucgugcu cccuuggaac   3240
ucugucucgu cugugcuccc cgugcgcugg gggggggcuu ccaagcucuc uucugcuacg   3300
cggggucuac cggcgcaugc ugauuggggg acuauuuacg ccuuugaccc ccguccuaau   3360
gagaagaaaa gcaccgcugu aaaacacgug gccguguaca uucgguacaa gaacgcacgu   3420
gccuggugcc ccagcaugcu ucccuuucgc agcuacaagc agaagaugcu gaugcaaucu   3480
ggcgauaucg agaccaaucc ugguccugcu ucugacaacc caauuuugga guuucuugaa   3540
gcagaaaaug aucuagucac ucuggccucu cucuggaaga uggugcacuc uguucaacag   3600
accuggagaa aguaugugaa gaacgaugau uuuuggccca auuuacucag cgagcuagug   3660
ggggaaggcu cugucgccuu ggccgccacg cuauccaacc aagcuucagu aaaggcucuu   3720
uugggccugc acuuucucuc ucgggggcuc aauuacacug acuuuuacuc uuuacugaua   3780
gagaaaugcu cuaguuucuu uaccguagaa ccaccuccuc caccagcuga aaaccugaug   3840
accaagcccu cagugaaguc gaaauuccga aaacuguuua agaugcaagg acccauggac   3900
aaagucaaag acuggaacca aauagcugcc ggcuugaaga auuucaauu uguucgugac   3960
cuagucaaag agguggucga uuggcugcag gccuggauca acaaagagaa agccagcccu   4020
guccuccagu accaguugga gaugaagaag cucgggccug uggccuuggc ucaugacgcu   4080
uucauggcug guuccgggcc cccucuuagc gacgaccaga uugaauaccu ccagaaccuc   4140
aaaucucuug cccuaacacu ggggaagacu aauuuggccc aaagucucac cacuaugauc   4200
aaugccaaac aaaguucagc ccaacgaguu gaacccguug ugguggaccu uagaggcaag   4260
ccgggaugcg gcaagagcuu ggccucuacg uugauugccc aggcuguguc caagcgccuc   4320
```

```
uauggcuccc aaaguguaua uucucuuccc ccagauccag auuucuucga uggauacaaa   4380
ggacaguucg ugaccuugau ggaugauuug ggacaaaacc cggauggaca agauuucucc   4440
accuuuuguc agauggugucuc gaccgcccaa uuucucccca acauggcgga ccuugcagag   4500
aaagggcguc ccuuuaccuc caaucucauc auugcaacua caaaucuccc ccacuucagu   4560
ccugucacca uugcugaucc uucugcaguc ucucgccgua ucaacuacga ucugacucua   4620
gaaguaucug aggccuacaa gaaacacaca cggcugaauu uugacuuggc uuucaggcgc   4680
acagacgccc cccccauuua uccuuuugcu gcccaugugc ccuuugugga cguagcugug   4740
cgcuucaaaa auggucacca gaauuuuaau cuccuagagu uggucgauuc cauuuguaca   4800
gacauucgag ccaagcaaca aggugcccga aacaugcaga cucugguucu acagagcccc   4860
aacgagaaug augacacccc cgucgacgag gcguugggua gaguucucuc ccccgcugcg   4920
gucgaugagg cgcuugucga ccucacucca gaggccgacc cgguuggccg uuuggcuauu   4980
cuugccaagc uaggucuugc ccuagcugcg gucaccccug gucugauaau cuuggcagug   5040
ggacucuaca gguacuucuc uggcucugau gcagaccaag aagaaacaga aagugaggga   5100
ucugucaagg cacccaggag cgaaaaugcu uaugacggcc cgaagaaaaa cucuaagccc   5160
ccuggagcac ucucucucau ggaaaugcaa cagcccaacg uggacauggg cuuugaggcu   5220
gcggucgcua agaaagugu cguccccauu accuucaugg uucccaacag accuucuggg   5280
cuuacacagu ccgcucuucu ggugaccggc cggaccuucc uaaucaauga acauacaugg   5340
uccaaucccu ccuggaccag cuucacaauc cgcggugagg uacacacucg ugaugagccc   5400
uuccaaacgg uucauuucac ucaccacggu auucccacag aucugaugau gguacgucuc   5460
ggaccgggca auucuuuccc uaacaaucua gacaaguuug gacuugacca gaugccggca   5520
cgcaacuccc gugugguugg cguuucgucc aguuacggaa acuucuucuu cucuggaaau   5580
uuccucggau uuguugauuc caucaccucu gaacaaggaa cuuacgcaag acucuuuagg   5640
uacagggugaa cgaccuacaa aggauggugc ggcucggccc uggucuguga ggccggguggc   5700
guccgacgca ucauuggccu gcauucugcu ggcgccgccg guaucggcgc cgggaccuau   5760
aucucaaaau uaggacuaau caaagcccug aaacaccucg gugaaccuuu ggccacaaug   5820
caaggacuga ugacugaauu agagccugga aucaccguac auguaccccg gaaauccaaa   5880
uugagaaaga cgaccgcaca cgcgguguac aaaccggagu uugagccugc uguguuguca   5940
aaauuugauc ccagacugaa caaggauguu gacuuggaug aaguaauuug gucuaaacac   6000
acugccaaug ucccuuacca accuccuuug uucuacacau acaugucaga guacgcucau   6060
cgagucuucu ccuucuuggg gaaagacaau gacauucuga ccgucaaaga agcaauucug   6120
ggcauccccg gacuagaccc cauggauccc cacacagcuc cggguccugcc uuacgccauc   6180
aacggccuuc gacguacuga ucucgucgau uuugugaacg guacaguaga ugcggcgcug   6240
gcuguacaaa uccagaaauu cuuagacggu gacuacucug accaugucuu ccaaacuuuu   6300
cugaaagaug agaucagacc cucagagaaa guccgagcgg gaaaaacccg cauuguugau   6360
gugcccuccc uggcgcauug cauugugggc agaauguugc uugggcgcuu ugcugccaag   6420
uuucaauccc auccuggcuu ucuccucggc ucugcuaucg ggucugaccc ugauguuuuc   6480
uggaccguca uaggggcuca acucgagggg agaaagaaca cguaugacgu ggacuacagu   6540
gccuuugacu cuucacacgg cacuggcucc uucgaggcuc ucaucucuca cuuuuucacc   6600
guggacaaug guuuuagccc ugcgcuggga ccguaucuca gaucccuggc ugucucggug   6660
```

```
cacgcuuacg gcgagcgucg caucaagauu accgguggcc uccccuccgg uugugccgcg   6720

accagccugc ugaacacagu gcucaacaau gugaucauca ggacugcucu ggcauugacu   6780

uacaaggaau uugaauauga cagguugau aucaucgccu acggugacga ccuucugguu   6840

ggcacggauu acgaucugga cuucaaugag guggcacgac gcgcugccaa guuggggguau   6900

aagaugacuc cugccaacaa ggguucuguc uucccuccga cuuccucucu uuccgaugcu   6960

guuuuucuaa agcgcaaauu cguccaaaac aacgacggcu uauacaaacc aguuauggau   7020

uuaaagaauu uggaagccau gcucuccuac uucaaaccag gaacacuacu cgagaagcug   7080

caaucuguuu cuauguuggc ucaacauucu ggaaaagaag aauaugauag auugaugcac   7140

cccuucgcug acuacggugc cguaccgagu cacgaguacc ugcaggcaag auggagggcc   7200

uuguucgacu gacccagaua gcccaaggcg cuucggugcu gccggcgauu cugggagaac   7260

ucagucggaa cagaaaaggg aaaaaaaaaa aaaaaaaaaa aaaaaaaaaa             7310
```

<210> SEQ ID NO 12
<211> LENGTH: 7310
<212> TYPE: RNA
<213> ORGANISM: Senecavirus

<400> SEQUENCE: 12

```
uuugaaaugg ggggcugggc ccugaugccc aguccuuccu uuccccuucc gggggguuaa     60

ccggcugugu uugcuagagg cacagagggg caacauccaa ccugcuuuug cggggaacgg    120

ugcggcuccg auuccugcgu cgccaaaggu guuagcgcac ccaaacggcg caccuaccaa    180

uguuauuggu guggucugcg aguucuagcc uacucguuuc ucccccgacc auucacucac    240

ccacgaaaag uguguuguaa ccauaagauu uaaccccccgc acgggaugug cgauaaccgu    300

aagacuggcu caagcgcgga aagcgcugua accacaugcu guuaguccu uuauggcugc    360

aagauggcua cccaccucgg aucacugaac uggagcucga cccuccuuag uaagggaacc    420

gagaggccuu cgugcaacaa gcuccgacac agaguccacg ugacugcuac caccaugagu    480

acaugguucu ccccucucga cccaggacuu cuuuuugaau auccacggcu cgauccagag    540

ggugggggcau gaccccuagc auagcgagcu acagcgggaa cuguagcuag gccuuagcgu    600

gccuuggaua cugccugaua gggcgacggc cuagucgugu cgguucuaua gguagcacau    660

acaaauaugc agaacucuca uuuuucuuuc gauacagccu cuggcaccuu ugaagaugua    720

accggaacaa aagucaagau cguugaauac cccagaucgg ugaacaaugg uguuuacgau    780

ucgucuacuc auuuggagau acugaaccua cagggugaaa uugaaauuuu aaggucuuuc    840

aaugaauacc aaauucgcgc cgccaaacaa caacucggac uggacaucgu guacgaacua    900

caggguaaug uucagacaac gucaaagaau gauuuugauu cccguggcaa uaaugguaac    960

augaccuuca auuacuacgc aaacacuuau cagaauucag uagacuucuc gaccuccucg   1020

ucggcgucag gcgccggacc cgggaacucc cggggcggau uagcgggucu ccucacaaau   1080

uucaguggaa ucuugaaccc ucuuggcuac cucaaagauc acaacaccga agaaauggaa   1140

aacucugcug aucgagucac aacgcaaacg gcgggcaaca cugccauaaa cacgcaauca   1200

ucauugggug uguugugugc cuacguugaa gacccgacca aaucugaucc uccguccagc   1260

agcacagauc aacccaccac cacuuucacu gccaucgaca ggugguacac uggacgucuc   1320

aauucuugga caaaagcugu aaaaaccuuc ucuuuucagg ccgucccgcu ucccggggcc   1380

uuucugucua ggcagggagg ccucaacgga ggggccuuca cagcuacccu acauagacac   1440

uuuuugauga agugcgggug gcaggugcag guccaaugua auuugacaca auuccaccaa   1500
```

```
ggcgcucuuc uuguugccau gguuccugaa accacccuug augucaagcc cgacgguaag   1560
gcaaagagcu uacaggagcu gaaugaagaa caguggugg aaaugucuga cgauuaccgg   1620
accgggaaaa acaugccuuu ucagucucuu ggcacauacu aucggccccc uaacuggacu   1680
ugggguccca auuucaucaa ccccuaucaa guaacgguuu ucccacacca aauucugaac   1740
gcgagaaccu cuaccucggu agacauaaac gucccauaca ucggggagac ccccacgcaa   1800
uccucagaga cacagaacuc cuggacccuc cucguuaugg ugcucguucc ccuagacuau   1860
aaggaaggag ccacaacuga cccagaaauu acauuuucug uaaggccuac aagucccuac   1920
uucaaugggc uucgcaaccg cuacacggcc gggacggacg aagaacaggg gcccauuccu   1980
acggcaccca gagaaaauuc gcuuauguuu cucucaaccc ucccugacga cacuguccu    2040
gcuuacggga augugcguac cccuccuguc aauuaccucc cuggugaaau aaccgaccuu   2100
uugcaacugg cccgcauacc cacucucaug gcauuugagc gggugccuga acccgugccu   2160
gccucagaca cauaugugcc cuacguugcc guucccaccc aguucgauga caggccucuc   2220
aucuccuucc cgaucacccu uucagauccc gucuaucaga acacccuggu uggcgccauc   2280
aguucaaauu ucgccaauua ccgugggugu auccaaauca cucugacauu uuguggaccc   2340
augauggcga gagggaaauu ccugcucucg uauucucccc caaauggaac gcaaccacag   2400
acucuuuccg aagcuaugca gugcacauac ucuauuuggg acauaggcuu gaacucuagu   2460
uggaccuucg ucguccccua caucucgccc agugacuacc gugaaacucg agccauuacc   2520
aacucgguuu acuccgcuga ugguugguuu agccugcaca aguugaccaa aauuacucua   2580
ccaccugacu guccgcaaag ucccugcauu cucuuuuucg cuucugcugg ugaggauuac   2640
acucuccguc uccccguuga uuguaauccu uccuaugugu uccacuccac cgacaacgcc   2700
gagaccgggg uuauugaggc ggguaacacu gacaccgauu ucucugguga acuggcggcu   2760
ccuggcucua accacacuaa ugucaaguuc cuguuugauc gaucucgauu auugaaugua   2820
aucaagguac uggagaagga cgccguuuuc ccccgcccuu ucccuacaca agaaggugcg   2880
cagcaggaug augguuacuu uugucuucug accccccgcc caacagucgc uucccgaccc   2940
gccacucguu ucggccugua cgccaauccg uccggcagug guguucuugc uaacacuuca   2999
cuggacuuca auuuuuauag cuuggccugu uucacuuacu uuagaucgga ccuugagguu   3060
acggugguc  cacuagagcc ggaucuggaa uuugcuguag gguggguuucc uucuggcagu  3120
gaauaccagg cuuccagcuu ugucuacgac cagcugcaug ugcccuucca cuuuacuggg   3180
cgcacucccc gcgcuuucgc uagcaagggu gggaagguau cuuucgugcu cccuuggaac   3240
ucugucucgu cugugcuccc cgugcgcugg gggggggcuu ccaagcucuc uucugcuacg   3300
cggggucuac cggcgcaugc ugauuggggg acuauuuacg ccuuugucccc ccguccuaau  3360
gagaagaaaa gcaccgcugu aaaacacgug gccguguaca uucgguacaa gaacgcacgu   3420
gccuggugcc ccagcaugcu ucccuuucgc agcuacaagc agaagaugcu gaugcaaucu   3480
ggcgauaucg agaccaaucc ugguccugcu ucugacaacc caauuuugga guuucuugaa   3540
gcagaaaaug aucuagucac ucuggccucu cucuggaaga uggugcacuc uguucaacag   3600
accuggagaa aguaugugaa gaacgaugau uuuuggccca auuuacucag cgagcuagug   3660
ggggaaggcu cugucgccuu ggccgccacg cuauccaacc aagcuucagu aaaggcucuu   3720
uugggccugc acuuucucuc ucgggggcuc aauuacacug acuuuuacuc uuuacugaua   3780
gagaaaugcu cuaguuucuu uaccguagaa ccaccuccuc caccagcuga aaaccugaug   3840
```

```
accaagcccu cagugaaguc gaaauuccga aaacuguuua agaugcaagg acccauggac   3900
aaagucaaag acuggaacca aauagcugcc ggcuugaaga auuuucaauu uguucgugac   3960
cuagucaaag agguggucga uuggcugcag gccuggauca acaaagagaa agccagcccu   4020
guccuccagu accaguugga gaugaagaag cucgggccug uggccuuggc ucaugacgcu   4080
uucauggcug guuccgggcc cccucuuagc gacgaccaga uugaauaccu ccagaaccuc   4140
aaaucucuug cccuaacacu ggggaagacu aauuuggccc aaagucucac cacuaugauc   4200
aaugccaaac aaaguucagc ccaacgaguu gaacccguug ugguuggucu uagaggcaag   4260
ccgggaugcg gcaagagcuu ggccucuacg uugauugccc aggcuguguc caagcgccuc   4320
uauggcuccc aaaguguaua uucucuuccc ccagauccag auuucuucga uggauacaaa   4380
ggacaguucg ugaccuugau ggaugauuug ggacaaaacc cggauggaca agauuucucc   4440
accuuuuguc agaugguguc gaccgcccaa uuucucccca acauggcgga ccuugcagag   4500
aaagggcguc ccuuuaccuc caaucucauc auugcaacua caaaucuccc ccacuucagu   4560
ccugucacca uugcugaucc uucugcaguc ucucgccgua ucaacuacga ucugacucua   4620
gaaguaucug aggccuacaa gaaacacaca cggcugaauu uugacuuggc uuucaggcgc   4680
acagacgccc cccccauuua ucccuuuugcu gcccaugugc ccuuugugga cguagcugug   4740
cgcuucaaaa auggucacca gaauuuuaau cuccuagagu uggucgauuc cauuuguaca   4800
gacauucgag ccaagcaaca aggugcccga aacaugcaga cucugguucu acagagcccc   4860
aacgagaaug augacacccc cgucgacgag gcguugggua gaguucucuc ccccgcugcg   4920
gucgaugagg cgcuugucga ccucacucca gaggccgacc cgguuggccg uuuggcuauu   4980
cuugccaagc uaggucuugc ccuagcugcg gucaccccug gucugauaau cuuggcagug   5040
ggacucuaca gguacuucuc uggcucugau gcagaccaag aagaaacaga aagugaggga   5100
ucugucaagg cacccaggag cgaaaaugcu uaugacggcc cgaagaaaaa cucuaagccc   5160
ccuggagcac ucucucucau ggaaaugcaa cagcccaacg uggacauggg cuuugaggcu   5220
gcggucgcua agaaagugu cguccccauu accuucaugg uucccaacag accuucuggg   5280
cuuacacagu ccgcucuucu ggugaccggc cggaccuucc uaaucaauga acauacaugg   5340
uccaaucccu ccuggaccag cuucacaauc cgcggugagg uacacacucg ugaugagccc   5400
uuccaaacgg uucauuucac ucaccacggu auucccacag aucugaugau gguacgucuc   5460
ggaccgggca auucuuuccc uaacaaucua gacaaguuug gacuugacca gaugccggca   5520
cgcaacuccc guguugguugg cguuucgucc aguuacggaa acuucuucuu cucuggaaau   5580
uuccucggau uuguugauuc caucaccucu gaacaaggaa cuuacgcaag acucuuuagg   5640
uacaggguga cgaccuacaa aggauggugc ggcucggccc uggucuguga ggccggugggc   5700
guccgacgca ucauuggccu gcauucugcu ggcgccgccg guaucggcgc cgggaccuau   5760
aucucaaaau uaggacuaau caaagcccug aaacaccucg gugaaccuuu ggccacaaug   5820
caaggacuga ugacugaauu agagccugga aucaccguac auguaccccg gaaauccaaa   5880
uugagaaaga cgaccgcaca cgcgguguac aaaccggagu uugagccugc uguguuguca   5940
aaauuugauc ccagacugaa caaggauguu gacuuggaug aaguaauuug gucuaaacac   6000
acugccaaug ucccuuacca accuccuuug uucuacacau acaugucaga guacgcucau   6060
cgagucuucu ccuucuuggg gaaagacaau gacauucuga ccgucaaaga agcaauucug   6120
ggcaucccccg gacuagaccc cauggauccc cacacagcuc cggggucugcc uuacgccauc   6180
aacggccuuc gacguacuga ucucgucgau uuugugaacg guacaguaga ugcggcgcug   6240
```

```
gcuguacaaa uccagaaauu cuuagacggu gacuacucug accaugucuu ccaaacuuuu   6300

cugaaagaug agaucagacc cucagagaaa guccgagcgg gaaaaacccg cauuguugau   6360

gugcccuccc uggcgcauug cauugugggc agaauguugc uugggcgcuu ugcugccaag   6420

uuucaauccc auccuggcuu ucuccucggc ucugcuaucg ggucugaccc ugauguuuuc   6480

uggaccguca uaggggcuca acucgagggg agaaagaaca cguaugacgu ggacuacagu   6540

gccuuugacu cuucacacgg cacuggcucc uucgaggcuc ucaucucuca cuuuuucacc   6600

guggacaaug guuuuagccc ugcgcuggga ccguaucuca gaucccuggc ugucucggug   6660

cacgcuuacg gcgagcgucg caucaagauu accgguggcc ucccccuccgg uugugccgcg   6720

accagccugc ugaacacagu gcucaacaau gugaucauca ggacugcucu ggcauugacu   6780

uacaaggaau uugaauauga caugguugau aucaucgccu acggugacga ccuucugguu   6840

ggcacggauu acgaucugga cuucaaugag guggcacgac gcgcugccaa guuggggguau   6900

aagaugacuc cugccaacaa ggguucuguc uucccuccga cuuccucucu uuccgaugcu   6960

guuuuucuaa agcgcaaauu cguccaaaac aacgacggcu uauacaaacc aguuauggau   7020

uuaaagaauu uggaagccau gcucuccuac uucaaaccag gaacacuacu cgagaagcug   7080

caaucuguuu cuauguuggc ucaacauucu ggaaaagaag aauaugauag auugaugcac   7140

cccuucgcug acuacggugc cguaccgagu cacgaguacc ugcaggcaag auggagggcc   7200

uuguucgacu gacccagaua gcccaaggcg cuucggugcu gccggcgauu cugggagaac   7260

ucagucggaa cagaaaaggg aaaaaaaaaa aaaaaaaaaa aaaaaaaaaa              7310
```

<210> SEQ ID NO 13
<211> LENGTH: 7310
<212> TYPE: RNA
<213> ORGANISM: Senecavirus

<400> SEQUENCE: 13

```
uuugaaaugg ggggcugggc ccugaugccc aguccuuccu uuccccuucc gggggguuaa     60

ccggcugugu uugcuagagg cacagagggg caacauccaa ccugcuuuug cggggaacgg    120

ugcggcuccg auuccugcgu cgccaaaggu guuagcgcac ccaaacggcg caccuaccaa    180

uguuauuggu guggucugcg aguucuagcc uacucguuuc ucccccgacc auucacucac    240

ccacgaaaag uguguuguaa ccauaagauu uaacccccgc acgggaugug cgauaaccgu    300

aagacuggcu caagcgcgga aagcgcugua accacaugcu guuagucccu uuauggcugc    360

aagauggcua cccaccucgg aucacugaac uggagcucga cccuccuuag uaagggaacc    420

gagaggccuu cgugcaacaa gcuccgacac agaguccacg ugacugcuac caccaugagu    480

acaugguucu ccccucucga cccaggacuu cuuuuugaau auccacggcu cgauccagag    540

gguggggcau gaccccuagc auagcgagcu acagcgggaa cuguagcuag gccuuagcgu    600

gccuuggaua cugccugaua gggcgacggc cuagucgugu cgguucuaua gguagcacau    660

acaaauaugc agaacucuca uuuuucuuuc gauacagccu cuggcaccuu ugaagaugua    720

accggaacaa aagucaagau cguugaauac cccagaucgg ugaacaaugg uguuuacgau    780

ucgucuacuc auuuggagau acugaaccua cagggugaaa uugaaauuuu aaggucuuuc    840

aaugaauacc aaauucgcgc cgccaaacaa caacucggac uggacaucgu guacgaacua    900

caggguaaug uucagacaac gucaaagaau gauuuugauu cccguggcaa uaaugguaac    960

augaccuuca auuacuacgc aaacacuuau cagaauucag uagacuucuc gaccuccucg   1020
```

```
ucggcgucag gcgccggacc cgggaacucc cggggcggau uagcgggucu ccucacaaau   1080
uucaguggaa ucuugaaccc ucuuggcuac cucaaagauc acaacaccga agaaauggaa   1140
aacucugcug aucgagucac aacgcaaacg gcgggcaaca cugccauaaa cacgcaauca   1200
ucauugggug uguugugugc cuacguugaa gacccgacca aaucugaucc uccguccagc   1260
agcacagauc aacccaccac cacuuucacu gccaucgaca ggugguacac uggacgucuc   1320
aauucuugga caaaagcugu aaaaaccuuc ucuuuucagg ccgucccgcu ucccggggcc   1380
uuucugucua ggcagggagg ccucaacgga ggggccuuca cagcuacccu acauagacac   1440
uuuuugauga agugcgggug gcaggugcag guccaaugua auuugacaca auuccaccaa   1500
ggcgcucuuc uuguugccau gguuccugaa accacccuug augucaagcc cgacgguaag   1560
gcaaagagcu uacaggagcu gaaugaagaa cagugggugg aaaugucuga cgauuaccgg   1620
accgggaaaa acaugccuuu ucagucucuu ggcacauacu aucggccccc uaacuggacu   1680
uggggguccca auuucaucaa ccccuaucaa guaacgguuu ucccacacca aauucugaac   1740
gcgagaaccu cuaccucggu agacauaaac gucccauaca ucggggagac ccccacgcaa   1800
uccucagaga cacagaacuc cuggacccuc cucguuaugg ugcucguucc ccuagacuau   1860
aaggaaggag ccacaacuga cccagaaauu acauuuucug uaaggccuac aagucccuac   1920
uucaaugggc uucgcaaccg cuacacggcc gggacggacg aagaacaggg gcccauuccu   1980
acggcaccca gagaaaauuc gcuuauguuu cucucaaccc ucccugacga cacugucccu   2040
gcuuacggga augugcguac cccuccuguc aauuaccucc cuggugaaau aaccgaccuu   2100
uugcaacugg cccgcauacc cacucucaug gcauuugagc gggugccuga acccgugccu   2160
gccucagaca cauaugugcc cuacguugcc guucccaccc aguucgauga caggccucuc   2220
aucuccuucc cgaucacccu uucagauccc gucuaucaga acacccuggu uggcgccauc   2280
aguucaaauu ucgccaauua ccgugggugu auccaaauca cucugacauu uuguggaccc   2340
augauggcga gagggaaauu ccugcucucg uauucucccc caaauggaac gcaaccacag   2400
acucuuuccg aagcuaugca gugcacauac ucuauuuggg acauaggcuu gaacucuagu   2460
uggaccuucg ucguccccua caucucgccc agugacuacc gugaaacucg agccauuacc   2520
aacucgguuu acuccgcuga ugguugguuu agccugcaca aguugaccaa aauuacucua   2580
ccaccugacu guccgcaaag ucccugcauu cucuuuuucg cuucugcugg ugaggauuac   2640
acucuccguc uccccguuga uuguaauccu uccuaugugu uccacuccac cgacaacgcc   2700
gagaccgggg uuauugaggc ggguaacacu gacaccgauu ucucugguga acuggcggcu   2760
ccuggcucua accacacuaa ugucaaguuc cuguuugauc gaucucgauu auugaaugua   2820
aucaagguac uggagaagga cgccguuuuc ccccgcccuu ucccuacaca agaaggugcg   2880
cagcaggaug augguuacuu uugucuucug accccccgcc caacagucgc uucccgaccc   2940
gccacucguu ucggccugua cgccaauccg uccggcagug guguucuugc uaacacuuca   3000
cuggacuuca auuuuuauag cuuggccugu uucacuuacu uuagaucgga ccuugagguu   3060
acgguggucu cacuagagcc ggaucuggaa uuugcuguag ggugguuucc uucuggcagu   3120
gaauaccagg cuuccagcuu ugucuacgac cagcugcaug ugcccuucca cuuuacuggg   3180
cgcacucccc gcgcuuucgc uagcaagggu gggaagguau cuuucgugcu cccuuggaac   3240
ucugucucgu cugugcuccc cgugcgcugg gggggggcuu ccaagcucuc uucugcuacg   3300
cggggucuac cggcgcaugc ugauuggggg acuauuuacg ccuuuguccc ccguccuaau   3360
gagaagaaaa gcaccgcugu aaaacacgug gccguguaca uucgguacaa gaacgcacgu   3420
```

```
gccuggugcc ccagcaugcu ucccuuucgc agcuacaagc agaagaugcu gaugcaaucu   3480
ggcgauaucg agaccaaucc ugguccugcu ucugacaacc caauuuugga guuucuugaa   3540
gcagaaaaug aucuagucac ucuggccucu cucuggaaga uggugcacuc uguucaacag   3600
accuggagaa aguaugugaa gaacgaugau uuuuggccca auuuacucag cgagcuagug   3660
ggggaaggcu cugucgccuu ggccgccacg cuauccaacc aagcuucagu aaaggcucuu   3720
uugggccugc acuuucucuc ucgggggcuc aauuacacug acuuuuacuc uuuacugaua   3780
gagaaaugcu cuaguuucuu uaccguagaa ccaccuccuc caccagcuga aaaccugaug   3840
accaagcccu cagugaaguc gaaauuccga aaacuguuua agaugcaagg acccauggac   3900
aaagucaaag acuggaacca aauagcugcc ggcuugaaga auuuucaauu uguucgugac   3960
cuagucaaag agguggucga uuggcugcag gccuggauca acaaagagaa agccagcccu   4020
guccuccagu accaguugga gaugaagaag cucgggccug uggccuuggc ucaugacgcu   4080
uucauggcug guuccgggcc cccucuuagc gacgaccaga uugaauaccu ccagaaccuc   4140
aaaucucuug cccuaacacu ggggaagacu aauuuggccc aaagucucac cacuaugauc   4200
aaugccaaac aaaguucagc ccaacgaguu gaacccguug ugguggucca uagaggcaag   4260
ccgggaugcg gcaagagcuu ggccucuacg uugauugccc aggcugugac caagcgccuc   4320
uauggcuccc aaaguguaua uucucuuccc ccagauccag auuucuucga uggauacaaa   4380
ggacaguucg ugaccuugau ggaugauuug ggacaaaacc cggauggaca agauuucucc   4440
accuuuuguc agauggguguc gaccgcccaa uuucucccca acauggcgga ccuugcagag   4500
aaagggcguc ccuuuaccuc caaucucauc auugcaacua caaaucuccc ccacuucagu   4560
ccugucacca uugcugaucc uucugcaguc ucucgccgua ucaacuacga ucugacucua   4620
gaaguaucug aggccuacaa gaaacacaca cggcugaauu uugacuuggc uuucaggcgc   4680
acagacgccc cccccauuua uccuuuugcu gcccaugugc ccuuugugga cguagcugug   4740
cgcuucaaaa augguCacca gaauuuuaau cuccuagagu uggucgauuc cauuuguaca   4800
gacauucgag ccaagcaaca aggugcccga aacaugcaga cucugguucu acagagcccc   4860
aacgagaaug augacacccc cgucgacgag gcguugggua gaguucucuc ccccgcugcg   4920
gucgaugagg cgcuugucga ccucacucca gaggccgacc cgguuggccg uuuggcuauu   4980
cuugccaagc uaggucuugc ccuagcugcg gucaccccug gucugauaau cuuggcagug   5040
ggacucuaca gguacuucuc uggcucugau gcagaccaag aagaaacaga aagugaggga   5100
ucugucaagg cacccaggag cgaaaaugcu uaugacggcc cgaagaaaaa cucuaagccc   5160
ccuggagcac ucucucucau ggaaaugcaa cagcccaacg uggacauggg cuuugaggcu   5220
gcggucgcua agaaaguggu cguccccauu accuucaugg uucccaacag accuucuggg   5280
cuuacacagu ccgcucuucu ggugaccggc cggaccuucc uaaucaauga acauacaugg   5340
uccaaucccu ccuggaccag cuucacaauc cgcggugagg uacacacucg ugaugagccc   5400
uuccaaacgg uucauuucac ucaccacggu auucccacag aucugaugau gguacgucuc   5460
ggaccgggca auucuuuccc uaacaaucua gacaaguuug gacuugacca gaugccggca   5520
cgcaacuccc gugugguugg cguuucgucc aguuacggaa acuucuucuu cucuggaaau   5580
uuccucggau uuguugauuc caucaccucu gaacaaggaa cuuacgcaag acucuuuagg   5640
uacaggguga cgaccuacaa aggaugguge ggcucggccc uggucuguga ggccggugge   5700
guccgacgca ucauuggccu gcauucugcu ggcgccgccg guaucggcgc cgggaccuau   5760
```

```
aucucaaaau uaggacuaau caaagcccug aaacaccucg gugaaccuuu ggccacaaug   5820
caaggacuga ugacugaauu agagccugga aucaccguac auguaccccg gaaauccaaa   5880
uugagaaaga cgaccgcaca cgcggugauac aaaccggagu uugagccugc uguguuguca   5940
aaauuugauc ccagacugaa caaggauguu gacuuggaug aaguaauuug gucuaaacac   6000
acugccaaug ucccuuacca accuccuuug uucuacacau acaugucaga guacgcucau   6060
cgagucuucu ccuucuuggg gaaagacaau gacauucuga ccgucaaaga agcaauucug   6120
ggcaucccccg gacuagaccc cauggauccc cacacagcuc cgggucugcc uuacgccauc   6180
aacggccuuc gacguacuga ucucgucgau uuugugaacg guacaguaga ugcggcgcug   6240
gcuguacaaa uccagaaauu cuuagacggu gacuacucug accaugucuu ccaaacuuuu   6300
cugaaagaug agaucagacc cucagagaaa guccgagcgg gaaaaacccg cauuguugau   6360
gugcccuccc uggcgcauug cauugugggc agaauguugc uugggcgcuu ugcugccaag   6420
uuucaauccc auccuggcuu ucuccucggc ucugcuaucg ggucugaccc ugauguuuuc   6480
uggaccguca uaggggcuca acucgagggg agaaagaaca cguaugacgu ggacuacagu   6540
gccuuugacu cuucacacgg cacuggcucc uucgaggcuc ucaucucuca cuuuuucacc   6600
guggacaaug guuuuagccc ugcgcuggga ccguaucuca gaucccuggc ugucucggug   6660
cacgcuuacg gcgagcgucg caucaagauu accgguggcc ucccccuccgg uugugccgcg   6720
accagccugc ugaacacagu gcucaacaau gugaucauca ggacugcucu ggcauugacu   6780
uacaaggaau uugaauauga caugguugau aucaucgccu acggugacga ccuucugguu   6840
ggcacggauu acgaucugga cuucaaugag guggcacgac gcgcugccaa guuggggguau   6900
aagaugacuc cugccaacaa ggguucuguc uucccuccga cuuccucucu uuccgaugcu   6960
guuuuucuaa agcgcaaauu cguccaaaac aacgacggcu uauacaaacc aguuauggau   7020
uuaaagaauu uggaagccau gcucuccuac uucaaaccag gaacacuacu cgagaagcug   7080
caaucuguuu cuauguuggc ucaacauucu ggaaaagaag aauaugauag auugaugcac   7140
cccuucgcug acuacggugc cguaccgagu cacgaguacc ugcaggcaag auggagggcc   7200
uuguucgacu gacccagaua gcccaaggcg cuucggugcu gccggcgauu cugggagaac   7260
ucagucggaa cagaaaaggg aaaaaaaaaa aaaaaaaaaa aaaaaaaaaa              7310
```

<210> SEQ ID NO 14
<211> LENGTH: 7310
<212> TYPE: RNA
<213> ORGANISM: Senecavirus

<400> SEQUENCE: 14

```
uuugaaaugg ggggcugggc ccugaugccc aguccuuccu uuccccuucc gggggguuaa     60
ccggcugugu uugcuagagg cacagagggg caacauccaa ccugcuuuug cggggaacgg    120
ugcggcuccg auuccugcgu cgccaaaggu guuagcgcac ccaaacggcg caccuaccaa    180
uguuauuggu guggucugcg aguucuagcc uacucguuuc ucccccgacc auucacucac    240
ccacgaaaag uguguuguaa ccauaagauu uaacccccgc acgggaugug cgauaaccgu    300
aagacuggcu caagcgcgga aagcgcugua accacaugcu guuagucccu uuauggcugc    360
aagauggcua cccaccucgg aucacugaac uggagcucga cccuccuuag uaagggaacc    420
gagaggccuu cgugcaacaa gcuccgacac agaguccacg ugacugcuac caccaugagu    480
acaugguucu ccccucucga cccaggacuu cuuuuugaau auccacggcu cgauccagag    540
gguggggcau gaccccuagc auagcgagcu acagcgggaa cuguagcuag gccuuagcgu    600
```

```
gccuuggaua cugccugaua gggcgacggc cuagucgugu cgguucuaua gguagcacau    660
acaaauaugc agaacucuca uuuuucuuuc gauacagccu cuggcaccuu ugaagaugua    720
accggaacaa aagucaagau cguugaauac cccagaucgg ugaacaaugg uguuuacgau    780
ucgucuacuc auuuggagau acugaaccua cagggugaaa uugaaauuuu aaggucuuuc    840
aaugaauacc aaauucgcgc cgccaaacaa caacucggac uggacaucgu guacgaacua    900
caggguaaug uucagacaac gucaaagaau gauuuugauu cccguggcaa uaaugguaac    960
augaccuuca auuacuacgc aaacacuuau cagaauucag uagacuucuc gaccuccucg   1020
ucggcgucag gcgccggacc cgggaacucc cggggcggau uagcggguau ccucacaaau   1080
uucaguggaa ucuugaaccc ucuuggcuac cucaaagauc acaacaccga agaaauggaa   1140
aacucugcug aucgagucac aacgcaaacg gcgggcaaca cugccauaaa cacgcaauca   1200
ucauugggug uguugugugc cuacguugaa gacccgacca aaucugaucc uccguccagc   1260
agcacagauc aacccaccac cacuuucacu gccaucgaca ggugguacac uggacgucuc   1320
aauucuugga caaaagcugu aaaaaccuuc ucuuuucagg ccgucccgcu ucccggggcc   1380
uuucugucua ggcagggagg ccucaacgga ggggccuuca cagcuacccu acauagacac   1440
uuuuugauga agugcgggug gcaggugcag guccaaugua auuugacaca auuccaccaa   1500
ggcgcucuuc uuguugccau gguuccugaa accacccuug augucaagcc cgacgguaag   1560
gcaaagagcu uacaggagcu gaaugaagaa caguggguggg aaaugucuga cgauuaccgg   1620
accgggaaaa acaugccuuu ucagucucuu ggcacauacu aucggccccc uaacuggacu   1680
uggggucccca auuucaucaa ccccuaucaa guaacgguuu ucccacacca aauucugaac   1740
gcgagaaccu cuaccucggu agacauaaac gucccauaca ucggggagac ccccacgcaa   1800
uccucagaga cacagaacuc cuggacccuc cucguuaugg ugcucguucc ccuagacuau   1860
aaggaaggag ccacaacuga cccagaaauu acauuuucug uaaggccuac aagucccuac   1920
uucaaugggc uucgcaaccg cuacacggcc gggacggacg aagaacaggg gcccauuccu   1980
acggcaccca gagaaaauuc gcuuauguuu cucucaaccc ucccugacga cacugucccu   2040
gcuuacggga augugcguac cccuccuguc aauuaccucc cuggugaaau aaccgaccuu   2100
uugcaacugg cccgcauacc cacucucaug gcauuugagc gggugccuga acccgugccu   2160
gccucagaca cauaugugcc cuacguugcc guucccaccc aguucgauga caggccucuc   2220
aucuccuucc cgaucacccu uucagauccc gucuaucaga acacccuggu uggcgccauc   2280
aguucaaauu ucgccaauua ccgugggugu auccaaauca cucugacauu uuguggaccc   2340
augauggcga gagggaaauu ccugcucucg uauucucccc caaauggaac gcaaccacag   2400
acucuuuccg aagcuaugca gugcacauac ucuauuuggg acauaggcuu gaacucuagu   2460
uggaccuucg ucguccccua caucucgccc agugacuacc gugaaacucg agccauuacc   2520
aacucgguuu acuccgcuga ugguugguuu agccugcaca aguugaccaa aauuacucua   2580
ccaccugacu guccgcaaag ucccugcauu cucuuuuucg cuucugcugg ugaggauuac   2640
acucuccguc uccccguuga uuguaauccu uccuaugugu uccacuccac cgacaacgcc   2700
gagaccgggg uuauugaggc ggguaacacu gacaccgauu ucucugguga acuggcggcu   2760
ccuggcucua accacacuaa ugucaaguuc cuguuugauc gaucucgauu auugaaugua   2820
aucaagguac uggagaagga cgccguuuuc ccccgcccuu ucccuacaca agaaggugcg   2880
cagcaggaug augguuacuu uugucuucug accccccgcc caacagucgc uucccgaccc   2940
```

```
gccacucguu ucggccugua cgccaauccg uccggcagug guguucuugc uaacacuuca   3000
cuggacuuca auuuuuauag cuuggccugu uucacuuacu uuagaucgga ccuugagguu   3060
acgguggucu cacuagagcc ggaucuggaa uuugcuguag ggugguuucc uucuggcagu   3120
gaauaccagg cuuccagcuu ugucuacgac cagcugcaug ugcccuucca cuuuacuggg   3180
cgcacucccc gcgcuuucgc uagcaagggu gggaagguau cuuucgugcu cccuuggaac   3240
ucugucucgu cugugcuccc cgugcgcugg ggggggcuu ccaagcucuc uucugcuacg   3300
cggggucuac cggcgcaugc ugauuggggg acuauuuacg ccuuuguccc ccguccuaau   3360
gagaagaaaa gcaccgcugu aaaacacgug gccguguaca uucgguacaa gaacgcacgu   3420
gccuggugcc ccagcaugcu ucccuuucgc agcuacaagc agaagaugcu gaugcaaucu   3480
ggcgauaucg agaccaaucc ugguccugcu ucugacaacc caauuuugga guuucuugaa   3540
gcagaaaaug aucuagucac ucuggccucu cucuggaaga uggugcacuc uguucaacag   3600
accuggagaa aguaugugaa gaacgaugau uuuuggccca auuuacucag cgagcuagug   3660
ggggaaggcu cugucgccuu ggccgccacg cuauccaacc aagcuucagu aaaggcucuu   3720
uugggccugc acuuucucuc ucgggggcuc aauuacacug acuuuuacuc uuuacugaua   3780
gagaaaugcu cuaguuucuu uaccguagaa ccaccuccuc caccagcuga aaaccugaug   3840
accaagcccu cagugaaguc gaaauuccga aaacuguuua agaugcaagg acccauggac   3900
aaagucaaag acuggaacca aauagcugcc ggcuugaaga auuuucaauu uguucgugac   3960
cuagucaaag agguggucga uuggcugcag gccuggauca acaaagagaa agccagcccu   4020
guccuccagu accaguugga gaugaagaag cucgggccug uggccuuggc ucaugacgcu   4080
uucauggcug guuccgggcc cccucuuagc gacgaccaga uugaauaccu ccagaaccuc   4140
aaaucucuug cccuaacacu ggggaagacu aauuuggccc aaagucucac cacuaugauc   4200
aaugccaaac aaaguucagc ccaacgaguu gaacccguug ugguggaccu uagaggcaag   4260
ccgggaugcg gcaagagcuu ggccucuacg uugauugccc aggcuguguc caagcgccuc   4320
uauggcuccc aaaguguaua uucucuuccc ccagauccag auuucuucga uggauacaaa   4380
ggacaguucg ugaccuugau ggaugauuug ggacaaaacc cggauggaca agauuucucc   4440
accuuuuguc agauggugac gaccgcccaa uuucucccca acauggcgga ccuugcagag   4500
aaagggcguc ccuuuaccuc caaucucauc auugcaacua caaaucuccc ccacuucagu   4560
ccugucacca uugcugaucc uucugcaguc ucucgccgua ucaacuacga ucugacucua   4620
gaaguaucug aggccuacaa gaaacacaca cggcugaauu uugacuuggc uuucaggcgc   4680
acagacgccc cccccauuua uccuuuugcu gcccaugugc ccuuugugga cguagcugug   4740
cgcuucaaaa auggucacca gaauuuuaau cuccuagagu uggucgauuc cauuuguaca   4800
gacauucgag ccaagcaaca aggugcccga aacaugcaga cucugguucu acagagcccc   4860
aacgagaaug augacacccc cgucgacgag gcguuggua gaguucucuc ccccgcugcg   4920
gucgaugagg cgcuugucga ccucacucca gaggccgacc cgguuggccg uuuggcuauu   4980
cuugccaagc uaggucuugc ccuagcugcg gucaccccug gucugauaau cuuggcagug   5040
ggacucuaca gguacuucuc uggcucugau gcagaccaag aagaaacaga aagugaggga   5100
ucugucaagg cacccaggag cgaaaaugcu uaugacggcc cgaagaaaaa cucuaagccc   5160
ccuggagcac ucucucucau ggaaaugcaa cagcccaacg uggacauggg cuuugaggcu   5220
gcggucgcua agaaaguggu cgucccauu accuucaugg uucccaacag accuucuggg   5280
cuuacacagu ccgcucuucu ggugaccggc cggaccuucc uaaucaauga acauacaugg   5340
```

```
uccaaucccu ccuggaccag cuucacaauc cgcggugagg uacacacucg ugaugagccc   5400

uuccaaacgg uucauuucac ucaccacggu auucccacag aucugaugau gguacgucuc   5460

ggaccgggca auucuuuccc uaacaaucua gacaaguuug gacuugacca gaugccggca   5520

cgcaacuccc gugugguugg cguuucgucc aguuacggaa acuucuucuu cucuggaaau   5580

uuccucggau uuguugauuc caucaccucu gaacaaggaa cuuacgcaag acucuuuagg   5640

uacaggguga cgaccuacaa aggauggugc ggcucggccc uggucuguga ggccggugge   5700

guccgacgca ucauuggccu gcauucugcu ggcgccgccg guaucggcgc cgggaccuau   5760

aucucaaaau uaggacuaau caaagcccug aaacaccucg gugaaccuuu ggccacaaug   5820

caaggacuga ugacugaauu agagccugga aucaccguac auguaccccg gaaauccaaa   5880

uugagaaaga cgaccgcaca cgcgguguac aaaccggagu uugagccugc uguguuguca   5940

aaauuugauc ccagacugaa caaggauguu gacuuggaug aaguaauuug gucuaaacac   6000

acugccaaug ucccuuacca accuccuuug uucuacacau acaugucaga guacgcucau   6060

cgagucuucu ccuucuuggg gaaagacaau gacauucuga ccgucaaaga agcaauucug   6120

ggcaucccgg gacuagaccc cauggauccc cacacagcuc cggguctgcc uuacgccauc   6180

aacggccuuc gacguacuga ucucgucgau uuugugaacg guacaguaga ugcggcgcug   6240

gcuguacaaa uccagaaauu cuuagacggu gacuacucug accaugucuu ccaaacuuuu   6300

cugaaagaug agaucagacc cucagagaaa guccgagcgg gaaaaacccg cauuguugau   6360

gugcccuccc uggcgcauug cauuguggge agaauguugc uugggcgcuu ugcugccaag   6420

uuucaauccc auccuggcuu ucuccucggc ucugcuaucg ggucugaccc ugauguuuuc   6480

uggaccguca uaggggcuca acucgagggg agaaagaaca cguaugacgu ggacuacagu   6540

gccuuugacu cuucacacgg cacuggcucc uucgaggcuc ucaucucuca cuuuuucacc   6600

guggacaaug guuuuagccc ugcgcuggga ccguaucuca gaucccuggc ugucucggug   6660

cacgcuuacg gcgagcgucg caucaagauu accgguggcc ucccuccgg uugugccgcg   6720

accagccugc ugaacacagu gcucaacaau gugaucauca ggacugcucu ggcauugacu   6780

uacaaggaau uugaauauga caugguugau aucaucgccu acggugacga ccuucugguu   6840

ggcacggauu acgaucugga cuucaaugag guggcacgac gcgcugccaa guuggggguau   6900

aagaugacuc cugccaacaa ggguucuguc uucccuccga cuuccucucu uuccgaugcu   6960

guuuuucuaa agcgcaaauu cguccaaaac aacgacggcu uauacaaacc aguuauggau   7020

uuaaagaauu uggaagccau gcucuccuac uucaaaccag gaacacuacu cgagaagcug   7080

caaucuguuu cuauguuggc ucaacauucu ggaaaagaag aauaugauag auugaugcac   7140

cccuucgcug acuacggugc cguaccgagu cacgaguacc ugcaggcaag auggagggcc   7200

uuguucgacu gacccagaua gcccaaggcg cuucggugcu gccggcgauu cugggagaac   7260

ucagucggaa cagaaaaggg aaaaaaaaaa aaaaaaaaaa aaaaaaaaaa             7310
```

<210> SEQ ID NO 15
<211> LENGTH: 2181
<212> TYPE: PRT
<213> ORGANISM: Senecavirus

<400> SEQUENCE: 15

```
Met Gln Asn Ser His Phe Ser Phe Asp Thr Ala Ser Gly Thr Phe Glu
1               5                   10                  15

Asp Val Thr Gly Thr Lys Val Lys Ile Val Glu Tyr Pro Arg Ser Val
```

```
            20                  25                  30

Asn Asn Gly Val Tyr Asp Ser Ser Thr His Leu Glu Ile Leu Asn Leu
        35                  40                  45

Gln Gly Glu Ile Glu Ile Leu Arg Ser Phe Asn Glu Tyr Gln Ile Arg
    50                  55                  60

Ala Ala Lys Gln Gln Leu Gly Leu Asp Ile Val Tyr Glu Leu Gln Gly
65                  70                  75                  80

Asn Val Gln Thr Thr Ser Lys Asn Asp Phe Asp Ser Arg Gly Asn Asn
                85                  90                  95

Gly Asn Met Thr Phe Asn Tyr Tyr Ala Asn Thr Tyr Gln Asn Ser Val
            100                 105                 110

Asp Phe Ser Thr Ser Ser Ser Ala Ser Gly Ala Gly Pro Gly Asn Ser
        115                 120                 125

Arg Gly Gly Leu Ala Gly Leu Leu Thr Asn Phe Ser Gly Ile Leu Asn
    130                 135                 140

Pro Leu Gly Tyr Leu Lys Asp His Asn Thr Glu Glu Met Glu Asn Ser
145                 150                 155                 160

Ala Asp Arg Val Thr Thr Gln Thr Ala Gly Asn Thr Ala Ile Asn Thr
                165                 170                 175

Gln Ser Ser Leu Gly Val Leu Cys Ala Tyr Val Glu Asp Pro Thr Lys
            180                 185                 190

Ser Asp Pro Pro Ser Ser Ser Thr Asp Gln Pro Thr Thr Thr Phe Thr
        195                 200                 205

Ala Ile Asp Arg Trp Tyr Thr Gly Arg Leu Asn Ser Trp Thr Lys Ala
    210                 215                 220

Val Lys Thr Phe Ser Phe Gln Ala Val Pro Leu Pro Gly Ala Phe Leu
225                 230                 235                 240

Ser Arg Gln Gly Gly Leu Asn Gly Gly Ala Phe Thr Ala Thr Leu His
                245                 250                 255

Arg His Phe Leu Met Lys Cys Gly Trp Gln Val Gln Val Gln Cys Asn
            260                 265                 270

Leu Thr Gln Phe His Gln Gly Ala Leu Leu Val Ala Met Val Pro Glu
        275                 280                 285

Thr Thr Leu Asp Val Lys Pro Asp Gly Lys Ala Lys Ser Leu Gln Glu
    290                 295                 300

Leu Asn Glu Glu Gln Trp Val Glu Met Ser Asp Asp Tyr Arg Thr Gly
305                 310                 315                 320

Lys Asn Met Pro Phe Gln Ser Leu Gly Thr Tyr Tyr Arg Pro Pro Asn
                325                 330                 335

Trp Thr Trp Gly Pro Asn Phe Ile Asn Pro Tyr Gln Val Thr Val Phe
            340                 345                 350

Pro His Gln Ile Leu Asn Ala Arg Thr Ser Thr Ser Val Asp Ile Asn
        355                 360                 365

Val Pro Tyr Ile Gly Glu Thr Pro Thr Gln Ser Ser Glu Thr Gln Asn
    370                 375                 380

Ser Trp Thr Leu Leu Val Met Val Leu Val Pro Leu Asp Tyr Lys Glu
385                 390                 395                 400

Gly Ala Thr Thr Asp Pro Glu Ile Thr Phe Ser Val Arg Pro Thr Ser
                405                 410                 415

Pro Tyr Phe Asn Gly Leu Arg Asn Arg Tyr Thr Ala Gly Thr Asp Glu
            420                 425                 430

Glu Gln Gly Pro Ile Pro Thr Ala Pro Arg Glu Asn Ser Leu Met Phe
        435                 440                 445
```

```
Leu Ser Thr Leu Pro Asp Asp Thr Val Pro Ala Tyr Gly Asn Val Arg
    450                 455                 460

Thr Pro Pro Val Asn Tyr Leu Pro Gly Glu Ile Thr Asp Leu Leu Gln
465                 470                 475                 480

Leu Ala Arg Ile Pro Thr Leu Met Ala Phe Glu Arg Val Pro Glu Pro
                485                 490                 495

Val Pro Ala Ser Asp Thr Tyr Val Pro Tyr Val Ala Val Pro Thr Gln
            500                 505                 510

Phe Asp Asp Arg Pro Leu Ile Ser Phe Pro Ile Thr Leu Ser Asp Pro
        515                 520                 525

Val Tyr Gln Asn Thr Leu Val Gly Ala Ile Ser Ser Asn Phe Ala Asn
    530                 535                 540

Tyr Arg Gly Cys Ile Gln Ile Thr Leu Thr Phe Cys Gly Pro Met Met
545                 550                 555                 560

Ala Arg Gly Lys Phe Leu Leu Ser Tyr Ser Pro Pro Asn Gly Thr Gln
                565                 570                 575

Pro Gln Thr Leu Ser Glu Ala Met Gln Cys Thr Tyr Ser Ile Trp Asp
            580                 585                 590

Ile Gly Leu Asn Ser Ser Trp Thr Phe Val Val Pro Tyr Ile Ser Pro
        595                 600                 605

Ser Asp Tyr Arg Glu Thr Arg Ala Ile Thr Asn Ser Val Tyr Ser Ala
    610                 615                 620

Asp Gly Trp Phe Ser Leu His Lys Leu Thr Lys Ile Thr Leu Pro Pro
625                 630                 635                 640

Asp Cys Pro Gln Ser Pro Cys Ile Leu Phe Phe Ala Ser Ala Gly Glu
                645                 650                 655

Asp Tyr Thr Leu Arg Leu Pro Val Asp Cys Asn Pro Ser Tyr Val Phe
            660                 665                 670

His Ser Thr Asp Asn Ala Glu Thr Gly Val Ile Glu Ala Gly Asn Thr
        675                 680                 685

Asp Thr Asp Phe Ser Gly Glu Leu Ala Ala Pro Gly Ser Asn His Thr
    690                 695                 700

Asn Val Lys Phe Leu Phe Asp Arg Ser Arg Leu Leu Asn Val Ile Lys
705                 710                 715                 720

Val Leu Glu Lys Asp Ala Val Phe Pro Arg Pro Phe Pro Thr Gln Glu
                725                 730                 735

Gly Ala Gln Gln Asp Asp Gly Tyr Phe Cys Leu Leu Thr Pro Arg Pro
            740                 745                 750

Thr Val Ala Ser Arg Pro Ala Thr Arg Phe Gly Leu Tyr Ala Asn Pro
        755                 760                 765

Ser Gly Ser Gly Val Leu Ala Asn Thr Ser Leu Asp Phe Asn Phe Tyr
    770                 775                 780

Ser Leu Ala Cys Phe Thr Tyr Phe Arg Ser Asp Leu Glu Val Thr Val
785                 790                 795                 800

Val Ser Leu Glu Pro Asp Leu Glu Phe Ala Val Gly Trp Phe Pro Ser
                805                 810                 815

Gly Ser Glu Tyr Gln Ala Ser Ser Phe Val Tyr Asp Gln Leu His Val
            820                 825                 830

Pro Phe His Phe Thr Gly Arg Thr Pro Arg Ala Phe Ala Ser Lys Gly
        835                 840                 845

Gly Lys Val Ser Phe Val Leu Pro Trp Asn Ser Val Ser Ser Val Leu
    850                 855                 860
```

```
Pro Val Arg Trp Gly Gly Ala Ser Lys Leu Ser Ser Ala Thr Arg Gly
865                 870                 875                 880

Leu Pro Ala His Ala Asp Trp Gly Thr Ile Tyr Ala Phe Val Pro Arg
                885                 890                 895

Pro Asn Glu Lys Lys Ser Thr Ala Val Lys His Val Ala Val Tyr Ile
            900                 905                 910

Arg Tyr Lys Asn Ala Arg Ala Trp Cys Pro Ser Met Leu Pro Phe Arg
        915                 920                 925

Ser Tyr Lys Gln Lys Met Leu Met Gln Ser Gly Asp Ile Glu Thr Asn
    930                 935                 940

Pro Gly Pro Ala Ser Asp Asn Pro Ile Leu Glu Phe Leu Glu Ala Glu
945                 950                 955                 960

Asn Asp Leu Val Thr Leu Ala Ser Leu Trp Lys Met Val His Ser Val
                965                 970                 975

Gln Gln Thr Trp Arg Lys Tyr Val Lys Asn Asp Asp Phe Trp Pro Asn
            980                 985                 990

Leu Leu Ser Glu Leu Val Gly Glu  Gly Ser Val Ala Leu  Ala Ala Thr
        995                 1000                1005

Leu Ser  Asn Gln Ala Ser Val  Lys Ala Leu Leu Gly  Leu His Phe
    1010                1015                1020

Leu Ser  Arg Gly Leu Asn Tyr  Thr Asp Phe Tyr Ser  Leu Leu Ile
    1025                1030                1035

Glu Lys  Cys Ser Ser Phe Phe  Thr Val Glu Pro Pro  Pro Pro Pro
    1040                1045                1050

Ala Glu  Asn Leu Met Thr Lys  Pro Ser Val Lys Ser  Lys Phe Arg
    1055                1060                1065

Lys Leu  Phe Lys Met Gln Gly  Pro Met Asp Lys Val  Lys Asp Trp
    1070                1075                1080

Asn Gln  Ile Ala Ala Gly Leu  Lys Asn Phe Gln Phe  Val Arg Asp
    1085                1090                1095

Leu Val  Lys Glu Val Val Asp  Trp Leu Gln Ala Trp  Ile Asn Lys
    1100                1105                1110

Glu Lys  Ala Ser Pro Val Leu  Gln Tyr Gln Leu Glu  Met Lys Lys
    1115                1120                1125

Leu Gly  Pro Val Ala Leu Ala  His Asp Ala Phe Met  Ala Gly Ser
    1130                1135                1140

Gly Pro  Pro Leu Ser Asp Asp  Gln Ile Glu Tyr Leu  Gln Asn Leu
    1145                1150                1155

Lys Ser  Leu Ala Leu Thr Leu  Gly Lys Thr Asn Leu  Ala Gln Ser
    1160                1165                1170

Leu Thr  Thr Met Ile Asn Ala  Lys Gln Ser Ser Ala  Gln Arg Val
    1175                1180                1185

Glu Pro  Val Val Val Val Leu  Arg Gly Lys Pro Gly  Cys Gly Lys
    1190                1195                1200

Ser Leu  Ala Ser Thr Leu Ile  Ala Gln Ala Val Ser  Lys Arg Leu
    1205                1210                1215

Tyr Gly  Ser Gln Ser Val Tyr  Ser Leu Pro Pro Asp  Pro Asp Phe
    1220                1225                1230

Phe Asp  Gly Tyr Lys Gly Gln  Phe Val Thr Leu Met  Asp Asp Leu
    1235                1240                1245

Gly Gln  Asn Pro Asp Gly Gln  Asp Phe Ser Thr Phe  Cys Gln Met
    1250                1255                1260

Val Ser  Thr Ala Gln Phe Leu  Pro Asn Met Ala Asp  Leu Ala Glu
```

```
    1265                1270                1275

Lys Gly  Arg Pro Phe Thr Ser  Asn Leu Ile Ile Ala  Thr Thr Asn
    1280                1285                1290

Leu Pro  His Phe Ser Pro Val  Thr Ile Ala Asp Pro  Ser Ala Val
    1295                1300                1305

Ser Arg  Arg Ile Asn Tyr Asp  Leu Thr Leu Glu Val  Ser Glu Ala
    1310                1315                1320

Tyr Lys  Lys His Thr Arg Leu  Asn Phe Asp Leu Ala  Phe Arg Arg
    1325                1330                1335

Thr Asp  Ala Pro Pro Ile Tyr  Pro Phe Ala Ala His  Val Pro Phe
    1340                1345                1350

Val Asp  Val Ala Val Arg Phe  Lys Asn Gly His Gln  Asn Phe Asn
    1355                1360                1365

Leu Leu  Glu Leu Val Asp Ser  Ile Cys Thr Asp Ile  Arg Ala Lys
    1370                1375                1380

Gln Gln  Gly Ala Arg Asn Met  Gln Thr Leu Val Leu  Gln Ser Pro
    1385                1390                1395

Asn Glu  Asn Asp Asp Thr Pro  Val Asp Glu Ala Leu  Gly Arg Val
    1400                1405                1410

Leu Ser  Pro Ala Ala Val Asp  Glu Ala Leu Val Asp  Leu Thr Pro
    1415                1420                1425

Glu Ala  Asp Pro Val Gly Arg  Leu Ala Ile Leu Ala  Lys Leu Gly
    1430                1435                1440

Leu Ala  Leu Ala Ala Val Thr  Pro Gly Leu Ile Ile  Leu Ala Val
    1445                1450                1455

Gly Leu  Tyr Arg Tyr Phe Ser  Gly Ser Asp Ala Asp  Gln Glu Glu
    1460                1465                1470

Thr Glu  Ser Glu Gly Ser Val  Lys Ala Pro Arg Ser  Glu Asn Ala
    1475                1480                1485

Tyr Asp  Gly Pro Lys Lys Asn  Ser Lys Pro Pro Gly  Ala Leu Ser
    1490                1495                1500

Leu Met  Glu Met Gln Gln Pro  Asn Val Asp Met Gly  Phe Glu Ala
    1505                1510                1515

Ala Val  Ala Lys Lys Val Val  Val Pro Ile Thr Phe  Met Val Pro
    1520                1525                1530

Asn Arg  Pro Ser Gly Leu Thr  Gln Ser Ala Leu Leu  Val Thr Gly
    1535                1540                1545

Arg Thr  Phe Leu Ile Asn Glu  His Thr Trp Ser Asn  Pro Ser Trp
    1550                1555                1560

Thr Ser  Phe Thr Ile Arg Gly  Glu Val His Thr Arg  Asp Glu Pro
    1565                1570                1575

Phe Gln  Thr Val His Phe Thr  His His Gly Ile Pro  Thr Asp Leu
    1580                1585                1590

Met Met  Val Arg Leu Gly Pro  Gly Asn Ser Phe Pro  Asn Asn Leu
    1595                1600                1605

Asp Lys  Phe Gly Leu Asp Gln  Met Pro Ala Arg Asn  Ser Arg Val
    1610                1615                1620

Val Gly  Val Ser Ser Ser Tyr  Gly Asn Phe Phe Phe  Ser Gly Asn
    1625                1630                1635

Phe Leu  Gly Phe Val Asp Ser  Ile Thr Ser Glu Gln  Gly Thr Tyr
    1640                1645                1650

Ala Arg  Leu Phe Arg Tyr Arg  Val Thr Thr Tyr Lys  Gly Trp Cys
    1655                1660                1665
```

```
Gly Ser  Ala Leu Val Cys Glu  Ala Gly Gly Val Arg  Arg Ile Ile
    1670                 1675                 1680

Gly Leu  His Ser Ala Gly Ala  Ala Gly Ile Gly Ala  Gly Thr Tyr
    1685                 1690                 1695

Ile Ser  Lys Leu Gly Leu Ile  Lys Ala Leu Lys His  Leu Gly Glu
    1700                 1705                 1710

Pro Leu  Ala Thr Met Gln Gly  Leu Met Thr Glu Leu  Glu Pro Gly
    1715                 1720                 1725

Ile Thr  Val His Val Pro Arg  Lys Ser Lys Leu Arg  Lys Thr Thr
    1730                 1735                 1740

Ala His  Ala Val Tyr Lys Pro  Glu Phe Glu Pro Ala  Val Leu Ser
    1745                 1750                 1755

Lys Phe  Asp Pro Arg Leu Asn  Lys Asp Val Asp Leu  Asp Glu Val
    1760                 1765                 1770

Ile Trp  Ser Lys His Thr Ala  Asn Val Pro Tyr Gln  Pro Pro Leu
    1775                 1780                 1785

Phe Tyr  Thr Tyr Met Ser Glu  Tyr Ala His Arg Val  Phe Ser Phe
    1790                 1795                 1800

Leu Gly  Lys Asp Asn Asp Ile  Leu Thr Val Lys Glu  Ala Ile Leu
    1805                 1810                 1815

Gly Ile  Pro Gly Leu Asp Pro  Met Asp Pro His Thr  Ala Pro Gly
    1820                 1825                 1830

Leu Pro  Tyr Ala Ile Asn Gly  Leu Arg Arg Thr Asp  Leu Val Asp
    1835                 1840                 1845

Phe Val  Asn Gly Thr Val Asp  Ala Ala Leu Ala Val  Gln Ile Gln
    1850                 1855                 1860

Lys Phe  Leu Asp Gly Asp Tyr  Ser Asp His Val Phe  Gln Thr Phe
    1865                 1870                 1875

Leu Lys  Asp Glu Ile Arg Pro  Ser Glu Lys Val Arg  Ala Gly Lys
    1880                 1885                 1890

Thr Arg  Ile Val Asp Val Pro  Ser Leu Ala His Cys  Ile Val Gly
    1895                 1900                 1905

Arg Met  Leu Leu Gly Arg Phe  Ala Ala Lys Phe Gln  Ser His Pro
    1910                 1915                 1920

Gly Phe  Leu Leu Gly Ser Ala  Ile Gly Ser Asp Pro  Asp Val Phe
    1925                 1930                 1935

Trp Thr  Val Ile Gly Ala Gln  Leu Glu Gly Arg Lys  Asn Thr Tyr
    1940                 1945                 1950

Asp Val  Asp Tyr Ser Ala Phe  Asp Ser Ser His Gly  Thr Gly Ser
    1955                 1960                 1965

Phe Glu  Ala Leu Ile Ser His  Phe Phe Thr Val Asp  Asn Gly Phe
    1970                 1975                 1980

Ser Pro  Ala Leu Gly Pro Tyr  Leu Arg Ser Leu Ala  Val Ser Val
    1985                 1990                 1995

His Ala  Tyr Gly Glu Arg Arg  Ile Lys Ile Thr Gly  Gly Leu Pro
    2000                 2005                 2010

Ser Gly  Cys Ala Ala Thr Ser  Leu Leu Asn Thr Val  Leu Asn Asn
    2015                 2020                 2025

Val Ile  Ile Arg Thr Ala Leu  Ala Leu Thr Tyr Lys  Glu Phe Glu
    2030                 2035                 2040

Tyr Asp  Met Val Asp Ile Ile  Ala Tyr Gly Asp Asp  Leu Leu Val
    2045                 2050                 2055
```

```
Gly Thr  Asp Tyr Asp Leu Asp  Phe Asn Glu Val Ala  Arg Arg Ala
    2060                 2065                 2070

Ala Lys  Leu Gly Tyr Lys Met  Thr Pro Ala Asn Lys  Gly Ser Val
    2075                 2080                 2085

Phe Pro  Pro Thr Ser Ser Leu  Ser Asp Ala Val Phe  Leu Lys Arg
    2090                 2095                 2100

Lys Phe  Val Gln Asn Asn Asp  Gly Leu Tyr Lys Pro  Val Met Asp
    2105                 2110                 2115

Leu Lys  Asn Leu Glu Ala Met  Leu Ser Tyr Phe Lys  Pro Gly Thr
    2120                 2125                 2130

Leu Leu  Glu Lys Leu Gln Ser  Val Ser Met Leu Ala  Gln His Ser
    2135                 2140                 2145

Gly Lys  Glu Glu Tyr Asp Arg  Leu Met His Pro Phe  Ala Asp Tyr
    2150                 2155                 2160

Gly Ala  Val Pro Ser His Glu  Tyr Leu Gln Ala Arg  Trp Arg Ala
    2165                 2170                 2175

Leu Phe  Asp
    2180


<210> SEQ ID NO 16
<211> LENGTH: 2181
<212> TYPE: PRT
<213> ORGANISM: Senecavirus

<400> SEQUENCE: 16

Met Gln Asn Ser His Phe Ser Phe Asp Thr Ala Ser Gly Thr Phe Glu
1               5                   10                  15

Asp Val Thr Gly Thr Lys Val Lys Ile Val Glu Tyr Pro Arg Ser Val
            20                  25                  30

Asn Asn Gly Val Tyr Asp Ser Ser Thr His Leu Glu Ile Leu Asn Leu
        35                  40                  45

Gln Gly Glu Ile Glu Ile Leu Arg Ser Phe Asn Glu Tyr Gln Ile Arg
    50                  55                  60

Ala Ala Lys Gln Gln Leu Gly Leu Asp Ile Val Tyr Glu Leu Gln Gly
65                  70                  75                  80

Asn Val Gln Thr Thr Ser Lys Asn Asp Phe Asp Ser Arg Gly Asn Asn
                85                  90                  95

Gly Asn Met Thr Phe Asn Tyr Tyr Ala Asn Thr Tyr Gln Asn Ser Val
            100                 105                 110

Asp Phe Ser Thr Ser Ser Ser Ala Ser Gly Ala Gly Pro Gly Asn Ser
        115                 120                 125

Arg Gly Gly Leu Ala Gly Leu Leu Thr Asn Phe Ser Gly Ile Leu Asn
    130                 135                 140

Pro Leu Gly Tyr Leu Lys Asp His Asn Thr Glu Glu Met Glu Asn Ser
145                 150                 155                 160

Ala Asp Arg Val Thr Thr Gln Thr Ala Gly Asn Thr Ala Ile Asn Thr
                165                 170                 175

Gln Ser Ser Leu Gly Val Leu Cys Ala Tyr Val Glu Asp Pro Thr Lys
            180                 185                 190

Ser Asp Pro Pro Ser Ser Ser Thr Asp Gln Pro Thr Thr Thr Phe Thr
        195                 200                 205

Ala Ile Asp Arg Trp Tyr Thr Gly Arg Leu Asn Ser Trp Thr Lys Ala
    210                 215                 220

Val Lys Thr Phe Ser Phe Gln Ala Val Pro Leu Pro Gly Ala Phe Leu
225                 230                 235                 240
```

```
Ser Arg Gln Gly Gly Leu Asn Gly Gly Ala Phe Thr Ala Thr Leu His
                245                 250                 255

Arg His Phe Leu Met Lys Cys Gly Trp Gln Val Gln Val Gln Cys Asn
            260                 265                 270

Leu Thr Gln Phe His Gln Gly Ala Leu Leu Val Ala Met Val Pro Glu
        275                 280                 285

Thr Thr Leu Asp Val Lys Pro Asp Gly Lys Ala Lys Ser Leu Gln Glu
    290                 295                 300

Leu Asn Glu Glu Gln Trp Val Glu Met Ser Asp Asp Tyr Arg Thr Gly
305                 310                 315                 320

Lys Asn Met Pro Phe Gln Ser Leu Gly Thr Tyr Tyr Arg Pro Pro Asn
                325                 330                 335

Trp Thr Trp Gly Pro Asn Phe Ile Asn Pro Tyr Gln Val Thr Val Phe
            340                 345                 350

Pro His Gln Ile Leu Asn Ala Arg Thr Ser Thr Ser Val Asp Ile Asn
        355                 360                 365

Val Pro Tyr Ile Gly Glu Thr Pro Thr Gln Ser Ser Glu Thr Gln Asn
    370                 375                 380

Ser Trp Thr Leu Leu Val Met Val Leu Val Pro Leu Asp Tyr Lys Glu
385                 390                 395                 400

Gly Ala Thr Thr Asp Pro Glu Ile Thr Phe Ser Val Arg Pro Thr Ser
                405                 410                 415

Pro Tyr Phe Asn Gly Leu Arg Asn Arg Tyr Thr Ala Gly Thr Asp Glu
            420                 425                 430

Glu Gln Gly Pro Ile Pro Thr Ala Pro Arg Glu Asn Ser Leu Met Phe
        435                 440                 445

Leu Ser Thr Leu Pro Asp Asp Thr Val Pro Ala Tyr Gly Asn Val Arg
    450                 455                 460

Thr Pro Pro Val Asn Tyr Leu Pro Gly Glu Ile Thr Asp Leu Leu Gln
465                 470                 475                 480

Leu Ala Arg Ile Pro Thr Leu Met Ala Phe Glu Arg Val Pro Glu Pro
                485                 490                 495

Val Pro Ala Ser Asp Thr Tyr Val Pro Tyr Val Ala Val Pro Thr Gln
            500                 505                 510

Phe Asp Asp Arg Pro Leu Ile Ser Phe Pro Ile Thr Leu Ser Asp Pro
        515                 520                 525

Val Tyr Gln Asn Thr Leu Val Gly Ala Ile Ser Ser Asn Phe Ala Asn
    530                 535                 540

Tyr Arg Gly Cys Ile Gln Ile Thr Leu Thr Phe Cys Gly Pro Met Met
545                 550                 555                 560

Ala Arg Gly Lys Phe Leu Leu Ser Tyr Ser Pro Pro Asn Gly Thr Gln
                565                 570                 575

Pro Gln Thr Leu Ser Glu Ala Met Gln Cys Thr Tyr Ser Ile Trp Asp
            580                 585                 590

Ile Gly Leu Asn Ser Ser Trp Thr Phe Val Val Pro Tyr Ile Ser Pro
        595                 600                 605

Ser Asp Tyr Arg Glu Thr Arg Ala Ile Thr Asn Ser Val Tyr Ser Ala
    610                 615                 620

Asp Gly Trp Phe Ser Leu His Lys Leu Thr Lys Ile Thr Leu Pro Pro
625                 630                 635                 640

Asp Cys Pro Gln Ser Pro Cys Ile Leu Phe Phe Ala Ser Ala Gly Glu
                645                 650                 655
```

```
Asp Tyr Thr Leu Arg Leu Pro Val Asp Cys Asn Pro Ser Tyr Val Phe
            660                 665                 670

His Ser Thr Asp Asn Ala Glu Thr Gly Val Ile Glu Ala Gly Asn Thr
        675                 680                 685

Asp Thr Asp Phe Ser Gly Glu Leu Ala Ala Pro Gly Ser Asn His Thr
    690                 695                 700

Asn Val Lys Phe Leu Phe Asp Arg Ser Arg Leu Leu Asn Val Ile Lys
705                 710                 715                 720

Val Leu Glu Lys Asp Ala Val Phe Pro Arg Pro Phe Pro Thr Gln Glu
                725                 730                 735

Gly Ala Gln Gln Asp Asp Gly Tyr Phe Cys Leu Leu Thr Pro Arg Pro
            740                 745                 750

Thr Val Ala Ser Arg Pro Ala Thr Arg Phe Gly Leu Tyr Ala Asn Pro
        755                 760                 765

Ser Gly Ser Gly Val Leu Ala Asn Thr Ser Leu Asp Phe Asn Phe Tyr
    770                 775                 780

Ser Leu Ala Cys Phe Thr Tyr Phe Arg Ser Asp Leu Glu Val Thr Val
785                 790                 795                 800

Val Ser Leu Glu Pro Asp Leu Glu Phe Ala Val Gly Trp Phe Pro Ser
                805                 810                 815

Gly Ser Glu Tyr Gln Ala Ser Ser Phe Val Tyr Asp Gln Leu His Val
            820                 825                 830

Pro Phe His Phe Thr Gly Arg Thr Pro Arg Ala Phe Ala Ser Lys Gly
        835                 840                 845

Gly Lys Val Ser Phe Val Leu Pro Trp Asn Ser Val Ser Ser Val Leu
    850                 855                 860

Pro Val Arg Trp Gly Gly Ala Ser Lys Leu Ser Ser Ala Thr Arg Gly
865                 870                 875                 880

Leu Pro Ala His Ala Asp Trp Gly Thr Ile Tyr Ala Phe Val Pro Arg
                885                 890                 895

Pro Asn Glu Lys Lys Ser Thr Ala Val Lys His Val Ala Val Tyr Ile
            900                 905                 910

Arg Tyr Lys Asn Ala Arg Ala Trp Cys Pro Ser Met Leu Pro Phe Arg
        915                 920                 925

Ser Tyr Lys Gln Lys Met Leu Met Gln Ser Gly Asp Ile Glu Thr Asn
    930                 935                 940

Pro Gly Pro Ala Ser Asp Asn Pro Ile Leu Glu Phe Leu Glu Ala Glu
945                 950                 955                 960

Asn Asp Leu Val Thr Leu Ala Ser Leu Trp Lys Met Val His Ser Val
                965                 970                 975

Gln Gln Thr Trp Arg Lys Tyr Val Lys Asn Asp Asp Phe Trp Pro Asn
            980                 985                 990

Leu Leu Ser Glu Leu Val Gly Glu  Gly Ser Val Ala Leu  Ala Ala Thr
        995                 1000                 1005

Leu Ser  Asn Gln Ala Ser Val  Lys Ala Leu Leu Gly  Leu His Phe
    1010                 1015                 1020

Leu Ser  Arg Gly Leu Asn Tyr  Thr Asp Phe Tyr Ser  Leu Leu Ile
    1025                 1030                 1035

Glu Lys  Cys Ser Ser Phe Phe  Thr Val Glu Pro Pro  Pro Pro Pro
    1040                 1045                 1050

Ala Glu  Asn Leu Met Thr Lys  Pro Ser Val Lys Ser  Lys Phe Arg
    1055                 1060                 1065

Lys Leu  Phe Lys Met Gln Gly  Pro Met Asp Lys Val  Lys Asp Trp
```

```
    1070                1075                1080

Asn Gln  Ile Ala Ala Gly Leu  Lys Asn Phe Gln Phe  Val Arg Asp
    1085                1090                1095

Leu Val  Lys Glu Val Val Asp  Trp Leu Gln Ala Trp  Ile Asn Lys
    1100                1105                1110

Glu Lys  Ala Ser Pro Val Leu  Gln Tyr Gln Leu Glu  Met Lys Lys
    1115                1120                1125

Leu Gly  Pro Val Ala Leu Ala  His Asp Ala Phe Met  Ala Gly Ser
    1130                1135                1140

Gly Pro  Pro Leu Ser Asp Asp  Gln Ile Glu Tyr Leu  Gln Asn Leu
    1145                1150                1155

Lys Ser  Leu Ala Leu Thr Leu  Gly Lys Thr Asn Leu  Ala Gln Ser
    1160                1165                1170

Leu Thr  Thr Met Ile Asn Ala  Lys Gln Ser Ser Ala  Gln Arg Val
    1175                1180                1185

Glu Pro  Val Val Val Val Leu  Arg Gly Lys Pro Gly  Cys Gly Lys
    1190                1195                1200

Ser Leu  Ala Ser Thr Leu Ile  Ala Gln Ala Val Ser  Lys Arg Leu
    1205                1210                1215

Tyr Gly  Ser Gln Ser Val Tyr  Ser Leu Pro Pro Asp  Pro Asp Phe
    1220                1225                1230

Phe Asp  Gly Tyr Lys Gly Gln  Phe Val Thr Leu Met  Asp Asp Leu
    1235                1240                1245

Gly Gln  Asn Pro Asp Gly Gln  Asp Phe Ser Thr Phe  Cys Gln Met
    1250                1255                1260

Val Ser  Thr Ala Gln Phe Leu  Pro Asn Met Ala Asp  Leu Ala Glu
    1265                1270                1275

Lys Gly  Arg Pro Phe Thr Ser  Asn Leu Ile Ile Ala  Thr Thr Asn
    1280                1285                1290

Leu Pro  His Phe Ser Pro Val  Thr Ile Ala Asp Pro  Ser Ala Val
    1295                1300                1305

Ser Arg  Arg Ile Asn Tyr Asp  Leu Thr Leu Glu Val  Ser Glu Ala
    1310                1315                1320

Tyr Lys  Lys His Thr Arg Leu  Asn Phe Asp Leu Ala  Phe Arg Arg
    1325                1330                1335

Thr Asp  Ala Pro Pro Ile Tyr  Pro Phe Ala Ala His  Val Pro Phe
    1340                1345                1350

Val Asp  Val Ala Val Arg Phe  Lys Asn Gly His Gln  Asn Phe Asn
    1355                1360                1365

Leu Leu  Glu Leu Val Asp Ser  Ile Cys Thr Asp Ile  Arg Ala Lys
    1370                1375                1380

Gln Gln  Gly Ala Arg Asn Met  Gln Thr Leu Val Leu  Gln Ser Pro
    1385                1390                1395

Asn Glu  Asn Asp Asp Thr Pro  Val Asp Glu Ala Leu  Gly Arg Val
    1400                1405                1410

Leu Ser  Pro Ala Ala Val Asp  Glu Ala Leu Val Asp  Leu Thr Pro
    1415                1420                1425

Glu Ala  Asp Pro Val Gly Arg  Leu Ala Ile Leu Ala  Lys Leu Gly
    1430                1435                1440

Leu Ala  Leu Ala Ala Val Thr  Pro Gly Leu Ile Ile  Leu Ala Val
    1445                1450                1455

Gly Leu  Tyr Arg Tyr Phe Ser  Gly Ser Asp Ala Asp  Gln Glu Glu
    1460                1465                1470
```

```
Thr Glu  Ser Glu Gly Ser Val  Lys Ala Pro Arg Ser  Glu Asn Ala
    1475                 1480                 1485

Tyr Asp  Gly Pro Lys Lys Asn  Ser Lys Pro Pro Gly  Ala Leu Ser
    1490                 1495                 1500

Leu Met  Glu Met Gln Gln Pro  Asn Val Asp Met Gly  Phe Glu Ala
    1505                 1510                 1515

Ala Val  Ala Lys Lys Val Val  Val Pro Ile Thr Phe  Met Val Pro
    1520                 1525                 1530

Asn Arg  Pro Ser Gly Leu Thr  Gln Ser Ala Leu Leu  Val Thr Gly
    1535                 1540                 1545

Arg Thr  Phe Leu Ile Asn Glu  His Thr Trp Ser Asn  Pro Ser Trp
    1550                 1555                 1560

Thr Ser  Phe Thr Ile Arg Gly  Glu Val His Thr Arg  Asp Glu Pro
    1565                 1570                 1575

Phe Gln  Thr Val His Phe Thr  His His Gly Ile Pro  Thr Asp Leu
    1580                 1585                 1590

Met Met  Val Arg Leu Gly Pro  Gly Asn Ser Phe Pro  Asn Asn Leu
    1595                 1600                 1605

Asp Lys  Phe Gly Leu Asp Gln  Met Pro Ala Arg Asn  Ser Arg Val
    1610                 1615                 1620

Val Gly  Val Ser Ser Ser Tyr  Gly Asn Phe Phe Phe  Ser Gly Asn
    1625                 1630                 1635

Phe Leu  Gly Phe Val Asp Ser  Ile Thr Ser Glu Gln  Gly Thr Tyr
    1640                 1645                 1650

Ala Arg  Leu Phe Arg Tyr Arg  Val Thr Thr Tyr Lys  Gly Trp Cys
    1655                 1660                 1665

Gly Ser  Ala Leu Val Cys Glu  Ala Gly Gly Val Arg  Arg Ile Ile
    1670                 1675                 1680

Gly Leu  His Ser Ala Gly Ala  Ala Gly Ile Gly Ala  Gly Thr Tyr
    1685                 1690                 1695

Ile Ser  Lys Leu Gly Leu Ile  Lys Ala Leu Lys His  Leu Gly Glu
    1700                 1705                 1710

Pro Leu  Ala Thr Met Gln Gly  Leu Met Thr Glu Leu  Glu Pro Gly
    1715                 1720                 1725

Ile Thr  Val His Val Pro Arg  Lys Ser Lys Leu Arg  Lys Thr Thr
    1730                 1735                 1740

Ala His  Ala Val Tyr Lys Pro  Glu Phe Glu Pro Ala  Val Leu Ser
    1745                 1750                 1755

Lys Phe  Asp Pro Arg Leu Asn  Lys Asp Val Asp Leu  Asp Glu Val
    1760                 1765                 1770

Ile Trp  Ser Lys His Thr Ala  Asn Val Pro Tyr Gln  Pro Pro Leu
    1775                 1780                 1785

Phe Tyr  Thr Tyr Met Ser Glu  Tyr Ala His Arg Val  Phe Ser Phe
    1790                 1795                 1800

Leu Gly  Lys Asp Asn Asp Ile  Leu Thr Val Lys Glu  Ala Ile Leu
    1805                 1810                 1815

Gly Ile  Pro Gly Leu Asp Pro  Met Asp Pro His Thr  Ala Pro Gly
    1820                 1825                 1830

Leu Pro  Tyr Ala Ile Asn Gly  Leu Arg Arg Thr Asp  Leu Val Asp
    1835                 1840                 1845

Phe Val  Asn Gly Thr Val Asp  Ala Ala Leu Ala Val  Gln Ile Gln
    1850                 1855                 1860
```

```
Lys Phe  Leu Asp Gly Asp Tyr  Ser Asp His Val Phe  Gln Thr Phe
    1865                 1870                 1875

Leu Lys  Asp Glu Ile Arg Pro  Ser Glu Lys Val Arg  Ala Gly Lys
    1880                 1885                 1890

Thr Arg  Ile Val Asp Val Pro  Ser Leu Ala His Cys  Ile Val Gly
    1895                 1900                 1905

Arg Met  Leu Leu Gly Arg Phe  Ala Ala Lys Phe Gln  Ser His Pro
    1910                 1915                 1920

Gly Phe  Leu Leu Gly Ser Ala  Ile Gly Ser Asp Pro  Asp Val Phe
    1925                 1930                 1935

Trp Thr  Val Ile Gly Ala Gln  Leu Glu Gly Arg Lys  Asn Thr Tyr
    1940                 1945                 1950

Asp Val  Asp Tyr Ser Ala Phe  Asp Ser Ser His Gly  Thr Gly Ser
    1955                 1960                 1965

Phe Glu  Ala Leu Ile Ser His  Phe Phe Thr Val Asp  Asn Gly Phe
    1970                 1975                 1980

Ser Pro  Ala Leu Gly Pro Tyr  Leu Arg Ser Leu Ala  Val Ser Val
    1985                 1990                 1995

His Ala  Tyr Gly Glu Arg Arg  Ile Lys Ile Thr Gly  Gly Leu Pro
    2000                 2005                 2010

Ser Gly  Cys Ala Ala Thr Ser  Leu Leu Asn Thr Val  Leu Asn Asn
    2015                 2020                 2025

Val Ile  Ile Arg Thr Ala Leu  Ala Leu Thr Tyr Lys  Glu Phe Glu
    2030                 2035                 2040

Tyr Asp  Met Val Asp Ile Ile  Ala Tyr Gly Asp Asp  Leu Leu Val
    2045                 2050                 2055

Gly Thr  Asp Tyr Asp Leu Asp  Phe Asn Glu Val Ala  Arg Arg Ala
    2060                 2065                 2070

Ala Lys  Leu Gly Tyr Lys Met  Thr Pro Ala Asn Lys  Gly Ser Val
    2075                 2080                 2085

Phe Pro  Pro Thr Ser Ser Leu  Ser Asp Ala Val Phe  Leu Lys Arg
    2090                 2095                 2100

Lys Phe  Val Gln Asn Asn Asp  Gly Leu Tyr Lys Pro  Val Met Asp
    2105                 2110                 2115

Leu Lys  Asn Leu Glu Ala Met  Leu Ser Tyr Phe Lys  Pro Gly Thr
    2120                 2125                 2130

Leu Leu  Glu Lys Leu Gln Ser  Val Ser Met Leu Ala  Gln His Ser
    2135                 2140                 2145

Gly Lys  Glu Glu Tyr Asp Arg  Leu Met His Pro Phe  Ala Asp Tyr
    2150                 2155                 2160

Gly Ala  Val Pro Ser His Glu  Tyr Leu Gln Ala Arg  Trp Arg Ala
    2165                 2170                 2175

Leu Phe  Asp
    2180


<210> SEQ ID NO 17
<211> LENGTH: 2181
<212> TYPE: PRT
<213> ORGANISM: Senecavirus

<400> SEQUENCE: 17

Met Gln Asn Ser His Phe Ser Phe Asp Thr Ala Ser Gly Thr Phe Glu
1               5                   10                  15

Asp Val Thr Gly Thr Lys Val Lys Ile Val Glu Tyr Pro Arg Ser Val
            20                  25                  30
```

```
Asn Asn Gly Val Tyr Asp Ser Ser Thr His Leu Glu Ile Leu Asn Leu
        35                  40                  45

Gln Gly Glu Ile Glu Ile Leu Arg Ser Phe Asn Glu Tyr Gln Ile Arg
    50                  55                  60

Ala Ala Lys Gln Gln Leu Gly Leu Asp Ile Val Tyr Glu Leu Gln Gly
65                  70                  75                  80

Asn Val Gln Thr Thr Ser Lys Asn Asp Phe Asp Ser Arg Gly Asn Asn
                85                  90                  95

Gly Asn Met Thr Phe Asn Tyr Tyr Ala Asn Thr Tyr Gln Asn Ser Val
            100                 105                 110

Asp Phe Ser Thr Ser Ser Ser Ala Ser Gly Ala Gly Pro Gly Asn Ser
        115                 120                 125

Arg Gly Gly Leu Ala Gly Leu Leu Thr Asn Phe Ser Gly Ile Leu Asn
    130                 135                 140

Pro Leu Gly Tyr Leu Lys Asp His Asn Thr Glu Glu Met Glu Asn Ser
145                 150                 155                 160

Ala Asp Arg Val Thr Thr Gln Thr Ala Gly Asn Thr Ala Ile Asn Thr
                165                 170                 175

Gln Ser Ser Leu Gly Val Leu Cys Ala Tyr Val Glu Asp Pro Thr Lys
            180                 185                 190

Ser Asp Pro Pro Ser Ser Ser Thr Asp Gln Pro Thr Thr Thr Phe Thr
        195                 200                 205

Ala Ile Asp Arg Trp Tyr Thr Gly Arg Leu Asn Ser Trp Thr Lys Ala
    210                 215                 220

Val Lys Thr Phe Ser Phe Gln Ala Val Pro Leu Pro Gly Ala Phe Leu
225                 230                 235                 240

Ser Arg Gln Gly Gly Leu Asn Gly Gly Ala Phe Thr Ala Thr Leu His
                245                 250                 255

Arg His Phe Leu Met Lys Cys Gly Trp Gln Val Gln Val Gln Cys Asn
            260                 265                 270

Leu Thr Gln Phe His Gln Gly Ala Leu Leu Val Ala Met Val Pro Glu
        275                 280                 285

Thr Thr Leu Asp Val Lys Pro Asp Gly Lys Ala Lys Ser Leu Gln Glu
    290                 295                 300

Leu Asn Glu Glu Gln Trp Val Glu Met Ser Asp Asp Tyr Arg Thr Gly
305                 310                 315                 320

Lys Asn Met Pro Phe Gln Ser Leu Gly Thr Tyr Tyr Arg Pro Pro Asn
                325                 330                 335

Trp Thr Trp Gly Pro Asn Phe Ile Asn Pro Tyr Gln Val Thr Val Phe
            340                 345                 350

Pro His Gln Ile Leu Asn Ala Arg Thr Ser Thr Ser Val Asp Ile Asn
        355                 360                 365

Val Pro Tyr Ile Gly Glu Thr Pro Thr Gln Ser Ser Glu Thr Gln Asn
    370                 375                 380

Ser Trp Thr Leu Leu Val Met Val Leu Val Pro Leu Asp Tyr Lys Glu
385                 390                 395                 400

Gly Ala Thr Thr Asp Pro Glu Ile Thr Phe Ser Val Arg Pro Thr Ser
                405                 410                 415

Pro Tyr Phe Asn Gly Leu Arg Asn Arg Tyr Thr Ala Gly Thr Asp Glu
            420                 425                 430

Glu Gln Gly Pro Ile Pro Thr Ala Pro Arg Glu Asn Ser Leu Met Phe
        435                 440                 445
```

```
Leu Ser Thr Leu Pro Asp Asp Thr Val Pro Ala Tyr Gly Asn Val Arg
    450                 455                 460

Thr Pro Pro Val Asn Tyr Leu Pro Gly Glu Ile Thr Asp Leu Leu Gln
465                 470                 475                 480

Leu Ala Arg Ile Pro Thr Leu Met Ala Phe Glu Arg Val Pro Glu Pro
                485                 490                 495

Val Pro Ala Ser Asp Thr Tyr Val Pro Tyr Val Ala Val Pro Thr Gln
            500                 505                 510

Phe Asp Asp Arg Pro Leu Ile Ser Phe Pro Ile Thr Leu Ser Asp Pro
        515                 520                 525

Val Tyr Gln Asn Thr Leu Val Gly Ala Ile Ser Ser Asn Phe Ala Asn
    530                 535                 540

Tyr Arg Gly Cys Ile Gln Ile Thr Leu Thr Phe Cys Gly Pro Met Met
545                 550                 555                 560

Ala Arg Gly Lys Phe Leu Leu Ser Tyr Ser Pro Pro Asn Gly Thr Gln
                565                 570                 575

Pro Gln Thr Leu Ser Glu Ala Met Gln Cys Thr Tyr Ser Ile Trp Asp
            580                 585                 590

Ile Gly Leu Asn Ser Ser Trp Thr Phe Val Val Pro Tyr Ile Ser Pro
        595                 600                 605

Ser Asp Tyr Arg Glu Thr Arg Ala Ile Thr Asn Ser Val Tyr Ser Ala
    610                 615                 620

Asp Gly Trp Phe Ser Leu His Lys Leu Thr Lys Ile Thr Leu Pro Pro
625                 630                 635                 640

Asp Cys Pro Gln Ser Pro Cys Ile Leu Phe Phe Ala Ser Ala Gly Glu
                645                 650                 655

Asp Tyr Thr Leu Arg Leu Pro Val Asp Cys Asn Pro Ser Tyr Val Phe
            660                 665                 670

His Ser Thr Asp Asn Ala Glu Thr Gly Val Ile Glu Ala Gly Asn Thr
        675                 680                 685

Asp Thr Asp Phe Ser Gly Glu Leu Ala Ala Pro Gly Ser Asn His Thr
    690                 695                 700

Asn Val Lys Phe Leu Phe Asp Arg Ser Arg Leu Leu Asn Val Ile Lys
705                 710                 715                 720

Val Leu Glu Lys Asp Ala Val Phe Pro Arg Pro Phe Pro Thr Gln Glu
                725                 730                 735

Gly Ala Gln Gln Asp Asp Gly Tyr Phe Cys Leu Leu Thr Pro Arg Pro
            740                 745                 750

Thr Val Ala Ser Arg Pro Ala Thr Arg Phe Gly Leu Tyr Ala Asn Pro
        755                 760                 765

Ser Gly Ser Gly Val Leu Ala Asn Thr Ser Leu Asp Phe Asn Phe Tyr
    770                 775                 780

Ser Leu Ala Cys Phe Thr Tyr Phe Arg Ser Asp Leu Glu Val Thr Val
785                 790                 795                 800

Val Ser Leu Glu Pro Asp Leu Glu Phe Ala Val Gly Trp Phe Pro Ser
                805                 810                 815

Gly Ser Glu Tyr Gln Ala Ser Ser Phe Val Tyr Asp Gln Leu His Val
            820                 825                 830

Pro Phe His Phe Thr Gly Arg Thr Pro Arg Ala Phe Ala Ser Lys Gly
        835                 840                 845

Gly Lys Val Ser Phe Val Leu Pro Trp Asn Ser Val Ser Ser Val Leu
    850                 855                 860

Pro Val Arg Trp Gly Gly Ala Ser Lys Leu Ser Ser Ala Thr Arg Gly
```

```
865                 870                 875                 880

Leu Pro Ala His Ala Asp Trp Gly Thr Ile Tyr Ala Phe Val Pro Arg
                885                 890                 895

Pro Asn Glu Lys Lys Ser Thr Ala Val Lys His Val Ala Val Tyr Ile
            900                 905                 910

Arg Tyr Lys Asn Ala Arg Ala Trp Cys Pro Ser Met Leu Pro Phe Arg
        915                 920                 925

Ser Tyr Lys Gln Lys Met Leu Met Gln Ser Gly Asp Ile Glu Thr Asn
    930                 935                 940

Pro Gly Pro Ala Ser Asp Asn Pro Ile Leu Glu Phe Leu Glu Ala Glu
945                 950                 955                 960

Asn Asp Leu Val Thr Leu Ala Ser Leu Trp Lys Met Val His Ser Val
                965                 970                 975

Gln Gln Thr Trp Arg Lys Tyr Val Lys Asn Asp Asp Phe Trp Pro Asn
            980                 985                 990

Leu Leu Ser Glu Leu Val Gly Glu  Gly Ser Val Ala Leu  Ala Ala Thr
        995                 1000                1005

Leu Ser  Asn Gln Ala Ser Val  Lys Ala Leu Leu Gly  Leu His Phe
    1010                 1015                 1020

Leu Ser  Arg Gly Leu Asn Tyr  Thr Asp Phe Tyr Ser  Leu Leu Ile
    1025                 1030                 1035

Glu Lys  Cys Ser Ser Phe Phe  Thr Val Glu Pro Pro  Pro Pro Pro
    1040                 1045                 1050

Ala Glu  Asn Leu Met Thr Lys  Pro Ser Val Lys Ser  Lys Phe Arg
    1055                 1060                 1065

Lys Leu  Phe Lys Met Gln Gly  Pro Met Asp Lys Val  Lys Asp Trp
    1070                 1075                 1080

Asn Gln  Ile Ala Ala Gly Leu  Lys Asn Phe Gln Phe  Val Arg Asp
    1085                 1090                 1095

Leu Val  Lys Glu Val Val Asp  Trp Leu Gln Ala Trp  Ile Asn Lys
    1100                 1105                 1110

Glu Lys  Ala Ser Pro Val Leu  Gln Tyr Gln Leu Glu  Met Lys Lys
    1115                 1120                 1125

Leu Gly  Pro Val Ala Leu Ala  His Asp Ala Phe Met  Ala Gly Ser
    1130                 1135                 1140

Gly Pro  Pro Leu Ser Asp Asp  Gln Ile Glu Tyr Leu  Gln Asn Leu
    1145                 1150                 1155

Lys Ser  Leu Ala Leu Thr Leu  Gly Lys Thr Asn Leu  Ala Gln Ser
    1160                 1165                 1170

Leu Thr  Thr Met Ile Asn Ala  Lys Gln Ser Ser Ala  Gln Arg Val
    1175                 1180                 1185

Glu Pro  Val Val Val Val Leu  Arg Gly Lys Pro Gly  Cys Gly Lys
    1190                 1195                 1200

Ser Leu  Ala Ser Thr Leu Ile  Ala Gln Ala Val Ser  Lys Arg Leu
    1205                 1210                 1215

Tyr Gly  Ser Gln Ser Val Tyr  Ser Leu Pro Pro Asp  Pro Asp Phe
    1220                 1225                 1230

Phe Asp  Gly Tyr Lys Gly Gln  Phe Val Thr Leu Met  Asp Asp Leu
    1235                 1240                 1245

Gly Gln  Asn Pro Asp Gly Gln  Asp Phe Ser Thr Phe  Cys Gln Met
    1250                 1255                 1260

Val Ser  Thr Ala Gln Phe Leu  Pro Asn Met Ala Asp  Leu Ala Glu
    1265                 1270                 1275
```

```
Lys Gly  Arg Pro Phe Thr Ser  Asn Leu Ile Ile Ala  Thr Thr Asn
    1280                 1285                 1290

Leu Pro  His Phe Ser Pro Val  Thr Ile Ala Asp Pro  Ser Ala Val
    1295                 1300                 1305

Ser Arg  Arg Ile Asn Tyr Asp  Leu Thr Leu Glu Val  Ser Glu Ala
    1310                 1315                 1320

Tyr Lys  Lys His Thr Arg Leu  Asn Phe Asp Leu Ala  Phe Arg Arg
    1325                 1330                 1335

Thr Asp  Ala Pro Pro Ile Tyr  Pro Phe Ala Ala His  Val Pro Phe
    1340                 1345                 1350

Val Asp  Val Ala Val Arg Phe  Lys Asn Gly His Gln  Asn Phe Asn
    1355                 1360                 1365

Leu Leu  Glu Leu Val Asp Ser  Ile Cys Thr Asp Ile  Arg Ala Lys
    1370                 1375                 1380

Gln Gln  Gly Ala Arg Asn Met  Gln Thr Leu Val Leu  Gln Ser Pro
    1385                 1390                 1395

Asn Glu  Asn Asp Asp Thr Pro  Val Asp Glu Ala Leu  Gly Arg Val
    1400                 1405                 1410

Leu Ser  Pro Ala Ala Val Asp  Glu Ala Leu Val Asp  Leu Thr Pro
    1415                 1420                 1425

Glu Ala  Asp Pro Val Gly Arg  Leu Ala Ile Leu Ala  Lys Leu Gly
    1430                 1435                 1440

Leu Ala  Leu Ala Ala Val Thr  Pro Gly Leu Ile Ile  Leu Ala Val
    1445                 1450                 1455

Gly Leu  Tyr Arg Tyr Phe Ser  Gly Ser Asp Ala Asp  Gln Glu Glu
    1460                 1465                 1470

Thr Glu  Ser Glu Gly Ser Val  Lys Ala Pro Arg Ser  Glu Asn Ala
    1475                 1480                 1485

Tyr Asp  Gly Pro Lys Lys Asn  Ser Lys Pro Pro Gly  Ala Leu Ser
    1490                 1495                 1500

Leu Met  Glu Met Gln Gln Pro  Asn Val Asp Met Gly  Phe Glu Ala
    1505                 1510                 1515

Ala Val  Ala Lys Lys Val Val  Val Pro Ile Thr Phe  Met Val Pro
    1520                 1525                 1530

Asn Arg  Pro Ser Gly Leu Thr  Gln Ser Ala Leu Leu  Val Thr Gly
    1535                 1540                 1545

Arg Thr  Phe Leu Ile Asn Glu  His Thr Trp Ser Asn  Pro Ser Trp
    1550                 1555                 1560

Thr Ser  Phe Thr Ile Arg Gly  Glu Val His Thr Arg  Asp Glu Pro
    1565                 1570                 1575

Phe Gln  Thr Val His Phe Thr  His His Gly Ile Pro  Thr Asp Leu
    1580                 1585                 1590

Met Met  Val Arg Leu Gly Pro  Gly Asn Ser Phe Pro  Asn Asn Leu
    1595                 1600                 1605

Asp Lys  Phe Gly Leu Asp Gln  Met Pro Ala Arg Asn  Ser Arg Val
    1610                 1615                 1620

Val Gly  Val Ser Ser Ser Tyr  Gly Asn Phe Phe Phe  Ser Gly Asn
    1625                 1630                 1635

Phe Leu  Gly Phe Val Asp Ser  Ile Thr Ser Glu Gln  Gly Thr Tyr
    1640                 1645                 1650

Ala Arg  Leu Phe Arg Tyr Arg  Val Thr Thr Tyr Lys  Gly Trp Cys
    1655                 1660                 1665
```

```
Gly Ser  Ala Leu Val Cys Glu  Ala Gly Gly Val Arg  Arg Ile Ile
    1670                 1675                 1680

Gly Leu  His Ser Ala Gly Ala  Ala Gly Ile Gly Ala  Gly Thr Tyr
    1685                 1690                 1695

Ile Ser  Lys Leu Gly Leu Ile  Lys Ala Leu Lys His  Leu Gly Glu
    1700                 1705                 1710

Pro Leu  Ala Thr Met Gln Gly  Leu Met Thr Glu Leu  Glu Pro Gly
    1715                 1720                 1725

Ile Thr  Val His Val Pro Arg  Lys Ser Lys Leu Arg  Lys Thr Thr
    1730                 1735                 1740

Ala His  Ala Val Tyr Lys Pro  Glu Phe Glu Pro Ala  Val Leu Ser
    1745                 1750                 1755

Lys Phe  Asp Pro Arg Leu Asn  Lys Asp Val Asp Leu  Asp Glu Val
    1760                 1765                 1770

Ile Trp  Ser Lys His Thr Ala  Asn Val Pro Tyr Gln  Pro Pro Leu
    1775                 1780                 1785

Phe Tyr  Thr Tyr Met Ser Glu  Tyr Ala His Arg Val  Phe Ser Phe
    1790                 1795                 1800

Leu Gly  Lys Asp Asn Asp Ile  Leu Thr Val Lys Glu  Ala Ile Leu
    1805                 1810                 1815

Gly Ile  Pro Gly Leu Asp Pro  Met Asp Pro His Thr  Ala Pro Gly
    1820                 1825                 1830

Leu Pro  Tyr Ala Ile Asn Gly  Leu Arg Arg Thr Asp  Leu Val Asp
    1835                 1840                 1845

Phe Val  Asn Gly Thr Val Asp  Ala Ala Leu Ala Val  Gln Ile Gln
    1850                 1855                 1860

Lys Phe  Leu Asp Gly Asp Tyr  Ser Asp His Val Phe  Gln Thr Phe
    1865                 1870                 1875

Leu Lys  Asp Glu Ile Arg Pro  Ser Glu Lys Val Arg  Ala Gly Lys
    1880                 1885                 1890

Thr Arg  Ile Val Asp Val Pro  Ser Leu Ala His Cys  Ile Val Gly
    1895                 1900                 1905

Arg Met  Leu Leu Gly Arg Phe  Ala Ala Lys Phe Gln  Ser His Pro
    1910                 1915                 1920

Gly Phe  Leu Leu Gly Ser Ala  Ile Gly Ser Asp Pro  Asp Val Phe
    1925                 1930                 1935

Trp Thr  Val Ile Gly Ala Gln  Leu Glu Gly Arg Lys  Asn Thr Tyr
    1940                 1945                 1950

Asp Val  Asp Tyr Ser Ala Phe  Asp Ser Ser His Gly  Thr Gly Ser
    1955                 1960                 1965

Phe Glu  Ala Leu Ile Ser His  Phe Phe Thr Val Asp  Asn Gly Phe
    1970                 1975                 1980

Ser Pro  Ala Leu Gly Pro Tyr  Leu Arg Ser Leu Ala  Val Ser Val
    1985                 1990                 1995

His Ala  Tyr Gly Glu Arg Arg  Ile Lys Ile Thr Gly  Gly Leu Pro
    2000                 2005                 2010

Ser Gly  Cys Ala Ala Thr Ser  Leu Leu Asn Thr Val  Leu Asn Asn
    2015                 2020                 2025

Val Ile  Ile Arg Thr Ala Leu  Ala Leu Thr Tyr Lys  Glu Phe Glu
    2030                 2035                 2040

Tyr Asp  Met Val Asp Ile Ile  Ala Tyr Gly Asp Asp  Leu Leu Val
    2045                 2050                 2055

Gly Thr  Asp Tyr Asp Leu Asp  Phe Asn Glu Val Ala  Arg Arg Ala
```

```
    2060                2065                2070

Ala Lys  Leu Gly Tyr Lys Met  Thr Pro Ala Asn Lys  Gly Ser Val
    2075                2080                2085

Phe Pro  Pro Thr Ser Ser Leu  Ser Asp Ala Val Phe  Leu Lys Arg
    2090                2095                2100

Lys Phe  Val Gln Asn Asn Asp  Gly Leu Tyr Lys Pro  Val Met Asp
    2105                2110                2115

Leu Lys  Asn Leu Glu Ala Met  Leu Ser Tyr Phe Lys  Pro Gly Thr
    2120                2125                2130

Leu Leu  Glu Lys Leu Gln Ser  Val Ser Met Leu Ala  Gln His Ser
    2135                2140                2145

Gly Lys  Glu Glu Tyr Asp Arg  Leu Met His Pro Phe  Ala Asp Tyr
    2150                2155                2160

Gly Ala  Val Pro Ser His Glu  Tyr Leu Gln Ala Arg  Trp Arg Ala
    2165                2170                2175

Leu Phe  Asp
    2180


<210> SEQ ID NO 18
<211> LENGTH: 3308
<212> TYPE: DNA
<213> ORGANISM: Senecavirus

<400> SEQUENCE: 18

ggatccgcca ccatgggtaa tgttcagaca acctcaaaga atgattttga ttcccgcggc     60

aataatggta acatgacctt caattactac gcaaacactt accagaattc agtagacttc    120

tcgacctcct cgtcggcgtc aggcgccgga cccgggaact cccggggcgg actagcgggt    180

ctcctcacaa atttcagtgg aatcttgaac cctcttggct acctcaaaga tcacaatacc    240

gaagaaatgg aaaactctgc tgatcgagtc ataacgcaaa cggcgggcaa cactgccata    300

aacacgcaat catcactggg tgtgttgtgt gcctacgttg aagacccgac caaatctgac    360

cctccgtcca gcagcacaga tcaacccacc accactttta ctgccatcga caggtggtac    420

actggacgcc tcaattcttg gacaaaagct gtaaaaacct tctcttttca ggccgtcccg    480

ctccctggag ccttcctgtc taaacaggga ggcctcaacg gaggggcctt cacggctacc    540

ctacatagac atttcttaat gaagtgcggg tggcaggtgc aggtccaatg caatttgacg    600

caattccacc aaggtgctct tcttgttgcc atggtccccg aaaccaccct tgatgtcaaa    660

cctgacggca aggcaaagag cttacaggag ctgaatgaag agcagtgggt ggaaatgtct    720

gacgattacc ggaccgggaa aaacatgcct tttcagtctc ttggcacata ctatcggccc    780

cctaactgga cttggggccc caatttcatc aacccctatc aagtaacagt tttcccacac    840

caaattctga acgcgagaac ctctacctcg gtagacataa gtgtcccata catcggggag    900

actcctacac aatcctcaga gacacagaac tcctggaccc tccttgttat ggtgcttgtc    960

cccctggact acaaggaggg agccacaact gacccagaaa ttacattttc tgtaaggcct   1020

acaagtccct acttcaatgg gcttcgtaac cgtttcacga ccgggacgga cgaggaacag   1080

gggcccattc ccacagcacc cagagaaaat tcgcttatgt ttctctcaac catccctgac   1140

gacactgtcc ctgcttacgg gaatgtgcgt accccctcccg tcaattacct ccccggtgaa   1200

ataaccgacc tcttacaact ggcccgtata cccactctca tggcgtttgg gcgggtgtct   1260

gaacccgagc ctgcctcaga cgcatatgtg ccctacgttg ccgttcctgc ccagttcgac   1320

gacaagcctc tcatctcctt cccgatcacc ctttcagatc ctgtctacca gaacaccctg   1380
```

```
gtaggcgcca tcagttcgaa cttcgccaac taccgggggt gtatccaaat cactctgaca   1440

ttttgtggac ccatgatggc aagagggaaa ttcctgctct cgtattctcc cccaaatgga   1500

gcacaaccac agaccctttc tgaagctatg cagtgcacat actctatttg ggatataggc   1560

ttgaactcta gttggacctt tgtcatcccc tacatctcgc ccagtgatta ccgtgaaact   1620

cgggctatta ccaactcagt ttattctgct gatggttggt ttagcttgca caagctgacc   1680

aaaattactc taccacctga ctgcccacag agtccctgta ttctcttttt cgcctctgct   1740

ggtgaggatt acaccctccg tctccctgtt gattgtaatc cttcctacgt gttccactcc   1800

accgacaacg ccgagactgg ggttattgag gcaggtaaca ctgacaccga tttctctggt   1860

gaactggcgg ctcctggctc taaccatact aatgtcaaat tcctgtttga ccgatctcga   1920

ctactgaatg taattaaggt actggagaag gacgccgtct tcccccgtcc tttccccaca   1980

gcaacaggtg cacagcagga cgatggttac ttttgtcttc taacaccccg cccaacagtc   2040

gcttcccgac ccgccactcg tttcggcctg tacgtcaacc cgtctgacag tggcgttctc   2100

gctaacactt cactggattt caatttttac agtttggcct gtttcactta ctttagatca   2160

gaccttgaag tcacggtggt ctcactggag ccagatttgg aattcgccgt ggggtggttc   2220

ccctctggca gtgagtacca ggcttctagc tttgtctacg accaactgca tgtaccctac   2280

cactttactg ggcgcactcc ccgcgctttc accagcaagg gtggaaaggt atctttcgtg   2340

ctcccttgga actctgtctc ttccgtgctt cccgtgcgct ggggggggcgc ttccaagctt   2400

tcttctgcca cgcggggtct gccggctcat gctgactggg ggaccattta cgcctttatc   2460

ccccgtccta acgagaagaa aagcaccgct gtaaagcacg tggcggtgta cgttcggtac   2520

aagaacgcgc gtgcttggtg ccccagcatg cttccctttc gcagctacaa gcaaaagatg   2580

ctgatgcaat caggcgacat cgagaccaac cctggccctg gttcaggtaa gccccctgga   2640

gcgctctctc ttatggaaat gcaacagccc aacgtggaca tgggctttga ggctgcggtc   2700

gctaagaaag tggtcgtccc cattaccttc atggttccca acagaccttc tggacttaca   2760

cagtccgctc ttcttgtggc cggccggacc ttcctaatca atgagcatac atggtccaac   2820

ccctcctgga ccagcttcac aatccgtggt gaggtgcaca ctcgtgatga gcctttccaa   2880

acggttcatt ttactcacca tggtcttccc acagatctga tgatggtacg tctcggaccg   2940

ggcaactctt tccctaacaa tctagacaag tttggacttg accagatgcc ggcacgtaac   3000

tcccgtgtgg ttggcgtttc ggctagttac ggtaacttct tcttctctgg gaacttcctc   3060

gggtttgttg actccatcac ctctgaccaa ggaacctatg cgagactttt caggtacagg   3120

gtgacgactt acaagggatg gtgcggttcg gccctggtct gtgaggccgg tggtgtccga   3180

cgcatcattg gcatgcattc tgctggtgcc gctggtatcg gcgccgggac ttacatctca   3240

aaattaggac tgatcaaagc ccttaaacac ctcggtgagc ctctggctac aatgcaatga   3300

gcggccgc                                                            3308
```

<210> SEQ ID NO 19
<211> LENGTH: 1095
<212> TYPE: PRT
<213> ORGANISM: Senecavirus

<400> SEQUENCE: 19

```
Met Gly Asn Val Gln Thr Thr Ser Lys Asn Asp Phe Asp Ser Arg Gly
1               5                   10                  15

Asn Asn Gly Asn Met Thr Phe Asn Tyr Tyr Ala Asn Thr Tyr Gln Asn
```

```
            20                  25                  30

Ser Val Asp Phe Ser Thr Ser Ser Ser Ala Ser Gly Ala Gly Pro Gly
        35                  40                  45

Asn Ser Arg Gly Gly Leu Ala Gly Leu Leu Thr Asn Phe Ser Gly Ile
    50                  55                  60

Leu Asn Pro Leu Gly Tyr Leu Lys Asp His Asn Thr Glu Glu Met Glu
65                  70                  75                  80

Asn Ser Ala Asp Arg Val Ile Thr Gln Thr Ala Gly Asn Thr Ala Ile
                85                  90                  95

Asn Thr Gln Ser Ser Leu Gly Val Leu Cys Ala Tyr Val Glu Asp Pro
            100                 105                 110

Thr Lys Ser Asp Pro Pro Ser Ser Ser Thr Asp Gln Pro Thr Thr Thr
        115                 120                 125

Phe Thr Ala Ile Asp Arg Trp Tyr Thr Gly Arg Leu Asn Ser Trp Thr
    130                 135                 140

Lys Ala Val Lys Thr Phe Ser Phe Gln Ala Val Pro Leu Pro Gly Ala
145                 150                 155                 160

Phe Leu Ser Lys Gln Gly Gly Leu Asn Gly Gly Ala Phe Thr Ala Thr
                165                 170                 175

Leu His Arg His Phe Leu Met Lys Cys Gly Trp Gln Val Gln Val Gln
            180                 185                 190

Cys Asn Leu Thr Gln Phe His Gln Gly Ala Leu Leu Val Ala Met Val
        195                 200                 205

Pro Glu Thr Thr Leu Asp Val Lys Pro Asp Gly Lys Ala Lys Ser Leu
    210                 215                 220

Gln Glu Leu Asn Glu Glu Gln Trp Val Glu Met Ser Asp Asp Tyr Arg
225                 230                 235                 240

Thr Gly Lys Asn Met Pro Phe Gln Ser Leu Gly Thr Tyr Tyr Arg Pro
                245                 250                 255

Pro Asn Trp Thr Trp Gly Pro Asn Phe Ile Asn Pro Tyr Gln Val Thr
            260                 265                 270

Val Phe Pro His Gln Ile Leu Asn Ala Arg Thr Ser Thr Ser Val Asp
        275                 280                 285

Ile Ser Val Pro Tyr Ile Gly Glu Thr Pro Thr Gln Ser Ser Glu Thr
    290                 295                 300

Gln Asn Ser Trp Thr Leu Leu Val Met Val Leu Val Pro Leu Asp Tyr
305                 310                 315                 320

Lys Glu Gly Ala Thr Thr Asp Pro Glu Ile Thr Phe Ser Val Arg Pro
                325                 330                 335

Thr Ser Pro Tyr Phe Asn Gly Leu Arg Asn Arg Phe Thr Thr Gly Thr
            340                 345                 350

Asp Glu Glu Gln Gly Pro Ile Pro Thr Ala Pro Arg Glu Asn Ser Leu
        355                 360                 365

Met Phe Leu Ser Thr Ile Pro Asp Asp Thr Val Pro Ala Tyr Gly Asn
    370                 375                 380

Val Arg Thr Pro Pro Val Asn Tyr Leu Pro Gly Glu Ile Thr Asp Leu
385                 390                 395                 400

Leu Gln Leu Ala Arg Ile Pro Thr Leu Met Ala Phe Gly Arg Val Ser
                405                 410                 415

Glu Pro Glu Pro Ala Ser Asp Ala Tyr Val Pro Tyr Val Ala Val Pro
            420                 425                 430

Ala Gln Phe Asp Asp Lys Pro Leu Ile Ser Phe Pro Ile Thr Leu Ser
        435                 440                 445
```

```
Asp Pro Val Tyr Gln Asn Thr Leu Val Gly Ala Ile Ser Ser Asn Phe
    450                 455                 460

Ala Asn Tyr Arg Gly Cys Ile Gln Ile Thr Leu Thr Phe Cys Gly Pro
465                 470                 475                 480

Met Met Ala Arg Gly Lys Phe Leu Leu Ser Tyr Ser Pro Pro Asn Gly
                485                 490                 495

Ala Gln Pro Gln Thr Leu Ser Glu Ala Met Gln Cys Thr Tyr Ser Ile
            500                 505                 510

Trp Asp Ile Gly Leu Asn Ser Ser Trp Thr Phe Val Ile Pro Tyr Ile
        515                 520                 525

Ser Pro Ser Asp Tyr Arg Glu Thr Arg Ala Ile Thr Asn Ser Val Tyr
    530                 535                 540

Ser Ala Asp Gly Trp Phe Ser Leu His Lys Leu Thr Lys Ile Thr Leu
545                 550                 555                 560

Pro Pro Asp Cys Pro Gln Ser Pro Cys Ile Leu Phe Phe Ala Ser Ala
                565                 570                 575

Gly Glu Asp Tyr Thr Leu Arg Leu Pro Val Asp Cys Asn Pro Ser Tyr
            580                 585                 590

Val Phe His Ser Thr Asp Asn Ala Glu Thr Gly Val Ile Glu Ala Gly
        595                 600                 605

Asn Thr Asp Thr Asp Phe Ser Gly Glu Leu Ala Ala Pro Gly Ser Asn
    610                 615                 620

His Thr Asn Val Lys Phe Leu Phe Asp Arg Ser Arg Leu Leu Asn Val
625                 630                 635                 640

Ile Lys Val Leu Glu Lys Asp Ala Val Phe Pro Arg Pro Phe Pro Thr
                645                 650                 655

Ala Thr Gly Ala Gln Gln Asp Asp Gly Tyr Phe Cys Leu Leu Thr Pro
            660                 665                 670

Arg Pro Thr Val Ala Ser Arg Pro Ala Thr Arg Phe Gly Leu Tyr Val
        675                 680                 685

Asn Pro Ser Asp Ser Gly Val Leu Ala Asn Thr Ser Leu Asp Phe Asn
    690                 695                 700

Phe Tyr Ser Leu Ala Cys Phe Thr Tyr Phe Arg Ser Asp Leu Glu Val
705                 710                 715                 720

Thr Val Val Ser Leu Glu Pro Asp Leu Glu Phe Ala Val Gly Trp Phe
                725                 730                 735

Pro Ser Gly Ser Glu Tyr Gln Ala Ser Ser Phe Val Tyr Asp Gln Leu
            740                 745                 750

His Val Pro Tyr His Phe Thr Gly Arg Thr Pro Arg Ala Phe Thr Ser
        755                 760                 765

Lys Gly Gly Lys Val Ser Phe Val Leu Pro Trp Asn Ser Val Ser Ser
    770                 775                 780

Val Leu Pro Val Arg Trp Gly Gly Ala Ser Lys Leu Ser Ser Ala Thr
785                 790                 795                 800

Arg Gly Leu Pro Ala His Ala Asp Trp Gly Thr Ile Tyr Ala Phe Ile
                805                 810                 815

Pro Arg Pro Asn Glu Lys Lys Ser Thr Ala Val Lys His Val Ala Val
            820                 825                 830

Tyr Val Arg Tyr Lys Asn Ala Arg Ala Trp Cys Pro Ser Met Leu Pro
        835                 840                 845

Phe Arg Ser Tyr Lys Gln Lys Met Leu Met Gln Ser Gly Asp Ile Glu
    850                 855                 860
```

```
Thr Asn Pro Gly Pro Gly Ser Gly Lys Pro Pro Gly Ala Leu Ser Leu
865                 870                 875                 880

Met Glu Met Gln Gln Pro Asn Val Asp Met Gly Phe Glu Ala Ala Val
                885                 890                 895

Ala Lys Lys Val Val Val Pro Ile Thr Phe Met Val Pro Asn Arg Pro
            900                 905                 910

Ser Gly Leu Thr Gln Ser Ala Leu Leu Val Ala Gly Arg Thr Phe Leu
        915                 920                 925

Ile Asn Glu His Thr Trp Ser Asn Pro Ser Trp Thr Ser Phe Thr Ile
    930                 935                 940

Arg Gly Glu Val His Thr Arg Asp Glu Pro Phe Gln Thr Val His Phe
945                 950                 955                 960

Thr His His Gly Leu Pro Thr Asp Leu Met Met Val Arg Leu Gly Pro
                965                 970                 975

Gly Asn Ser Phe Pro Asn Asn Leu Asp Lys Phe Gly Leu Asp Gln Met
            980                 985                 990

Pro Ala Arg Asn Ser Arg Val Val  Gly Val Ser Ala Ser  Tyr Gly Asn
        995                 1000                1005

Phe Phe  Phe Ser Gly Asn Phe  Leu Gly Phe Val Asp  Ser Ile Thr
    1010                1015                1020

Ser Asp  Gln Gly Thr Tyr Ala  Arg Leu Phe Arg Tyr  Arg Val Thr
    1025                1030                1035

Thr Tyr  Lys Gly Trp Cys Gly  Ser Ala Leu Val Cys  Glu Ala Gly
    1040                1045                1050

Gly Val  Arg Arg Ile Ile Gly  Met His Ser Ala Gly  Ala Ala Gly
    1055                1060                1065

Ile Gly  Ala Gly Thr Tyr Ile  Ser Lys Leu Gly Leu  Ile Lys Ala
    1070                1075                1080

Leu Lys  His Leu Gly Glu Pro  Leu Ala Thr Met Gln
    1085                1090                1095


<210> SEQ ID NO 20
<211> LENGTH: 3308
<212> TYPE: DNA
<213> ORGANISM: Senecavirus

<400> SEQUENCE: 20

ggatccgcca ccatgggcaa cgttcaaact acctccaaga atgattttga ctcccgcggc      60

aacaacggca acatgacttt taactactac gccaatacgt atcaaaactc tgttgatttc     120

tcgacatcga gttccgcttc cggcgcggga cctggaaatt cccgcggtgg actggccggt     180

ctgctcacaa acttttccgg tatcctgaac cccctcggtt atctgaaaga tcacaatacg     240

gaagagatgg agaactctgc cgatcgtgtg attacgcaga cagctggtaa cacggctatc     300

aacactcaat cgtctctggg agtactctgt gcttacgtcg aggacccaac aaaatccgac     360

cctccatctt cctcgaccga tcaacctacg actaccttca cggccataga caggtggtat     420

acaggtcgcc tgaattcgtg gacaaaggct gttaaaacct ttagcttcca ggctgtgcca     480

ttgcccggtg ctttcctttc ccgccagggc ggcctcaacg gtggagcttt tactgctaca     540

ctgcacagac actttctgat gaaatgcggt tggcaggtgc aggtacagtg caatttgact     600

caattccacc aaggtgcact tctcgttgct atggttcccg agactacgct tgacgttaag     660

cctgacggca aggccaagtc tctccaagag ctgaatgagg aacagtgggt tgagatgagc     720

gatgactata gaaccggtaa aaacatgcca ttccagtccc tgggcacata ctacagaccc     780
```

-continued

```
ccaaattgga cttggggccc gaactttatc aatccgtatc aggtcaccgt gtttccacac    840

caaatcctga atgccaggac tagtaccagc gtcgatatta gcgtgcccta tatcggcgaa    900

acgccaaccc aatcctccga aactcagaac agctggacgc ttctggtaat ggtgttggta    960

cccttggatt ataaggaggg agccactacc gaccctgaaa tcactttttc ggtaaggccc   1020

actagccctt acttcaacgg actgcgcaac cgtttcacca ccggcactga tgaggagcaa   1080

ggccctatcc ctactgcccc cagagaaaat agcctgatgt ttctgagcac aattcctgac   1140

gacaccgtac ctgcctatgg taacgttcgt acgcctcccg taaactacct gcctggtgaa   1200

attacggacc tcttgcagct ggcccgcatc cctacactga tggccttcgg tcgtgtcagt   1260

gagcccgaac cagccagcga cgcttacgtt ccatatgttg cggtacctgc tcagttcgac   1320

gacaagccgt tgataagttt cccaatcact ttgagcgacc ctgtatacca gaacactttg   1380

gttggagcta tctcctcgaa ctttgcgaac taccgtggtt gtattcaaat cacccttaca   1440

ttctgcggcc cgatgatggc tcgtggcaag ttcctgttga gctactcccc ccccaacgga   1500

gcacaaccac agacactgtc cgaggccatg cagtgcacat actccatctg ggatatcggt   1560

ctcaacagct catggacctt tgtaatacca tacatctcgc catccgatta tagagagacc   1620

cgcgccatca ccaacagtgt gtactcagcc gatggatggt tcagtctcca taagcttaca   1680

aagatcactc tgcccccga ctgcccacaa tcaccctgca tattgttctt tgcctcagct   1740

ggtgaagatt acacgcttcg tttgcccgtc gactgtaacc cgtcttacgt gttccactcc   1800

acggacaatg ctgagaccgg tgtaattgag gctggtaaca ccgacacgga tttctctggt   1860

gagctggcgg ctcccggttc taaccatacc aacgtgaagt tccttttcga ccgttcacgt   1920

cttttgaacg taatcaaggt cttggaaaag gacgctgtgt tccctcgccc attccccaca   1980

gcaacgggag cacaacaaga cgacggctat ttctgcctgc tgacaccacg tcctactgtg   2040

gctagccgtc cggccacacg ctttggtctc tacgttaacc ctagcgactc tggtgtactg   2100

gctaacacct ccctggactt caatttctac tctctggcct gcttcacgta cttcaggagc   2160

gacctggagg tcactgtggt gtctctggaa ccagatctgg aatttgcggt aggatggttc   2220

ccttcaggaa gcgagtacca ggcatcgtcc tttgtgtacg accaacttca tgttccctac   2280

catttcaccg gtagaacccc acgtgccttc accagtaagg gaggcaaagt ttcttttgta   2340

ctgccctgga attctgtcag ttccgttctc ccggtccgct ggggcggagc gtcaaagctc   2400

tcatccgcga cccgcggatt gcccgcacac gcggattggg gaactatcta cgctttcatt   2460

ccacgcccta atgaaaagaa gtctacagca gtgaagcacg tggccgtcta tgtgcgttac   2520

aagaatgcaa gggcgtggtg tccgtctatg ttgccattcc gtagctataa acagaagatg   2580

cttatgcaaa gcggtgatat tgagacgaat cctggacctg gttcaggtaa gccccctgga   2640

gcgctctctc ttatggaaat gcaacagccc aacgtggaca tgggctttga ggctgcggtc   2700

gctaagaaag tggtcgtccc cattaccttc atggttccca acagaccttc tggacttaca   2760

cagtccgctc ttcttgtggc cggccggacc ttcctaatca atgagcatac atggtccaac   2820

ccctcctgga ccagcttcac aatccgtggt gaggtgcaca ctcgtgatga gcctttccaa   2880

acggttcatt ttactcacca tggtcttccc acagatctga tgatggtacg tctcggaccg   2940

ggcaactctt tccctaacaa tctagacaag tttggacttg accagatgcc ggcacgtaac   3000

tcccgtgtgg ttggcgtttc ggctagttac ggtaacttct tcttctctgg gaacttcctc   3060

gggtttgttg actccatcac ctctgaccaa ggaacctatg cgagactttt caggtacagg   3120

gtgacgactt acaagggatg gtgcggttcg gccctggtct gtgaggccgg tggtgtccga   3180
```

cgcatcattg gcatgcattc tgctggtgcc gctggtatcg gcgccgggac ttacatctca 3240
aaattaggac tgatcaaagc ccttaaacac ctcggtgagc ctctggctac aatgcaatga 3300
gcggccgc 3308

<210> SEQ ID NO 21
<211> LENGTH: 1095
<212> TYPE: PRT
<213> ORGANISM: Senecavirus

<400> SEQUENCE: 21

Met Gly Asn Val Gln Thr Thr Ser Lys Asn Asp Phe Asp Ser Arg Gly
1 5 10 15

Asn Asn Gly Asn Met Thr Phe Asn Tyr Tyr Ala Asn Thr Tyr Gln Asn
20 25 30

Ser Val Asp Phe Ser Thr Ser Ser Ser Ala Ser Gly Ala Gly Pro Gly
35 40 45

Asn Ser Arg Gly Gly Leu Ala Gly Leu Leu Thr Asn Phe Ser Gly Ile
50 55 60

Leu Asn Pro Leu Gly Tyr Leu Lys Asp His Asn Thr Glu Glu Met Glu
65 70 75 80

Asn Ser Ala Asp Arg Val Ile Thr Gln Thr Ala Gly Asn Thr Ala Ile
85 90 95

Asn Thr Gln Ser Ser Leu Gly Val Leu Cys Ala Tyr Val Glu Asp Pro
100 105 110

Thr Lys Ser Asp Pro Pro Ser Ser Ser Thr Asp Gln Pro Thr Thr Thr
115 120 125

Phe Thr Ala Ile Asp Arg Trp Tyr Thr Gly Arg Leu Asn Ser Trp Thr
130 135 140

Lys Ala Val Lys Thr Phe Ser Phe Gln Ala Val Pro Leu Pro Gly Ala
145 150 155 160

Phe Leu Ser Arg Gln Gly Gly Leu Asn Gly Gly Ala Phe Thr Ala Thr
165 170 175

Leu His Arg His Phe Leu Met Lys Cys Gly Trp Gln Val Gln Val Gln
180 185 190

Cys Asn Leu Thr Gln Phe His Gln Gly Ala Leu Leu Val Ala Met Val
195 200 205

Pro Glu Thr Thr Leu Asp Val Lys Pro Asp Gly Lys Ala Lys Ser Leu
210 215 220

Gln Glu Leu Asn Glu Glu Gln Trp Val Glu Met Ser Asp Asp Tyr Arg
225 230 235 240

Thr Gly Lys Asn Met Pro Phe Gln Ser Leu Gly Thr Tyr Tyr Arg Pro
245 250 255

Pro Asn Trp Thr Trp Gly Pro Asn Phe Ile Asn Pro Tyr Gln Val Thr
260 265 270

Val Phe Pro His Gln Ile Leu Asn Ala Arg Thr Ser Thr Ser Val Asp
275 280 285

Ile Ser Val Pro Tyr Ile Gly Glu Thr Pro Thr Gln Ser Ser Glu Thr
290 295 300

Gln Asn Ser Trp Thr Leu Leu Val Met Val Leu Val Pro Leu Asp Tyr
305 310 315 320

Lys Glu Gly Ala Thr Thr Asp Pro Glu Ile Thr Phe Ser Val Arg Pro
325 330 335

Thr Ser Pro Tyr Phe Asn Gly Leu Arg Asn Arg Phe Thr Thr Gly Thr

```
            340                 345                 350

Asp Glu Glu Gln Gly Pro Ile Pro Thr Ala Pro Arg Glu Asn Ser Leu
        355                 360                 365

Met Phe Leu Ser Thr Ile Pro Asp Asp Thr Val Pro Ala Tyr Gly Asn
    370                 375                 380

Val Arg Thr Pro Pro Val Asn Tyr Leu Pro Gly Glu Ile Thr Asp Leu
385                 390                 395                 400

Leu Gln Leu Ala Arg Ile Pro Thr Leu Met Ala Phe Gly Arg Val Ser
                405                 410                 415

Glu Pro Glu Pro Ala Ser Asp Ala Tyr Val Pro Tyr Val Ala Val Pro
            420                 425                 430

Ala Gln Phe Asp Asp Lys Pro Leu Ile Ser Phe Pro Ile Thr Leu Ser
        435                 440                 445

Asp Pro Val Tyr Gln Asn Thr Leu Val Gly Ala Ile Ser Ser Asn Phe
    450                 455                 460

Ala Asn Tyr Arg Gly Cys Ile Gln Ile Thr Leu Thr Phe Cys Gly Pro
465                 470                 475                 480

Met Met Ala Arg Gly Lys Phe Leu Leu Ser Tyr Ser Pro Pro Asn Gly
                485                 490                 495

Ala Gln Pro Gln Thr Leu Ser Glu Ala Met Gln Cys Thr Tyr Ser Ile
            500                 505                 510

Trp Asp Ile Gly Leu Asn Ser Ser Trp Thr Phe Val Ile Pro Tyr Ile
        515                 520                 525

Ser Pro Ser Asp Tyr Arg Glu Thr Arg Ala Ile Thr Asn Ser Val Tyr
    530                 535                 540

Ser Ala Asp Gly Trp Phe Ser Leu His Lys Leu Thr Lys Ile Thr Leu
545                 550                 555                 560

Pro Pro Asp Cys Pro Gln Ser Pro Cys Ile Leu Phe Phe Ala Ser Ala
                565                 570                 575

Gly Glu Asp Tyr Thr Leu Arg Leu Pro Val Asp Cys Asn Pro Ser Tyr
            580                 585                 590

Val Phe His Ser Thr Asp Asn Ala Glu Thr Gly Val Ile Glu Ala Gly
        595                 600                 605

Asn Thr Asp Thr Asp Phe Ser Gly Glu Leu Ala Ala Pro Gly Ser Asn
    610                 615                 620

His Thr Asn Val Lys Phe Leu Phe Asp Arg Ser Arg Leu Leu Asn Val
625                 630                 635                 640

Ile Lys Val Leu Glu Lys Asp Ala Val Phe Pro Arg Pro Phe Pro Thr
                645                 650                 655

Ala Thr Gly Ala Gln Gln Asp Asp Gly Tyr Phe Cys Leu Leu Thr Pro
            660                 665                 670

Arg Pro Thr Val Ala Ser Arg Pro Ala Thr Arg Phe Gly Leu Tyr Val
        675                 680                 685

Asn Pro Ser Asp Ser Gly Val Leu Ala Asn Thr Ser Leu Asp Phe Asn
    690                 695                 700

Phe Tyr Ser Leu Ala Cys Phe Thr Tyr Phe Arg Ser Asp Leu Glu Val
705                 710                 715                 720

Thr Val Val Ser Leu Glu Pro Asp Leu Glu Phe Ala Val Gly Trp Phe
                725                 730                 735

Pro Ser Gly Ser Glu Tyr Gln Ala Ser Ser Phe Val Tyr Asp Gln Leu
            740                 745                 750

His Val Pro Tyr His Phe Thr Gly Arg Thr Pro Arg Ala Phe Thr Ser
        755                 760                 765
```

```
Lys Gly Gly Lys Val Ser Phe Val Leu Pro Trp Asn Ser Val Ser Ser
    770                 775                 780

Val Leu Pro Val Arg Trp Gly Gly Ala Ser Lys Leu Ser Ser Ala Thr
785                 790                 795                 800

Arg Gly Leu Pro Ala His Ala Asp Trp Gly Thr Ile Tyr Ala Phe Ile
                805                 810                 815

Pro Arg Pro Asn Glu Lys Lys Ser Thr Ala Val Lys His Val Ala Val
            820                 825                 830

Tyr Val Arg Tyr Lys Asn Ala Arg Ala Trp Cys Pro Ser Met Leu Pro
        835                 840                 845

Phe Arg Ser Tyr Lys Gln Lys Met Leu Met Gln Ser Gly Asp Ile Glu
    850                 855                 860

Thr Asn Pro Gly Pro Gly Ser Gly Lys Pro Pro Gly Ala Leu Ser Leu
865                 870                 875                 880

Met Glu Met Gln Gln Pro Asn Val Asp Met Gly Phe Glu Ala Ala Val
                885                 890                 895

Ala Lys Lys Val Val Val Pro Ile Thr Phe Met Val Pro Asn Arg Pro
            900                 905                 910

Ser Gly Leu Thr Gln Ser Ala Leu Leu Val Ala Gly Arg Thr Phe Leu
        915                 920                 925

Ile Asn Glu His Thr Trp Ser Asn Pro Ser Trp Thr Ser Phe Thr Ile
    930                 935                 940

Arg Gly Glu Val His Thr Arg Asp Glu Pro Phe Gln Thr Val His Phe
945                 950                 955                 960

Thr His His Gly Leu Pro Thr Asp Leu Met Met Val Arg Leu Gly Pro
                965                 970                 975

Gly Asn Ser Phe Pro Asn Asn Leu Asp Lys Phe Gly Leu Asp Gln Met
            980                 985                 990

Pro Ala Arg Asn Ser Arg Val Val  Gly Val Ser Ala Ser  Tyr Gly Asn
        995                 1000                 1005

Phe Phe  Phe Ser Gly Asn Phe  Leu Gly Phe Val Asp  Ser Ile Thr
    1010                 1015                 1020

Ser Asp  Gln Gly Thr Tyr Ala  Arg Leu Phe Arg Tyr  Arg Val Thr
    1025                 1030                 1035

Thr Tyr  Lys Gly Trp Cys Gly  Ser Ala Leu Val Cys  Glu Ala Gly
    1040                 1045                 1050

Gly Val  Arg Arg Ile Ile Gly  Met His Ser Ala Gly  Ala Ala Gly
    1055                 1060                 1065

Ile Gly  Ala Gly Thr Tyr Ile  Ser Lys Leu Gly Leu  Ile Lys Ala
    1070                 1075                 1080

Leu Lys  His Leu Gly Glu Pro  Leu Ala Thr Met Gln
    1085                 1090                 1095
```

<210> SEQ ID NO 22
<211> LENGTH: 3308
<212> TYPE: DNA
<213> ORGANISM: Senecavirus

<400> SEQUENCE: 22

```
ggatccgcca ccatgggtaa tgttcagaca acctcaaaga atgattttga ttcccgcggc      60

aataatggta acatgacctt caattactac gcaaacactt accagaattc agtagacttc     120

tcgacctcct cgtcggcgtc aggcgccgga cccgggaact cccggggcgg actagcgggt     180

ctcctcacaa atttcagtgg aatcttgaac cctcttggct acctcaaaga tcacaatacc     240
```

```
gaagaaatgg aaaactctgc tgatcgagtc ataacgcaaa cggcgggcaa cactgccata    300
aacacgcaat catcactggg tgtgttgtgt gcctacgttg aagacccgac caaatctgac    360
cctccgtcca gcagcacaga tcaacccacc accactttta ctgccatcga caggtggtac    420
actggacgcc tcaattcttg gacaaaagct gtaaaaacct tctcttttca ggccgtcccg    480
ctccctggag ccttcctgtc taaacaggga ggcctcaacg gaggggcctt cacggctacc    540
ctacatagac atttcttaat gaagtgcggg tggcaggtgc aggtccaatg caatttgacg    600
caattccacc aaggtgctct tcttgttgcc atggtccccg aaaccaccct tgatgtcaaa    660
cctgacggca aggcaaagag cttacaggag ctgaatgaag agcagtgggt ggaaatgtct    720
gacgattacc ggaccgggaa aaacatgcct tttcagtctc ttggcacata ctatcggccc    780
cctaactgga cttggggccc caatttcatc aacccctatc aagtaacagt tttcccacac    840
caaattctga acgcgagaac ctctacctcg gtagacataa gtgtcccata catcggggag    900
actcctacac aatcctcaga gacacagaac tcctggaccc tccttgttat ggtgcttgtc    960
cccctggact acaaggaggg agccacaact gacccagaaa ttacattttc tgtaaggcct   1020
acaagtccct acttcaatgg gcttcgtaac cgtttcacga ccgggacgga cgaggaacag   1080
gggcccattc ccacagcacc cagagaaaat tcgcttatgt ttctctcaac catccctgac   1140
gacactgtcc ctgcttacgg gaatgtgcgt acccctcccg tcaattacct ccccggtgaa   1200
ataaccgacc tcttacaact ggcccgtata cccactctca tggcgtttgg gcgggtgtct   1260
gaacccgagc ctgcctcaga cgcatatgtg ccctacgttg ccgttcctgc ccagttcgac   1320
gacaagcctc tcatctcctt cccgatcacc ctttcagatc ctgtctacca gaacaccctg   1380
gtaggcgcca tcagttcgaa cttcgccaac taccgggggt gtatccaaat cactctgaca   1440
ttttgtggac ccatgatggc aagagggaaa ttcctgctct cgtattctcc cccaaatgga   1500
gcacaaccac agaccctttc tgaagctatg cagtgcacat actctatttg ggatataggc   1560
ttgaactcta gttggacctt tgtcatcccc tacatctcgc ccagtgatta ccgtgaaact   1620
cgggctatta ccaactcagt ttattctgct gatggttggt ttagcttgca caagctgacc   1680
aaaattactc taccacctga ctgcccacag agtccctgta ttctcttttt cgcctctgct   1740
ggtgaggatt acaccctccg tctccctgtt gattgtaatc cttcctacgt gcctcagggg   1800
gttgacaacg ccgagactgg ggttattgag gcaggtaaca ctgacaccga tttctctggt   1860
gaactggcgg ctcctggctc taaccatact aatgtcaaat tcctgtttga ccgatctcga   1920
ctactgaatg taattaaggt actggagaag gacgccgtct tcccccgtcc tttccccaca   1980
gcaacaggtg cacagcagga cgatggttac ttttgtcttc taacaccccg cccaacagtc   2040
gcttcccgac ccgccactcg tttcggcctg tacgtcaacc cgtctgacag tggcgttctc   2100
gctaacactt cactggattt caatttttac agtttggcct gtttcactta ctttagatca   2160
gaccttgaag tcacggtggt ctcactggag ccagatttgg aattcgccgt ggggtggttc   2220
ccctctggca gtgagtacca ggcttctagc tttgtctacg accaactgca tgtaccctac   2280
cactttactg ggcgcactcc ccgcgctttc accagcaagg gtggaaaggt atctttcgtg   2340
ctcccttgga actctgtctc ttccgtgctt cccgtgcgct ggggggggcgc ttccaagctt   2400
tcttctgcca cgcggggtct gccggctcat gctgactggg ggaccattta cgcctttatc   2460
ccccgtccta acgagaagaa aagcaccgct gtaaagcacg tggcggtgta cgttcggtac   2520
aagaacgcgc gtgcttggtg ccccagcatg cttccctttc gcagctacaa gcaaaagatg   2580
```

```
ctgatgcaat caggcgacat cgagaccaac cctggccctg gttcaggtaa gccccctgga   2640

gcgctctctc ttatggaaat gcaacagccc aacgtggaca tgggctttga ggctgcggtc   2700

gctaagaaag tggtcgtccc cattaccttc atggttccca acagaccttc tggacttaca   2760

cagtccgctc ttcttgtggc cggccggacc ttcctaatca atgagcatac atggtccaac   2820

ccctcctgga ccagcttcac aatccgtggt gaggtgcaca ctcgtgatga gcctttccaa   2880

acggttcatt ttactcacca tggtcttccc acagatctga tgatggtacg tctcggaccg   2940

ggcaactctt tccctaacaa tctagacaag tttggacttg accagatgcc ggcacgtaac   3000

tcccgtgtgg ttggcgtttc ggctagttac ggtaacttct tcttctctgg gaacttcctc   3060

gggtttgttg actccatcac ctctgaccaa ggaacctatg cgagactttt caggtacagg   3120

gtgacgactt acaagggatg gtgcggttcg gccctggtct gtgaggccgg tggtgtccga   3180

cgcatcattg gcatgcattc tgctggtgcc gctggtatcg gcgccgggac ttacatctca   3240

aaattaggac tgatcaaagc ccttaaacac ctcggtgagc ctctggctac aatgcaatga   3300

gcggccgc                                                            3308
```

```
<210> SEQ ID NO 23
<211> LENGTH: 1095
<212> TYPE: PRT
<213> ORGANISM: Senecavirus

<400> SEQUENCE: 23

Met Gly Asn Val Gln Thr Thr Ser Lys Asn Asp Phe Asp Ser Arg Gly
1               5                   10                  15

Asn Asn Gly Asn Met Thr Phe Asn Tyr Tyr Ala Asn Thr Tyr Gln Asn
            20                  25                  30

Ser Val Asp Phe Ser Thr Ser Ser Ser Ala Ser Gly Ala Gly Pro Gly
        35                  40                  45

Asn Ser Arg Gly Gly Leu Ala Gly Leu Leu Thr Asn Phe Ser Gly Ile
    50                  55                  60

Leu Asn Pro Leu Gly Tyr Leu Lys Asp His Asn Thr Glu Glu Met Glu
65                  70                  75                  80

Asn Ser Ala Asp Arg Val Ile Thr Gln Thr Ala Gly Asn Thr Ala Ile
                85                  90                  95

Asn Thr Gln Ser Ser Leu Gly Val Leu Cys Ala Tyr Val Glu Asp Pro
            100                 105                 110

Thr Lys Ser Asp Pro Pro Ser Ser Ser Thr Asp Gln Pro Thr Thr Thr
        115                 120                 125

Phe Thr Ala Ile Asp Arg Trp Tyr Thr Gly Arg Leu Asn Ser Trp Thr
    130                 135                 140

Lys Ala Val Lys Thr Phe Ser Phe Gln Ala Val Pro Leu Pro Gly Ala
145                 150                 155                 160

Phe Leu Ser Lys Gln Gly Gly Leu Asn Gly Gly Ala Phe Thr Ala Thr
                165                 170                 175

Leu His Arg His Phe Leu Met Lys Cys Gly Trp Gln Val Gln Val Gln
            180                 185                 190

Cys Asn Leu Thr Gln Phe His Gln Gly Ala Leu Leu Val Ala Met Val
        195                 200                 205

Pro Glu Thr Thr Leu Asp Val Lys Pro Asp Gly Lys Ala Lys Ser Leu
    210                 215                 220

Gln Glu Leu Asn Glu Glu Gln Trp Val Glu Met Ser Asp Asp Tyr Arg
225                 230                 235                 240
```

```
Thr Gly Lys Asn Met Pro Phe Gln Ser Leu Gly Thr Tyr Tyr Arg Pro
                245                 250                 255

Pro Asn Trp Thr Trp Gly Pro Asn Phe Ile Asn Pro Tyr Gln Val Thr
            260                 265                 270

Val Phe Pro His Gln Ile Leu Asn Ala Arg Thr Ser Thr Ser Val Asp
        275                 280                 285

Ile Ser Val Pro Tyr Ile Gly Glu Thr Pro Thr Gln Ser Ser Glu Thr
    290                 295                 300

Gln Asn Ser Trp Thr Leu Leu Val Met Val Leu Val Pro Leu Asp Tyr
305                 310                 315                 320

Lys Glu Gly Ala Thr Thr Asp Pro Glu Ile Thr Phe Ser Val Arg Pro
                325                 330                 335

Thr Ser Pro Tyr Phe Asn Gly Leu Arg Asn Arg Phe Thr Thr Gly Thr
            340                 345                 350

Asp Glu Glu Gln Gly Pro Ile Pro Thr Ala Pro Arg Glu Asn Ser Leu
        355                 360                 365

Met Phe Leu Ser Thr Ile Pro Asp Asp Thr Val Pro Ala Tyr Gly Asn
    370                 375                 380

Val Arg Thr Pro Pro Val Asn Tyr Leu Pro Gly Glu Ile Thr Asp Leu
385                 390                 395                 400

Leu Gln Leu Ala Arg Ile Pro Thr Leu Met Ala Phe Gly Arg Val Ser
                405                 410                 415

Glu Pro Glu Pro Ala Ser Asp Ala Tyr Val Pro Tyr Val Ala Val Pro
            420                 425                 430

Ala Gln Phe Asp Asp Lys Pro Leu Ile Ser Phe Pro Ile Thr Leu Ser
        435                 440                 445

Asp Pro Val Tyr Gln Asn Thr Leu Val Gly Ala Ile Ser Ser Asn Phe
    450                 455                 460

Ala Asn Tyr Arg Gly Cys Ile Gln Ile Thr Leu Thr Phe Cys Gly Pro
465                 470                 475                 480

Met Met Ala Arg Gly Lys Phe Leu Leu Ser Tyr Ser Pro Pro Asn Gly
                485                 490                 495

Ala Gln Pro Gln Thr Leu Ser Glu Ala Met Gln Cys Thr Tyr Ser Ile
            500                 505                 510

Trp Asp Ile Gly Leu Asn Ser Ser Trp Thr Phe Val Ile Pro Tyr Ile
        515                 520                 525

Ser Pro Ser Asp Tyr Arg Glu Thr Arg Ala Ile Thr Asn Ser Val Tyr
    530                 535                 540

Ser Ala Asp Gly Trp Phe Ser Leu His Lys Leu Thr Lys Ile Thr Leu
545                 550                 555                 560

Pro Pro Asp Cys Pro Gln Ser Pro Cys Ile Leu Phe Phe Ala Ser Ala
                565                 570                 575

Gly Glu Asp Tyr Thr Leu Arg Leu Pro Val Asp Cys Asn Pro Ser Tyr
            580                 585                 590

Val Pro Gln Gly Val Asp Asn Ala Glu Thr Gly Val Ile Glu Ala Gly
        595                 600                 605

Asn Thr Asp Thr Asp Phe Ser Gly Glu Leu Ala Ala Pro Gly Ser Asn
    610                 615                 620

His Thr Asn Val Lys Phe Leu Phe Asp Arg Ser Arg Leu Leu Asn Val
625                 630                 635                 640

Ile Lys Val Leu Glu Lys Asp Ala Val Phe Pro Arg Pro Phe Pro Thr
                645                 650                 655

Ala Thr Gly Ala Gln Gln Asp Asp Gly Tyr Phe Cys Leu Leu Thr Pro
```

```
            660                 665                 670

Arg Pro Thr Val Ala Ser Arg Pro Ala Thr Arg Phe Gly Leu Tyr Val
        675                 680                 685

Asn Pro Ser Asp Ser Gly Val Leu Ala Asn Thr Ser Leu Asp Phe Asn
    690                 695                 700

Phe Tyr Ser Leu Ala Cys Phe Thr Tyr Phe Arg Ser Asp Leu Glu Val
705                 710                 715                 720

Thr Val Val Ser Leu Glu Pro Asp Leu Glu Phe Ala Val Gly Trp Phe
                725                 730                 735

Pro Ser Gly Ser Glu Tyr Gln Ala Ser Ser Phe Val Tyr Asp Gln Leu
            740                 745                 750

His Val Pro Tyr His Phe Thr Gly Arg Thr Pro Arg Ala Phe Thr Ser
        755                 760                 765

Lys Gly Gly Lys Val Ser Phe Val Leu Pro Trp Asn Ser Val Ser Ser
    770                 775                 780

Val Leu Pro Val Arg Trp Gly Gly Ala Ser Lys Leu Ser Ser Ala Thr
785                 790                 795                 800

Arg Gly Leu Pro Ala His Ala Asp Trp Gly Thr Ile Tyr Ala Phe Ile
                805                 810                 815

Pro Arg Pro Asn Glu Lys Lys Ser Thr Ala Val Lys His Val Ala Val
            820                 825                 830

Tyr Val Arg Tyr Lys Asn Ala Arg Ala Trp Cys Pro Ser Met Leu Pro
        835                 840                 845

Phe Arg Ser Tyr Lys Gln Lys Met Leu Met Gln Ser Gly Asp Ile Glu
    850                 855                 860

Thr Asn Pro Gly Pro Gly Ser Gly Lys Pro Pro Gly Ala Leu Ser Leu
865                 870                 875                 880

Met Glu Met Gln Gln Pro Asn Val Asp Met Gly Phe Glu Ala Ala Val
                885                 890                 895

Ala Lys Lys Val Val Val Pro Ile Thr Phe Met Val Pro Asn Arg Pro
            900                 905                 910

Ser Gly Leu Thr Gln Ser Ala Leu Leu Val Ala Gly Arg Thr Phe Leu
        915                 920                 925

Ile Asn Glu His Thr Trp Ser Asn Pro Ser Trp Thr Ser Phe Thr Ile
    930                 935                 940

Arg Gly Glu Val His Thr Arg Asp Glu Pro Phe Gln Thr Val His Phe
945                 950                 955                 960

Thr His His Gly Leu Pro Thr Asp Leu Met Met Val Arg Leu Gly Pro
                965                 970                 975

Gly Asn Ser Phe Pro Asn Asn Leu Asp Lys Phe Gly Leu Asp Gln Met
            980                 985                 990

Pro Ala Arg Asn Ser Arg Val Val  Gly Val Ser Ala Ser  Tyr Gly Asn
        995                 1000                1005

Phe Phe  Phe Ser Gly Asn Phe  Leu Gly Phe Val Asp  Ser Ile Thr
    1010                1015                1020

Ser Asp  Gln Gly Thr Tyr Ala  Arg Leu Phe Arg Tyr  Arg Val Thr
    1025                1030                1035

Thr Tyr  Lys Gly Trp Cys Gly  Ser Ala Leu Val Cys  Glu Ala Gly
    1040                1045                1050

Gly Val  Arg Arg Ile Ile Gly  Met His Ser Ala Gly  Ala Ala Gly
    1055                1060                1065

Ile Gly  Ala Gly Thr Tyr Ile  Ser Lys Leu Gly Leu  Ile Lys Ala
    1070                1075                1080
```

```
Leu Lys  His Leu Gly Glu Pro  Leu Ala Thr Met Gln
    1085                 1090                1095
```

<210> SEQ ID NO 24
<211> LENGTH: 4694
<212> TYPE: DNA
<213> ORGANISM: Senecavirus

<400> SEQUENCE: 24

```
ggatccgcca ccatgggtaa tgttcagaca acctcaaaga atgattttga ttcccgcggc     60

aataatggta acatgacctt caattactac gcaaacactt accagaattc agtagacttc    120

tcgacctcct cgtcggcgtc aggcgccgga cccgggaact cccggggcgg actagcgggt    180

ctcctcacaa atttcagtgg aatcttgaac cctcttggct acctcaaaga tcacaatacc    240

gaagaaatgg aaaactctgc tgatcgagtc ataacgcaaa cggcgggcaa cactgccata    300

aacacgcaat catcactggg tgtgttgtgt gcctacgttg aagacccgac caaatctgac    360

cctccgtcca gcagcacaga tcaacccacc accactttta ctgccatcga caggtggtac    420

actggacgcc tcaattcttg gacaaaagct gtaaaaacct tctcttttca ggccgtcccg    480

ctccctggag ccttcctgtc taaacaggga ggcctcaacg gaggggcctt cacggctacc    540

ctacatagac atttcttaat gaagtgcggg tggcaggtgc aggtccaatg caatttgacg    600

caattccacc aaggtgctct tcttgttgcc atggtccccg aaaccaccct tgatgtcaaa    660

cctgacggca aggcaaagag cttacaggag ctgaatgaag agcagtgggt ggaaatgtct    720

gacgattacc ggaccgggaa aaacatgcct tttcagtctc ttggcacata ctatcggccc    780

cctaactgga cttggggccc caatttcatc aacccctatc aagtaacagt tttcccacac    840

caaattctga acgcgagaac ctctacctcg gtagacataa gtgtcccata catcggggag    900

actcctacac aatcctcaga gacacagaac tcctggaccc tccttgttat ggtgcttgtc    960

cccctggact acaaggaggg agccacaact gacccagaaa ttacattttc tgtaaggcct   1020

acaagtccct acttcaatgg gcttcgtaac cgtttcacga ccgggacgga cgaggaacag   1080

gggcccattc ccacagcacc cagagaaaat tcgcttatgt ttctctcaac catccctgac   1140

gacactgtcc ctgcttacgg gaatgtgcgt acccctcccg tcaattacct ccccggtgaa   1200

ataaccgacc tcttacaact ggcccgtata cccactctca tggcgtttgg gcgggtgtct   1260

gaacccgagc ctgcctcaga cgcatatgtg ccctacgttg ccgttcctgc ccagttcgac   1320

gacaagcctc tcatctcctt cccgatcacc ctttcagatc ctgtctacca gaacaccctg   1380

gtaggcgcca tcagttcgaa cttcgccaac taccgggggt gtatccaaat cactctgaca   1440

ttttgtggac ccatgatggc aagagggaaa ttcctgctct cgtattctcc cccaaatgga   1500

gcacaaccac agaccctttc tgaagctatg cagtgcacat actctatttg ggatataggc   1560

ttgaactcta gttggacctt tgtcatcccc tacatctcgc ccagtgatta ccgtgaaact   1620

cgggctatta ccaactcagt ttattctgct gatggttggt ttagcttgca caagctgacc   1680

aaaattactc taccacctga ctgcccacag agtccctgta ttctcttttt cgcctctgct   1740

ggtgaggatt acaccctccg tctccctgtt gattgtaatc cttcctacgt gttccactcc   1800

accgacaacg ccgagactgg ggttattgag gcaggtaaca ctgacaccga tttctctggt   1860

gaactggcgg ctcctggctc taaccatact aatgtcaaat tcctgtttga ccgatctcga   1920

ctactgaatg taattaaggt actggagaag gacgccgtct tcccccgtcc tttccccaca   1980

gcaacaggtg cacagcagga cgatggttac ttttgtcttc taacaccccg cccaacagtc   2040
```

```
gcttcccgac ccgccactcg tttcggcctg tacgtcaacc cgtctgacag tggcgttctc   2100
gctaacactt cactggattt caatttttac agtttggcct gtttcactta ctttagatca   2160
gaccttgaag tcacggtggt ctcactggag ccagatttgg aattcgccgt ggggtggttc   2220
ccctctggca gtgagtacca ggcttctagc tttgtctacg accaactgca tgtaccctac   2280
cactttactg ggcgcactcc ccgcgctttc accagcaagg gtggaaaggt atctttcgtg   2340
ctcccttgga actctgtctc ttccgtgctt cccgtgcgct gggggggcgc ttccaagctt   2400
tcttctgcca cgcggggtct gccggctcat gctgactggg ggaccattta cgcctttatc   2460
ccccgtccta acgagaagaa aagcaccgct gtaaagcacg tggcggtgta cgttcggtac   2520
aagaacgcgc gtgcttggtg ccccagcatg cttccctttc gcagctacaa gcaaaagatg   2580
ctgatgcaat caggcgacat cgagaccaac cctggccctg gttcaggtaa gccccctgga   2640
gcgctctctc ttatggaaat gcaacagccc aacgtggaca tgggctttga ggctgcggtc   2700
gctaagaaag tggtcgtccc cattaccttc atggttccca acagaccttc tggacttaca   2760
cagtccgctc ttcttgtggc cggccggacc ttcctaatca atgagcatac atggtccaac   2820
ccctcctgga ccagcttcac aatccgtggt gaggtgcaca ctcgtgatga gcctttccaa   2880
acggttcatt ttactcacca tggtcttccc acagatctga tgatggtacg tctcggaccg   2940
ggcaactctt tccctaacaa tctagacaag tttggacttg accagatgcc ggcacgtaac   3000
tcccgtgtgg ttggcgtttc ggctagttac ggtaacttct tcttctctgg gaacttcctc   3060
gggtttgttg actccatcac ctctgaccaa ggaacctatg cgagactttt caggtacagg   3120
gtgacgactt acaagggatg gtgcggttcg gccctggtct gtgaggccgg tggtgtccga   3180
cgcatcattg gcatgcattc tgctggtgcc gctggtatcg gcgccgggac ttacatctca   3240
aaattaggac tgatcaaagc ccttaaacac ctcggtgagc ctctggctac aatgcaagga   3300
ctgatgactg agctagagcc tggagtcacc gtacatgtac cccgaaaatc taaattgaga   3360
aagacgaccg cacacgcggt gtacaaaccg gagtttgaac ctgctgtgtt gtcaaaattt   3420
gatcccagac tgaacaagga tgttgaccta gatgaggtaa tttggtctaa acacaccgcc   3480
aacgtccctt atcaacctcc tttgttctac acatacatgt cagagtacgc tcatcgggtt   3540
ttctcctttt tgggaaaaga caatgacatt ctgaccgtca aagaagcaat cctgggcatc   3600
cctggactag accctatgga tccccacaca gctccgggtt tgccctacgc cattagcggc   3660
cttcgacgta ctgatctcgt cgattttgcg aacggcacgg tagacccggc actggccatg   3720
cagatccaga aattcttaga cggtgactac tctgatcatg tcttccaaac ttttctgaaa   3780
gatgaaatca gaccctcaga gaaggtccgg gcgggaaaaa cccgcattgt cgatgtgccc   3840
tccctggcgc actgcattgt gggcagaatg ctgcttgggc gctttgccgc caagtttcaa   3900
tcccatcctg gctttctcct tggctccgct atcgggtctg accctgatgt cttctggacc   3960
gtcatagggg ctcagctcga gggaagaaag aacacgtatg acgtggacta cagtgccttt   4020
gactcttcac acggcactgg ctccttcgag gctctcatct ctcacttttt caccgtggac   4080
aatggtttca gccctgcgct gggaccgtat ctcagatccc tggctgtctc ggtgcacgct   4140
tacggcgagc gtcgcatcaa gattaccgga ggcctcccct ctggttgtgc cgcgaccagc   4200
ctgctgaaca cagtgctcaa caatgtgatc atcaggactg ctctggcatt gacctacaag   4260
gaatttgaat atgacatggt tgatatcatc gcctacggtg acgaccttct ggttggtacg   4320
gattatgatc tggacttcaa tgaggtggcg cggcgcgctg ccaaactggg gtataagatg   4380
```

```
actcctgcca acaagggttc tgtcttccct ccgacttcct ctctctccga tgctgttttt   4440

ctaaaacgca aattcgtcca aaacaatgac ggcttatata aaccagttat ggatttaaag   4500

aatttggaag ccatgctctc ctacttcaaa ccaggaacac tactcgagaa gctgcaatct   4560

gtttctatgt tggctcaaca ttctggaaaa gaagaatacg atagattgat gcaccccttc   4620

gctgactatg gtgccgtacc gagtcacgag tacctgcagg caagatggag ggccttgttc   4680

gactgagcgg ccgc                                                      4694
```

<210> SEQ ID NO 25
<211> LENGTH: 1557
<212> TYPE: PRT
<213> ORGANISM: Senecavirus

<400> SEQUENCE: 25

```
Met Gly Asn Val Gln Thr Thr Ser Lys Asn Asp Phe Asp Ser Arg Gly
1               5                   10                  15

Asn Asn Gly Asn Met Thr Phe Asn Tyr Tyr Ala Asn Thr Tyr Gln Asn
            20                  25                  30

Ser Val Asp Phe Ser Thr Ser Ser Ser Ala Ser Gly Ala Gly Pro Gly
        35                  40                  45

Asn Ser Arg Gly Gly Leu Ala Gly Leu Leu Thr Asn Phe Ser Gly Ile
    50                  55                  60

Leu Asn Pro Leu Gly Tyr Leu Lys Asp His Asn Thr Glu Glu Met Glu
65                  70                  75                  80

Asn Ser Ala Asp Arg Val Ile Thr Gln Thr Ala Gly Asn Thr Ala Ile
                85                  90                  95

Asn Thr Gln Ser Ser Leu Gly Val Leu Cys Ala Tyr Val Glu Asp Pro
            100                 105                 110

Thr Lys Ser Asp Pro Pro Ser Ser Ser Thr Asp Gln Pro Thr Thr Thr
        115                 120                 125

Phe Thr Ala Ile Asp Arg Trp Tyr Thr Gly Arg Leu Asn Ser Trp Thr
    130                 135                 140

Lys Ala Val Lys Thr Phe Ser Phe Gln Ala Val Pro Leu Pro Gly Ala
145                 150                 155                 160

Phe Leu Ser Lys Gln Gly Gly Leu Asn Gly Gly Ala Phe Thr Ala Thr
                165                 170                 175

Leu His Arg His Phe Leu Met Lys Cys Gly Trp Gln Val Gln Val Gln
            180                 185                 190

Cys Asn Leu Thr Gln Phe His Gln Gly Ala Leu Leu Val Ala Met Val
        195                 200                 205

Pro Glu Thr Thr Leu Asp Val Lys Pro Asp Gly Lys Ala Lys Ser Leu
    210                 215                 220

Gln Glu Leu Asn Glu Glu Gln Trp Val Glu Met Ser Asp Asp Tyr Arg
225                 230                 235                 240

Thr Gly Lys Asn Met Pro Phe Gln Ser Leu Gly Thr Tyr Tyr Arg Pro
                245                 250                 255

Pro Asn Trp Thr Trp Gly Pro Asn Phe Ile Asn Pro Tyr Gln Val Thr
            260                 265                 270

Val Phe Pro His Gln Ile Leu Asn Ala Arg Thr Ser Thr Ser Val Asp
        275                 280                 285

Ile Ser Val Pro Tyr Ile Gly Glu Thr Pro Thr Gln Ser Ser Glu Thr
    290                 295                 300

Gln Asn Ser Trp Thr Leu Leu Val Met Val Leu Val Pro Leu Asp Tyr
305                 310                 315                 320
```

```
Lys Glu Gly Ala Thr Thr Asp Pro Glu Ile Thr Phe Ser Val Arg Pro
                325                 330                 335

Thr Ser Pro Tyr Phe Asn Gly Leu Arg Asn Arg Phe Thr Thr Gly Thr
            340                 345                 350

Asp Glu Glu Gln Gly Pro Ile Pro Thr Ala Pro Arg Glu Asn Ser Leu
        355                 360                 365

Met Phe Leu Ser Thr Ile Pro Asp Asp Thr Val Pro Ala Tyr Gly Asn
    370                 375                 380

Val Arg Thr Pro Pro Val Asn Tyr Leu Pro Gly Glu Ile Thr Asp Leu
385                 390                 395                 400

Leu Gln Leu Ala Arg Ile Pro Thr Leu Met Ala Phe Gly Arg Val Ser
                405                 410                 415

Glu Pro Glu Pro Ala Ser Asp Ala Tyr Val Pro Tyr Val Ala Val Pro
            420                 425                 430

Ala Gln Phe Asp Asp Lys Pro Leu Ile Ser Phe Pro Ile Thr Leu Ser
        435                 440                 445

Asp Pro Val Tyr Gln Asn Thr Leu Val Gly Ala Ile Ser Ser Asn Phe
    450                 455                 460

Ala Asn Tyr Arg Gly Cys Ile Gln Ile Thr Leu Thr Phe Cys Gly Pro
465                 470                 475                 480

Met Met Ala Arg Gly Lys Phe Leu Leu Ser Tyr Ser Pro Pro Asn Gly
                485                 490                 495

Ala Gln Pro Gln Thr Leu Ser Glu Ala Met Gln Cys Thr Tyr Ser Ile
            500                 505                 510

Trp Asp Ile Gly Leu Asn Ser Ser Trp Thr Phe Val Ile Pro Tyr Ile
        515                 520                 525

Ser Pro Ser Asp Tyr Arg Glu Thr Arg Ala Ile Thr Asn Ser Val Tyr
    530                 535                 540

Ser Ala Asp Gly Trp Phe Ser Leu His Lys Leu Thr Lys Ile Thr Leu
545                 550                 555                 560

Pro Pro Asp Cys Pro Gln Ser Pro Cys Ile Leu Phe Phe Ala Ser Ala
                565                 570                 575

Gly Glu Asp Tyr Thr Leu Arg Leu Pro Val Asp Cys Asn Pro Ser Tyr
            580                 585                 590

Val Phe His Ser Thr Asp Asn Ala Glu Thr Gly Val Ile Glu Ala Gly
        595                 600                 605

Asn Thr Asp Thr Asp Phe Ser Gly Glu Leu Ala Ala Pro Gly Ser Asn
    610                 615                 620

His Thr Asn Val Lys Phe Leu Phe Asp Arg Ser Arg Leu Leu Asn Val
625                 630                 635                 640

Ile Lys Val Leu Glu Lys Asp Ala Val Phe Pro Arg Pro Phe Pro Thr
                645                 650                 655

Ala Thr Gly Ala Gln Gln Asp Asp Gly Tyr Phe Cys Leu Leu Thr Pro
            660                 665                 670

Arg Pro Thr Val Ala Ser Arg Pro Ala Thr Arg Phe Gly Leu Tyr Val
        675                 680                 685

Asn Pro Ser Asp Ser Gly Val Leu Ala Asn Thr Ser Leu Asp Phe Asn
    690                 695                 700

Phe Tyr Ser Leu Ala Cys Phe Thr Tyr Phe Arg Ser Asp Leu Glu Val
705                 710                 715                 720

Thr Val Val Ser Leu Glu Pro Asp Leu Glu Phe Ala Val Gly Trp Phe
                725                 730                 735
```

```
Pro Ser Gly Ser Glu Tyr Gln Ala Ser Ser Phe Val Tyr Asp Gln Leu
            740                 745                 750

His Val Pro Tyr His Phe Thr Gly Arg Thr Pro Arg Ala Phe Thr Ser
        755                 760                 765

Lys Gly Gly Lys Val Ser Phe Val Leu Pro Trp Asn Ser Val Ser Ser
    770                 775                 780

Val Leu Pro Val Arg Trp Gly Gly Ala Ser Lys Leu Ser Ser Ala Thr
785                 790                 795                 800

Arg Gly Leu Pro Ala His Ala Asp Trp Gly Thr Ile Tyr Ala Phe Ile
                805                 810                 815

Pro Arg Pro Asn Glu Lys Lys Ser Thr Ala Val Lys His Val Ala Val
            820                 825                 830

Tyr Val Arg Tyr Lys Asn Ala Arg Ala Trp Cys Pro Ser Met Leu Pro
        835                 840                 845

Phe Arg Ser Tyr Lys Gln Lys Met Leu Met Gln Ser Gly Asp Ile Glu
    850                 855                 860

Thr Asn Pro Gly Pro Gly Ser Gly Lys Pro Pro Gly Ala Leu Ser Leu
865                 870                 875                 880

Met Glu Met Gln Gln Pro Asn Val Asp Met Gly Phe Glu Ala Ala Val
                885                 890                 895

Ala Lys Lys Val Val Val Pro Ile Thr Phe Met Val Pro Asn Arg Pro
            900                 905                 910

Ser Gly Leu Thr Gln Ser Ala Leu Leu Val Ala Gly Arg Thr Phe Leu
        915                 920                 925

Ile Asn Glu His Thr Trp Ser Asn Pro Ser Trp Thr Ser Phe Thr Ile
    930                 935                 940

Arg Gly Glu Val His Thr Arg Asp Glu Pro Phe Gln Thr Val His Phe
945                 950                 955                 960

Thr His His Gly Leu Pro Thr Asp Leu Met Met Val Arg Leu Gly Pro
                965                 970                 975

Gly Asn Ser Phe Pro Asn Asn Leu Asp Lys Phe Gly Leu Asp Gln Met
            980                 985                 990

Pro Ala Arg Asn Ser Arg Val Val  Gly Val Ser Ala Ser  Tyr Gly Asn
        995                 1000                 1005

Phe Phe  Phe Ser Gly Asn Phe  Leu Gly Phe Val Asp  Ser Ile Thr
    1010                 1015                 1020

Ser Asp  Gln Gly Thr Tyr Ala  Arg Leu Phe Arg Tyr  Arg Val Thr
    1025                 1030                 1035

Thr Tyr  Lys Gly Trp Cys Gly  Ser Ala Leu Val Cys  Glu Ala Gly
    1040                 1045                 1050

Gly Val  Arg Arg Ile Ile Gly  Met His Ser Ala Gly  Ala Ala Gly
    1055                 1060                 1065

Ile Gly  Ala Gly Thr Tyr Ile  Ser Lys Leu Gly Leu  Ile Lys Ala
    1070                 1075                 1080

Leu Lys  His Leu Gly Glu Pro  Leu Ala Thr Met Gln  Gly Leu Met
    1085                 1090                 1095

Thr Glu  Leu Glu Pro Gly Val  Thr Val His Val Pro  Arg Lys Ser
    1100                 1105                 1110

Lys Leu  Arg Lys Thr Thr Ala  His Ala Val Tyr Lys  Pro Glu Phe
    1115                 1120                 1125

Glu Pro  Ala Val Leu Ser Lys  Phe Asp Pro Arg Leu  Asn Lys Asp
    1130                 1135                 1140

Val Asp  Leu Asp Glu Val Ile  Trp Ser Lys His Thr  Ala Asn Val
```

```
    1145                1150                1155

Pro Tyr  Gln Pro Pro Leu Phe  Tyr Thr Tyr Met Ser  Glu Tyr Ala
    1160                1165                1170

His Arg  Val Phe Ser Phe Leu  Gly Lys Asp Asn Asp  Ile Leu Thr
    1175                1180                1185

Val Lys  Glu Ala Ile Leu Gly  Ile Pro Gly Leu Asp  Pro Met Asp
    1190                1195                1200

Pro His  Thr Ala Pro Gly Leu  Pro Tyr Ala Ile Ser  Gly Leu Arg
    1205                1210                1215

Arg Thr  Asp Leu Val Asp Phe  Ala Asn Gly Thr Val  Asp Pro Ala
    1220                1225                1230

Leu Ala  Met Gln Ile Gln Lys  Phe Leu Asp Gly Asp  Tyr Ser Asp
    1235                1240                1245

His Val  Phe Gln Thr Phe Leu  Lys Asp Glu Ile Arg  Pro Ser Glu
    1250                1255                1260

Lys Val  Arg Ala Gly Lys Thr  Arg Ile Val Asp Val  Pro Ser Leu
    1265                1270                1275

Ala His  Cys Ile Val Gly Arg  Met Leu Leu Gly Arg  Phe Ala Ala
    1280                1285                1290

Lys Phe  Gln Ser His Pro Gly  Phe Leu Leu Gly Ser  Ala Ile Gly
    1295                1300                1305

Ser Asp  Pro Asp Val Phe Trp  Thr Val Ile Gly Ala  Gln Leu Glu
    1310                1315                1320

Gly Arg  Lys Asn Thr Tyr Asp  Val Asp Tyr Ser Ala  Phe Asp Ser
    1325                1330                1335

Ser His  Gly Thr Gly Ser Phe  Glu Ala Leu Ile Ser  His Phe Phe
    1340                1345                1350

Thr Val  Asp Asn Gly Phe Ser  Pro Ala Leu Gly Pro  Tyr Leu Arg
    1355                1360                1365

Ser Leu  Ala Val Ser Val His  Ala Tyr Gly Glu Arg  Arg Ile Lys
    1370                1375                1380

Ile Thr  Gly Gly Leu Pro Ser  Gly Cys Ala Ala Thr  Ser Leu Leu
    1385                1390                1395

Asn Thr  Val Leu Asn Asn Val  Ile Ile Arg Thr Ala  Leu Ala Leu
    1400                1405                1410

Thr Tyr  Lys Glu Phe Glu Tyr  Asp Met Val Asp Ile  Ile Ala Tyr
    1415                1420                1425

Gly Asp  Asp Leu Leu Val Gly  Thr Asp Tyr Asp Leu  Asp Phe Asn
    1430                1435                1440

Glu Val  Ala Arg Arg Ala Ala  Lys Leu Gly Tyr Lys  Met Thr Pro
    1445                1450                1455

Ala Asn  Lys Gly Ser Val Phe  Pro Pro Thr Ser Ser  Leu Ser Asp
    1460                1465                1470

Ala Val  Phe Leu Lys Arg Lys  Phe Val Gln Asn Asn  Asp Gly Leu
    1475                1480                1485

Tyr Lys  Pro Val Met Asp Leu  Lys Asn Leu Glu Ala  Met Leu Ser
    1490                1495                1500

Tyr Phe  Lys Pro Gly Thr Leu  Leu Glu Lys Leu Gln  Ser Val Ser
    1505                1510                1515

Met Leu  Ala Gln His Ser Gly  Lys Glu Glu Tyr Asp  Arg Leu Met
    1520                1525                1530

His Pro  Phe Ala Asp Tyr Gly  Ala Val Pro Ser His  Glu Tyr Leu
    1535                1540                1545
```

```
Gln Ala  Arg Trp Arg Ala Leu  Phe Asp
    1550                 1555


<210> SEQ ID NO 26
<211> LENGTH: 2618
<212> TYPE: DNA
<213> ORGANISM: Senecavirus

<400> SEQUENCE: 26

ggatccgcca ccatgggtaa tgttcagaca acctcaaaga atgattttga ttcccgcggc     60

aataatggta acatgacctt caattactac gcaaacactt accagaattc agtagacttc    120

tcgacctcct cgtcggcgtc aggcgccgga cccgggaact cccggggcgg actagcgggt    180

ctcctcacaa atttcagtgg aatcttgaac cctcttggct acctcaaaga tcacaatacc    240

gaagaaatgg aaaactctgc tgatcgagtc ataacgcaaa cggcgggcaa cactgccata    300

aacacgcaat catcactggg tgtgttgtgt gcctacgttg aagacccgac caaatctgac    360

cctccgtcca gcagcacaga tcaacccacc accactttta ctgccatcga caggtggtac    420

actggacgcc tcaattcttg gacaaaagct gtaaaaacct tctcttttca ggccgtcccg    480

ctccctggag ccttcctgtc taaacaggga ggcctcaacg gaggggcctt cacggctacc    540

ctacatagac atttcttaat gaagtgcggg tggcaggtgc aggtccaatg caatttgacg    600

caattccacc aaggtgctct tcttgttgcc atggtccccg aaaccaccct tgatgtcaaa    660

cctgacggca aggcaaagag cttacaggag ctgaatgaag agcagtgggt ggaaatgtct    720

gacgattacc ggaccgggaa aaacatgcct tttcagtctc ttggcacata ctatcggccc    780

cctaactgga cttggggccc caatttcatc aacccctatc aagtaacagt tttcccacac    840

caaattctga acgcgagaac ctctacctcg gtagacataa gtgtcccata catcggggag    900

actcctacac aatcctcaga gacacagaac tcctggaccc tccttgttat ggtgcttgtc    960

cccctggact acaaggaggg agccacaact gacccagaaa ttacattttc tgtaaggcct   1020

acaagtccct acttcaatgg gcttcgtaac cgtttcacga ccgggacgga cgaggaacag   1080

gggcccattc ccacagcacc cagagaaaat tcgcttatgt ttctctcaac catccctgac   1140

gacactgtcc ctgcttacgg gaatgtgcgt acccctcccg tcaattacct ccccggtgaa   1200

ataaccgacc tcttacaact ggcccgtata cccactctca tggcgtttgg gcgggtgtct   1260

gaacccgagc ctgcctcaga cgcatatgtg ccctacgttg ccgttcctgc ccagttcgac   1320

gacaagcctc tcatctcctt cccgatcacc ctttcagatc ctgtctacca gaacaccctg   1380

gtaggcgcca tcagttcgaa cttcgccaac taccgggggt gtatccaaat cactctgaca   1440

ttttgtggac ccatgatggc aagagggaaa ttcctgctct cgtattctcc cccaaatgga   1500

gcacaaccac agaccctttc tgaagctatg cagtgcacat actctatttg ggatataggc   1560

ttgaactcta gttggacctt tgtcatcccc tacatctcgc ccagtgatta ccgtgaaact   1620

cgggctatta ccaactcagt ttattctgct gatggttggt ttagcttgca caagctgacc   1680

aaaattactc taccacctga ctgcccacag agtccctgta ttctcttttt cgcctctgct   1740

ggtgaggatt acaccctccg tctccctgtt gattgtaatc cttcctacgt gttccactcc   1800

accgacaacg ccgagactgg ggttattgag gcaggtaaca ctgacaccga tttctctggt   1860

gaactggcgg ctcctggctc taaccatact aatgtcaaat tcctgtttga ccgatctcga   1920

ctactgaatg taattaaggt actggagaag gacgccgtct tcccccgtcc tttccccaca   1980

gcaacaggtg cacagcagga cgatggttac ttttgtcttc taacaccccg cccaacagtc   2040
```

```
gcttcccgac ccgccactcg tttcggcctg tacgtcaacc cgtctgacag tggcgttctc   2100

gctaacactt cactggattt caatttttac agtttggcct gtttcactta ctttagatca   2160

gaccttgaag tcacggtggt ctcactggag ccagatttgg aattcgccgt ggggtggttc   2220

ccctctggca gtgagtacca ggcttctagc tttgtctacg accaactgca tgtaccctac   2280

cactttactg ggcgcactcc ccgcgctttc accagcaagg gtggaaaggt atctttcgtg   2340

ctcccttgga actctgtctc ttccgtgctt cccgtgcgct ggggggcgc ttccaagctt    2400

tcttctgcca cgcggtgtct gccggctcat gctgactggg ggaccattta cgcctttatc   2460

ccccgtccta acgagaagaa aagcaccgct gtaaagcacg tggcggtgta cgttcggtac   2520

aagaacgcgc gtgcttggtg ccccagcatg cttccctttc gcagctacaa gcaaaagatg   2580

ctgatgcaac accaccacca ccaccactga gcggccgc                           2618
```

```
<210> SEQ ID NO 27
<211> LENGTH: 855
<212> TYPE: PRT
<213> ORGANISM: Senecavirus

<400> SEQUENCE: 27

Met Gly Asn Val Gln Thr Thr Ser Lys Asn Asp Phe Asp Ser Arg Gly
1               5                   10                  15

Asn Asn Gly Asn Met Thr Phe Asn Tyr Tyr Ala Asn Thr Tyr Gln Asn
            20                  25                  30

Ser Val Asp Phe Ser Thr Ser Ser Ser Ala Ser Gly Ala Gly Pro Gly
        35                  40                  45

Asn Ser Arg Gly Gly Leu Ala Gly Leu Leu Thr Asn Phe Ser Gly Ile
    50                  55                  60

Leu Asn Pro Leu Gly Tyr Leu Lys Asp His Asn Thr Glu Glu Met Glu
65                  70                  75                  80

Asn Ser Ala Asp Arg Val Ile Thr Gln Thr Ala Gly Asn Thr Ala Ile
                85                  90                  95

Asn Thr Gln Ser Ser Leu Gly Val Leu Cys Ala Tyr Val Glu Asp Pro
            100                 105                 110

Thr Lys Ser Asp Pro Pro Ser Ser Ser Thr Asp Gln Pro Thr Thr Thr
        115                 120                 125

Phe Thr Ala Ile Asp Arg Trp Tyr Thr Gly Arg Leu Asn Ser Trp Thr
    130                 135                 140

Lys Ala Val Lys Thr Phe Ser Phe Gln Ala Val Pro Leu Pro Gly Ala
145                 150                 155                 160

Phe Leu Ser Lys Gln Gly Gly Leu Asn Gly Gly Ala Phe Thr Ala Thr
                165                 170                 175

Leu His Arg His Phe Leu Met Lys Cys Gly Trp Gln Val Gln Val Gln
            180                 185                 190

Cys Asn Leu Thr Gln Phe His Gln Gly Ala Leu Leu Val Ala Met Val
        195                 200                 205

Pro Glu Thr Thr Leu Asp Val Lys Pro Asp Gly Lys Ala Lys Ser Leu
    210                 215                 220

Gln Glu Leu Asn Glu Glu Gln Trp Val Glu Met Ser Asp Asp Tyr Arg
225                 230                 235                 240

Thr Gly Lys Asn Met Pro Phe Gln Ser Leu Gly Thr Tyr Tyr Arg Pro
                245                 250                 255

Pro Asn Trp Thr Trp Gly Pro Asn Phe Ile Asn Pro Tyr Gln Val Thr
            260                 265                 270
```

```
Val Phe Pro His Gln Ile Leu Asn Ala Arg Thr Ser Thr Ser Val Asp
        275                 280                 285

Ile Ser Val Pro Tyr Ile Gly Glu Thr Pro Thr Gln Ser Ser Glu Thr
    290                 295                 300

Gln Asn Ser Trp Thr Leu Leu Val Met Val Leu Val Pro Leu Asp Tyr
305                 310                 315                 320

Lys Glu Gly Ala Thr Thr Asp Pro Glu Ile Thr Phe Ser Val Arg Pro
                325                 330                 335

Thr Ser Pro Tyr Phe Asn Gly Leu Arg Asn Arg Phe Thr Thr Gly Thr
            340                 345                 350

Asp Glu Glu Gln Gly Pro Ile Pro Thr Ala Pro Arg Glu Asn Ser Leu
        355                 360                 365

Met Phe Leu Ser Thr Ile Pro Asp Asp Thr Val Pro Ala Tyr Gly Asn
    370                 375                 380

Val Arg Thr Pro Pro Val Asn Tyr Leu Pro Gly Glu Ile Thr Asp Leu
385                 390                 395                 400

Leu Gln Leu Ala Arg Ile Pro Thr Leu Met Ala Phe Gly Arg Val Ser
                405                 410                 415

Glu Pro Glu Pro Ala Ser Asp Ala Tyr Val Pro Tyr Val Ala Val Pro
            420                 425                 430

Ala Gln Phe Asp Asp Lys Pro Leu Ile Ser Phe Pro Ile Thr Leu Ser
        435                 440                 445

Asp Pro Val Tyr Gln Asn Thr Leu Val Gly Ala Ile Ser Ser Asn Phe
    450                 455                 460

Ala Asn Tyr Arg Gly Cys Ile Gln Ile Thr Leu Thr Phe Cys Gly Pro
465                 470                 475                 480

Met Met Ala Arg Gly Lys Phe Leu Leu Ser Tyr Ser Pro Pro Asn Gly
                485                 490                 495

Ala Gln Pro Gln Thr Leu Ser Glu Ala Met Gln Cys Thr Tyr Ser Ile
            500                 505                 510

Trp Asp Ile Gly Leu Asn Ser Ser Trp Thr Phe Val Ile Pro Tyr Ile
        515                 520                 525

Ser Pro Ser Asp Tyr Arg Glu Thr Arg Ala Ile Thr Asn Ser Val Tyr
    530                 535                 540

Ser Ala Asp Gly Trp Phe Ser Leu His Lys Leu Thr Lys Ile Thr Leu
545                 550                 555                 560

Pro Pro Asp Cys Pro Gln Ser Pro Cys Ile Leu Phe Phe Ala Ser Ala
                565                 570                 575

Gly Glu Asp Tyr Thr Leu Arg Leu Pro Val Asp Cys Asn Pro Ser Tyr
            580                 585                 590

Val Phe His Ser Thr Asp Asn Ala Glu Thr Gly Val Ile Glu Ala Gly
        595                 600                 605

Asn Thr Asp Thr Asp Phe Ser Gly Glu Leu Ala Ala Pro Gly Ser Asn
    610                 615                 620

His Thr Asn Val Lys Phe Leu Phe Asp Arg Ser Arg Leu Leu Asn Val
625                 630                 635                 640

Ile Lys Val Leu Glu Lys Asp Ala Val Phe Pro Arg Pro Phe Pro Thr
                645                 650                 655

Ala Thr Gly Ala Gln Gln Asp Asp Gly Tyr Phe Cys Leu Leu Thr Pro
            660                 665                 670

Arg Pro Thr Val Ala Ser Arg Pro Ala Thr Arg Phe Gly Leu Tyr Val
        675                 680                 685
```

```
Asn Pro Ser Asp Ser Gly Val Leu Ala Asn Thr Ser Leu Asp Phe Asn
    690                 695                 700

Phe Tyr Ser Leu Ala Cys Phe Thr Tyr Phe Arg Ser Asp Leu Glu Val
705                 710                 715                 720

Thr Val Val Ser Leu Glu Pro Asp Leu Glu Phe Ala Val Gly Trp Phe
                725                 730                 735

Pro Ser Gly Ser Glu Tyr Gln Ala Ser Ser Phe Val Tyr Asp Gln Leu
            740                 745                 750

His Val Pro Tyr His Phe Thr Gly Arg Thr Pro Arg Ala Phe Thr Ser
        755                 760                 765

Lys Gly Gly Lys Val Ser Phe Val Leu Pro Trp Asn Ser Val Ser Ser
    770                 775                 780

Val Leu Pro Val Arg Trp Gly Gly Ala Ser Lys Leu Ser Ser Ala Thr
785                 790                 795                 800

Arg Cys Leu Pro Ala His Ala Asp Trp Gly Thr Ile Tyr Ala Phe Ile
                805                 810                 815

Pro Arg Pro Asn Glu Lys Lys Ser Thr Ala Val Lys His Val Ala Val
            820                 825                 830

Tyr Val Arg Tyr Lys Asn Ala Arg Ala Trp Cys Pro Ser Met Leu Pro
        835                 840                 845

Phe Arg Ser Tyr Lys Gln Lys
    850                 855
```

<210> SEQ ID NO 28
<211> LENGTH: 2618
<212> TYPE: DNA
<213> ORGANISM: Senecavirus

<400> SEQUENCE: 28

```
ggatccgcca ccatgggcaa cgttcaaact acctccaaga atgattttga ctcccgcggc      60

aacaacggca acatgacttt taactactac gccaatacgt atcaaaactc tgttgatttc     120

tcgacatcga gttccgcttc cggcgcggga cctggaaatt cccgcggtgg actggccggt     180

ctgctcacaa acttttccgg tatcctgaac cccctcggtt atctgaaaga tcacaatacg     240

gaagagatgg agaactctgc cgatcgtgtg attacgcaga cagctggtaa cacggctatc     300

aacactcaat cgtctctggg agtactctgt gcttacgtcg aggacccaac aaaatccgac     360

cctccatctt cctcgaccga tcaacctacg actaccttca cggccataga caggtggtat     420

acaggtcgcc tgaattcgtg gacaaaggct gttaaaacct ttagcttcca ggctgtgcca     480

ttgcccggtg ctttcctttc ccgccagggc ggcctcaacg gtggagcttt tactgctaca     540

ctgcacagac actttctgat gaaatgcggt tggcaggtgc aggtacagtg caatttgact     600

caattccacc aaggtgcact tctcgttgct atggttcccg agactacgct tgacgttaag     660

cctgacggca aggccaagtc tctccaagag ctgaatgagg aacagtgggt tgagatgagc     720

gatgactata gaaccggtaa aaacatgcca ttccagtccc tgggcacata ctacagaccc     780

ccaaattgga cttggggccc gaactttatc aatccgtatc aggtcaccgt gtttccacac     840

caaatcctga atgccaggac tagtaccagc gtcgatatta gcgtgcccta tatcggcgaa     900

acgccaaccc aatcctccga aactcagaac agctggacgc ttctggtaat ggtgttggta     960

cccttggatt ataaggaggg agccactacc gaccctgaaa tcactttttc ggtaaggccc    1020

actagccctt acttcaacgg actgcgcaac cgtttcacca ccggcactga tgaggagcaa    1080

ggccctatcc ctactgcccc cagagaaaat agcctgatgt ttctgagcac aattcctgac    1140
```

```
gacaccgtac ctgcctatgg taacgttcgt acgcctcccg taaactacct gcctggtgaa   1200

attacggacc tcttgcagct ggcccgcatc cctacactga tggccttcgg tcgtgtcagt   1260

gagcccgaac cagccagcga cgcttacgtt ccatatgttg cggtacctgc tcagttcgac   1320

gacaagccgt tgataagttt cccaatcact ttgagcgacc ctgtatacca gaacactttg   1380

gttggagcta tctcctcgaa ctttgcgaac taccgtggtt gtattcaaat cacccttaca   1440

ttctgcggcc cgatgatggc tcgtggcaag ttcctgttga gctactcccc ccccaacgga   1500

gcacaaccac agacactgtc cgaggccatg cagtgcacat actccatctg ggatatcggt   1560

ctcaacagct catggacctt tgtaatacca tacatctcgc catccgatta tagagagacc   1620

cgcgccatca ccaacagtgt gtactcagcc gatggatggt tcagtctcca taagcttaca   1680

aagatcactc tgccccccga ctgcccacaa tcaccctgca tattgttctt tgcctcagct   1740

ggtgaagatt acacgcttcg tttgcccgtc gactgtaacc cgtcttacgt gttccactcc   1800

acggacaatg ctgagaccgg tgtaattgag gctggtaaca ccgacacgga tttctctggt   1860

gagctggcgg ctcccggttc taaccatacc aacgtgaagt tcctttcga ccgttcacgt   1920

cttttgaacg taatcaaggt cttggaaaag gacgctgtgt tccctcgccc attccccaca   1980

gcaacgggag cacaacaaga cgacggctat ttctgcctgc tgacaccacg tcctactgtg   2040

gctagccgtc cggccacacg ctttggtctc tacgttaacc ctagcgactc tggtgtactg   2100

gctaacacct ccctggactt caatttctac tctctggcct gcttcacgta cttcaggagc   2160

gacctggagg tcactgtggt gtctctggaa ccagatctgg aatttgcggt aggatggttc   2220

ccttcaggaa gcgagtacca ggcatcgtcc tttgtgtacg accaacttca tgttccctac   2280

catttcaccg gtagaacccc acgtgccttc accagtaagg gaggcaaagt ttcttttgta   2340

ctgccctgga attctgtcag ttccgttctc ccggtccgct ggggcggagc gtcaaagctc   2400

tcatccgcga cccgcggatt gcccgcacac gcggattggg gaactatcta cgctttcatt   2460

ccacgcccta atgaaaagaa gtctacagca gtgaagcacg tggccgtcta tgtgcgttac   2520

aagaatgcaa gggcgtggtg tccgtctatg ttgccattcc gtagctataa acagaagatg   2580

cttatgcaac accaccacca ccaccactga gcggccgc                           2618
```

<210> SEQ ID NO 29
<211> LENGTH: 865
<212> TYPE: PRT
<213> ORGANISM: Senecavirus

<400> SEQUENCE: 29

```
Met Gly Asn Val Gln Thr Thr Ser Lys Asn Asp Phe Asp Ser Arg Gly
1               5                   10                  15

Asn Asn Gly Asn Met Thr Phe Asn Tyr Tyr Ala Asn Thr Tyr Gln Asn
            20                  25                  30

Ser Val Asp Phe Ser Thr Ser Ser Ser Ala Ser Gly Ala Gly Pro Gly
        35                  40                  45

Asn Ser Arg Gly Gly Leu Ala Gly Leu Leu Thr Asn Phe Ser Gly Ile
    50                  55                  60

Leu Asn Pro Leu Gly Tyr Leu Lys Asp His Asn Thr Glu Glu Met Glu
65                  70                  75                  80

Asn Ser Ala Asp Arg Val Ile Thr Gln Thr Ala Gly Asn Thr Ala Ile
                85                  90                  95

Asn Thr Gln Ser Ser Leu Gly Val Leu Cys Ala Tyr Val Glu Asp Pro
            100                 105                 110
```

```
Thr Lys Ser Asp Pro Pro Ser Ser Ser Thr Asp Gln Pro Thr Thr Thr
        115                 120                 125

Phe Thr Ala Ile Asp Arg Trp Tyr Thr Gly Arg Leu Asn Ser Trp Thr
    130                 135                 140

Lys Ala Val Lys Thr Phe Ser Phe Gln Ala Val Pro Leu Pro Gly Ala
145                 150                 155                 160

Phe Leu Ser Arg Gln Gly Gly Leu Asn Gly Gly Ala Phe Thr Ala Thr
                165                 170                 175

Leu His Arg His Phe Leu Met Lys Cys Gly Trp Gln Val Gln Val Gln
            180                 185                 190

Cys Asn Leu Thr Gln Phe His Gln Gly Ala Leu Leu Val Ala Met Val
        195                 200                 205

Pro Glu Thr Thr Leu Asp Val Lys Pro Asp Gly Lys Ala Lys Ser Leu
    210                 215                 220

Gln Glu Leu Asn Glu Glu Gln Trp Val Glu Met Ser Asp Asp Tyr Arg
225                 230                 235                 240

Thr Gly Lys Asn Met Pro Phe Gln Ser Leu Gly Thr Tyr Tyr Arg Pro
                245                 250                 255

Pro Asn Trp Thr Trp Gly Pro Asn Phe Ile Asn Pro Tyr Gln Val Thr
            260                 265                 270

Val Phe Pro His Gln Ile Leu Asn Ala Arg Thr Ser Thr Ser Val Asp
        275                 280                 285

Ile Ser Val Pro Tyr Ile Gly Glu Thr Pro Thr Gln Ser Ser Glu Thr
    290                 295                 300

Gln Asn Ser Trp Thr Leu Leu Val Met Val Leu Val Pro Leu Asp Tyr
305                 310                 315                 320

Lys Glu Gly Ala Thr Thr Asp Pro Glu Ile Thr Phe Ser Val Arg Pro
                325                 330                 335

Thr Ser Pro Tyr Phe Asn Gly Leu Arg Asn Arg Phe Thr Thr Gly Thr
            340                 345                 350

Asp Glu Glu Gln Gly Pro Ile Pro Thr Ala Pro Arg Glu Asn Ser Leu
        355                 360                 365

Met Phe Leu Ser Thr Ile Pro Asp Asp Thr Val Pro Ala Tyr Gly Asn
    370                 375                 380

Val Arg Thr Pro Pro Val Asn Tyr Leu Pro Gly Glu Ile Thr Asp Leu
385                 390                 395                 400

Leu Gln Leu Ala Arg Ile Pro Thr Leu Met Ala Phe Gly Arg Val Ser
                405                 410                 415

Glu Pro Glu Pro Ala Ser Asp Ala Tyr Val Pro Tyr Val Ala Val Pro
            420                 425                 430

Ala Gln Phe Asp Asp Lys Pro Leu Ile Ser Phe Pro Ile Thr Leu Ser
        435                 440                 445

Asp Pro Val Tyr Gln Asn Thr Leu Val Gly Ala Ile Ser Ser Asn Phe
    450                 455                 460

Ala Asn Tyr Arg Gly Cys Ile Gln Ile Thr Leu Thr Phe Cys Gly Pro
465                 470                 475                 480

Met Met Ala Arg Gly Lys Phe Leu Leu Ser Tyr Ser Pro Pro Asn Gly
                485                 490                 495

Ala Gln Pro Gln Thr Leu Ser Glu Ala Met Gln Cys Thr Tyr Ser Ile
            500                 505                 510

Trp Asp Ile Gly Leu Asn Ser Ser Trp Thr Phe Val Ile Pro Tyr Ile
        515                 520                 525

Ser Pro Ser Asp Tyr Arg Glu Thr Arg Ala Ile Thr Asn Ser Val Tyr
```

```
    530                 535                 540

Ser Ala Asp Gly Trp Phe Ser Leu His Lys Leu Thr Lys Ile Thr Leu
545                 550                 555                 560

Pro Pro Asp Cys Pro Gln Ser Pro Cys Ile Leu Phe Phe Ala Ser Ala
                565                 570                 575

Gly Glu Asp Tyr Thr Leu Arg Leu Pro Val Asp Cys Asn Pro Ser Tyr
            580                 585                 590

Val Phe His Ser Thr Asp Asn Ala Glu Thr Gly Val Ile Glu Ala Gly
        595                 600                 605

Asn Thr Asp Thr Asp Phe Ser Gly Glu Leu Ala Ala Pro Gly Ser Asn
    610                 615                 620

His Thr Asn Val Lys Phe Leu Phe Asp Arg Ser Arg Leu Leu Asn Val
625                 630                 635                 640

Ile Lys Val Leu Glu Lys Asp Ala Val Phe Pro Arg Pro Phe Pro Thr
                645                 650                 655

Ala Thr Gly Ala Gln Gln Asp Asp Gly Tyr Phe Cys Leu Leu Thr Pro
            660                 665                 670

Arg Pro Thr Val Ala Ser Arg Pro Ala Thr Arg Phe Gly Leu Tyr Val
        675                 680                 685

Asn Pro Ser Asp Ser Gly Val Leu Ala Asn Thr Ser Leu Asp Phe Asn
    690                 695                 700

Phe Tyr Ser Leu Ala Cys Phe Thr Tyr Phe Arg Ser Asp Leu Glu Val
705                 710                 715                 720

Thr Val Val Ser Leu Glu Pro Asp Leu Glu Phe Ala Val Gly Trp Phe
                725                 730                 735

Pro Ser Gly Ser Glu Tyr Gln Ala Ser Ser Phe Val Tyr Asp Gln Leu
            740                 745                 750

His Val Pro Tyr His Phe Thr Gly Arg Thr Pro Arg Ala Phe Thr Ser
        755                 760                 765

Lys Gly Gly Lys Val Ser Phe Val Leu Pro Trp Asn Ser Val Ser Ser
    770                 775                 780

Val Leu Pro Val Arg Trp Gly Gly Ala Ser Lys Leu Ser Ser Ala Thr
785                 790                 795                 800

Arg Gly Leu Pro Ala His Ala Asp Trp Gly Thr Ile Tyr Ala Phe Ile
                805                 810                 815

Pro Arg Pro Asn Glu Lys Lys Ser Thr Ala Val Lys His Val Ala Val
            820                 825                 830

Tyr Val Arg Tyr Lys Asn Ala Arg Ala Trp Cys Pro Ser Met Leu Pro
        835                 840                 845

Phe Arg Ser Tyr Lys Gln Lys Met Leu Met Gln His His His His His
    850                 855                 860

His
865


<210> SEQ ID NO 30
<211> LENGTH: 651
<212> TYPE: DNA
<213> ORGANISM: Senecavirus

<400> SEQUENCE: 30

actagtatgc agcccaacgt ggacatgggc tttgaggctg cggtcgctaa gaaagtggtc      60

gtccccatta ccttcatggt tcccaacaga ccttctggac ttacacagtc cgctcttctt     120

gtggccggcc ggaccttcat aatcaatgag catacatggt ccaacccctc ctggaccagc     180
```

```
ttcacaatcc gtggtgaggt gcacactcgt gatgagcctt tccaaacggt tcattttact    240

caccatggtc ttcccacaga tctgatgatg gtacgtctcg gaccgggcaa ctctttccct    300

aacaatctag acaagtttgg acttgaccag atgccggcac gtaactcccg tgtggttggc    360

gtttcggcta gttacggtaa cttcttcttc tctgggaact tcctcgggtt tgttgactcc    420

atcacctctg accaaggaac ctatgcgaga cttttcaggt acagggtgac gacttacaag    480

ggatggtgcg gttcggccct ggtctgtgag gccggtggtg tccgacgcat cattggcatg    540

cattctgctg gtgccgctgg tatcggcgcc gggacttaca tctcaaaatt aggactgatc    600

aaagccctta aacacctcgg tgagcctctg gctacaatgc aatgagagct c             651
```

<210> SEQ ID NO 31
<211> LENGTH: 212
<212> TYPE: PRT
<213> ORGANISM: Senecavirus

<400> SEQUENCE: 31

```
Met Gln Pro Asn Val Asp Met Gly Phe Glu Ala Ala Val Ala Lys Lys
1               5                   10                  15

Val Val Val Pro Ile Thr Phe Met Val Pro Asn Arg Pro Ser Gly Leu
            20                  25                  30

Thr Gln Ser Ala Leu Leu Val Ala Gly Arg Thr Phe Ile Ile Asn Glu
        35                  40                  45

His Thr Trp Ser Asn Pro Ser Trp Thr Ser Phe Thr Ile Arg Gly Glu
    50                  55                  60

Val His Thr Arg Asp Glu Pro Phe Gln Thr Val His Phe Thr His His
65                  70                  75                  80

Gly Leu Pro Thr Asp Leu Met Met Val Arg Leu Gly Pro Gly Asn Ser
                85                  90                  95

Phe Pro Asn Asn Leu Asp Lys Phe Gly Leu Asp Gln Met Pro Ala Arg
            100                 105                 110

Asn Ser Arg Val Val Gly Val Ser Ala Ser Tyr Gly Asn Phe Phe Phe
        115                 120                 125

Ser Gly Asn Phe Leu Gly Phe Val Asp Ser Ile Thr Ser Asp Gln Gly
    130                 135                 140

Thr Tyr Ala Arg Leu Phe Arg Tyr Arg Val Thr Thr Tyr Lys Gly Trp
145                 150                 155                 160

Cys Gly Ser Ala Leu Val Cys Glu Ala Gly Gly Val Arg Arg Ile Ile
                165                 170                 175

Gly Met His Ser Ala Gly Ala Ala Gly Ile Gly Ala Gly Thr Tyr Ile
            180                 185                 190

Ser Lys Leu Gly Leu Ile Lys Ala Leu Lys His Leu Gly Glu Pro Leu
        195                 200                 205

Ala Thr Met Gln
    210
```

<210> SEQ ID NO 32
<211> LENGTH: 3489
<212> TYPE: DNA
<213> ORGANISM: Senecavirus

<400> SEQUENCE: 32

```
ggatccgcca ccatgggtaa tgttcagaca acctcaaaga atgattttga ttcccgcggc     60

aataatggta acatgacctt caattactac gcaaacactt accagaattc agtagacttc    120

tcgacctcct cgtcggcgtc aggcgccgga cccgggaact cccggggcgg actagcgggt    180
```

```
ctcctcacaa atttcagtgg aatcttgaac cctcttggct acctcaaaga tcacaatacc    240
gaagaaatgg aaaactctgc tgatcgagtc ataacgcaaa cggcgggcaa cactgccata    300
aacacgcaat catcactggg tgtgttgtgt gcctacgttg aagacccgac caaatctgac    360
cctccgtcca gcagcacaga tcaacccacc accactttta ctgccatcga caggtggtac    420
actggacgcc tcaattcttg gacaaaagct gtaaaaacct tctcttttca ggccgtcccg    480
ctccctggag ccttcctgtc taaacaggga ggcctcaacg gaggggcctt cacggctacc    540
ctacatagac atttcttaat gaagtgcggg tggcaggtgc aggtccaatg caatttgacg    600
caattccacc aaggtgctct tcttgttgcc atggtccccg aaaccaccct tgatgtcaaa    660
cctgacggca aggcaaagag cttacaggag ctgaatgaag agcagtgggt ggaaatgtct    720
gacgattacc ggaccgggaa aaacatgcct tttcagtctc ttggcacata ctatcggccc    780
cctaactgga cttggggccc caatttcatc aacccctatc aagtaacagt tttcccacac    840
caaattctga acgcgagaac ctctacctcg gtagacataa gtgtcccata catcggggag    900
actcctacac aatcctcaga gacacagaac tcctggaccc tccttgttat ggtgcttgtc    960
cccctggact acaaggaggg agccacaact gacccagaaa ttacattttc tgtaaggcct   1020
acaagtccct acttcaatgg gcttcgtaac cgtttcacga ccgggacgga cgaggaacag   1080
gggcccattc ccacagcacc cagagaaaat tcgcttatgt ttctctcaac catccctgac   1140
gacactgtcc ctgcttacgg gaatgtgcgt accccctcccg tcaattacct ccccggtgaa   1200
ataaccgacc tcttacaact ggcccgtata cccactctca tggcgtttgg gcgggtgtct   1260
gaacccgagc ctgcctcaga cgcatatgtg ccctacgttg ccgttcctgc ccagttcgac   1320
gacaagcctc tcatctcctt cccgatcacc ctttcagatc ctgtctacca gaacaccctg   1380
gtaggcgcca tcagttcgaa cttcgccaac taccgggggt gtatccaaat cactctgaca   1440
ttttgtggac ccatgatggc aagagggaaa ttcctgctct cgtattctcc cccaaatgga   1500
gcacaaccac agaccctttc tgaagctatg cagtgcacat actctatttg ggatataggc   1560
ttgaactcta gttggacctt tgtcatcccc tacatctcgc ccagtgatta ccgtgaaact   1620
cgggctatta ccaactcagt ttattctgct gatggttggt ttagcttgca caagctgacc   1680
aaaattactc taccacctga ctgcccacag agtccctgta ttctcttttt cgcctctgct   1740
ggtgaggatt acaccctccg tctccctgtt gattgtaatc cttcctacgt gttccactcc   1800
accgacaacg ccgagactgg ggttattgag gcaggtaaca ctgacaccga tttctctggt   1860
gaactggcgg ctcctggctc taaccatact aatgtcaaat tcctgtttga ccgatctcga   1920
ctactgaatg taattaaggt actggagaag gacgccgtct tcccccgtcc tttccccaca   1980
gcaacaggtg cacagcagga cgatggttac ttttgtcttc taacaccccg cccaacagtc   2040
gcttcccgac ccgccactcg tttcggcctg tacgtcaacc cgtctgacag tggcgttctc   2100
gctaacactt cactggattt caatttttac agtttggcct gtttcactta ctttagatca   2160
gaccttgaag tcacggtggt ctcactggag ccagatttgg aattcgccgt ggggtggttc   2220
ccctctggca gtgagtacca ggcttctagc tttgtctacg accaactgca tgtaccctac   2280
cactttactg ggcgcactcc ccgcgctttc accagcaagg gtggaaaggt atctttcgtg   2340
ctcccttgga actctgtctc ttccgtgctt cccgtgcgct ggggggcgc ttccaagctt   2400
tcttctgcca cgcggtgtct gccggctcat gctgactggg ggaccattta cgcctttatc   2460
ccccgtccta acgagaagaa aagcaccgct gtaaagcacg tggcggtgta cgttcggtac   2520
```

```
aagaacgcgc gtgcttggtg ccccagcatg cttccctttc gcagctacaa gcaaaagatg   2580
ctgatgcaac accaccacca ccaccactga gcggccgcga actgtggagc cagggcggcc   2640
ttggccaccc tggcttactg taacagaaaa aagagtaaaa ggcgacagct cgcttgccaa   2700
ttgtcctgtt acgtactctg tggtttcacg aggttgtcat caccaaaggt aacctttttt   2760
tttgtcctcg ccgacaaaac gacatcttaa taaccaagca acgttcgata aagaaaaaaa   2820
ctcgtcctta agtcgcgaac tagtatgcag cccaacgtgg acatgggctt tgaggctgcg   2880
gtcgctaaga aagtggtcgt ccccattacc ttcatggttc ccaacagacc ttctggactt   2940
acacagtccg ctcttcttgt ggccggccgg accttcataa tcaatgagca tacatggtcc   3000
aacccctcct ggaccagctt cacaatccgt ggtgaggtgc acactcgtga tgagcctttc   3060
caaacggttc attttactca ccatggtctt cccacagatc tgatgatggt acgtctcgga   3120
ccgggcaact ctttccctaa caatctagac aagtttggac ttgaccagat gccggcacgt   3180
aactcccgtg tggttggcgt ttcggctagt tacggtaact tcttcttctc tgggaacttc   3240
ctcgggtttg ttgactccat cacctctgac caaggaacct atgcgagact tttcaggtac   3300
agggtgacga cttacaaggg atggtgcggt tcggccctgg tctgtgaggc cggtggtgtc   3360
cgacgcatca ttggcatgca ttctgctggt gccgctggta tcggcgccgg gacttacatc   3420
tcaaaattag gactgatcaa agcccttaaa cacctcggtg agcctctggc tacaatgcaa   3480
tgagagctc                                                           3489
```

<210> SEQ ID NO 33
<211> LENGTH: 3489
<212> TYPE: DNA
<213> ORGANISM: Senecavirus

<400> SEQUENCE: 33

```
ggatccgcca ccatgggcaa cgttcaaact acctccaaga atgattttga ctcccgcggc     60
aacaacggca acatgacttt taactactac gccaatacgt atcaaaactc tgttgatttc    120
tcgacatcga gttccgcttc cggcgcggga cctggaaatt cccgcggtgg actggccggt    180
ctgctcacaa acttttccgg tatcctgaac cccctcggtt atctgaaaga tcacaatacg    240
gaagagatgg agaactctgc cgatcgtgtg attacgcaga cagctggtaa cacggctatc    300
aacactcaat cgtctctggg agtactctgt gcttacgtcg aggacccaac aaaatccgac    360
cctccatctt cctcgaccga tcaacctacg actaccttca cggccataga caggtggtat    420
acaggtcgcc tgaattcgtg gacaaaggct gttaaaacct ttagcttcca ggctgtgcca    480
ttgcccggtg ctttcctttc ccgccagggc ggcctcaacg gtggagcttt tactgctaca    540
ctgcacagac actttctgat gaaatgcggt tggcaggtgc aggtacagtg caatttgact    600
caattccacc aaggtgcact tctcgttgct atggttcccg agactacgct tgacgttaag    660
cctgacggca aggccaagtc tctccaagag ctgaatgagg aacagtgggt tgagatgagc    720
gatgactata gaaccggtaa aaacatgcca ttccagtccc tgggcacata ctacagaccc    780
ccaaattgga cttggggccc gaactttatc aatccgtatc aggtcaccgt gtttccacac    840
caaatcctga atgccaggac tagtaccagc gtcgatatta gcgtgcccta tatcggcgaa    900
acgccaaccc aatcctccga aactcagaac agctggacgc ttctggtaat ggtgttggta    960
cccttggatt ataaggaggg agccactacc gaccctgaaa tcactttttc ggtaaggccc   1020
actagccctt acttcaacgg actgcgcaac cgtttcacca ccggcactga tgaggagcaa   1080
ggccctatcc ctactgcccc cagagaaaat agcctgatgt ttctgagcac aattcctgac   1140
```

```
gacaccgtac ctgcctatgg taacgttcgt acgcctcccg taaactacct gcctggtgaa   1200
attacggacc tcttgcagct ggcccgcatc cctacactga tggccttcgg tcgtgtcagt   1260
gagcccgaac cagccagcga cgcttacgtt ccatatgttg cggtacctgc tcagttcgac   1320
gacaagccgt tgataagttt cccaatcact ttgagcgacc ctgtatacca gaacactttg   1380
gttggagcta tctcctcgaa ctttgcgaac taccgtggtt gtattcaaat caccctaaca   1440
ttctgcggcc cgatgatggc tcgtggcaag ttcctgttga gctactcccc ccccaacgga   1500
gcacaaccac agacactgtc cgaggccatg cagtgcacat actccatctg ggatatcggt   1560
ctcaacagct catggacctt tgtaatacca tacatctcgc catccgatta tagagagacc   1620
cgcgccatca ccaacagtgt gtactcagcc gatggatggt tcagtctcca taagcttaca   1680
aagatcactc tgccccccga ctgcccacaa tcaccctgca tattgttctt tgcctcagct   1740
ggtgaagatt acacgcttcg tttgcccgtc gactgtaacc cgtcttacgt gttccactcc   1800
acggacaatg ctgagaccgg tgtaattgag gctggtaaca ccgacacgga tttctctggt   1860
gagctggcgg ctcccggttc taaccatacc aacgtgaagt tcctttcga ccgttcacgt   1920
cttttgaacg taatcaaggt cttggaaaag gacgctgtgt tccctcgccc attccccaca   1980
gcaacgggag cacaacaaga cgacggctat ttctgcctgc tgacaccacg tcctactgtg   2040
gctagccgtc cggccacacg ctttggtctc tacgttaacc ctagcgactc tggtgtactg   2100
gctaacacct ccctggactt caatttctac tctctggcct gcttcacgta cttcaggagc   2160
gacctggagg tcactgtggt gtctctggaa ccagatctgg aatttgcggt aggatggttc   2220
ccttcaggaa gcgagtacca ggcatcgtcc tttgtgtacg accaacttca tgttccctac   2280
catttcaccg gtagaacccc acgtgccttc accagtaagg gaggcaaagt ttcttttgta   2340
ctgccctgga attctgtcag ttccgttctc ccggtccgct ggggcggagc gtcaaagctc   2400
tcatccgcga cccgcggatt gcccgcacac gcggattggg gaactatcta cgctttcatt   2460
ccacgcccta atgaaaagaa gtctacagca gtgaagcacg tggccgtcta tgtgcgttac   2520
aagaatgcaa gggcgtggtg tccgtctatg ttgccattcc gtagctataa acagaagatg   2580
cttatgcaac accaccacca ccaccactga gcggccgcga actgtggagc cagggcggcc   2640
ttggccaccc tggcttactg taacagaaaa aagagtaaaa ggcgacagct cgcttgccaa   2700
ttgtcctgtt acgtactctg tggtttcacg aggttgtcat caccaaaggt aacctttttt   2760
tttgtcctcg ccgacaaaac gacatcttaa taaccaagca acgttcgata aagaaaaaaa   2820
ctcgtcctta agtcgcgaac tagtatgcag cccaacgtgg acatgggctt tgaggctgcg   2880
gtcgctaaga aagtggtcgt ccccattacc ttcatggttc ccaacagacc ttctggactt   2940
acacagtccg ctcttcttgt ggccggccgg accttcataa tcaatgagca tacatggtcc   3000
aacccctcct ggaccagctt cacaatccgt ggtgaggtgc acactcgtga tgagcctttc   3060
caaacggttc attttactca ccatggtctt cccacagatc tgatgatggt acgtctcgga   3120
ccgggcaact ctttccctaa caatctagac aagtttggac ttgaccagat gccggcacgt   3180
aactcccgtg tggttggcgt ttcggctagt tacggtaact tcttcttctc tgggaacttc   3240
ctcgggtttg ttgactccat cacctctgac caaggaacct atgcgagact tttcaggtac   3300
agggtgacga cttacaaggg atggtgcggt tcggccctgg tctgtgaggc cggtggtgtc   3360
cgacgcatca ttggcatgca ttctgctggt gccgctggta tcggcgccgg gacttacatc   3420
tcaaaattag gactgatcaa agcccttaaa cacctcggtg agcctctggc tacaatgcaa   3480
```

tgagagctc 3489

<210> SEQ ID NO 34
<211> LENGTH: 26
<212> TYPE: DNA
<213> ORGANISM: Artificial Sequence
<220> FEATURE:
<223> OTHER INFORMATION: Primer

<400> SEQUENCE: 34
ggatccgcca ccatgggtaa tgttca 26

<210> SEQ ID NO 35
<211> LENGTH: 58
<212> TYPE: DNA
<213> ORGANISM: Artificial Sequence
<220> FEATURE:
<223> OTHER INFORMATION: Primer

<400> SEQUENCE: 35
gcggccgctc agtggtggtg gtggtggtgt tgcatcagca tcttttgctt gtagctgc 58

<210> SEQ ID NO 36
<211> LENGTH: 22
<212> TYPE: DNA
<213> ORGANISM: Artificial Sequence
<220> FEATURE:
<223> OTHER INFORMATION: Primer

<400> SEQUENCE: 36
ggatccgcca ccatgggcaa cg 22

<210> SEQ ID NO 37
<211> LENGTH: 60
<212> TYPE: DNA
<213> ORGANISM: Artificial Sequence
<220> FEATURE:
<223> OTHER INFORMATION: Primer

<400> SEQUENCE: 37
gcggccgctc agtggtggtg gtggtggtgt tgcataagca tcttctgttt atagctacgg 60

<210> SEQ ID NO 38
<211> LENGTH: 33
<212> TYPE: DNA
<213> ORGANISM: Artificial Sequence
<220> FEATURE:
<223> OTHER INFORMATION: Primer

<400> SEQUENCE: 38
actagtatgc agcccaacgt ggacatgggc ttt 33

<210> SEQ ID NO 39
<211> LENGTH: 35
<212> TYPE: DNA
<213> ORGANISM: Artificial Sequence
<220> FEATURE:
<223> OTHER INFORMATION: Primer

<400> SEQUENCE: 39
gagctctcat tgcattgtag ccagaggctc accga 35

<210> SEQ ID NO 40
<211> LENGTH: 41
<212> TYPE: DNA
<213> ORGANISM: Artificial Sequence
<220> FEATURE:
<223> OTHER INFORMATION: Primer

<400> SEQUENCE: 40
cttcctacgt gcctcagggg gttgacaacg ccgagactgg g 41

<210> SEQ ID NO 41
<211> LENGTH: 41
<212> TYPE: DNA
<213> ORGANISM: Artificial Sequence
<220> FEATURE:
<223> OTHER INFORMATION: Primer

<400> SEQUENCE: 41
cccagtctcg gcgttgtcaa ccccctgagg cacgtaggaa g 41

<210> SEQ ID NO 42
<211> LENGTH: 35
<212> TYPE: DNA
<213> ORGANISM: Artificial Sequence
<220> FEATURE:
<223> OTHER INFORMATION: Primer

<400> SEQUENCE: 42
tacaatgcaa ggactgatga ctgagctaga gcctg 35

<210> SEQ ID NO 43
<211> LENGTH: 31
<212> TYPE: DNA
<213> ORGANISM: Artificial Sequence
<220> FEATURE:
<223> OTHER INFORMATION: Primer

<400> SEQUENCE: 43
tcagtcatca gtccttgcat tgtagccaga g 31

<210> SEQ ID NO 44
<211> LENGTH: 32
<212> TYPE: DNA
<213> ORGANISM: Artificial Sequence
<220> FEATURE:
<223> OTHER INFORMATION: Primer

<400> SEQUENCE: 44
gcggccgctc agtcgaacaa ggccctccat ct 32

<210> SEQ ID NO 45
<211> LENGTH: 1389
<212> TYPE: DNA
<213> ORGANISM: Senecavirus

<400> SEQUENCE: 45
ggactgatga ctgagctaga gcctggagtc accgtacatg taccccgaaa atctaaattg 60
agaaagacga ccgcacacgc ggtgtacaaa ccggagtttg aacctgctgt gttgtcaaaa 120
tttgatccca gactgaacaa ggatgttgac ctagatgagg taatttggtc taaacacacc 180
gccaacgtcc cttatcaacc tcctttgttc tacacataca tgtcagagta cgctcatcgg 240
gttttctcct ttttgggaaa agacaatgac attctgaccg tcaaagaagc aatcctgggc 300
atccctggac tagaccctat ggatccccac acagctccgg gtttgcccta cgccattagc 360
ggccttcgac gtactgatct cgtcgatttt gcgaacggca cggtagaccc ggcactggcc 420
atgcagatcc agaaattctt agacggtgac tactctgatc atgtcttcca aacttttctg 480

-continued

```
aaagatgaaa tcagaccctc agagaaggtc cgggcgggaa aaacccgcat tgtcgatgtg    540

ccctccctgg cgcactgcat tgtgggcaga atgctgcttg ggcgctttgc cgccaagttt    600

caatcccatc ctggctttct ccttggctcc gctatcgggt ctgaccctga tgtcttctgg    660

accgtcatag ggctcagct cgagggaaga aagaacacgt atgacgtgga ctacagtgcc    720

tttgactctt cacacggcac tggctccttc gaggctctca tctctcactt tttcaccgtg    780

gacaatggtt tcagccctgc gctgggaccg tatctcagat ccctggctgt ctcggtgcac    840

gcttacggcg agcgtcgcat caagattacc ggaggcctcc cctctggttg tgccgcgacc    900

agcctgctga acacagtgct caacaatgtg atcatcagga ctgctctggc attgacctac    960

aaggaatttg aatatgacat ggttgatatc atcgcctacg gtgacgacct tctggttggt   1020

acggattatg atctggactt caatgaggtg gcgcggcgcg ctgccaaact ggggtataag   1080

atgactcctg ccaacaaggg ttctgtcttc cctccgactt cctctctctc cgatgctgtt   1140

tttctaaaac gcaaattcgt ccaaaacaat gacggcttat ataaaccagt tatggattta   1200

aagaatttgg aagccatgct ctcctacttc aaaccaggaa cactactcga gaagctgcaa   1260

tctgtttcta tgttggctca acattctgga aaagaagaat acgatagatt gatgcacccc   1320

ttcgctgact atggtgccgt accgagtcac gagtacctgc aggcaagatg gagggccttg   1380

ttcgactga                                                            1389
```